US012492244B2

(12) United States Patent
Kim et al.

(10) Patent No.: US 12,492,244 B2
(45) **Date of Patent: *Dec. 9, 2025**

(54) ANTI-FAMILY WITH SEQUENCE SIMILARITY 19, MEMBER A5 ANTIBODIES AND METHOD OF USE THEREOF

(71) Applicant: NEURACLE SCIENCE CO., LTD., Seoul (KR)

(72) Inventors: Bongcheol Kim, Seongnam-si (KR); Wonkyum Kim, Seoul (KR); Dong Sik Kim, Seoul (KR); Jae-Keun Lee, Seoul (KR); Jeongwon Yoon, Sejong-si (KR); Junho Chung, Seongnam-si (KR); Junyeong Jin, Gwachun-si (KR)

(73) Assignee: NEURACLE SCIENCE CO., LTD., Seoul (KR)

( * ) Notice: Subject to any disclaimer, the term of this patent is extended or adjusted under 35 U.S.C. 154(b) by 881 days.

This patent is subject to a terminal disclaimer.

(21) Appl. No.: 17/290,154

(22) PCT Filed: Dec. 31, 2019

(86) PCT No.: PCT/IB2019/061461

§ 371 (c)(1),
(2) Date: Apr. 29, 2021

(87) PCT Pub. No.: WO2020/141452

PCT Pub. Date: Jul. 9, 2020

(65) Prior Publication Data

US 2022/0144932 A1 May 12, 2022

Related U.S. Application Data

(60) Provisional application No. 62/787,711, filed on Jan. 2, 2019, provisional application No. 62/838,190, filed on Apr. 24, 2019.

(51) Int. Cl.
*C07K 16/00* (2006.01)
*C07K 16/24* (2006.01)

(52) U.S. Cl.
CPC .......... *C07K 16/24* (2013.01); *C07K 2317/24* (2013.01); *C07K 2317/34* (2013.01); *C07K 2317/54* (2013.01); *C07K 2317/55* (2013.01); *C07K 2317/56* (2013.01); *C07K 2317/622* (2013.01); *C07K 2317/76* (2013.01); *C07K 2317/92* (2013.01)

(58) Field of Classification Search
CPC ................ C07K 16/24; C07K 2317/24; C07K 2317/34; C07K 2317/54; C07K 2317/55; C07K 2317/56; C07K 2317/622; C07K 2317/76; C07K 2317/92
See application file for complete search history.

(56) References Cited

U.S. PATENT DOCUMENTS

| | | | |
|---|---|---|---|
| 4,044,126 | A | 8/1977 | Cook et al. |
| 4,364,923 | A | 12/1982 | Cook et al. |
| 4,414,209 | A | 11/1983 | Cook et al. |
| 4,444,887 | A | 4/1984 | Hoffmann |
| 4,716,111 | A | 12/1987 | Osband et al. |
| 4,816,397 | A | 3/1989 | Boss et al. |
| 4,816,567 | A | 3/1989 | Cabilly et al. |
| 4,881,175 | A | 11/1989 | Ladner |
| 4,946,778 | A | 8/1990 | Ladner et al. |
| 5,013,653 | A | 5/1991 | Huston et al. |
| 5,091,513 | A | 2/1992 | Huston et al. |
| 5,122,464 | A | 6/1992 | Wilson et al. |
| 5,132,405 | A | 7/1992 | Huston et al. |
| 5,223,409 | A | 6/1993 | Ladner et al. |
| 5,225,539 | A | 7/1993 | Winter |
| 5,258,498 | A | 11/1993 | Huston et al. |
| 5,260,203 | A | 11/1993 | Ladner et al. |
| 5,403,484 | A | 4/1995 | Ladner et al. |
| 5,413,923 | A | 5/1995 | Kucherlapati et al. |

(Continued)

FOREIGN PATENT DOCUMENTS

| | | |
|---|---|---|
| EP | 0239400 A2 | 9/1987 |
| EP | 0519596 A1 | 12/1992 |

(Continued)

OTHER PUBLICATIONS

Aarts, L.H., et al., "The role of the neural growth associated protein B-50/GAP-43 in morphogenesis," Adv Exp Med Biol 446:85-106, Springer, United States (1998).
Ames, R.S., et al., "Conversion of murine Fabs isolated from a combinatorial phage display library to full length immunoglobulins," J Immunol Methods 184(2):177-186, Elsevier, Netherlands (Aug. 1995).
An, Z., et al., "IgG2m4, an engineered antibody isotype with reduced Fc function," Mabs 1(6):572-579, Landes Bioscience, United States (Nov.-Dec. 2009).
Baca, M., et al., "Antibody humanization using monovalent phage display," J Biol Chem 272(16):10678-10684, American Society for Biochemistry and Molecular Biology Inc., United States (Apr. 1997).

(Continued)

*Primary Examiner* — Lei Yao
(74) *Attorney, Agent, or Firm* — Sterne, Kessler, Goldstein & Fox P.L.L.C.

(57) ABSTRACT

The present disclosure provides antibodies that specifically bind to human FAM19A5 and compositions comprising such antibodies. In some embodiments, antibodies are deimmunized to reduce immunogenicity in a human subject. In certain embodiments, antibodies have undergone affinity maturation. In some embodiments, the anti-FAM19A5 antibodies can modulate FAM19A5 activity, e.g., inhibit, suppress, reduce, or reverse the onset of reactive gliosis and/or excessive proliferation of reactive astrocytes, utilizing such antibodies. The present disclosure also provides methods for treating disorders, such as central nervous system damage, a degenerative brain disorder, a neuropathic pain, or a cancer, by administering an antibody that specifically binds to human FAM19A5.

18 Claims, 51 Drawing Sheets

Specification includes a Sequence Listing.

(56) References Cited

U.S. PATENT DOCUMENTS

| | | | |
|---|---|---|---|
| 5,427,908 | A | 6/1995 | Dower et al. |
| 5,455,030 | A | 10/1995 | Ladner et al. |
| 5,476,786 | A | 12/1995 | Huston et al. |
| 5,482,858 | A | 1/1996 | Huston et al. |
| 5,516,637 | A | 5/1996 | Huang et al. |
| 5,530,101 | A | 6/1996 | Queen et al. |
| 5,545,806 | A | 8/1996 | Lonberg et al. |
| 5,565,332 | A | 10/1996 | Hoogenboom et al. |
| 5,569,825 | A | 10/1996 | Lonberg et al. |
| 5,571,698 | A | 11/1996 | Ladner et al. |
| 5,580,717 | A | 12/1996 | Dower et al. |
| 5,585,089 | A | 12/1996 | Queen et al. |
| 5,625,126 | A | 4/1997 | Lonberg et al. |
| 5,633,425 | A | 5/1997 | Lonberg et al. |
| 5,658,727 | A | 8/1997 | Barbas et al. |
| 5,661,016 | A | 8/1997 | Lonberg et al. |
| 5,693,780 | A | 12/1997 | Newman et al. |
| 5,698,426 | A | 12/1997 | Huse |
| 5,709,874 | A | 1/1998 | Hanson et al. |
| 5,733,743 | A | 3/1998 | Johnson et al. |
| 5,750,753 | A | 5/1998 | Kimae et al. |
| 5,759,542 | A | 6/1998 | Gurewich |
| 5,766,886 | A | 6/1998 | Studnicka et al. |
| 5,780,225 | A | 7/1998 | Wigler et al. |
| 5,807,715 | A | 9/1998 | Morrison et al. |
| 5,814,318 | A | 9/1998 | Lonberg et al. |
| 5,821,047 | A | 10/1998 | Garrard et al. |
| 5,837,242 | A | 11/1998 | Holliger et al. |
| 5,840,674 | A | 11/1998 | Yatvin et al. |
| 5,860,957 | A | 1/1999 | Jacobsen et al. |
| 5,869,620 | A | 2/1999 | Whitlow et al. |
| 5,885,793 | A | 3/1999 | Griffiths et al. |
| 5,900,252 | A | 5/1999 | Calanchi et al. |
| 5,939,598 | A | 8/1999 | Kucherlapati et al. |
| 5,948,433 | A | 9/1999 | Burton et al. |
| 5,969,108 | A | 10/1999 | Mccafferty et al. |
| 5,972,366 | A | 10/1999 | Haynes et al. |
| 5,983,134 | A | 11/1999 | Ostrow |
| 5,985,307 | A | 11/1999 | Hanson et al. |
| 5,985,317 | A | 11/1999 | Venkateshwaran et al. |
| 5,989,830 | A | 11/1999 | Davis et al. |
| 6,004,534 | A | 12/1999 | Langer et al. |
| 6,005,079 | A | 12/1999 | Casterman et al. |
| 6,010,715 | A | 1/2000 | Wick et al. |
| 6,024,975 | A | 2/2000 | D Angelo et al. |
| 6,039,975 | A | 3/2000 | Shah et al. |
| 6,048,736 | A | 4/2000 | Kosak |
| 6,060,082 | A | 5/2000 | Chen et al. |
| 6,071,495 | A | 6/2000 | Unger et al. |
| 6,075,181 | A | 6/2000 | Kucherlapati et al. |
| 6,120,751 | A | 9/2000 | Unger |
| 6,131,570 | A | 10/2000 | Schuster et al. |
| 6,132,992 | A | 10/2000 | Ledbetter et al. |
| 6,139,865 | A | 10/2000 | Friend et al. |
| 6,150,184 | A | 11/2000 | Evans et al. |
| 6,167,301 | A | 12/2000 | Flower et al. |
| 6,253,872 | B1 | 7/2001 | Neumann |
| 6,256,533 | B1 | 7/2001 | Yuzhakov et al. |
| 6,261,595 | B1 | 7/2001 | Stanley et al. |
| 6,267,983 | B1 | 7/2001 | Fujii et al. |
| 6,271,359 | B1 | 8/2001 | Norris et al. |
| 6,274,552 | B1 | 8/2001 | Tamarkin et al. |
| 6,316,652 | B1 | 11/2001 | Steliou |
| 6,331,415 | B1 | 12/2001 | Cabilly et al. |
| 6,407,213 | B1 | 6/2002 | Carter et al. |
| 7,183,076 | B2 | 2/2007 | Arathoon et al. |
| 7,951,917 | B1 | 5/2011 | Arathoon et al. |
| 8,227,577 | B2 | 7/2012 | Klein et al. |
| 8,586,713 | B2 | 11/2013 | Davis et al. |
| 2004/0014194 | A1 | 1/2004 | Beyer et al. |
| 2005/0042664 | A1 | 2/2005 | Wu et al. |
| 2012/0100140 | A1 | 4/2012 | Reyes et al. |
| 2015/0118230 | A1 | 4/2015 | Seong et al. |
| 2015/0118320 | A1 | 4/2015 | Inokunchi et al. |
| 2021/0070849 | A1* | 3/2021 | Kim ........................ A61P 25/02 |
| 2021/0388382 | A1* | 12/2021 | Kim ........................ C12N 15/86 |

FOREIGN PATENT DOCUMENTS

| | | | |
|---|---|---|---|
| EP | 0592106 | A1 | 4/1994 |
| EP | 1074563 | A1 | 2/2001 |
| KR | 20160101786 | A | 8/2016 |
| WO | WO-8605807 | A1 | 10/1986 |
| WO | WO-8901036 | A1 | 2/1989 |
| WO | WO-9002809 | A1 | 3/1990 |
| WO | WO-9109967 | A1 | 7/1991 |
| WO | WO-9110737 | A1 | 7/1991 |
| WO | WO-9110741 | A1 | 7/1991 |
| WO | WO-9201047 | A1 | 1/1992 |
| WO | WO-9218619 | A1 | 10/1992 |
| WO | WO-9222324 | A1 | 12/1992 |
| WO | WO-9311236 | A1 | 6/1993 |
| WO | WO-9317105 | A1 | 9/1993 |
| WO | WO-9404678 | A1 | 3/1994 |
| WO | WO-9425591 | A1 | 11/1994 |
| WO | WO-9515982 | A2 | 6/1995 |
| WO | WO-9517886 | A1 | 7/1995 |
| WO | WO-9520401 | A1 | 8/1995 |
| WO | WO-9633735 | A1 | 10/1996 |
| WO | WO-9634096 | A1 | 10/1996 |
| WO | WO-9712622 | A1 | 4/1997 |
| WO | WO-9713844 | A1 | 4/1997 |
| WO | WO-9816654 | A1 | 4/1998 |
| WO | WO-9817815 | A1 | 4/1998 |
| WO | WO-9817816 | A1 | 4/1998 |
| WO | WO-9818934 | A1 | 5/1998 |
| WO | WO-9824893 | A2 | 6/1998 |
| WO | WO-9846645 | A2 | 10/1998 |
| WO | WO-9850433 | A2 | 11/1998 |
| WO | WO-9852976 | A1 | 11/1998 |
| WO | WO-9931251 | A1 | 6/1999 |
| WO | WO-0034317 | A2 | 6/2000 |
| WO | WO-0144301 | A1 | 6/2001 |
| WO | WO-02092780 | A2 | 11/2002 |
| WO | WO-03074679 | A2 | 9/2003 |
| WO | WO-2009059278 | A1 | 5/2009 |
| WO | WO-2018083538 | A1 | 5/2018 |
| WO | WO-2019003159 | A1 | 1/2019 |
| WO | WO-2019003162 | A1 | 1/2019 |
| WO | WO-2019003164 | A1 | 1/2019 |
| WO | WO-2019003165 | A1 | 1/2019 |
| WO | WO2019207513 | * | 10/2019 |
| WO | WO-2020141452 | A1 | 7/2020 |

OTHER PUBLICATIONS

Baek, D.S., and Kim, Y.S., "Humanization of a phosphothreonine peptide-specific chicken antibody by combinatorial library optimization of the phosphoepitope-binding motif," Biochem Biophys Res Commun 463(3):414-420, Elsevier B.V., United States (Jul. 2015).

Balasingam, V., et al., "Reactive astrogliosis in the neonatal mouse brain and its modulation by cytokines," J Neurosci 14(2):846-856, Society for Neuroscience, United States (Feb. 1994).

Benowitz, L.I., and Routtenberg, A., "GAP-43: an intrinsic determinant of neuronal development and plasticity," Trends Neurosci 20(2):84-91, Elsevier Ltd., United Kingdom (Feb. 1997).

Better, M., et al., "*Escherichia coli* secretion of an active chimeric antibody fragment," Science 240(4855):1041-1043, American Association for the Advancement of Science, United States (May 1988).

Bird, R.E., et al., "Single-chain antigen-binding proteins," Science 242(4877):423-426, American Association for the Advancement of Science, United States (Oct. 1988).

Bitter, G.A., et al., "Expression and secretion vectors for yeast," Methods Enzymol 153:516-544, Academic Press Inc., United States (1987).

Boussif, O., et al., "A versatile vector for gene and oligonucleotide transfer into cells in culture and in vivo: polyethylenimine," Proc Natl Acad Sci USA 92(16):7297-7301, National Academy of Sciences, United States (Aug. 1995).

(56) References Cited

OTHER PUBLICATIONS

Brennan, M., et al., "Preparation of bispecific antibodies by chemical recombination of monoclonal immunoglobulin G1 fragments," Science 229(4708):81-83, American Association for the Advancement of Science, United States (Jul. 1985).
Bricogne, G., "[23] Bayesian statistical viewpoint on structure determination: Basic concepts and examples," Methods Enzymol 276:361-423, Academic Press Inc., United States (1997).
Bricogne, G., "Direct phase determination by entropy maximization and likelihood ranking: status report and perspectives," Acta Crystallogr D Biol Crystallogr 49(Pt 1):37-60, John Wiley & Sons Inc., United States (Jan. 1993).
Brinkman, U., et al., "Phage display of disulfide-stabilized Fv fragments," J Immunol Methods 182(1):41-50, Elsevier, Netherlands (May 1995).
Brodeur, B.R., et al., "Mouse-Human Myeloma Partners for the Production of Heterohybridomas," in Monoclonal Antibody Production Techniques and Applications, Schook, L.B., ed., pp. 51-63, Marcel Dekker Inc., United States (1987).
Burton, D.R., and Barbas, C.F., "Human antibodies from combinatorial libraries," Adv Immunol 57:191-280, Academic Press Inc., United States (1994).
Caldas, C., et al., "Design and synthesis of germline-based hemi-humanized single-chain Fv against the CD18 surface antigen," Protein Eng 13(5):353-360, Oxford University Press, United Kingdom (May 2000).
Champe, M., et al., "Monoclonal antibodies that block the activity of leukocyte function-associated antigen 1 recognize three discrete epitopes in the inserted domain of CD11a," J Biol Chem 270(3):1388-1394, American Society for Biochemistry and Molecular Biology Inc., United States (Jan. 1995).
Chayen, N.E., "The role of oil in macromolecular crystallization," Structure 5(10):1269-1274, Cell Press, United States (Oct. 1997).
Cheung, R.C., et al., "Epitope-specific antibody response to the surface antigen of duck hepatitis B virus in infected ducks," Virology 176(2):546-552, Academic Press Inc., United States (Jun. 1990).
Chothia, C., and Lesk, A.M., "Canonical structures for the hypervariable regions of immunoglobulins," J Mol Biol 196(4):901-917, Academic Press, United States (Aug. 1987).
Cockett, M.I., et al., "High level expression of tissue inhibitor of metalloproteinases in Chinese hamster ovary cells using glutamine synthetase gene amplification," Biotechnology (NY) 8(7):662-667, Mary Ann Liebert, United States (Jul. 1990).
Colbere-Garapin, F., et al., "A new dominant hybrid selective marker for higher eukaryotic cells," J Mol Biol 150(1):1-14, Academic Press, United States (Jul. 1981).
Couto, J.R., et al., "Anti-BA46 monoclonal antibody Mc3: humanization using a novel positional consensus and in vivo and in vitro characterization," Cancer Res 55(8):1717-1722, American Association for Cancer Research Inc., United States (Apr. 1995).
Couto, J.R., et al., "Designing human consensus antibodies with minimal positional templates," Cancer Res 55(23 Suppl):5973s-5977s, American Association for Cancer Research Inc., United States (Dec. 1995).
Crouse, G.F., et al., "Expression and amplification of engineered mouse dihydrofolate reductase minigenes," Mol Cell Biol 3(2):257-266, Taylor and Francis Inc., United States (Feb. 1983).
Cunningham, B.C., and Wells, J.A., "High-resolution epitope mapping of hGH-receptor interactions by alanine-scanning mutagenesis," Science 244(4908):1081-1085, American Association for the Advancement of Science, United States (Jun. 1989).
De Graaf, A.J., et al., "Nonnatural amino acids for site-specific protein conjugation," Bioconjug Chem 20(7):1281-1295, American Chemical Society, United States (Jul. 2009).
Edelman, G.M., et al., "The covalent structure of an entire gammaG immunoglobulin molecule," Proc Natl Acad Sci USA 63(1):78-85, National Academy of Sciences, United States (May 1969).
Foecking, M.K., and Hofstetter, H., "Powerful and versatile enhancer-promoter unit for mammalian expression vectors," Gene 45(1):101-105, Elsevier B.V., Netherlands (1986).
Frese, M.A., and Dierks, T., "Formylglycine aldehyde Tag—protein engineering through a novel post-translational modification," Chembiochem 10(3):425-427, John Wiley and Sons Inc., Germany (Feb. 2009).
Gao, Y.J., and Ji, R.R., "c-Fos and pERK, which is a better marker for neuronal activation and central sensitization after noxious stimulation and tissue injury?," Open Pain J 2:11-17, Bentham Science Publishers B.V., Netherlands (Jan. 2009).
Gautier, A., et al., "An engineered protein tag for multiprotein labeling in living cells," Chem Biol 15(2):128-136, American Chemical Society, United States (Feb. 2008).
Genbank, "*Homo sapiens* family with sequence similarity 19 (chemokine (C-C motif)-like), member A5, mRNA (cDNA clone MGC:44558 IMAGE:5299791), complete cds," Accession No. BC039396, accessed at https://www.ncbi.nlm.nih.gov/nuccore/BC039396, accessed on May 1, 2024, 2 pages.
Giege, R., et al., "Crystallogenesis of biological macromolecules: facts and perspectives," Acta Crystallogr D Biol Crystallogr 50(Pt 4):339-350, John Wiley & Sons Inc., United States (Jul. 1994).
Gillies, S.D., et al., "High-level expression of chimeric antibodies using adapted cDNA variable region cassettes," J Immunol Methods 125(1-2):191-202, Elsevier, Netherlands (Dec. 1989).
Glennie, M.J., et al., "Preparation and performance of bispecific F(ab' gamma)2 antibody containing thioether-linked Fab' gamma fragments," J Immunol 139(7):2367-2375, American Association of Immunologists, United States (Oct. 1987).
Goding, J.W., "Production of Monoclonal Antibodies," in Monoclonal Antibodies: Principles and Practice, pp. 59-103, Elsevier, Netherlands (1986).
Greenspan, N.S., and Bona, C.A., "Idiotypes: structure and immunogenicity," FASEB J 7(5):437-444, John Wiley & Sons Inc., United States (Mar. 1993).
Hackenberger, C.P.R., and Schwarzer, D., "Chemoselective ligation and modification strategies for peptides and proteins," Angew Chem Int Ed Engl 47(52):10030-10074, Wiley-VCH, Germany (2008).
Han, J., et al., "A phosphorylation pattern-recognizing antibody specifically reacts to RNA polymerase II bound to exons," Exp Mol Med 48(11):e271, Korean Society of Med Biochemistry and Mol Biology, South Korea (Nov. 2016).
Harmsen, M.M., and De Haard, H.J., "Properties, production, and applications of camelid single-domain antibody fragments," Appl Microbiol Biotechnol 77(1):13-22, Springer Verlag, Germany (Nov. 2007).
Herrmann, J.E., et al., "STAT3 is a critical regulator of astrogliosis and scar formation after spinal cord injury," J Neurosci 28(28):7231-7243, Society for Neuroscience, United States (Jul. 2008).
Houde, D., and Engen, J.R., "Conformational analysis of recombinant monoclonal antibodies with hydrogen/deuterium exchange mass spectrometry," Methods Mol Biol 988:269-289, Humana Press, United States (2013).
Huston, J.S., et al., "Protein engineering of antibody binding sites: recovery of specific activity in an anti-digoxin single-chain Fv analogue produced in *Escherichia coli*," Proc Natl Acad Sci USA 85(16):5879-5883, National Academy of Sciences, United States (Aug. 1988).
Inouye, S., and Inouye, M., "Up-promoter mutations in the lpp gene of *Escherichia coli*," Nucleic Acids Res 13(9):3101-3110, Oxford University Press, United Kingdom (May 1985).
Jefferis, R., and Lefranc, M.P., et al., "Human immunoglobulin allotypes: possible implications for immunogenicity," Mabs 1(4):332-338, Landes Bioscience, United States (Jul.-Aug. 2009).
Ji, R.R., et al., "Nociceptive-specific activation of ERK in spinal neurons contributes to pain hypersensitivity," Nat Neurosci 2(12):1114-1119, Nature Research, United Kingdom (Dec. 1999).
Kabat, E.A., and Wu, T.T., "Attempts to locate complementarity-determining residues in the variable positions of light and heavy chains," Ann NY Acad Sci 190:382-393, Wiley-Blackwell, United States (Dec. 1971).
Karpovsky, B., et al., "Production of target-specific effector cells using hetero-cross-linked aggregates containing anti-target cell and

(56) References Cited

OTHER PUBLICATIONS anti-Fc gamma receptor antibodies," J Exp Med 160(6):1686-1701, Rockefeller University Press, United States (Dec. 1984).
Kettleborough, C.A., et al., "Isolation of tumor cell-specific single-chain Fv from immunized mice using phage-antibody libraries and the re-construction of whole antibodies from these antibody fragments," Eur J Immunol 24(4):952-958, Wiley-VCH Verlag, Germany (Apr. 1994).
Kilpatrick, K.E., et al., "Rapid development of affinity matured monoclonal antibodies using RIMMS," Hybridoma 16(4):381-389, Mary Ann Liebert Inc., United States (Aug. 1997).
Kim, M., et al., "Gremlin-1 induces BMP-independent tumor cell proliferation, migration, and invasion," PLoS One 7(4):e35100, Public Library of Science, United States (2012).
Kirkland, T.N., et al., "Analysis of the fine specificity and cross-reactivity of monoclonal anti-lipid A antibodies," J Immunol 137(11):3614-3619, American Association of Immunologists, United States (Dec. 1986).
Kohler, G., "Immunoglobulin chain loss in hybridoma lines," Proc Natl Acad Sci USA 77(4):2197-2199, National Academy of Sciences, United States (Apr. 1980).
Kohler, G., and Milstein, C., "Continuous cultures of fused cells secreting antibody of predefined specificity," Nature 256(5517):495-497, Nature Research, United Kingdom (Aug. 1975).
Kosik, K.S., et al., "Human GAP-43: its deduced amino acid sequence and chromosomal localization in mouse and human," Neuron 1(2):127-132, Cell Press, United States (Apr. 1988).
Kostelny, S.A., et al., "Formation of a bispecific antibody by the use of leucine zippers," J Immunol 148(5):1547-1553, American Association of Immunologists, United States (Mar. 1992).
Kozbor, D., et al., "A human hybrid myeloma for production of human monoclonal antibodies," J Immunol 133(6):3001-3005, American Association of Immunologists, United States (Dec. 1984).
Lau, C., et al., "Chimeric anti-CD14 IGG2/4 Hybrid antibodies for therapeutic intervention in pig and human models of inflammation," J Immunol 191(9):4769-4777, American Association of Immunologists, United States (Nov. 2013).
Lee, J.Y., et al., "Structural basis of checkpoint blockade by monoclonal antibodies in cancer immunotherapy," Nat Commun 7:13354, Nature Publishing Group, United Kingdom (Oct. 2016).
Lee, Y., et al., "An antibody reactive to the Gly63-Lys68 epitope of NT-proBNP exhibits O-glycosylation-independent binding," Exp Mol Med 46(9):e114, Korean Society of Med Biochemistry and Mol Biology, South Korea (Sep. 2014).
Lefranc, M.P., et al., "IMGT unique numbering for immunoglobulin and T cell receptor variable domains and Ig superfamily V-like domains," Dev Comp Immunol 27(1):55-77, Elsevier Ltd., United Kingdom (Jan. 2003).
Liu, M.A., et al., "Heteroantibody duplexes target cells for lysis by cytotoxic T lymphocytes," Proc Natl Acad Sci USA 82(24):8648-8652, National Academy of Sciences, United States (Dec. 1985).
Logan, J., and Shenk, T., "Adenovirus tripartite leader sequence enhances translation of mRNAs late after infection," Proc Natl Acad Sci USA 81(12):3655-3659, National Academy of Sciences, United States (Jun. 1984).
Lonberg, N., "Human antibodies from transgenic animals," Nat Biotechnol 23(9):1117-1125, Nature Publishing Group, United Kingdom (Sep. 2005).
Lonberg, N., and Huszar, D., "Human antibodies from transgenic mice," Int Rev Immunol 13(1):65-93, Informa Healthcare, United Kingdom (1995).
Lowy, I., et al., "Isolation of transforming DNA: cloning the hamster aprt gene," Cell 22(3):817-823, Elsevier B.V., United States (Dec. 1980).
McCafferty, J., et al., "Phage antibodies: filamentous phage displaying antibody variable domains," Nature 348(6301):552-554, Nature Research, United Kingdom (Dec. 1990).
McGraw, J., et al., "Modulating astrogliosis after neurotrauma," J Neurosci Res 63(2):109-115, Wiley-Liss Inc., United States (Jan. 2001).
McPherson, A., "Crystallization of proteins from polyethylene glycol," J Biol Chem 251(20):6300-6303, American Society for Biochemistry and Molecular Biology Inc., United States (Oct. 1976).
McPherson, A., "Current approaches to macromolecular crystallization," Eur J Biochem 189(1):1-23, Cell Physiol Biochem Press, Switzerland (Apr. 1990).
Moldenhauer, G., et al., "Identity of HML-1 antigen on intestinal intraepithelial T cells and of B-ly7 antigen on hairy cell leukaemia," Scand J Immunol 32(2):77-82, Wiley-Blackwell Publishing Ltd., United Kingdom (Aug. 1990).
Morea, V., et al., "Antibody modeling: implications for engineering and design," Methods 20(3):267-279, Academic Press Inc., United States (Mar. 2000).
Morel, G.A., et al., "Monoclonal antibodies to bovine serum albumin: affinity and specificity determinations," Mol Immunol 25(1):7-15, Elsevier Ltd., United Kingdom (Jan. 1988).
Morgan, R.A., and Anderson, W.F., "Human gene therapy," Annu Rev Biochem 62:191-217, Annual Reviews Inc., United States (1993).
Morrison, S.L., "Transfectomas provide novel chimeric antibodies," Science 229(4719):1202-1207, American Association for the Advancement of Science, United States (Sep. 1985).
Mulligan, R.C., "The basic science of gene therapy," Science 260(5110):926-932, American Association for the Advancement of Science, United States (May 1993).
Mulligan, R.C., and Berg, P., "Selection for animal cells that express the *Escherichia coli* gene coding for xanthine-guanine phosphoribosyltransferase," Proc Natl Acad Sci USA 78(4):2072-2076, National Academy of Sciences, United States (Apr. 1981).
Mullinax, R.L., et al., "Expression of a heterodimeric Fab antibody protein in one cloning step," Biotechniques 12(6):864-869, Taylor and Francis Ltd., United Kingdom (Jun. 1992).
Muyldermans, S., "Single domain camel antibodies: current status," J Biotechnol 74(4):277-302, Elsevier B.V., Netherlands (Jun. 2001).
Nabel, G.J., and Felgner, P.L., "Direct gene transfer for immunotherapy and immunization," Trends Biotechnol 11(5):211-215, Elsevier Ltd., United Kingdom (May 1993).
Naganawa, Y., et al., "Generation of mouse-human hybridomas secreting human monoclonal antibodies to Japanese cedar pollen allergen Cry j1," Hum Antibodies 14(1-2):27-31, IOS Press BV, Netherlands (2005).
Ng, S.C., et al., "Cloning of human GAP-43: growth association and ischemic resurgence," Neuron 1(2):133-139, Cell Press, United States (Apr. 1988).
Nisonoff, A., "Idiotypes: concepts and applications," J Immunol 147(8):2429-2438, American Association of Immunologists, United States (Oct. 1991).
Nuttall, S.D., et al., "Immunoglobulin VH domains and beyond: design and selection of single-domain binding and targeting reagents," Curr Pharm Biotechnol 1(3):253-263, Bentham Science Publishers B.V., Netherlands (Nov. 2000).
O'Hare, K., et al., "Transformation of mouse fibroblasts to methotrexate resistance by a recombinant plasmid expressing a prokaryotic dihydrofolate reductase," Proc Natl Acad Sci USA 78(3):1527-1531, National Academy of Sciences, United States (Mar. 1981).
Oi, V.T., and Morrison, S.L., "Chimeric Antibodies," Biotechniques 4(3):214-221, Taylor and Francis Ltd., United Kingdom (1986).
Padlan, E.A., "A possible procedure for reducing the immunogenicity of antibody variable domains while preserving their ligand-binding properties," Mol Immunol 28(4-5):489-498, Elsevier Ltd., United Kingdom (Apr.-May 1991).
Paulus, H., "Preparation and biomedical applications of bispecific antibodies," Behring Inst Mit 78:118-132, Behringwerke AG, Germany (Dec. 1985).
Pedersen, J.T., et al., "Comparison of surface accessible residues in human and murine immunoglobulin Fv domains. Implication for humanization of murine antibodies," J Mol Biol 235(3):959-973, Academic Press, United States (Jan. 1994).
Persic, L., et al., "An integrated vector system for the eukaryotic expression of antibodies or their fragments after selection from phage display libraries," Gene 187(1):9-18, Elsevier, Netherlands (Mar. 1997).

(56) References Cited

OTHER PUBLICATIONS

Proudfoot, N.J., "Transcriptional interference and termination between duplicated alpha-globin gene constructs suggests a novel mechanism for gene regulation," Nature 322(6079):562-565, Nature Research, United Kingdom (Aug. 1986).
Ren, H., et al., "A biocompatible condensation reaction for the labeling of terminal cysteine residues on proteins," Angew Chem Int Ed Engl 48(51):9658-9662, Wiley-VCH, Germany (2009).
Rhodes, K.E., and Fawcett, J.W., "Chondroitin sulphate proteoglycans: preventing plasticity or protecting the CNS?," J Anat 204(1):33-48, Wiley-Blackwell Publishing Ltd., United Kingdom (Jan. 2004).
Riechmann, L., and Muyldermans, S., "Single domain antibodies: comparison of camel VH and camelised human VH domains," J Immunol Methods 231(1-2):25-38, Elsevier B.V., Netherlands (Dec. 1999).
Roguska, M.A., et al., "A comparison of two murine monoclonal antibodies humanized by CDR-grafting and variable domain resurfacing," Protein Eng 9(10):895-904, Oxford University Press, United Kingdom (Oct. 1996).
Roguska, M.A., et al., "Humanization of murine monoclonal antibodies through variable domain resurfacing," Proc Natl Acad Sci USA 91(3):969-973, National Academy of Sciences, United States (Feb. 1994).
Roux, K.H., et al., "Comparisons of the ability of human IgG3 hinge mutants, IgM, IgE, and IgA2, to form small immune complexes: a role for flexibility and geometry," J Immunol 161(8):4083-4090, American Association of Immunologists, United States (Oct. 1998).
Ruther, U., and Muller-Hill, B., "Easy identification of cDNA clones," EMBO J 2(10):1791-1794, Springer Nature, Germany (1983).
Sandhu, J.S., "A rapid procedure for the humanization of monoclonal antibodies," Gene 150(2):409-410, Elsevier B.V., Netherlands (Dec. 1994).
Santerre, R.F., et al., "Expression of prokaryotic genes for hygromycin B and G418 resistance as dominant-selection markers in mouse L cells," Gene 30(1-3):147-156, Elsevier B.V., Netherlands (Oct. 1984).
Senter, P.D., "Potent antibody drug conjugates for cancer therapy," Curr Opin Chem Biol 13(3):235-244, Elsevier Ltd., United Kingdom (Jun. 2009).
Shinmoto, H., et al., "Generation of mouse-human hybridomas secreting antibodies against peanut allergen Ara h1," Cytotechnology 46(1):19-23, Springer Netherlands, Netherlands (Sep. 2004).
Sofroniew, M.V., "Molecular dissection of reactive astrogliosis and glial scar formation," Trends Neurosci 32(12):638-647, Elsevier Ltd. United Kingdom (Dec. 2009).
Sofroniew, M.V., "Reactive astrocytes in neural repair and protection," Neuroscientist 11(5):400-407, SAGE Publications Inc., United States (Oct. 2005).
Songsivilai, S., and Lachman, P.J., "Bispecific antibody: a tool for diagnosis and treatment of disease," Clin Exp Immunol 79(3):315-321, Oxford University Press, United Kingdom (Mar. 1990).
Sormanni, P., et al., "Rapid and accurate in silico solubility screening of a monoclonal antibody library," Sci Rep 7(1):8200, Nature Publishing Group, United Kingdom (Aug. 2017).
Stahli, C., et al., "Distinction of epitopes by monoclonal antibodies," Methods Enzymol 92:242-253, Academic Press Inc., United States (1983).
Studnicka, G.M., et al., "Human-engineered monoclonal antibodies retain full specific binding activity by preserving non-CDR complementarity-modulating residues," Protein Eng 7(6):805-814, Oxford University Press, United Kingdom (Jun. 1994).
Sunbul, M., and Yin, J., "Site specific protein labeling by enzymatic posttranslational modification," Org Biomol Chem 7(17):3361-3371, Royal Society of Chemistry, United Kingdom (Sep. 2009).
Szybalska, E.H., and Szybalski, W., "Genetics of human cell line. IV. DNA-mediated heritable transformation of a biochemical trait," Proc Natl Acad Sci USA 48(12):2026-2034, National Academy of Sciences, United States (Dec. 1962).
Taki, M., et al., "Transglutaminase-mediated N- and C-terminal fluorescein labeling of a protein can support the native activity of the modified protein," Protein Eng Des Sel 17(2):119-126, Oxford University Press, United Kingdom (Feb. 2004).
Tan, P., et al., ""Superhumanized" antibodies: reduction of immunogenic potential by complementarity-determining region grafting with human germline sequences: application to an anti-CD28," J Immunol 169(2):1119-1125, American Association of Immunologists, United States (Jul. 2002).
Tang, T.Y., et al., "TAFA: a novel secreted family with conserved cysteine residues and restricted expression in the brain," Genomics 83(4):727-734, Academic Press, United States (Apr. 2004).
Taylor, E.V., and Imperiali, B., "Native Chemical Ligation: SemiSynthesis of Post-translationally Modified Proteins and Biological Probes," Protein Engineering 22:65-96, Oxford University Press, United Kingdom (2009).
Tolstoshev, P., "Gene therapy, concepts, current trials and future directions," Annu Rev Pharmacol Toxicol 33:573-596, Annual Reviews Inc., United States (1993).
Van Heeke, G., and Schuster, S.M., "Expression of human asparagine synthetase in *Escherichia coli*," J Biol Chem 264(10):5503-5509, American Society for Biochemistry and Molecular Biology Inc., United States (Apr. 1989).
Vidarsson, G., et al., "IgG subclasses and allotypes: from structure to effector functions," Front Immunol 5:520, Frontiers Media SA, Switzerland (Oct. 2014).
Ward, E.S., et al., "Binding activities of a repertoire of single immunoglobulin variable domains secreted from *Escherichia coli*," Nature 341(6242):544-546, Nature Research, United Kingdom (Oct. 1989).
Wigler, M., et al., "Transfer of purified herpes virus thymidine kinase gene to cultured mouse cells," Cell 11(1):223-232, Elsevier B.V., United States (May 1977).
Wigler, M., et al., "Transformation of mammalian cells with an amplifiable dominant-acting gene," Proc Natl Acad Sci USA 77(6):3567-3570, National Academy of Sciences, United States (Jun. 1980).
Winter, C.G., et al., "A role for ciliary neurotrophic factor as an inducer of reactive gliosis, the glial response to central nervous system injury," Proc Natl Acad Sci USA 92(13):5865-5869, National Academy of Sciences, United States (Jun. 1995).
Wu, G.Y., and Wu, C.H., "Delivery systems for gene therapy," Biotherapy 3(1):87-95, Springer International Publishing AG, Switzerland (1991).
Yoon, A., et al., "Chicken scFvs with an Artificial Cysteine for Site-Directed Conjugation," PLoS One 11(1):e0146907, Public Library of Science, United States (Jan. 2016).
Boussif, O., et al., "A versatile vector for gene and oligonucleotide transfer into cells in culture and in vivo: polyethylenimine," Proceedings of the National Academy of Sciences of the United States of America 92(16):7297-7301, United States national Academy of Sciences, United States (Aug. 1995).
Han, Jungwon, et al., "A phosphorylation pattern-recognizing antibody specifically reacts to RNA polymerase II bound to exons," Experimental & Molecular Medicine 48(11): e271-e271, Nature Publishing, United Kingdom (Nov. 2016).
Houde, D., et al., "Conformational analysis of recombinant monoclonal antibodies with hydrogen/deuterium exchange mass spectrometry," Methods Mol Bio 988:269-289, SpringerLink, United States (Dec. 2013).
International Search Report and Written Opinion mailed May 1, 2020 in International Application No. PCT/IB2019/061461, KIPO, Korea, 12 pages.
Kim, M., et al., "Gremlin-1 Induces BMP-Independent Tumor Cell Proliferation, Migration, and Invasion," PLoS One 7(4):e35100, Public Library of Science, United States (Apr. 2012).
Korea University, "Discovery and functional characterization of novel peptidome," Brain Science Source Technology Development Project Final Report, 1-46, Korea (Nov. 2017).
Lee, Y., et al., "An antibody reactive to the $Gly_{62}$-$Lys_{68}$ epitope of NT-proBNP exhibits O-glycosylation-independent binding," Exp Mol Med 46:e114, Springer Nature, United Kingdom (Sep. 2014).

(56) References Cited

OTHER PUBLICATIONS

Sormanni, P., et al., "Rapid and accurate in silico solubility screening of a monoclonal antibody library," Sci Rep 7(1): 8200, Nature Publishing Group, England (Aug. 2017).
Wang, Y., et al., "Novel adipoline, FAM19A5, inhibits neointima formation after injury through sphingosine-1-phosphate receptor 2," Circulation 138:48-63, American Heart Association, United States (Jul. 2018).
U.S. Appl. No. 19/054,436, inventors Kim, B., et al., filed Feb. 14, 2025 (Not yet Published).
Bordusa, F., "Protease-catalyzed Formation of C—N Bonds," Highlights in Bioorganic Chemistry 389-403, Wiley-VCH, Germany (Jan. 2004).
Tian, F., et al., "A general approach to site-specific antibody drug conjugates," Proc Natl Acad Sci USA, 111(5):1766-71, United States (Feb. 2014).
Hammerling, G.J., et al., "Appendix: Production of Antibody-Producing Hybridomas in the RodentSystems," in: Monoclonal Antibodies and T-Cell Hybridomas: Perspectives and Technical Advances, pp. 563-587, Elsevier, Netherlands (1981).
Harlow, E., and Lane, D., "Epitope Mapping by Competition Assay," CSH protocol, Cold Spring Harbor Laboratory, United States (2006).
Roversi, P., et al., "Modelling Prior Distributions of Atoms for Macromolecular Refinement and Completion," Acta Crystallographica. Section D, Biological Crystallography 56(Pt10):1316-1323, Wiley-Blackwell, United States (Oct. 2000).
Sawai, H., et al., "Direct Production of the Fab Fragment Derived From the Sperm Immobilizing Antibody Using Polymerase Chain Reaction and cDNA Expression Vectors," American Journal of reproductive immunology 34(1):26-34, Wiley-Blackwell, Denmark (1995).
UniProt, "Neum Human," Accession No. P17677, accessed at https://www.uniprot.org/uniprotkb/P17677/entry, accessed on Jun. 13, 2025, 10 pages.
UniProt, "TAFA5_HUMAN," Accession No. Q7Z5A7, accessed at https://www.uniprot.org/uniprotkb/Q775A7/entry, accessed on Jun. 13, 2025, 9 pages.
Chen, C., et al., "Enhancement and destruction of antibody function by somatic mutation: unequal occurrence is controlled by V gene combinatorial associations," EMBO J 14(12):2784-94, Springer, United Kingdom (Jun. 1995).
Colman, P.M., "Effects of amino acid sequence changes on antibody-antigen interactions," Res Immunol 145(1):33-6, Elsevier, Netherlands (Jan. 1994).
Foote, J., et al., "Antibody framework residues affecting the conformation of the hypervariable loops," J Mol Biol 224(2):487-99, Elsevier, Netherlands (Mar. 1992).
Winter, G., et al., "Humanized antibodies," Immunol Today 14(6):243-6, Elsevier, Netherlands (Jun. 1993).

* cited by examiner

QFLKEGQLAAGTCEIVTLDRDSSQPRRTIARQTARCACRKGQIAGTTRARPACVDARIIKTKQWCDMLPCLEGEGCDLLINRSGWTCTQPGGRIKTTTVS

QFLKEGQLAAGTSEIVTLDRDSSQPRRTIARQTARSASRKGQIAGTTRARPASVDARIIKTKQWSDMLPSLEGEGSDLLINRSGWTSTQPGGRIKTTTVS

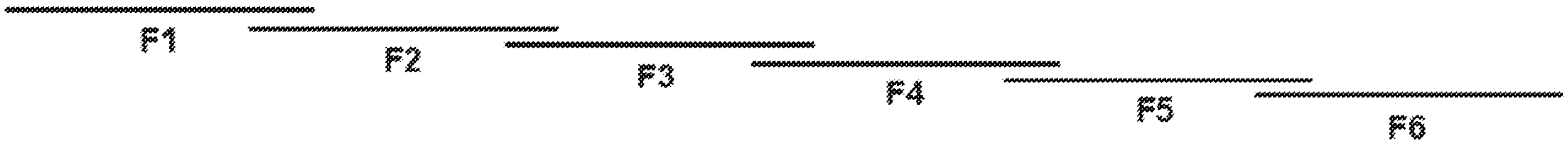

F1 : QFLKEGQLAAGTSEIVTLDRGGGSC~BSA

F2 : TLDRDSSQPRRTIARQTARSGGGSC~BSA

F3 : TARSASRKGQIAGTTRARPAGGGSC~BSA

F4 : ARPASVDARIIKTKQWSDMLGGGSC~BSA

F5 : SDMLPSLEGEGSDLLINRSGGGGSC~BSA

F6 : NRSGWTSTQPGGRIKTTTVSGGGSC~BSA

FIG. 4

| Clone | CamSol score | GRAVY score |
|---|---|---|
| Original | 0.177 | -0.384 |
| Low pI | 0.991 | -0.465 |
| 1-17 | 0.734 | -0.445 |
| 1-30 | 0.906 | -0.465 |
| 1-32 | 0.717 | -0.445 |
| 4-11 | 0.681 | -0.441 |
| 6-10 | 0.378 | -0.401 |

| Sample Conc. | Quench condition | Roxy system or Gradient type | Pepsin (on ice 5min) | Quench holding time (min) | Coverage (%) |
|---|---|---|---|---|---|
| Pepsin column(on), C18 | | | | | |
| 30pmol | 100mM K.phosphate pH 2.66 | FG | | | 19.1 |
| 30pmol | 100mM K.phosphate, 500mM TCEP, 2M guanidine-HCl pH 2.66 | FG | | | 65.0 |
| 30pmol | 100mM K.phosphate, 500mM TCEP, 4M guanidine-HCl pH 2.66 | FG | | | 19.6 |
| 30pmol | 100mM K.phosphate, 500mM TCEP pH 2.66 | FG | | | 65.0 |
| 40pmol | 100mM K.phosphate, 250mM TCEP, 2M guanidine-HCl pH 2.66 | FG | | | 43.9 |
| 40pmol | 200mM Na.phosphate, 500mM TCEP, 2M guanidine-HCl pH 2.66 | FG | | | 26.5 |
| 40pmol | His-tag) 100mM K.phosphate, 500mM TCEP, 2M guanidine-HCl pH 2.66 | FG | | | 37.6 |
| 40pmol | 100mM K.phosphate, 500mM TCEP, 2M guanidine-HCl pH 2.66 | FG | 5 | | 72.0 |
| 40pmol | 100mM K.phosphate, 500mM TCEP, 2M guanidine-HCl pH 2.66 | FG | 5 | | 72.0 |
| 40pmol | 100mM K.phosphate, 500mM TCEP, 2M guanidine-HCl pH 2.66 | FG | 5 | | 89.0 |
| 40pmol | 100mM K.phosphate, 500mM TCEP, 2M guanidine-HCl pH 2.66 | FG | 5 | | 93.0 |
| 40pmol | 100mM K.phosphate, 500mM TCEP, 2M guanidine-HCl pH 2.66 | FG | 5 | | 80.0 |
| 40pmol | 100mM K.phosphate, 500mM TCEP, 2M guanidine-HCl pH 2.66 | FG | 5 | | 72.0 |
| 40pmol | 100mM K.phosphate, 500mM TCEP, 2M guanidine-HCl pH 2.66 | FG | 5 | | 72.0 |
| Pepsin column(on), C18, Concentration sample | | | | | |
| 40pmol | 100mM K.phosphate, 500mM TCEP, 2M guanidine-HCl pH 2.66 | FG | 5 | | 90.0 |
| 40pmol | 100mM K.phosphate, 500mM TCEP, 2M guanidine-HCl pH 2.66 | FG | 5 | | 92.0 |
| 40pmol | 100mM K.phosphate, 500mM TCEP, 2M guanidine-HCl pH 2.66 | FG | 5 | | 72.0 |
| 40pmol | 100mM K.phosphate, 500mM TCEP, 2M guanidine-HCl pH 2.66 | FG | 5 | | 76.0 |
| 40pmol | 100mM K.phosphate, 500mM TCEP, 2M guanidine-HCl pH 2.66 | FG | 5 | | 77.6 |
| 40pmol | 100mM K.phosphate, 500mM TCEP, 2M guanidine-HCl pH 2.66 | FG | 5 | | 92.0 |
| 40pmol | 100mM K.phosphate, 150mM TCEP pH 2.66 | FG | | | 43.9 |
| 40pmol | 200mM Na.phosphate, 750mM TCEP, 4M guanidine-HCl pH 2.66 | FG | | | 19.0 |
| 40pmol | 100mM K.phosphate, 750mM TCEP, 2M guanidine-HCl pH 2.66 | FG | | | 38.8 |
| 40pmol | 100mM TCEP, 400mM guanidine-HCl pH 2.66 | FG | | | 38.8 |
| 40pmol | 500mM K.phosphate, 375mM TCEP, 1M guanidine-HCl pH 2.66 | FG | | | 43.9 |
| 40pmol | 100mM K.phosphate, 500mM TCEP, 1M guanidine-HCl pH 2.66 | FG | | | 84.1 |
| 40pmol | 1M TCEP, 2M U pH 2.66 | FG | | | 68.4 |
| 40pmol | 500mM TCEP, 1M U pH 2.66 | FG | | | 48.0 |
| 40pmol | 1M TCEP, 2M U pH 1.7 | FG | 5 | | 95.0 |
| 45pmol | 1M TCEP, 2M U pH 2.66 | FG | | | 96.0 |
| 45pmol | 1M TCEP, 2M U pH 2.66 | FG | 5 | | 98.0 |
| 45pmol | 1M TCEP, 2M U pH 2.66 | FG | | 5 | 79.0 |

FIG. 19

| Sample Conc. | Quench condition | Roxy system or Gradient type | Pepsin (on ice 5min) | Quench holding time (min) | Coverage (%) |
|---|---|---|---|---|---|
| **Pepsin column(on), C18, Concentration sample** | | | | | |
| 45pmol | 1M TCEP, 2M U pH 2.66 | FG | 1:2(5) | | 92.0 |
| 45pmol | 1M TCEP, 2M U pH 2.66 | FG | 1:2(5) | | 93.9 |
| 45pmol | 1M TCEP, 2M U pH 2.66 | FG | 1:2(5) | | 94.0 |
| 45pmol | 1M TCEP, 2M U pH 2.66 | FG | 1:2(5) | | 76.0 |
| 45pmol | 1M TCEP, 2M U pH 2.66 | FG | 1:2(5) | | 94.0 |
| 45pmol | 1M TCEP, 2M U pH 2.66 | FG | 1:2(5) | | 80.0 |
| 45pmol | 1M TCEP, 2M U pH 2.66 | FG | 1:3(5) | | 85.0 |
| **Waters Pepsin column(on), C18** | | | | | |
| 45pmol | 1M TCEP, 2M U pH 2.66 | FG | 1:2(5) | | **99.0** |
| 45pmol | 1M TCEP, 2M U pH 2.66 | FG | 1:2(5) | | **97.0** |
| 45pmol | 1M TCEP, 2M U pH 2.66 | FG | 1:2(5) | | **97.0** |
| 45pmol | 1M TCEP, 2M U pH 2.66 | FG | 1:2(5) | | **92.0** |
| 45pmol | 1M TCEP, 2M U pH 2.66 | FG | 1:2(5) | | **97.0** |
| 45pmol | 1M TCEP, 2M U pH 2.66 | FG | 1:2(5) | | **92.0** |
| **Pepsin column(on), C8** | | | | | |
| 40pmol | His-tag) 100mM K.phosphate, 500mM TCEP, 2M guanidine-HCl pH 2.66 | FG | | | 29.5 |
| 40pmol | His-tag) 100mM K.phosphate, 500mM TCEP, 2M guanidine-HCl pH 2.66 | FG | 5 | | 52.0 |
| 40pmol | 100mM K.phosphate, 500mM TCEP, 2M guanidine-HCl pH 2.66 | FG | | | 57.0 |
| 40pmol | 100mM K.phosphate, 500mM TCEP, 2M guanidine-HCl pH 2.66 | FG | 5 | | 79.8 |
| **Pepsin column(off), C8** | | | | | |
| 40pmol | 100mM K.phosphate, 500mM TCEP, 2M guanidine-HCl pH 2.66 | FG | 5 | | 20.8 |

FIG. 19
(cont'd)

| Sequence | Start | End | MHP | RT |
|---|---|---|---|---|
| FAM19A5_HUMAN | | | | |
| FLKEGQL | 2 | 8 | 834.4720 | 6.56 |
| FLKEGQLAAGTCE | 2 | 14 | 1366.6671 | 6.34 |
| LKEGQLAAG | 3 | 11 | 886.4993 | 5.30 |
| LKEGQLAAGTCE | 3 | 14 | 1219.5987 | 5.69 |
| LKEGQLAAGTCEI | 3 | 15 | 1332.6828 | 6.83 |
| LKEGQLAAGTCEIVTL | 3 | 18 | 1645.8829 | 7.71 |
| KEGQLAAGTCEIVTLDRDS | 4 | 22 | 2005.9859 | 5.04 |
| AAGTCEI | 9 | 15 | 664.2971 | 6.41 |
| DRDSSQPPRTIARQTARC | 19 | 36 | 2058.0257 | 4.56 |
| RDSSQPPRTIARQTARCAC | 20 | 38 | 2117.0451 | 4.65 |
| QPPRTIARQTA | 24 | 34 | 1238.6964 | 6.41 |
| PRTIARQTARCA | 26 | 37 | 1343.7325 | 6.38 |
| PRTIARQTARCACRK | 26 | 40 | 1730.9377 | 4.56 |
| TARCACRKGQIAGTTRARPACVI | 33 | 55 | 2405.2071 | 5.89 |
| ARCACRKGQI | 34 | 43 | 1105.5717 | 5.45 |
| ACRKGQIAGTTRARPAC | 37 | 53 | 1759.9167 | 4.32 |
| ACRKGQIAGTTRARPACVD | 37 | 55 | 1974.0120 | 4.63 |
| ACRKGQIAGTTRARPACVDA | 37 | 56 | 2045.0491 | 4.77 |
| CRKGQIAGTTRARPAC | 38 | 53 | 1688.8795 | 4.96 |
| RKGQIAGTTRARPACVD | 39 | 55 | 1799.9657 | 5.77 |
| IAGTTRARPA | 43 | 52 | 1013.5851 | 6.21 |
| GTTRARPACVDA | 45 | 56 | 1217.6055 | 6.29 |
| VDARIIKTKQWCDM | 54 | 67 | 1706.8717 | 6.78 |
| ARIIKTKQWC | 56 | 65 | 1246.7089 | 5.65 |
| ARIIKTKQWCDM | 56 | 67 | 1492.7763 | 6.38 |
| ARIIKTKQWCDML | 56 | 68 | 1605.8604 | 7.27 |
| ARIIKTKQWCDMLPCL | 56 | 71 | 1919.0064 | 8.15 |
| RIIKTKQWCDM | 57 | 67 | 1421.7392 | 6.37 |
| RIIKTKQWCDML | 57 | 68 | 1534.8233 | 7.28 |
| IKTKQWCDML | 59 | 68 | 1265.6381 | 7.60 |
| WCDMLPCL | 64 | 71 | 980.4038 | 9.97 |
| LPCLEGEG | 68 | 75 | 817.3760 | 6.85 |
| PCLEGEG | 69 | 75 | 704.2920 | 5.73 |
| PCLEGEGCD | 69 | 77 | 922.3281 | 6.05 |
| PCLEGEGCDL | 69 | 78 | 1035.4122 | 7.42 |
| PCLEGEGCDLLINRSGWTCTQPC | 69 | 93 | 2662.2170 | 8.79 |
| EGEGCDL | 72 | 78 | 722.2661 | 6.48 |
| EGEGCDLL | 72 | 79 | 835.3502 | 7.72 |
| LLINRSGWTCTQPGGRIKTTT | 78 | 98 | 2303.2289 | 6.42 |
| LINRSGWTCTQPGGRIKTTT | 79 | 98 | 2190.1448 | 5.90 |
| INRSGWTCTQPGGRIKTTT | 80 | 98 | 2077.0607 | 5.79 |
| NRSGWTCTQPGGRIKTTT | 81 | 98 | 1963.9767 | 5.71 |
| TCTQPGGRIKTTT | 86 | 98 | 1363.6998 | 5.67 |
| TQPGGRIKTTT | 88 | 98 | 1159.6430 | 5.40 |

FIG. 20B

SEQUENCE LISTING

```
<160> NUMBER OF SEQ ID NOS: 190

<210> SEQ ID NO 1
<211> LENGTH: 132
<212> TYPE: PRT
<213> ORGANISM: Homo sapiens

<400> SEQUENCE: 1

Met Ala Pro Ser Pro Arg Thr Gly Ser Arg Gln Asp Ala Thr Ala Leu
1               5                   10                  15
```

```
Pro Ser Met Ser Ser Thr Phe Trp Ala Phe Met Ile Leu Ala Ser Leu
            20                  25                  30

Leu Ile Ala Tyr Cys Ser Gln Leu Ala Ala Gly Thr Cys Glu Ile Val
        35                  40                  45

Thr Leu Asp Arg Asp Ser Ser Gln Pro Arg Arg Thr Ile Ala Arg Gln
    50                  55                  60

Thr Ala Arg Cys Ala Cys Arg Lys Gly Gln Ile Ala Gly Thr Thr Arg
65                  70                  75                  80

Ala Arg Pro Ala Cys Val Asp Ala Arg Ile Ile Lys Thr Lys Gln Trp
                85                  90                  95

Cys Asp Met Leu Pro Cys Leu Glu Gly Glu Gly Cys Asp Leu Leu Ile
            100                 105                 110

Asn Arg Ser Gly Trp Thr Cys Thr Gln Pro Gly Gly Arg Ile Lys Thr
        115                 120                 125

Thr Thr Val Ser
    130


<210> SEQ ID NO 2
<211> LENGTH: 125
<212> TYPE: PRT
<213> ORGANISM: Homo sapiens

<400> SEQUENCE: 2

Met Gln Leu Leu Lys Ala Leu Trp Ala Leu Ala Gly Ala Ala Leu Cys
1               5                   10                  15

Cys Phe Leu Val Leu Val Ile His Ala Gln Phe Leu Lys Glu Gly Gln
            20                  25                  30

Leu Ala Ala Gly Thr Cys Glu Ile Val Thr Leu Asp Arg Asp Ser Ser
        35                  40                  45

Gln Pro Arg Arg Thr Ile Ala Arg Gln Thr Ala Arg Cys Ala Cys Arg
    50                  55                  60

Lys Gly Gln Ile Ala Gly Thr Thr Arg Ala Arg Pro Ala Cys Val Asp
65                  70                  75                  80

Ala Arg Ile Ile Lys Thr Lys Gln Trp Cys Asp Met Leu Pro Cys Leu
                85                  90                  95

Glu Gly Glu Gly Cys Asp Leu Leu Ile Asn Arg Ser Gly Trp Thr Cys
            100                 105                 110

Thr Gln Pro Gly Gly Arg Ile Lys Thr Thr Thr Val Ser
        115                 120                 125


<210> SEQ ID NO 3
<211> LENGTH: 53
<212> TYPE: PRT
<213> ORGANISM: Homo sapiens

<400> SEQUENCE: 3

Met Tyr His His Arg Glu Trp Pro Ala Arg Ile Ile Lys Thr Lys Gln
1               5                   10                  15

Trp Cys Asp Met Leu Pro Cys Leu Glu Gly Glu Gly Cys Asp Leu Leu
            20                  25                  30

Ile Asn Arg Ser Gly Trp Thr Cys Thr Gln Pro Gly Gly Arg Ile Lys
        35                  40                  45

Thr Thr Thr Val Ser
    50


<210> SEQ ID NO 4
```

<211> LENGTH: 1501
<212> TYPE: DNA
<213> ORGANISM: Homo sapiens

<400> SEQUENCE: 4
ggcggcggag gatggcgcgc gcggggcccg cacgtggagg ccggcgcggg ggcgcgggca 60
gggccggctg ctgagacgcg ctgctgcccc ccgcgcgggc gccgcggctt caatggcgcc 120
atcgcccagg accggcagcc ggcaagatgc gaccgccctg cccagcatgt cctcaacttt 180
ctgggcgttc atgatcctgg ccagcctgct catcgcctac tgcagtcagc tggccgccgg 240
cacctgtgag attgtgacct tggaccggga cagcagccag cctcggagga cgatcgcccg 300
gcagaccgcc cgctgtgcgt gtagaaaggg gcagatcgcc ggcaccacga gagcccggcc 360
cgcctgtgtg gacgcaagaa tcatcaagac caagcagtgg tgtgacatgc ttccgtgtct 420
ggagggggaa ggctgcgact tgttaatcaa ccggtcaggc tggacgtgca cgcagcccgg 480
cgggaggata aagaccacca cggtctcctg acaaacacag cccctgaggg ggccccggga 540
gtggccttgg ctccctggag agcccacgtc tcagccacag ttctccactc gcctcggact 600
tcacccgttc tctgccgccc gcccactccg tttccctgtg gtccgtgaag gacggcctca 660
ggccttggca tcctgagctt cggtctgtcc agccgacccg aggaggccgg actcagacac 720
ataggcgggg ggcggcacct ggcatcagca atacgcagtc tgtgggagcc cggccgcgcc 780
cagcccccgc cgaccgtggc gttggccctg ctgtcctcag aggaggagga ggaggaggca 840
gctccggcag ccacagaagg ctgcagccca gcccgcctga gacacgacgc ctgccccagg 900
ggactgtcag gcacagaagc ggcctcctcc cgtgccccag actgtccgaa ttgcttttat 960
tttcttatac tttcagtata ctccatagac caaagagcaa aatctatctg aacctggacg 1020
caccctcact gtcagggtcc ctggggtcgc ttgtgcgggc gggagggcaa tggtggcaga 1080
gacatgctgg tggccccggc ggagcggaga gggcggccgt ggtggaggcc tccaccccag 1140
gagcaccccg cacaccctcg gaggacgggc ttcggctgcg cggaggccgt ggcacacctg 1200
cgggaggcag cgacggcccc cacgcagacg ccgggaacgc aggccgcttt attcctctgt 1260
acttagatca acttgaccgt actaaaatcc ctttctgttt taaccagtta aacatgcctc 1320
ttctacagct ccatttttga tagttggata atccagtatc tgccaagagc atgttgggtc 1380
tcccgtgact gctgcctcat cgatacccca tttagctcca gaaagcaaag aaaactcgag 1440
taacacttgt ttgaaagaga tcattaaatg tattttgcaa agcccaaaaa aaaaaaaaaa 1500
a 1501

<210> SEQ ID NO 5
<211> LENGTH: 10
<212> TYPE: PRT
<213> ORGANISM: Artificial Sequence
<220> FEATURE:
<223> OTHER INFORMATION: Heavy Chain CDR1 - 3-2; 1-7A-IT Abs

<400> SEQUENCE: 5

Gly Phe Thr Phe Ser Ser Phe Asn Met Phe
1               5                   10

<210> SEQ ID NO 6
<211> LENGTH: 17
<212> TYPE: PRT
<213> ORGANISM: Artificial Sequence
<220> FEATURE:
<223> OTHER INFORMATION: Heavy Chain CDR2 - 3-2 Ab

<400> SEQUENCE: 6

Gln Ile Ser Ser Ser Gly Ser Ser Thr Asn Tyr Ala Pro Ala Val Arg
1 5 10 15

Gly

<210> SEQ ID NO 7
<211> LENGTH: 22
<212> TYPE: PRT
<213> ORGANISM: Artificial Sequence
<220> FEATURE:
<223> OTHER INFORMATION: Heavy Chain CDR3 - 3-2; 1-7A-IT; Low-PI; 1-30; 1-17; 1-32; 4-11; 6-10 Abs

<400> SEQUENCE: 7

Ser Ser Tyr Asp Cys Pro Tyr Gly His Cys Ser Ser Gly Val Asp Ser
1 5 10 15

Ala Gly Glu Ile Asp Ala
20

<210> SEQ ID NO 8
<211> LENGTH: 13
<212> TYPE: PRT
<213> ORGANISM: Artificial Sequence
<220> FEATURE:
<223> OTHER INFORMATION: Light Chain CDR1 - 3-2; 1-7A-IT; 1-17; 1-32; 4-11; 6-10 Abs

<400> SEQUENCE: 8

Ser Gly Gly Gly Ser Tyr Ala Gly Ser Tyr Tyr Tyr Gly
1 5 10

<210> SEQ ID NO 9
<211> LENGTH: 7
<212> TYPE: PRT
<213> ORGANISM: Artificial Sequence
<220> FEATURE:
<223> OTHER INFORMATION: Light Chain CDR2 - 3-2 Ab

<400> SEQUENCE: 9

Glu Ser Asn Lys Arg Pro Ser
1 5

<210> SEQ ID NO 10
<211> LENGTH: 10
<212> TYPE: PRT
<213> ORGANISM: Artificial Sequence
<220> FEATURE:
<223> OTHER INFORMATION: Light Chain CDR3 - 3-2; 1-7A-IT Abs

<400> SEQUENCE: 10

Gly Ser Trp Asp Ser Ser Asn Gly Gly Ile
1 5 10

<210> SEQ ID NO 11
<211> LENGTH: 131
<212> TYPE: PRT
<213> ORGANISM: Artificial Sequence
<220> FEATURE:
<223> OTHER INFORMATION: VH - 3-2 Ab

<400> SEQUENCE: 11

Ala Val Thr Leu Asp Glu Ser Gly Gly Gly Leu Gln Thr Pro Gly Gly
1 5 10 15

Ala Leu Ser Leu Val Cys Lys Ala Ser Gly Phe Thr Phe Ser Ser Phe
20 25 30

```
Asn Met Phe Trp Val Arg Gln Ala Pro Gly Lys Gly Leu Glu Tyr Val
        35                  40                  45

Ala Gln Ile Ser Ser Ser Gly Ser Ser Thr Asn Tyr Ala Pro Ala Val
    50                  55                  60

Arg Gly Arg Ala Thr Ile Ser Arg Asp Asn Gly Gln Ser Thr Val Arg
65                  70                  75                  80

Leu Gln Leu Asn Asn Pro Gly Ala Glu Asp Thr Gly Thr Tyr Tyr Cys
                85                  90                  95

Ala Lys Ser Ser Tyr Asp Cys Pro Tyr Gly His Cys Ser Ser Gly Val
            100                 105                 110

Asp Ser Ala Gly Glu Ile Asp Ala Trp Gly His Gly Thr Glu Val Ile
        115                 120                 125

Val Ser Ser
    130


<210> SEQ ID NO 12
<211> LENGTH: 108
<212> TYPE: PRT
<213> ORGANISM: Artificial Sequence
<220> FEATURE:
<223> OTHER INFORMATION: VL - 3-2 Ab

<400> SEQUENCE: 12

Ala Leu Thr Gln Pro Ser Ser Val Ser Ala Asn Pro Gly Glu Thr Val
1               5                   10                  15

Lys Ile Thr Cys Ser Gly Gly Gly Ser Tyr Ala Gly Ser Tyr Tyr Tyr
            20                  25                  30

Gly Trp Tyr Gln Gln Lys Ala Pro Gly Ser Ala Pro Val Thr Leu Ile
        35                  40                  45

Tyr Glu Ser Asn Lys Arg Pro Ser Asp Ile Pro Ser Arg Phe Ser Gly
    50                  55                  60

Ser Thr Ser Gly Ser Thr Ala Thr Leu Thr Ile Thr Gly Val Gln Ala
65                  70                  75                  80

Asp Asp Glu Ala Ile Tyr Tyr Cys Gly Ser Trp Asp Ser Ser Asn Gly
                85                  90                  95

Gly Ile Phe Gly Ala Gly Thr Thr Leu Thr Val Leu
            100                 105


<210> SEQ ID NO 13
<211> LENGTH: 17
<212> TYPE: PRT
<213> ORGANISM: Artificial Sequence
<220> FEATURE:
<223> OTHER INFORMATION: Heavy Chain CDR2 - 1-7A-IT Ab

<400> SEQUENCE: 13

Gln Ile Ser Ser Ser Gly Ser Ser Thr Asn Tyr Ala Pro Ala Val Lys
1               5                   10                  15

Gly


<210> SEQ ID NO 14
<211> LENGTH: 10
<212> TYPE: PRT
<213> ORGANISM: Artificial Sequence
<220> FEATURE:
<223> OTHER INFORMATION: Heavy Chain CDR1 - Low-PI; 1-30; 1-17; 1-32;
      4-11; 6-10 Abs

<400> SEQUENCE: 14
```

Gly Phe Asp Phe Glu Ser Phe Asn Met Phe
1 5 10

<210> SEQ ID NO 15
<211> LENGTH: 17
<212> TYPE: PRT
<213> ORGANISM: Artificial Sequence
<220> FEATURE:
<223> OTHER INFORMATION: Heavy Chain CDR2 - Low-PI; 1-30; 1-17; 1-32; 4-11; 6-10 Abs

<400> SEQUENCE: 15

Gln Ile Ser Ser Ser Glu Glu Asp Glu Asn Tyr Ala Pro Ala Val Lys
1 5 10 15

Gly

<210> SEQ ID NO 16
<211> LENGTH: 10
<212> TYPE: PRT
<213> ORGANISM: Artificial Sequence
<220> FEATURE:
<223> OTHER INFORMATION: Heavy Chain CDR1 - 2-13; 2-13D Abs

<400> SEQUENCE: 16

Gly Phe Thr Phe Ser Ser His Gly Met Phe
1 5 10

<210> SEQ ID NO 17
<211> LENGTH: 17
<212> TYPE: PRT
<213> ORGANISM: Artificial Sequence
<220> FEATURE:
<223> OTHER INFORMATION: Heavy Chain CDR2 - 2-13; 2-13D; 2-13D-37 Abs

<400> SEQUENCE: 17

Glu Ile Thr Asn Asp Gly Ser Gly Thr Asn Tyr Gly Ser Ala Val Lys
1 5 10 15

Gly

<210> SEQ ID NO 18
<211> LENGTH: 20
<212> TYPE: PRT
<213> ORGANISM: Artificial Sequence
<220> FEATURE:
<223> OTHER INFORMATION: Heavy Chain CDR3 - 2-13; 2-13D; 2-13D-37 Abs

<400> SEQUENCE: 18

Ser Thr Tyr Glu Cys Pro Gly Gly Phe Ser Cys Trp Gly Asp Thr Gly
1 5 10 15

Gln Ile Asp Ala
20

<210> SEQ ID NO 19
<211> LENGTH: 10
<212> TYPE: PRT
<213> ORGANISM: Artificial Sequence
<220> FEATURE:
<223> OTHER INFORMATION: Heavy Chain CDR1 - 2-13D-37 Ab

<400> SEQUENCE: 19

Gly Phe Asp Phe Ser Ser His Gly Met Phe
1 5 10

<210> SEQ ID NO 20
<211> LENGTH: 7

<212> TYPE: PRT
<213> ORGANISM: Artificial Sequence
<220> FEATURE:
<223> OTHER INFORMATION: Light Chain CDR2 - 1-7A-IT

<400> SEQUENCE: 20

Glu Asn Asn Lys Arg Pro Ser
1 5

<210> SEQ ID NO 21
<211> LENGTH: 13
<212> TYPE: PRT
<213> ORGANISM: Artificial Sequence
<220> FEATURE:
<223> OTHER INFORMATION: Light Chain CDR1 - Low-PI; 1-30 Abs

<400> SEQUENCE: 21

Ser Gly Gly Gly Ser Glu Glu Glu Gln Tyr Tyr Tyr Gly
1 5 10

<210> SEQ ID NO 22
<211> LENGTH: 7
<212> TYPE: PRT
<213> ORGANISM: Artificial Sequence
<220> FEATURE:
<223> OTHER INFORMATION: Light Chain CDR2 - Low-PI Ab

<400> SEQUENCE: 22

Glu Asp Glu Glu Arg Pro Ser
1 5

<210> SEQ ID NO 23
<211> LENGTH: 10
<212> TYPE: PRT
<213> ORGANISM: Artificial Sequence
<220> FEATURE:
<223> OTHER INFORMATION: Light Chain CDR3 - Low-PI; 1-30; 1-17; 1-32 Abs

<400> SEQUENCE: 23

Gly Ser Trp Asp Ser Glu Asp Glu Asp His
1 5 10

<210> SEQ ID NO 24
<211> LENGTH: 7
<212> TYPE: PRT
<213> ORGANISM: Artificial Sequence
<220> FEATURE:
<223> OTHER INFORMATION: Light Chain CDR2 - 1-30; 1-32 Abs

<400> SEQUENCE: 24

Gln Asp Glu Glu Arg Pro Ser
1 5

<210> SEQ ID NO 25
<211> LENGTH: 7
<212> TYPE: PRT
<213> ORGANISM: Artificial Sequence
<220> FEATURE:
<223> OTHER INFORMATION: Light Chain CDR2 - 1-17 Ab

<400> SEQUENCE: 25

Glu Asp Glu Gln Arg Pro Ser
1 5

<210> SEQ ID NO 26
<211> LENGTH: 7
<212> TYPE: PRT

```
<213> ORGANISM: Artificial Sequence
<220> FEATURE:
<223> OTHER INFORMATION: Light Chain CDR2 - 4-11 Ab

<400> SEQUENCE: 26

Glu Asp His Glu Arg Pro Ser
1               5


<210> SEQ ID NO 27
<211> LENGTH: 10
<212> TYPE: PRT
<213> ORGANISM: Artificial Sequence
<220> FEATURE:
<223> OTHER INFORMATION: Light Chain CDR3 - 4-11 Ab

<400> SEQUENCE: 27

Gly Ser Trp Asp Ser Ser Asp Glu Asp His
1               5                   10


<210> SEQ ID NO 28
<211> LENGTH: 7
<212> TYPE: PRT
<213> ORGANISM: Artificial Sequence
<220> FEATURE:
<223> OTHER INFORMATION: Light Chain CDR2 - 6-10 Ab

<400> SEQUENCE: 28

Gln Asp Leu Leu Arg Pro Ser
1               5


<210> SEQ ID NO 29
<211> LENGTH: 10
<212> TYPE: PRT
<213> ORGANISM: Artificial Sequence
<220> FEATURE:
<223> OTHER INFORMATION: Light Chain CDR3 - 6-10 Ab

<400> SEQUENCE: 29

Gly Ser Trp Asp Ser Leu Ser Ser Ser His
1               5                   10


<210> SEQ ID NO 30
<211> LENGTH: 8
<212> TYPE: PRT
<213> ORGANISM: Artificial Sequence
<220> FEATURE:
<223> OTHER INFORMATION: Light Chain CDR1 - 2-13 Ab

<400> SEQUENCE: 30

Ser Gly Gly Ser Tyr Ser Tyr Gly
1               5


<210> SEQ ID NO 31
<211> LENGTH: 7
<212> TYPE: PRT
<213> ORGANISM: Artificial Sequence
<220> FEATURE:
<223> OTHER INFORMATION: Light Chain CDR2 - 2-13; 2-13D; 2-13D-37 Abs

<400> SEQUENCE: 31

Trp Asp Asp Glu Arg Pro Ser
1               5


<210> SEQ ID NO 32
<211> LENGTH: 11
<212> TYPE: PRT
<213> ORGANISM: Artificial Sequence
```

<220> FEATURE:
<223> OTHER INFORMATION: Light Chain CDR3 - 2-13; 2-13D; 2-13D-37 Abs

<400> SEQUENCE: 32

```
Gly Thr Glu Asp Ile Ser Gly Thr Ala Gly Val
1               5                   10
```

<210> SEQ ID NO 33
<211> LENGTH: 131
<212> TYPE: PRT
<213> ORGANISM: Artificial Sequence
<220> FEATURE:
<223> OTHER INFORMATION: VH - 1-7A-IT Ab

<400> SEQUENCE: 33

```
Ala Val Thr Leu Asp Glu Ser Gly Gly Gly Leu Gln Thr Pro Gly Gly
1               5                   10                  15

Ala Leu Arg Leu Ser Cys Lys Ala Ser Gly Phe Thr Phe Ser Ser Phe
            20                  25                  30

Asn Met Phe Trp Val Arg Gln Ala Pro Gly Lys Gly Leu Glu Tyr Val
        35                  40                  45

Ser Gln Ile Ser Ser Ser Gly Ser Ser Thr Asn Tyr Ala Pro Ala Val
    50                  55                  60

Lys Gly Arg Ala Thr Ile Ser Arg Asp Asn Gly Gln Ser Thr Leu Tyr
65                  70                  75                  80

Leu Gln Met Asn Ser Leu Arg Ala Glu Asp Thr Gly Thr Tyr Tyr Cys
                85                  90                  95

Ala Lys Ser Ser Tyr Asp Cys Pro Tyr Gly His Cys Ser Ser Gly Val
            100                 105                 110

Asp Ser Ala Gly Glu Ile Asp Ala Trp Gly His Gly Thr Glu Val Ile
        115                 120                 125

Val Ser Ser
    130
```

<210> SEQ ID NO 34
<211> LENGTH: 131
<212> TYPE: PRT
<213> ORGANISM: Artificial Sequence
<220> FEATURE:
<223> OTHER INFORMATION: VH - Low-PI; 1-30; 1-17; 1-32; 4-11; 6-10 Abs

<400> SEQUENCE: 34

```
Ala Val Thr Leu Asp Glu Ser Gly Gly Gly Leu Gln Thr Pro Gly Gly
1               5                   10                  15

Ala Leu Arg Leu Ser Cys Lys Ala Ser Gly Phe Asp Phe Glu Ser Phe
            20                  25                  30

Asn Met Phe Trp Val Arg Gln Ala Pro Gly Lys Gly Leu Glu Tyr Val
        35                  40                  45

Ser Gln Ile Ser Ser Ser Glu Glu Asp Glu Asn Tyr Ala Pro Ala Val
    50                  55                  60

Lys Gly Arg Ala Thr Ile Ser Arg Asp Asn Gly Gln Ser Thr Leu Tyr
65                  70                  75                  80

Leu Gln Met Asn Ser Leu Arg Ala Glu Asp Thr Gly Thr Tyr Tyr Cys
                85                  90                  95

Ala Lys Ser Ser Tyr Asp Cys Pro Tyr Gly His Cys Ser Ser Gly Val
            100                 105                 110

Asp Ser Ala Gly Glu Ile Asp Ala Trp Gly His Gly Thr Glu Val Ile
        115                 120                 125
```

```
Val Ser Ser
    130


<210> SEQ ID NO 35
<211> LENGTH: 129
<212> TYPE: PRT
<213> ORGANISM: Artificial Sequence
<220> FEATURE:
<223> OTHER INFORMATION: VH - 2-13 Ab

<400> SEQUENCE: 35

Ala Val Thr Leu Asp Glu Ser Gly Gly Gly Leu Gln Thr Pro Gly Gly
1               5                   10                  15

Ala Leu Ser Leu Val Cys Lys Ala Ser Gly Phe Thr Phe Ser Ser His
            20                  25                  30

Gly Met Phe Trp Val Arg Gln Thr Pro Gly Lys Gly Leu Glu Tyr Val
        35                  40                  45

Ala Glu Ile Thr Asn Asp Gly Ser Gly Thr Asn Tyr Gly Ser Ala Val
    50                  55                  60

Lys Gly Arg Ala Thr Ile Ser Arg Asp Asn Gly Gln Ser Thr Val Arg
65                  70                  75                  80

Leu Gln Leu Asn Asn Leu Arg Ala Glu Asp Thr Gly Thr Tyr Phe Cys
                85                  90                  95

Ala Arg Ser Thr Tyr Glu Cys Pro Gly Gly Phe Ser Cys Trp Gly Asp
            100                 105                 110

Thr Gly Gln Ile Asp Ala Trp Gly His Gly Thr Glu Val Ile Val Ser
        115                 120                 125

Ser


<210> SEQ ID NO 36
<211> LENGTH: 129
<212> TYPE: PRT
<213> ORGANISM: Artificial Sequence
<220> FEATURE:
<223> OTHER INFORMATION: VH - 2-13D Ab

<400> SEQUENCE: 36

Ala Val Thr Leu Asp Glu Ser Gly Gly Gly Leu Gln Thr Pro Gly Gly
1               5                   10                  15

Ala Leu Arg Leu Ser Cys Ser Ala Ser Gly Phe Thr Phe Ser Ser His
            20                  25                  30

Gly Met Phe Trp Val Arg Gln Ala Pro Gly Lys Gly Leu Glu Tyr Val
        35                  40                  45

Ser Glu Ile Thr Asn Asp Gly Ser Gly Thr Asn Tyr Gly Ser Ala Val
    50                  55                  60

Lys Gly Arg Ala Thr Ile Ser Arg Asp Asn Gly Gln Ser Thr Leu Tyr
65                  70                  75                  80

Leu Gln Met Asn Ser Leu Arg Ala Glu Asp Thr Gly Thr Tyr Phe Cys
                85                  90                  95

Ala Arg Ser Thr Tyr Glu Cys Pro Gly Gly Phe Ser Cys Trp Gly Asp
            100                 105                 110

Thr Gly Gln Ile Asp Ala Trp Gly His Gly Thr Glu Val Ile Val Ser
        115                 120                 125

Ser


<210> SEQ ID NO 37
<211> LENGTH: 129
<212> TYPE: PRT
```

<213> ORGANISM: Artificial Sequence
<220> FEATURE:
<223> OTHER INFORMATION: VH - 2-13D-37 Ab

<400> SEQUENCE: 37

Ala Val Thr Leu Asp Glu Ser Gly Gly Gly Leu Gln Thr Pro Gly Gly
1 5 10 15

Ala Leu Arg Leu Ser Cys Ser Ala Ser Gly Phe Asp Phe Ser Ser His
20 25 30

Gly Met Phe Trp Val Arg Gln Ala Pro Gly Lys Gly Leu Glu Tyr Val
35 40 45

Ser Glu Ile Thr Asn Asp Gly Ser Gly Thr Asn Tyr Gly Ser Ala Val
50 55 60

Lys Gly Arg Ala Thr Ile Ser Arg Asp Asn Gly Gln Ser Thr Leu Tyr
65 70 75 80

Leu Gln Met Asn Ser Leu Arg Ala Glu Asp Thr Gly Thr Tyr Phe Cys
85 90 95

Ala Arg Ser Thr Tyr Glu Cys Pro Gly Gly Phe Ser Cys Trp Gly Asp
100 105 110

Thr Gly Gln Ile Asp Ala Trp Gly His Gly Thr Glu Val Ile Val Ser
115 120 125

Ser

<210> SEQ ID NO 38
<211> LENGTH: 107
<212> TYPE: PRT
<213> ORGANISM: Artificial Sequence
<220> FEATURE:
<223> OTHER INFORMATION: VL - 1-7A-IT Ab

<400> SEQUENCE: 38

Ala Leu Thr Gln Pro Ser Ser Val Ser Ala Asn Pro Gly Glu Thr Val
1 5 10 15

Lys Ile Thr Cys Ser Gly Gly Gly Ser Tyr Ala Gly Ser Tyr Tyr Tyr
20 25 30

Gly Trp Tyr Gln Gln Lys Pro Gly Ser Ala Pro Val Thr Leu Ile Tyr
35 40 45

Glu Asn Asn Lys Arg Pro Ser Asp Ile Pro Ser Arg Phe Ser Gly Ser
50 55 60

Thr Ser Gly Ser Thr Ala Thr Leu Thr Ile Thr Gly Val Gln Ala Gly
65 70 75 80

Asp Glu Ala Asp Tyr Tyr Cys Gly Ser Trp Asp Ser Ser Asn Gly Gly
85 90 95

Ile Phe Gly Ala Gly Thr Thr Leu Thr Val Leu
100 105

<210> SEQ ID NO 39
<211> LENGTH: 107
<212> TYPE: PRT
<213> ORGANISM: Artificial Sequence
<220> FEATURE:
<223> OTHER INFORMATION: VL - Low-PI Ab

<400> SEQUENCE: 39

Ala Leu Thr Gln Pro Ser Ser Val Ser Ala Asn Pro Gly Glu Thr Val
1 5 10 15

Lys Ile Thr Cys Ser Gly Gly Gly Ser Glu Glu Glu Gln Tyr Tyr Tyr
20 25 30

```
Gly Trp Tyr Gln Gln Lys Pro Gly Ser Ala Pro Val Thr Leu Ile Tyr
        35                  40                  45

Glu Asp Glu Glu Arg Pro Ser Asp Ile Pro Ser Arg Phe Ser Gly Ser
    50                  55                  60

Thr Ser Gly Ser Thr Ala Thr Leu Thr Ile Thr Gly Val Gln Ala Gly
65                  70                  75                  80

Asp Glu Ala Asp Tyr Tyr Cys Gly Ser Trp Asp Ser Glu Asp Glu Asp
                85                  90                  95

His Phe Gly Ala Gly Thr Thr Leu Thr Val Leu
            100                 105


<210> SEQ ID NO 40
<211> LENGTH: 107
<212> TYPE: PRT
<213> ORGANISM: Artificial Sequence
<220> FEATURE:
<223> OTHER INFORMATION: VL - 1-30 Ab

<400> SEQUENCE: 40

Ala Leu Thr Gln Pro Ser Ser Val Ser Ala Asn Pro Gly Glu Thr Val
1               5                   10                  15

Lys Ile Thr Cys Ser Gly Gly Gly Ser Glu Glu Glu Gln Tyr Tyr Tyr
            20                  25                  30

Gly Trp Tyr Gln Gln Lys Pro Gly Ser Ala Pro Val Thr Leu Ile Tyr
        35                  40                  45

Gln Asp Glu Glu Arg Pro Ser Asp Ile Pro Ser Arg Phe Ser Gly Ser
    50                  55                  60

Thr Ser Gly Ser Thr Ala Thr Leu Thr Ile Thr Gly Val Gln Ala Gly
65                  70                  75                  80

Asp Glu Ala Asp Tyr Tyr Cys Gly Ser Trp Asp Ser Glu Asp Glu Asp
                85                  90                  95

His Phe Gly Ala Gly Thr Thr Leu Thr Val Leu
            100                 105


<210> SEQ ID NO 41
<211> LENGTH: 107
<212> TYPE: PRT
<213> ORGANISM: Artificial Sequence
<220> FEATURE:
<223> OTHER INFORMATION: VL - 1-17 Ab

<400> SEQUENCE: 41

Ala Leu Thr Gln Pro Ser Ser Val Ser Ala Asn Pro Gly Glu Thr Val
1               5                   10                  15

Lys Ile Thr Cys Ser Gly Gly Gly Ser Tyr Ala Gly Ser Tyr Tyr Tyr
            20                  25                  30

Gly Trp Tyr Gln Gln Lys Pro Gly Ser Ala Pro Val Thr Leu Ile Tyr
        35                  40                  45

Glu Asp Glu Gln Arg Pro Ser Asp Ile Pro Ser Arg Phe Ser Gly Ser
    50                  55                  60

Thr Ser Gly Ser Thr Ala Thr Leu Thr Ile Thr Gly Val Gln Ala Gly
65                  70                  75                  80

Asp Glu Ala Asp Tyr Tyr Cys Gly Ser Trp Asp Ser Glu Asp Glu Asp
                85                  90                  95

His Phe Gly Ala Gly Thr Thr Leu Thr Val Leu
            100                 105


<210> SEQ ID NO 42
```

<211> LENGTH: 107
<212> TYPE: PRT
<213> ORGANISM: Artificial Sequence
<220> FEATURE:
<223> OTHER INFORMATION: VL - 1-32 Ab

<400> SEQUENCE: 42

```
Ala Leu Thr Gln Pro Ser Ser Val Ser Ala Asn Pro Gly Glu Thr Val
1               5                   10                  15

Lys Ile Thr Cys Ser Gly Gly Gly Ser Tyr Ala Gly Ser Tyr Tyr Tyr
            20                  25                  30

Gly Trp Tyr Gln Gln Lys Pro Gly Ser Ala Pro Val Thr Leu Ile Tyr
        35                  40                  45

Gln Asp Glu Glu Arg Pro Ser Asp Ile Pro Ser Arg Phe Ser Gly Ser
    50                  55                  60

Thr Ser Gly Ser Thr Ala Thr Leu Thr Ile Thr Gly Val Gln Ala Gly
65                  70                  75                  80

Asp Glu Ala Asp Tyr Tyr Cys Gly Ser Trp Asp Ser Glu Asp Glu Asp
                85                  90                  95

His Phe Gly Ala Gly Thr Thr Leu Thr Val Leu
            100                 105
```

<210> SEQ ID NO 43
<211> LENGTH: 107
<212> TYPE: PRT
<213> ORGANISM: Artificial Sequence
<220> FEATURE:
<223> OTHER INFORMATION: VL - 4-11 Ab

<400> SEQUENCE: 43

```
Ala Leu Thr Gln Pro Ser Ser Val Ser Ala Asn Pro Gly Glu Thr Val
1               5                   10                  15

Lys Ile Thr Cys Ser Gly Gly Gly Ser Tyr Ala Gly Ser Tyr Tyr Tyr
            20                  25                  30

Gly Trp Tyr Gln Gln Lys Pro Gly Ser Ala Pro Val Thr Leu Ile Tyr
        35                  40                  45

Glu Asp His Glu Arg Pro Ser Asp Ile Pro Ser Arg Phe Ser Gly Ser
    50                  55                  60

Thr Ser Gly Ser Thr Ala Thr Leu Thr Ile Thr Gly Val Gln Ala Gly
65                  70                  75                  80

Asp Glu Ala Asp Tyr Tyr Cys Gly Ser Trp Asp Ser Ser Asp Glu Asp
                85                  90                  95

His Phe Gly Ala Gly Thr Thr Leu Thr Val Leu
            100                 105
```

<210> SEQ ID NO 44
<211> LENGTH: 107
<212> TYPE: PRT
<213> ORGANISM: Artificial Sequence
<220> FEATURE:
<223> OTHER INFORMATION: VL - 6-10 Ab

<400> SEQUENCE: 44

```
Ala Leu Thr Gln Pro Ser Ser Val Ser Ala Asn Pro Gly Glu Thr Val
1               5                   10                  15

Lys Ile Thr Cys Ser Gly Gly Gly Ser Tyr Ala Gly Ser Tyr Tyr Tyr
            20                  25                  30

Gly Trp Tyr Gln Gln Lys Pro Gly Ser Ala Pro Val Thr Leu Ile Tyr
        35                  40                  45
```

Gln Asp Leu Leu Arg Pro Ser Asp Ile Pro Ser Arg Phe Ser Gly Ser
50 55 60

Thr Ser Gly Ser Thr Ala Thr Leu Thr Ile Thr Gly Val Gln Ala Gly
65 70 75 80

Asp Glu Ala Asp Tyr Tyr Cys Gly Ser Trp Asp Ser Leu Ser Ser Ser
85 90 95

His Phe Gly Ala Gly Thr Thr Leu Thr Val Leu
100 105

<210> SEQ ID NO 45
<211> LENGTH: 104
<212> TYPE: PRT
<213> ORGANISM: Artificial Sequence
<220> FEATURE:
<223> OTHER INFORMATION: VL - 2-13 Ab

<400> SEQUENCE: 45

Ala Leu Thr Gln Pro Ser Ser Val Ser Ala Asn Pro Gly Glu Thr Val
1 5 10 15

Lys Ile Thr Cys Ser Gly Gly Ser Tyr Ser Tyr Gly Trp Phe Gln Gln
20 25 30

Lys Ser Pro Gly Ser Ala Leu Val Thr Val Ile Tyr Trp Asp Asp Glu
35 40 45

Arg Pro Ser Asp Ile Pro Ser Arg Phe Ser Gly Ala Leu Ser Gly Ser
50 55 60

Thr Asn Thr Leu Thr Ile Thr Gly Val Gln Ala Asp Asp Glu Ala Val
65 70 75 80

Tyr Phe Cys Gly Thr Glu Asp Ile Ser Gly Thr Ala Gly Val Phe Gly
85 90 95

Ala Gly Thr Thr Leu Thr Val Leu
100

<210> SEQ ID NO 46
<211> LENGTH: 103
<212> TYPE: PRT
<213> ORGANISM: Artificial Sequence
<220> FEATURE:
<223> OTHER INFORMATION: VL - 2-13D; 2-13D-37 Abs

<400> SEQUENCE: 46

Ala Leu Thr Gln Pro Ser Ser Val Ser Ala Asn Pro Gly Glu Thr Ala
1 5 10 15

Lys Ile Thr Cys Ser Gly Gly Val Tyr Ser Tyr Gly Trp Phe Gln Gln
20 25 30

Lys Pro Gly Ser Ala Leu Val Thr Val Ile Tyr Trp Asp Asp Glu Arg
35 40 45

Pro Ser Asp Ile Pro Ser Arg Phe Ser Gly Ala Leu Ser Gly Ser Thr
50 55 60

Asn Thr Leu Thr Ile Thr Gly Val Gln Ala Glu Asp Glu Ala Asp Tyr
65 70 75 80

Tyr Cys Gly Thr Glu Asp Ile Ser Gly Thr Ala Gly Val Phe Gly Ala
85 90 95

Gly Thr Thr Leu Thr Val Leu
100

<210> SEQ ID NO 47
<211> LENGTH: 257
<212> TYPE: PRT
<213> ORGANISM: Artificial Sequence
<220> FEATURE:
<223> OTHER INFORMATION: scFv - 3-2 Ab

<400> SEQUENCE: 47

```
Ala Leu Thr Gln Pro Ser Ser Val Ser Ala Asn Pro Gly Glu Thr Val
1               5                   10                  15

Lys Ile Thr Cys Ser Gly Gly Gly Ser Tyr Ala Gly Ser Tyr Tyr Tyr
            20                  25                  30

Gly Trp Tyr Gln Gln Lys Ala Pro Gly Ser Ala Pro Val Thr Leu Ile
        35                  40                  45

Tyr Glu Ser Asn Lys Arg Pro Ser Asp Ile Pro Ser Arg Phe Ser Gly
    50                  55                  60

Ser Thr Ser Gly Ser Thr Ala Thr Leu Thr Ile Thr Gly Val Gln Ala
65                  70                  75                  80

Asp Asp Glu Ala Ile Tyr Tyr Cys Gly Ser Trp Asp Ser Ser Asn Gly
                85                  90                  95

Gly Ile Phe Gly Ala Gly Thr Thr Leu Thr Val Leu Gly Gln Ser Ser
            100                 105                 110

Arg Ser Ser Gly Gly Gly Gly Ser Ser Gly Gly Gly Gly Ser Ala Val
        115                 120                 125

Thr Leu Asp Glu Ser Gly Gly Gly Leu Gln Thr Pro Gly Gly Ala Leu
    130                 135                 140

Ser Leu Val Cys Lys Ala Ser Gly Phe Thr Phe Ser Ser Phe Asn Met
145                 150                 155                 160

Phe Trp Val Arg Gln Ala Pro Gly Lys Gly Leu Glu Tyr Val Ala Gln
                165                 170                 175

Ile Ser Ser Ser Gly Ser Ser Thr Asn Tyr Ala Pro Ala Val Arg Gly
            180                 185                 190

Arg Ala Thr Ile Ser Arg Asp Asn Gly Gln Ser Thr Val Arg Leu Gln
        195                 200                 205

Leu Asn Asn Pro Gly Ala Glu Asp Thr Gly Thr Tyr Tyr Cys Ala Lys
    210                 215                 220

Ser Ser Tyr Asp Cys Pro Tyr Gly His Cys Ser Ser Gly Val Asp Ser
225                 230                 235                 240

Ala Gly Glu Ile Asp Ala Trp Gly His Gly Thr Glu Val Ile Val Ser
                245                 250                 255

Ser
```

<210> SEQ ID NO 48
<211> LENGTH: 256
<212> TYPE: PRT
<213> ORGANISM: Artificial Sequence
<220> FEATURE:
<223> OTHER INFORMATION: scFV - 1-7A-IT Ab

<400> SEQUENCE: 48

```
Ala Leu Thr Gln Pro Ser Ser Val Ser Ala Asn Pro Gly Glu Thr Val
1               5                   10                  15

Lys Ile Thr Cys Ser Gly Gly Gly Ser Tyr Ala Gly Ser Tyr Tyr Tyr
            20                  25                  30

Gly Trp Tyr Gln Gln Lys Pro Gly Ser Ala Pro Val Thr Leu Ile Tyr
        35                  40                  45

Glu Asn Asn Lys Arg Pro Ser Asp Ile Pro Ser Arg Phe Ser Gly Ser
    50                  55                  60

Thr Ser Gly Ser Thr Ala Thr Leu Thr Ile Thr Gly Val Gln Ala Gly
65                  70                  75                  80
```

```
Asp Glu Ala Asp Tyr Tyr Cys Gly Ser Trp Asp Ser Ser Asn Gly Gly
                85                  90                  95

Ile Phe Gly Ala Gly Thr Thr Leu Thr Val Leu Gly Gln Ser Ser Arg
            100                 105                 110

Ser Ser Gly Gly Gly Gly Ser Ser Gly Gly Gly Gly Ser Ala Val Thr
        115                 120                 125

Leu Asp Glu Ser Gly Gly Gly Leu Gln Thr Pro Gly Gly Ala Leu Arg
    130                 135                 140

Leu Ser Cys Lys Ala Ser Gly Phe Thr Phe Ser Ser Phe Asn Met Phe
145                 150                 155                 160

Trp Val Arg Gln Ala Pro Gly Lys Gly Leu Glu Tyr Val Ser Gln Ile
                165                 170                 175

Ser Ser Ser Gly Ser Ser Thr Asn Tyr Ala Pro Ala Val Lys Gly Arg
            180                 185                 190

Ala Thr Ile Ser Arg Asp Asn Gly Gln Ser Thr Leu Tyr Leu Gln Met
        195                 200                 205

Asn Ser Leu Arg Ala Glu Asp Thr Gly Thr Tyr Tyr Cys Ala Lys Ser
    210                 215                 220

Ser Tyr Asp Cys Pro Tyr Gly His Cys Ser Ser Gly Val Asp Ser Ala
225                 230                 235                 240

Gly Glu Ile Asp Ala Trp Gly His Gly Thr Glu Val Ile Val Ser Ser
                245                 250                 255


<210> SEQ ID NO 49
<211> LENGTH: 256
<212> TYPE: PRT
<213> ORGANISM: Artificial Sequence
<220> FEATURE:
<223> OTHER INFORMATION: scFv - Low-PI Ab

<400> SEQUENCE: 49

Ala Leu Thr Gln Pro Ser Ser Val Ser Ala Asn Pro Gly Glu Thr Val
1               5                   10                  15

Lys Ile Thr Cys Ser Gly Gly Gly Ser Glu Glu Glu Gln Tyr Tyr Tyr
            20                  25                  30

Gly Trp Tyr Gln Gln Lys Pro Gly Ser Ala Pro Val Thr Leu Ile Tyr
        35                  40                  45

Glu Asp Glu Glu Arg Pro Ser Asp Ile Pro Ser Arg Phe Ser Gly Ser
    50                  55                  60

Thr Ser Gly Ser Thr Ala Thr Leu Thr Ile Thr Gly Val Gln Ala Gly
65                  70                  75                  80

Asp Glu Ala Asp Tyr Tyr Cys Gly Ser Trp Asp Ser Glu Asp Glu Asp
                85                  90                  95

His Phe Gly Ala Gly Thr Thr Leu Thr Val Leu Gly Gln Ser Ser Arg
            100                 105                 110

Ser Ser Gly Gly Gly Gly Ser Ser Gly Gly Gly Gly Ser Ala Val Thr
        115                 120                 125

Leu Asp Glu Ser Gly Gly Gly Leu Gln Thr Pro Gly Gly Ala Leu Arg
    130                 135                 140

Leu Ser Cys Lys Ala Ser Gly Phe Asp Phe Glu Ser Phe Asn Met Phe
145                 150                 155                 160

Trp Val Arg Gln Ala Pro Gly Lys Gly Leu Glu Tyr Val Ser Gln Ile
                165                 170                 175

Ser Ser Ser Glu Glu Asp Glu Asn Tyr Ala Pro Ala Val Lys Gly Arg
            180                 185                 190
```

```
Ala Thr Ile Ser Arg Asp Asn Gly Gln Ser Thr Leu Tyr Leu Gln Met
        195                 200                 205

Asn Ser Leu Arg Ala Glu Asp Thr Gly Thr Tyr Tyr Cys Ala Lys Ser
    210                 215                 220

Ser Tyr Asp Cys Pro Tyr Gly His Cys Ser Ser Gly Val Asp Ser Ala
225                 230                 235                 240

Gly Glu Ile Asp Ala Trp Gly His Gly Thr Glu Val Ile Val Ser Ser
                245                 250                 255


<210> SEQ ID NO 50
<211> LENGTH: 256
<212> TYPE: PRT
<213> ORGANISM: Artificial Sequence
<220> FEATURE:
<223> OTHER INFORMATION: scFv - 1-30 Ab

<400> SEQUENCE: 50

Ala Leu Thr Gln Pro Ser Ser Val Ser Ala Asn Pro Gly Glu Thr Val
1               5                   10                  15

Lys Ile Thr Cys Ser Gly Gly Gly Ser Glu Glu Glu Gln Tyr Tyr Tyr
            20                  25                  30

Gly Trp Tyr Gln Gln Lys Pro Gly Ser Ala Pro Val Thr Leu Ile Tyr
        35                  40                  45

Gln Asp Glu Glu Arg Pro Ser Asp Ile Pro Ser Arg Phe Ser Gly Ser
    50                  55                  60

Thr Ser Gly Ser Thr Ala Thr Leu Thr Ile Thr Gly Val Gln Ala Gly
65                  70                  75                  80

Asp Glu Ala Asp Tyr Tyr Cys Gly Ser Trp Asp Ser Glu Asp Glu Asp
                85                  90                  95

His Phe Gly Ala Gly Thr Thr Leu Thr Val Leu Gly Gln Ser Ser Arg
            100                 105                 110

Ser Ser Gly Gly Gly Gly Ser Ser Gly Gly Gly Gly Ser Ala Val Thr
        115                 120                 125

Leu Asp Glu Ser Gly Gly Gly Leu Gln Thr Pro Gly Gly Ala Leu Arg
    130                 135                 140

Leu Ser Cys Lys Ala Ser Gly Phe Asp Phe Glu Ser Phe Asn Met Phe
145                 150                 155                 160

Trp Val Arg Gln Ala Pro Gly Lys Gly Leu Glu Tyr Val Ser Gln Ile
                165                 170                 175

Ser Ser Ser Glu Glu Asp Glu Asn Tyr Ala Pro Ala Val Lys Gly Arg
            180                 185                 190

Ala Thr Ile Ser Arg Asp Asn Gly Gln Ser Thr Leu Tyr Leu Gln Met
        195                 200                 205

Asn Ser Leu Arg Ala Glu Asp Thr Gly Thr Tyr Tyr Cys Ala Lys Ser
    210                 215                 220

Ser Tyr Asp Cys Pro Tyr Gly His Cys Ser Ser Gly Val Asp Ser Ala
225                 230                 235                 240

Gly Glu Ile Asp Ala Trp Gly His Gly Thr Glu Val Ile Val Ser Ser
                245                 250                 255


<210> SEQ ID NO 51
<211> LENGTH: 256
<212> TYPE: PRT
<213> ORGANISM: Artificial Sequence
<220> FEATURE:
<223> OTHER INFORMATION: scFv - 1-17 Ab
```

<400> SEQUENCE: 51

Ala Leu Thr Gln Pro Ser Ser Val Ser Ala Asn Pro Gly Glu Thr Val
1 5 10 15

Lys Ile Thr Cys Ser Gly Gly Gly Ser Tyr Ala Gly Ser Tyr Tyr Tyr
20 25 30

Gly Trp Tyr Gln Gln Lys Pro Gly Ser Ala Pro Val Thr Leu Ile Tyr
35 40 45

Glu Asp Glu Gln Arg Pro Ser Asp Ile Pro Ser Arg Phe Ser Gly Ser
50 55 60

Thr Ser Gly Ser Thr Ala Thr Leu Thr Ile Thr Gly Val Gln Ala Gly
65 70 75 80

Asp Glu Ala Asp Tyr Tyr Cys Gly Ser Trp Asp Ser Glu Asp Glu Asp
85 90 95

His Phe Gly Ala Gly Thr Thr Leu Thr Val Leu Gly Gln Ser Ser Arg
100 105 110

Ser Ser Gly Gly Gly Gly Ser Ser Gly Gly Gly Gly Ser Ala Val Thr
115 120 125

Leu Asp Glu Ser Gly Gly Gly Leu Gln Thr Pro Gly Gly Ala Leu Arg
130 135 140

Leu Ser Cys Lys Ala Ser Gly Phe Asp Phe Glu Ser Phe Asn Met Phe
145 150 155 160

Trp Val Arg Gln Ala Pro Gly Lys Gly Leu Glu Tyr Val Ser Gln Ile
165 170 175

Ser Ser Ser Glu Glu Asp Glu Asn Tyr Ala Pro Ala Val Lys Gly Arg
180 185 190

Ala Thr Ile Ser Arg Asp Asn Gly Gln Ser Thr Leu Tyr Leu Gln Met
195 200 205

Asn Ser Leu Arg Ala Glu Asp Thr Gly Thr Tyr Tyr Cys Ala Lys Ser
210 215 220

Ser Tyr Asp Cys Pro Tyr Gly His Cys Ser Ser Gly Val Asp Ser Ala
225 230 235 240

Gly Glu Ile Asp Ala Trp Gly His Gly Thr Glu Val Ile Val Ser Ser
245 250 255

<210> SEQ ID NO 52
<211> LENGTH: 256
<212> TYPE: PRT
<213> ORGANISM: Artificial Sequence
<220> FEATURE:
<223> OTHER INFORMATION: scFv - 1-32 Ab

<400> SEQUENCE: 52

Ala Leu Thr Gln Pro Ser Ser Val Ser Ala Asn Pro Gly Glu Thr Val
1 5 10 15

Lys Ile Thr Cys Ser Gly Gly Gly Ser Tyr Ala Gly Ser Tyr Tyr Tyr
20 25 30

Gly Trp Tyr Gln Gln Lys Pro Gly Ser Ala Pro Val Thr Leu Ile Tyr
35 40 45

Gln Asp Glu Glu Arg Pro Ser Asp Ile Pro Ser Arg Phe Ser Gly Ser
50 55 60

Thr Ser Gly Ser Thr Ala Thr Leu Thr Ile Thr Gly Val Gln Ala Gly
65 70 75 80

Asp Glu Ala Asp Tyr Tyr Cys Gly Ser Trp Asp Ser Glu Asp Glu Asp
85 90 95

His Phe Gly Ala Gly Thr Thr Leu Thr Val Leu Gly Gln Ser Ser Arg

```
            100                 105                 110

Ser Ser Gly Gly Gly Gly Ser Ser Gly Gly Gly Gly Ser Ala Val Thr
        115                 120                 125

Leu Asp Glu Ser Gly Gly Gly Leu Gln Thr Pro Gly Gly Ala Leu Arg
    130                 135                 140

Leu Ser Cys Lys Ala Ser Gly Phe Asp Phe Glu Ser Phe Asn Met Phe
145                 150                 155                 160

Trp Val Arg Gln Ala Pro Gly Lys Gly Leu Glu Tyr Val Ser Gln Ile
                165                 170                 175

Ser Ser Ser Glu Glu Asp Glu Asn Tyr Ala Pro Ala Val Lys Gly Arg
            180                 185                 190

Ala Thr Ile Ser Arg Asp Asn Gly Gln Ser Thr Leu Tyr Leu Gln Met
        195                 200                 205

Asn Ser Leu Arg Ala Glu Asp Thr Gly Thr Tyr Tyr Cys Ala Lys Ser
    210                 215                 220

Ser Tyr Asp Cys Pro Tyr Gly His Cys Ser Ser Gly Val Asp Ser Ala
225                 230                 235                 240

Gly Glu Ile Asp Ala Trp Gly His Gly Thr Glu Val Ile Val Ser Ser
                245                 250                 255


<210> SEQ ID NO 53
<211> LENGTH: 256
<212> TYPE: PRT
<213> ORGANISM: Artificial Sequence
<220> FEATURE:
<223> OTHER INFORMATION: scFv - 4-11 Ab

<400> SEQUENCE: 53

Ala Leu Thr Gln Pro Ser Ser Val Ser Ala Asn Pro Gly Glu Thr Val
1               5                   10                  15

Lys Ile Thr Cys Ser Gly Gly Gly Ser Tyr Ala Gly Ser Tyr Tyr Tyr
            20                  25                  30

Gly Trp Tyr Gln Gln Lys Pro Gly Ser Ala Pro Val Thr Leu Ile Tyr
        35                  40                  45

Glu Asp His Glu Arg Pro Ser Asp Ile Pro Ser Arg Phe Ser Gly Ser
    50                  55                  60

Thr Ser Gly Ser Thr Ala Thr Leu Thr Ile Thr Gly Val Gln Ala Gly
65                  70                  75                  80

Asp Glu Ala Asp Tyr Tyr Cys Gly Ser Trp Asp Ser Ser Asp Glu Asp
                85                  90                  95

His Phe Gly Ala Gly Thr Thr Leu Thr Val Leu Gly Gln Ser Ser Arg
            100                 105                 110

Ser Ser Gly Gly Gly Gly Ser Ser Gly Gly Gly Gly Ser Ala Val Thr
        115                 120                 125

Leu Asp Glu Ser Gly Gly Gly Leu Gln Thr Pro Gly Gly Ala Leu Arg
    130                 135                 140

Leu Ser Cys Lys Ala Ser Gly Phe Asp Phe Glu Ser Phe Asn Met Phe
145                 150                 155                 160

Trp Val Arg Gln Ala Pro Gly Lys Gly Leu Glu Tyr Val Ser Gln Ile
                165                 170                 175

Ser Ser Ser Glu Glu Asp Glu Asn Tyr Ala Pro Ala Val Lys Gly Arg
            180                 185                 190

Ala Thr Ile Ser Arg Asp Asn Gly Gln Ser Thr Leu Tyr Leu Gln Met
        195                 200                 205

Asn Ser Leu Arg Ala Glu Asp Thr Gly Thr Tyr Tyr Cys Ala Lys Ser
```

```
    210                 215                 220

Ser Tyr Asp Cys Pro Tyr Gly His Cys Ser Ser Gly Val Asp Ser Ala
225                 230                 235                 240

Gly Glu Ile Asp Ala Trp Gly His Gly Thr Glu Val Ile Val Ser Ser
                245                 250                 255


<210> SEQ ID NO 54
<211> LENGTH: 256
<212> TYPE: PRT
<213> ORGANISM: Artificial Sequence
<220> FEATURE:
<223> OTHER INFORMATION: scFv - 6-10 Ab

<400> SEQUENCE: 54

Ala Leu Thr Gln Pro Ser Ser Val Ser Ala Asn Pro Gly Glu Thr Val
1               5                   10                  15

Lys Ile Thr Cys Ser Gly Gly Gly Ser Tyr Ala Gly Ser Tyr Tyr Tyr
            20                  25                  30

Gly Trp Tyr Gln Gln Lys Pro Gly Ser Ala Pro Val Thr Leu Ile Tyr
        35                  40                  45

Gln Asp Leu Leu Arg Pro Ser Asp Ile Pro Ser Arg Phe Ser Gly Ser
    50                  55                  60

Thr Ser Gly Ser Thr Ala Thr Leu Thr Ile Thr Gly Val Gln Ala Gly
65                  70                  75                  80

Asp Glu Ala Asp Tyr Tyr Cys Gly Ser Trp Asp Ser Leu Ser Ser Ser
                85                  90                  95

His Phe Gly Ala Gly Thr Thr Leu Thr Val Leu Gly Gln Ser Ser Arg
            100                 105                 110

Ser Ser Gly Gly Gly Gly Ser Ser Gly Gly Gly Gly Ser Ala Val Thr
        115                 120                 125

Leu Asp Glu Ser Gly Gly Gly Leu Gln Thr Pro Gly Gly Ala Leu Arg
    130                 135                 140

Leu Ser Cys Lys Ala Ser Gly Phe Asp Phe Glu Ser Phe Asn Met Phe
145                 150                 155                 160

Trp Val Arg Gln Ala Pro Gly Lys Gly Leu Glu Tyr Val Ser Gln Ile
                165                 170                 175

Ser Ser Ser Glu Glu Asp Glu Asn Tyr Ala Pro Ala Val Lys Gly Arg
            180                 185                 190

Ala Thr Ile Ser Arg Asp Asn Gly Gln Ser Thr Leu Tyr Leu Gln Met
        195                 200                 205

Asn Ser Leu Arg Ala Glu Asp Thr Gly Thr Tyr Tyr Cys Ala Lys Ser
    210                 215                 220

Ser Tyr Asp Cys Pro Tyr Gly His Cys Ser Ser Gly Val Asp Ser Ala
225                 230                 235                 240

Gly Glu Ile Asp Ala Trp Gly His Gly Thr Glu Val Ile Val Ser Ser
                245                 250                 255


<210> SEQ ID NO 55
<211> LENGTH: 251
<212> TYPE: PRT
<213> ORGANISM: Artificial Sequence
<220> FEATURE:
<223> OTHER INFORMATION: scFv - 2-13 Ab

<400> SEQUENCE: 55

Ala Leu Thr Gln Pro Ser Ser Val Ser Ala Asn Pro Gly Glu Thr Val
1               5                   10                  15
```

```
Lys Ile Thr Cys Ser Gly Gly Ser Tyr Ser Tyr Gly Trp Phe Gln Gln
            20                  25                  30

Lys Ser Pro Gly Ser Ala Leu Val Thr Val Ile Tyr Trp Asp Asp Glu
        35                  40                  45

Arg Pro Ser Asp Ile Pro Ser Arg Phe Ser Gly Ala Leu Ser Gly Ser
    50                  55                  60

Thr Asn Thr Leu Thr Ile Thr Gly Val Gln Ala Asp Asp Glu Ala Val
65                  70                  75                  80

Tyr Phe Cys Gly Thr Glu Asp Ile Ser Gly Thr Ala Gly Val Phe Gly
                85                  90                  95

Ala Gly Thr Thr Leu Thr Val Leu Gly Gln Ser Ser Arg Ser Ser Gly
            100                 105                 110

Gly Gly Gly Ser Ser Gly Gly Gly Gly Ser Ala Val Thr Leu Asp Glu
        115                 120                 125

Ser Gly Gly Gly Leu Gln Thr Pro Gly Gly Ala Leu Ser Leu Val Cys
    130                 135                 140

Lys Ala Ser Gly Phe Thr Phe Ser Ser His Gly Met Phe Trp Val Arg
145                 150                 155                 160

Gln Thr Pro Gly Lys Gly Leu Glu Tyr Val Ala Glu Ile Thr Asn Asp
                165                 170                 175

Gly Ser Gly Thr Asn Tyr Gly Ser Ala Val Lys Gly Arg Ala Thr Ile
            180                 185                 190

Ser Arg Asp Asn Gly Gln Ser Thr Val Arg Leu Gln Leu Asn Asn Leu
        195                 200                 205

Arg Ala Glu Asp Thr Gly Thr Tyr Phe Cys Ala Arg Ser Thr Tyr Glu
    210                 215                 220

Cys Pro Gly Gly Phe Ser Cys Trp Gly Asp Thr Gly Gln Ile Asp Ala
225                 230                 235                 240

Trp Gly His Gly Thr Glu Val Ile Val Ser Ser
                245                 250


<210> SEQ ID NO 56
<211> LENGTH: 250
<212> TYPE: PRT
<213> ORGANISM: Artificial Sequence
<220> FEATURE:
<223> OTHER INFORMATION: scFv - 2-13D Ab

<400> SEQUENCE: 56

Ala Leu Thr Gln Pro Ser Ser Val Ser Ala Asn Pro Gly Glu Thr Ala
1               5                   10                  15

Lys Ile Thr Cys Ser Gly Gly Val Tyr Ser Tyr Gly Trp Phe Gln Gln
            20                  25                  30

Lys Pro Gly Ser Ala Leu Val Thr Val Ile Tyr Trp Asp Asp Glu Arg
        35                  40                  45

Pro Ser Asp Ile Pro Ser Arg Phe Ser Gly Ala Leu Ser Gly Ser Thr
    50                  55                  60

Asn Thr Leu Thr Ile Thr Gly Val Gln Ala Glu Asp Glu Ala Asp Tyr
65                  70                  75                  80

Tyr Cys Gly Thr Glu Asp Ile Ser Gly Thr Ala Gly Val Phe Gly Ala
                85                  90                  95

Gly Thr Thr Leu Thr Val Leu Gly Gln Ser Ser Arg Ser Ser Gly Gly
            100                 105                 110

Gly Gly Ser Ser Gly Gly Gly Gly Ser Ala Val Thr Leu Asp Glu Ser
        115                 120                 125
```

```
Gly Gly Gly Leu Gln Thr Pro Gly Gly Ala Leu Arg Leu Ser Cys Ser
    130                 135                 140

Ala Ser Gly Phe Thr Phe Ser Ser His Gly Met Phe Trp Val Arg Gln
145                 150                 155                 160

Ala Pro Gly Lys Gly Leu Glu Tyr Val Ser Glu Ile Thr Asn Asp Gly
                165                 170                 175

Ser Gly Thr Asn Tyr Gly Ser Ala Val Lys Gly Arg Ala Thr Ile Ser
            180                 185                 190

Arg Asp Asn Gly Gln Ser Thr Leu Tyr Leu Gln Met Asn Ser Leu Arg
        195                 200                 205

Ala Glu Asp Thr Gly Thr Tyr Phe Cys Ala Arg Ser Thr Tyr Glu Cys
    210                 215                 220

Pro Gly Gly Phe Ser Cys Trp Gly Asp Thr Gly Gln Ile Asp Ala Trp
225                 230                 235                 240

Gly His Gly Thr Glu Val Ile Val Ser Ser
                245                 250


<210> SEQ ID NO 57
<211> LENGTH: 250
<212> TYPE: PRT
<213> ORGANISM: Artificial Sequence
<220> FEATURE:
<223> OTHER INFORMATION: scFv - 2-13D-37 Ab

<400> SEQUENCE: 57

Ala Leu Thr Gln Pro Ser Ser Val Ser Ala Asn Pro Gly Glu Thr Ala
1               5                   10                  15

Lys Ile Thr Cys Ser Gly Gly Val Tyr Ser Tyr Gly Trp Phe Gln Gln
            20                  25                  30

Lys Pro Gly Ser Ala Leu Val Thr Val Ile Tyr Trp Asp Asp Glu Arg
        35                  40                  45

Pro Ser Asp Ile Pro Ser Arg Phe Ser Gly Ala Leu Ser Gly Ser Thr
    50                  55                  60

Asn Thr Leu Thr Ile Thr Gly Val Gln Ala Glu Asp Glu Ala Asp Tyr
65                  70                  75                  80

Tyr Cys Gly Thr Glu Asp Ile Ser Gly Thr Ala Gly Val Phe Gly Ala
                85                  90                  95

Gly Thr Thr Leu Thr Val Leu Gly Gln Ser Ser Arg Ser Ser Gly Gly
            100                 105                 110

Gly Gly Ser Ser Gly Gly Gly Gly Ser Ala Val Thr Leu Asp Glu Ser
        115                 120                 125

Gly Gly Gly Leu Gln Thr Pro Gly Gly Ala Leu Arg Leu Ser Cys Ser
    130                 135                 140

Ala Ser Gly Phe Asp Phe Ser Ser His Gly Met Phe Trp Val Arg Gln
145                 150                 155                 160

Ala Pro Gly Lys Gly Leu Glu Tyr Val Ser Glu Ile Thr Asn Asp Gly
                165                 170                 175

Ser Gly Thr Asn Tyr Gly Ser Ala Val Lys Gly Arg Ala Thr Ile Ser
            180                 185                 190

Arg Asp Asn Gly Gln Ser Thr Leu Tyr Leu Gln Met Asn Ser Leu Arg
        195                 200                 205

Ala Glu Asp Thr Gly Thr Tyr Phe Cys Ala Arg Ser Thr Tyr Glu Cys
    210                 215                 220

Pro Gly Gly Phe Ser Cys Trp Gly Asp Thr Gly Gln Ile Asp Ala Trp
225                 230                 235                 240
```

Gly His Gly Thr Glu Val Ile Val Ser Ser
245 250

<210> SEQ ID NO 58
<211> LENGTH: 393
<212> TYPE: DNA
<213> ORGANISM: Artificial Sequence
<220> FEATURE:
<223> OTHER INFORMATION: VH -3-2 Ab

<400> SEQUENCE: 58
gccgtgacgt tggacgagtc cgggggcggc ctccagacgc ccggaggagc gctcagcctc 60
gtctgcaagg cctccgggtt caccttcagc agcttcaaca tgttctgggt gcgacaggcg 120
cccggcaagg ggctggaata cgtcgctcaa attagcagca gtggtagtag cacaaactac 180
gcacccgcgg tgaggggccg tgccaccatc tcgagggaca acgggcagag cacagtgagg 240
ctgcagctga acaaccccgg ggctgaagac accggcacct actactgcgc caaaagtagt 300
tatgactgtc cttacggtca ttgtagtagt ggtgttgata gtgctggtga gatcgacgca 360
tggggccacg ggaccgaagt catcgtctcc tcc 393

<210> SEQ ID NO 59
<211> LENGTH: 393
<212> TYPE: DNA
<213> ORGANISM: Artificial Sequence
<220> FEATURE:
<223> OTHER INFORMATION: VH - 1-7A-IT Ab

<400> SEQUENCE: 59
gccgtgacgt tggatgaatc cgggggcggc ctccagacgc ccggaggagc gctccgcctc 60
agctgcaagg cctctgggtt caccttcagc agcttcaaca tgttctgggt gcgacaggcg 120
cccggcaagg ggctggaata cgtctcgcag attagcagca gtggtagtag cacaaactac 180
gcacccgcgg tgaaaggccg tgccaccatc tcgagggaca acgggcagag cacactgtat 240
ctgcagatga acagcctgcg cgctgaagac accggcacct actactgcgc caaaagtagt 300
tatgactgtc cttacggtca ttgtagtagt ggtgttgata gtgctggtga gatcgacgca 360
tggggccacg ggaccgaagt catcgtctcc tcc 393

<210> SEQ ID NO 60
<211> LENGTH: 393
<212> TYPE: DNA
<213> ORGANISM: Artificial Sequence
<220> FEATURE:
<223> OTHER INFORMATION: VH - Low-PI Ab

<400> SEQUENCE: 60
gccgtgacgt tggatgaatc cgggggcggc ctccagacgc ccggaggagc gctccgcctc 60
agctgcaagg cctctgggtt caccttcagc agcttcaaca tgttctgggt gcgacaggcg 120
cccggcaagg ggctggaata cgtctcgcag attagcagca gtggtagtag cacaaactac 180
gcacccgcgg tgaaaggccg tgccaccatc tcgagggaca acgggcagag cacactgtat 240
ctgcagatga acagcctgcg cgctgaagac accggcacct actactgcgc caaaagtagt 300
tatgactgtc cttacggtca ttgtagtagt ggtgttgata gtgctggtga gatcgacgca 360
tggggccacg ggaccgaagt catcgtctcc tcc 393

<210> SEQ ID NO 61
<211> LENGTH: 393
<212> TYPE: DNA

<213> ORGANISM: Artificial Sequence
<220> FEATURE:
<223> OTHER INFORMATION: VH - 1-30 Ab

<400> SEQUENCE: 61
gccgtgacgt tggatgaatc cgggggcggc ctccagacgc ccggaggagc gctccgcctc 60
agctgcaagg cctctggctt tgattttgaa agcttcaaca tgttctgggt gcgacaggcg 120
cccggcaagg ggctggaata cgtctcgcag attagcagca gtgaagaaga tgaaaactac 180
gcacccgcgg tgaaaggccg tgccaccatc tcgagggaca acgggcagag cacactgtat 240
ctgcagatga acagcctgcg cgctgaagac accggcacct actactgcgc caaaagtagt 300
tatgactgtc cttacggtca ttgtagtagt ggtgttgata gtgctggtga gatcgacgca 360
tggggccacg ggaccgaagt catcgtctcc tcc 393

<210> SEQ ID NO 62
<211> LENGTH: 393
<212> TYPE: DNA
<213> ORGANISM: Artificial Sequence
<220> FEATURE:
<223> OTHER INFORMATION: VH - 1-17 Ab

<400> SEQUENCE: 62
gccgtgacgt tggatgaatc cgggggcggc ctccagacgc ccggaggagc gctccgcctc 60
agctgcaagg cctctggctt tgattttgaa agcttcaaca tgttctgggt gcgacaggcg 120
cccggcaagg ggctggaata cgtctcgcag attagcagca gtgaagaaga tgaaaactac 180
gcacccgcgg tgaaaggccg tgccaccatc tcgagggaca acgggcagag cacactgtat 240
ctgcagatga acagcctgcg cgctgaagac accggcacct actactgcgc caaaagtagt 300
tatgactgtc cttacggtca ttgtagtagt ggtgttgata gtgctggtga gatcgacgca 360
tggggccacg ggaccgaagt catcgtctcc tcc 393

<210> SEQ ID NO 63
<211> LENGTH: 393
<212> TYPE: DNA
<213> ORGANISM: Artificial Sequence
<220> FEATURE:
<223> OTHER INFORMATION: VH - 1-32 Ab

<400> SEQUENCE: 63
gccgtgacgt tggatgaatc cgggggcggc ctccagacgc ccggaggagc gctccgcctc 60
agctgcaagg cctctggctt tgattttgaa agcttcaaca tgttctgggt gcgacaggcg 120
cccggcaagg ggctggaata cgtctcgcag attagcagca gtgaagaaga tgaaaactac 180
gcacccgcgg tgaaaggccg tgccaccatc tcgagggaca acgggcagag cacactgtat 240
ctgcagatga acagcctgcg cgctgaagac accggcacct actactgcgc caaaagtagt 300
tatgactgtc cttacggtca ttgtagtagt ggtgttgata gtgctggtga gatcgacgca 360
tggggccacg ggaccgaagt catcgtctcc tcc 393

<210> SEQ ID NO 64
<211> LENGTH: 393
<212> TYPE: DNA
<213> ORGANISM: Artificial Sequence
<220> FEATURE:
<223> OTHER INFORMATION: VH - 4-11 Ab

<400> SEQUENCE: 64
gccgtgacgt tggatgaatc cgggggcggc ctccagacgc ccggaggagc gctccgcctc 60
agctgcaagg cctctggctt tgattttgaa agcttcaaca tgttctgggt gcgacaggcg 120
cccggcaagg ggctggaata cgtctcgcag attagcagca gtgaagaaga tgaaaactac 180
gcacccgcgg tgaaaggccg tgccaccatc tcgagggaca acgggcagag cacactgtat 240
ctgcagatga acagcctgcg cgctgaagac accggcacct actactgcgc caaaagtagt 300
tatgactgtc cttacggtca ttgtagtagt ggtgttgata gtgctggtga gatcgacgca 360
tggggccacg ggaccgaagt catcgtctcc tcc 393

<210> SEQ ID NO 65
<211> LENGTH: 393
<212> TYPE: DNA
<213> ORGANISM: Artificial Sequence
<220> FEATURE:
<223> OTHER INFORMATION: VH - 6-10 Ab

<400> SEQUENCE: 65
gccgtgacgt tggatgaatc cgggggcggc ctccagacgc ccggaggagc gctccgcctc 60
agctgcaagg cctctggctt tgattttgaa agcttcaaca tgttctgggt gcgacaggcg 120
cccggcaagg ggctggaata cgtctcgcag attagcagca gtgaagaaga tgaaaactac 180
gcacccgcgg tgaaaggccg tgccaccatc tcgagggaca acgggcagag cacactgtat 240
ctgcagatga acagcctgcg cgctgaagac accggcacct actactgcgc caaaagtagt 300
tatgactgtc cttacggtca ttgtagtagt ggtgttgata gtgctggtga gatcgacgca 360
tggggccacg ggaccgaagt catcgtctcc tcc 393

<210> SEQ ID NO 66
<211> LENGTH: 387
<212> TYPE: DNA
<213> ORGANISM: Artificial Sequence
<220> FEATURE:
<223> OTHER INFORMATION: VH - 2-13 Ab

<400> SEQUENCE: 66
gccgtgacgt tggacgagtc cgggggcggc ctccagacgc ccggaggagc gctcagcctc 60
gtctgcaagg cctccgggtt caccttcagc agccatggca tgttctgggt gcgacagacg 120
cccggcaagg ggttggaata tgtcgctgaa attaccaatg atggtagtgg cacaaactac 180
gggtcggcgg tgaagggccg tgccaccatc tcgagggaca acgggcagag cacagtgagg 240
ctgcagctga acaacctcag ggctgaggac accggcacct acttctgcgc cagatctact 300
tatgaatgtc ctggtggttt tagttgttgg ggtgatactg gtcaaataga cgcatggggc 360
cacgggaccg aagtcatcgt ctcctcc 387

<210> SEQ ID NO 67
<211> LENGTH: 387
<212> TYPE: DNA
<213> ORGANISM: Artificial Sequence
<220> FEATURE:
<223> OTHER INFORMATION: VH - 2-13D Ab

<400> SEQUENCE: 67
gccgtgacgt tggacgagtc cgggggcggc ctccagacgc ccggaggagc gctccgcctt 60
agctgcagcg cctccgggtt caccttcagc agccatggca tgttctgggt gcgacaggcg 120
cccggcaagg ggttggaata tgtctcggag attaccaatg atggtagtgg cacaaactac 180
gggtcggcgg tgaagggccg tgccaccatc tcgagggaca acgggcagag cacactgtat 240

```
ctgcagatga acagcctcag ggctgaggac accggcacct acttctgcgc cagatctact    300

tatgaatgtc ctggtggttt tagttgttgg ggtgatactg gtcaaataga cgcatggggc    360

cacgggaccg aagtcatcgt ctcctcc                                        387
```

<210> SEQ ID NO 68
<211> LENGTH: 387
<212> TYPE: DNA
<213> ORGANISM: Artificial Sequence
<220> FEATURE:
<223> OTHER INFORMATION: VH - 2-13D-37 Ab

<400> SEQUENCE: 68

```
gccgtgacgt tggacgagtc cgggggcggc ctccagacgc ccggaggagc gctccgcctt     60

agctgcagcg cctccgggtt cgatttcagc agccatggca tgttctgggt gcgacaggcg    120

cccggcaagg ggttggaata tgtctcggag attaccaatg atggtagtgg cacaaactac    180

gggtcggcgg tgaagggccg tgccaccatc tcgagggaca acgggcagag cacactgtat    240

ctgcagatga acagcctcag ggctgaggac accggcacct acttctgcgc cagatctact    300

tatgaatgtc ctggtggttt tagttgttgg ggtgatactg gtcaaataga cgcatggggc    360

cacgggaccg aagtcatcgt ctcctcc                                        387
```

<210> SEQ ID NO 69
<211> LENGTH: 324
<212> TYPE: DNA
<213> ORGANISM: Artificial Sequence
<220> FEATURE:
<223> OTHER INFORMATION: VL - 3-2 Ab

<400> SEQUENCE: 69

```
gccctgactc agccgtcctc ggtgtcagca aacccaggag aaaccgtcaa gatcacctgc     60

tccgggggtg gcagctatgc tggaagttac tattatggct ggtaccagca gaaggcacct    120

ggcagtgccc ctgtcactct gatctatgaa agcaacaaga gaccctcgga catcccttca    180

cgattctccg gttccacatc tggctccaca gccacactaa ccatcactgg ggtccaagcc    240

gatgacgagg ctatctatta ctgtgggagc tgggacagta gcaatggtgg tatatttggg    300

gccgggacaa ccctgaccgt ccta                                           324
```

<210> SEQ ID NO 70
<211> LENGTH: 321
<212> TYPE: DNA
<213> ORGANISM: Artificial Sequence
<220> FEATURE:
<223> OTHER INFORMATION: VL - 1-7A-IT Ab

<400> SEQUENCE: 70

```
gccctgactc agccgtcctc ggtgtcagca aacccaggag aaaccgtcaa gatcacctgc     60

tccgggggtg gcagctatgc tggaagttac tattatggct ggtatcagca gaagcctggc    120

agtgcccctg tcactctgat ctatgaaaac aacaagagac cctcggacat cccttcacga    180

ttctccggtt ccacatctgg ctccacagcc acactaacca tcactggggt ccaagccggc    240

gacgaggctg attattactg tgggagctgg gacagtagca atggtggtat atttggggcc    300

gggacaaccc tgaccgtcct a                                              321
```

<210> SEQ ID NO 71
<211> LENGTH: 321
<212> TYPE: DNA
<213> ORGANISM: Artificial Sequence
<220> FEATURE:
<223> OTHER INFORMATION: VL - Low-PI Ab

<400> SEQUENCE: 71
gccctgactc agccgtcctc ggtgtcagca aacccaggag aaaccgtcaa gatcacctgc 60
tccgggggtg gcagctatgc tggaagttac tattatggct ggtatcagca gaagcctggc 120
agtgcccctg tcactctgat ctatgaaaac aacaagagac cctcggacat cccttcacga 180
ttctccggtt ccacatctgg ctccacagcc acactaacca tcactggggt ccaagccggc 240
gacgaggctg attattactg tgggagctgg gacagtagca atggtggtat atttggggcc 300
gggacaaccc tgaccgtcct a 321

<210> SEQ ID NO 72
<211> LENGTH: 321
<212> TYPE: DNA
<213> ORGANISM: Artificial Sequence
<220> FEATURE:
<223> OTHER INFORMATION: VL - 1-30 Ab

<400> SEQUENCE: 72
gccctgactc agccgtcctc ggtgtcagca aacccaggag aaaccgtcaa gatcacctgc 60
tccgggggtg gcagcgaaga agaacagtac tattatggct ggtatcagca gaagcctggc 120
agtgcccctg tcactctgat ctatcaggat gaagaaagac cctcggacat cccttcacga 180
ttctccggtt ccacatctgg ctccacagcc acactaacca tcactggggt ccaagccggc 240
gacgaggctg attattactg tgggagctgg gacagtgaag atgaagatca ttttggggcc 300
gggacaaccc tgaccgtcct a 321

<210> SEQ ID NO 73
<211> LENGTH: 321
<212> TYPE: DNA
<213> ORGANISM: Artificial Sequence
<220> FEATURE:
<223> OTHER INFORMATION: VL 1-17 Ab

<400> SEQUENCE: 73
gccctgactc agccgtcctc ggtgtcagca aacccaggag aaaccgtcaa gatcacctgc 60
tccgggggtg gcagctatgc tggaagttac tattatggct ggtatcagca gaagcctggc 120
agtgcccctg tcactctgat ctatgaagat gaacagagac cctcggacat cccttcacga 180
ttctccggtt ccacatctgg ctccacagcc acactaacca tcactggggt ccaagccggc 240
gacgaggctg attattactg tgggagctgg gacagtgaag atgaagatca ttttggggcc 300
gggacaaccc tgaccgtcct a 321

<210> SEQ ID NO 74
<211> LENGTH: 321
<212> TYPE: DNA
<213> ORGANISM: Artificial Sequence
<220> FEATURE:
<223> OTHER INFORMATION: VL 1-32 Ab

<400> SEQUENCE: 74
gccctgactc agccgtcctc ggtgtcagca aacccaggag aaaccgtcaa gatcacctgc 60
tccgggggtg gcagctatgc tggaagttac tattatggct ggtatcagca gaagcctggc 120
agtgcccctg tcactctgat ctatcaggat gaagaaagac cctcggacat cccttcacga 180
ttctccggtt ccacatctgg ctccacagcc acactaacca tcactggggt ccaagccggc 240
gacgaggctg attattactg tgggagctgg gacagtgaag atgaagatca ttttggggcc 300
gggacaaccc tgaccgtcct a 321

<210> SEQ ID NO 75
<211> LENGTH: 321
<212> TYPE: DNA
<213> ORGANISM: Artificial Sequence
<220> FEATURE:
<223> OTHER INFORMATION: VL 4-11 Ab

<400> SEQUENCE: 75
gccctgactc agccgtcctc ggtgtcagca aacccaggag aaaccgtcaa gatcacctgc 60
tccgggggtg gcagctatgc tggaagttac tattatggct ggtatcagca gaagcctggc 120
agtgcccctg tcactctgat ctatgaagac cacgagagac cctcggacat cccttcacga 180
ttctccggtt ccacatctgg ctccacagcc acactaacca tcactggggt ccaagccggc 240
gacgaggctg attattactg tgggagctgg gacagtagcg atgaagatca ttttggggcc 300
gggacaaccc tgaccgtcct a 321

<210> SEQ ID NO 76
<211> LENGTH: 321
<212> TYPE: DNA
<213> ORGANISM: Artificial Sequence
<220> FEATURE:
<223> OTHER INFORMATION: VL 6-10 Ab

<400> SEQUENCE: 76
gccctgactc agccgtcctc ggtgtcagca aacccaggag aaaccgtcaa gatcacctgc 60
tccgggggtg gcagctatgc tggaagttac tattatggct ggtatcagca gaagcctggc 120
agtgcccctg tcactctgat ctatcaggat ctgctgagac cctcggacat cccttcacga 180
ttctccggtt ccacatctgg ctccacagcc acactaacca tcactggggt ccaagccggc 240
gacgaggctg attattactg tgggagctgg gacagtctga gcagcagcca ttttggggcc 300
gggacaaccc tgaccgtcct a 321

<210> SEQ ID NO 77
<211> LENGTH: 312
<212> TYPE: DNA
<213> ORGANISM: Artificial Sequence
<220> FEATURE:
<223> OTHER INFORMATION: VL 2-13 Ab

<400> SEQUENCE: 77
gccctgactc agccgtcctc ggtgtcagca aacccaggag aaaccgtcaa gataacctgc 60
tccgggggta gctatagcta tggctggttc cagcagaagt ctcctggcag tgcccttgtc 120
actgtgatct actgggatga tgagagaccc tcggacatcc cttcacgatt ctccggtgcc 180
ctatccggct ccacaaacac attaaccatc actggggtcc aagccgacga cgaggctgtc 240
tatttctgtg ggactgaaga catcagcggc actgctggtg tatttggggc cgggacaacc 300
ctgaccgtcc tg 312

<210> SEQ ID NO 78
<211> LENGTH: 309
<212> TYPE: DNA
<213> ORGANISM: Artificial Sequence
<220> FEATURE:
<223> OTHER INFORMATION: VL 2-13D Ab

<400> SEQUENCE: 78

```
gccctgactc agccgtcctc ggtgtcagca aacccaggag aaaccgcgaa gataacctgc     60

tccgggggtg tgtatagcta tggctggttc cagcagaagc ctggcagtgc ccttgtcact    120

gtgatctact gggatgatga gagaccctcg gacatccctt cacgattctc cggtgcccta    180

tccggctcca caaacacatt aaccatcact ggggtccaag ccgaagacga ggctgattat    240

tattgtggga ctgaagacat cagcggcact gctggtgtat ttggggccgg gacaaccctg    300

accgtcctg                                                            309


<210> SEQ ID NO 79
<211> LENGTH: 309
<212> TYPE: DNA
<213> ORGANISM: Artificial Sequence
<220> FEATURE:
<223> OTHER INFORMATION: VL 2-13D-37 Ab

<400> SEQUENCE: 79

gccctgactc agccgtcctc ggtgtcagca aacccaggag aaaccgcgaa gataacctgc     60

tccgggggtg tgtatagcta tggctggttc cagcagaagc ctggcagtgc ccttgtcact    120

gtgatctact gggatgatga gagaccctcg gacatccctt cacgattctc cggtgcccta    180

tccggctcca caaacacatt aaccatcact ggggtccaag ccgaagacga ggctgattat    240

tattgtggga ctgaagacat cagcggcact gctggtgtat ttggggccgg gacaaccctg    300

accgtcctg                                                            309


<210> SEQ ID NO 80
<211> LENGTH: 8
<212> TYPE: PRT
<213> ORGANISM: Artificial Sequence
<220> FEATURE:
<223> OTHER INFORMATION: Light Chain CDR1 - 2-13D; 2-13D-37 Abs

<400> SEQUENCE: 80

Ser Gly Gly Val Tyr Ser Tyr Gly
1               5


<210> SEQ ID NO 81
<211> LENGTH: 5
<212> TYPE: PRT
<213> ORGANISM: Artificial Sequence
<220> FEATURE:
<223> OTHER INFORMATION: EP1 Epitope

<400> SEQUENCE: 81

Ile Val Thr Leu Asp
1               5


<210> SEQ ID NO 82
<211> LENGTH: 5
<212> TYPE: PRT
<213> ORGANISM: Artificial Sequence
<220> FEATURE:
<223> OTHER INFORMATION: EP2 Epitope

<400> SEQUENCE: 82

Asp Ser Ser Gln Pro
1               5


<210> SEQ ID NO 83
<211> LENGTH: 5
<212> TYPE: PRT
<213> ORGANISM: Artificial Sequence
```

<220> FEATURE:
<223> OTHER INFORMATION: EP3 Epitope

<400> SEQUENCE: 83

Arg Thr Ile Ala Arg
1               5

<210> SEQ ID NO 84
<211> LENGTH: 7
<212> TYPE: PRT
<213> ORGANISM: Artificial Sequence
<220> FEATURE:
<223> OTHER INFORMATION: EP4 Epitope

<400> SEQUENCE: 84

Ala Arg Cys Ala Cys Arg Lys
1               5

<210> SEQ ID NO 85
<211> LENGTH: 4
<212> TYPE: PRT
<213> ORGANISM: Artificial Sequence
<220> FEATURE:
<223> OTHER INFORMATION: EP5 Epitope

<400> SEQUENCE: 85

Ala Arg Pro Ala
1

<210> SEQ ID NO 86
<211> LENGTH: 9
<212> TYPE: PRT
<213> ORGANISM: Artificial Sequence
<220> FEATURE:
<223> OTHER INFORMATION: EP6 Epitope

<400> SEQUENCE: 86

Lys Thr Lys Gln Trp Cys Asp Met Leu
1               5

<210> SEQ ID NO 87
<211> LENGTH: 8
<212> TYPE: PRT
<213> ORGANISM: Artificial Sequence
<220> FEATURE:
<223> OTHER INFORMATION: EP7 Epitope

<400> SEQUENCE: 87

Gly Cys Asp Leu Leu Ile Asn Arg
1               5

<210> SEQ ID NO 88
<211> LENGTH: 8
<212> TYPE: PRT
<213> ORGANISM: Artificial Sequence
<220> FEATURE:
<223> OTHER INFORMATION: EP8 Epitope

<400> SEQUENCE: 88

Thr Cys Thr Gln Pro Gly Gly Arg
1               5

<210> SEQ ID NO 89
<211> LENGTH: 14
<212> TYPE: PRT
<213> ORGANISM: Artificial Sequence
<220> FEATURE:

<223> OTHER INFORMATION: Epitope F1

<400> SEQUENCE: 89

```
Gln Leu Ala Ala Gly Thr Cys Glu Ile Val Thr Leu Asp Arg
1               5                   10
```

<210> SEQ ID NO 90
<211> LENGTH: 20
<212> TYPE: PRT
<213> ORGANISM: Artificial Sequence
<220> FEATURE:
<223> OTHER INFORMATION: Epitope F2

<400> SEQUENCE: 90

```
Thr Leu Asp Arg Asp Ser Ser Gln Pro Arg Arg Thr Ile Ala Arg Gln
1               5                   10                  15

Thr Ala Arg Cys
            20
```

<210> SEQ ID NO 91
<211> LENGTH: 20
<212> TYPE: PRT
<213> ORGANISM: Artificial Sequence
<220> FEATURE:
<223> OTHER INFORMATION: Epitope F3

<400> SEQUENCE: 91

```
Thr Ala Arg Cys Ala Cys Arg Lys Gly Gln Ile Ala Gly Thr Thr Arg
1               5                   10                  15

Ala Arg Pro Ala
            20
```

<210> SEQ ID NO 92
<211> LENGTH: 20
<212> TYPE: PRT
<213> ORGANISM: Artificial Sequence
<220> FEATURE:
<223> OTHER INFORMATION: Epitope F4

<400> SEQUENCE: 92

```
Ala Arg Pro Ala Cys Val Asp Ala Arg Ile Ile Lys Thr Lys Gln Trp
1               5                   10                  15

Cys Asp Met Leu
            20
```

<210> SEQ ID NO 93
<211> LENGTH: 20
<212> TYPE: PRT
<213> ORGANISM: Artificial Sequence
<220> FEATURE:
<223> OTHER INFORMATION: Epitope F5

<400> SEQUENCE: 93

```
Cys Asp Met Leu Pro Cys Leu Glu Gly Glu Gly Cys Asp Leu Leu Ile
1               5                   10                  15

Asn Arg Ser Gly
            20
```

<210> SEQ ID NO 94
<211> LENGTH: 20
<212> TYPE: PRT
<213> ORGANISM: Artificial Sequence
<220> FEATURE:
<223> OTHER INFORMATION: Epitope F6

<400> SEQUENCE: 94

Asn Arg Ser Gly Trp Thr Cys Thr Gln Pro Gly Gly Arg Ile Lys Thr
1 5 10 15

Thr Thr Val Ser
20

<210> SEQ ID NO 95
<211> LENGTH: 12
<212> TYPE: PRT
<213> ORGANISM: Artificial Sequence
<220> FEATURE:
<223> OTHER INFORMATION: Linker

<400> SEQUENCE: 95

Ser Gly Gly Gly Gly Ser Ser Gly Gly Gly Gly Ser
1 5 10

<210> SEQ ID NO 96
<211> LENGTH: 13
<212> TYPE: PRT
<213> ORGANISM: Artificial Sequence
<220> FEATURE:
<223> OTHER INFORMATION: 2-13 binding epitope 1

<400> SEQUENCE: 96

Cys Arg Lys Gly Gln Ile Ala Gly Thr Thr Arg Ala Arg
1 5 10

<210> SEQ ID NO 97
<211> LENGTH: 14
<212> TYPE: PRT
<213> ORGANISM: Artificial Sequence
<220> FEATURE:
<223> OTHER INFORMATION: 2-13 binding epitope 2

<400> SEQUENCE: 97

Pro Ala Cys Val Asp Ala Arg Ile Ile Lys Thr Lys Gln Trp
1 5 10

<210> SEQ ID NO 98
<211> LENGTH: 8
<212> TYPE: PRT
<213> ORGANISM: Artificial Sequence
<220> FEATURE:
<223> OTHER INFORMATION: binding epitope
<220> FEATURE:
<221> NAME/KEY: BINDING
<222> LOCATION: (1)..(2)
<223> OTHER INFORMATION: Antibody specifically binds to respective residue
<220> FEATURE:
<221> NAME/KEY: BINDING
<222> LOCATION: (6)..(8)
<223> OTHER INFORMATION: Antibody specifically binds to respective residue

<400> SEQUENCE: 98

Arg Asp Ser Ser Gln Pro Arg Arg
1 5

<210> SEQ ID NO 99
<211> LENGTH: 8
<212> TYPE: PRT
<213> ORGANISM: Artificial Sequence
<220> FEATURE:
<223> OTHER INFORMATION: binding epitope
<220> FEATURE:
<221> NAME/KEY: BINDING

```
<222> LOCATION: (1)..(1)
<223> OTHER INFORMATION: Antibody Specifically binds to respective
      residue
<220> FEATURE:
<221> NAME/KEY: BINDING
<222> LOCATION: (6)..(8)
<223> OTHER INFORMATION: Antibody Specifically binds to respective
      residue

<400> SEQUENCE: 99

Arg Asp Ser Ser Gln Pro Arg Arg
1               5


<210> SEQ ID NO 100
<211> LENGTH: 8
<212> TYPE: PRT
<213> ORGANISM: Artificial Sequence
<220> FEATURE:
<223> OTHER INFORMATION: binding epitope
<220> FEATURE:
<221> NAME/KEY: BINDING
<222> LOCATION: (1)..(1)
<223> OTHER INFORMATION: Antibody Specifically binds to respective
      residue
<220> FEATURE:
<221> NAME/KEY: BINDING
<222> LOCATION: (7)..(8)
<223> OTHER INFORMATION: Antibody Specifically binds to respective
      residue

<400> SEQUENCE: 100

Arg Asp Ser Ser Gln Pro Arg Arg
1               5


<210> SEQ ID NO 101
<211> LENGTH: 100
<212> TYPE: PRT
<213> ORGANISM: Artificial Sequence
<220> FEATURE:
<223> OTHER INFORMATION: Mature Human FAM19A5 Isoform 2

<400> SEQUENCE: 101

Gln Phe Leu Lys Glu Gly Gln Leu Ala Ala Gly Thr Cys Glu Ile Val
1               5                   10                  15

Thr Leu Asp Arg Asp Ser Ser Gln Pro Arg Arg Thr Ile Ala Arg Gln
            20                  25                  30

Thr Ala Arg Cys Ala Cys Arg Lys Gly Gln Ile Ala Gly Thr Thr Arg
        35                  40                  45

Ala Arg Pro Ala Cys Val Asp Ala Arg Ile Ile Lys Thr Lys Gln Trp
    50                  55                  60

Cys Asp Met Leu Pro Cys Leu Glu Gly Glu Gly Cys Asp Leu Leu Ile
65                  70                  75                  80

Asn Arg Ser Gly Trp Thr Cys Thr Gln Pro Gly Gly Arg Ile Lys Thr
                85                  90                  95

Thr Thr Val Ser
            100


<210> SEQ ID NO 102
<211> LENGTH: 7
<212> TYPE: PRT
<213> ORGANISM: Artificial Sequence
<220> FEATURE:
<223> OTHER INFORMATION: Peptide Sequence #1 (residues 2-8 of SEQ ID NO:
      101)

<400> SEQUENCE: 102
```

```
Phe Leu Lys Glu Gly Gln Leu
1               5


<210> SEQ ID NO 103
<211> LENGTH: 13
<212> TYPE: PRT
<213> ORGANISM: Artificial Sequence
<220> FEATURE:
<223> OTHER INFORMATION: Peptide Sequence #2 (residues 2-14 of SEQ ID
      NO: 101)

<400> SEQUENCE: 103

Phe Leu Lys Glu Gly Gln Leu Ala Ala Gly Thr Cys Glu
1               5                   10


<210> SEQ ID NO 104
<211> LENGTH: 9
<212> TYPE: PRT
<213> ORGANISM: Artificial Sequence
<220> FEATURE:
<223> OTHER INFORMATION: Peptide Sequence #3 (residues 3-11 of SEQ ID
      NO: 101)

<400> SEQUENCE: 104

Leu Lys Glu Gly Gln Leu Ala Ala Gly
1               5


<210> SEQ ID NO 105
<211> LENGTH: 13
<212> TYPE: PRT
<213> ORGANISM: Artificial Sequence
<220> FEATURE:
<223> OTHER INFORMATION: Peptide Sequence #4 (residues 3-15 of SEQ ID
      NO: 101)

<400> SEQUENCE: 105

Leu Lys Glu Gly Gln Leu Ala Ala Gly Thr Cys Glu Ile
1               5                   10


<210> SEQ ID NO 106
<211> LENGTH: 16
<212> TYPE: PRT
<213> ORGANISM: Artificial Sequence
<220> FEATURE:
<223> OTHER INFORMATION: Peptide Sequence #5 (residues 3-18 of SEQ ID
      NO: 101)

<400> SEQUENCE: 106

Leu Lys Glu Gly Gln Leu Ala Ala Gly Thr Cys Glu Ile Val Thr Leu
1               5                   10                  15


<210> SEQ ID NO 107
<211> LENGTH: 7
<212> TYPE: PRT
<213> ORGANISM: Artificial Sequence
<220> FEATURE:
<223> OTHER INFORMATION: Peptide Sequence #6 (residues 9-15 of SEQ ID
      NO: 101)

<400> SEQUENCE: 107

Ala Ala Gly Thr Cys Glu Ile
1               5


<210> SEQ ID NO 108
<211> LENGTH: 19
<212> TYPE: PRT
<213> ORGANISM: Artificial Sequence
<220> FEATURE:
```

<223> OTHER INFORMATION: Peptide Sequence #7 (residues 20-38 of SEQ ID NO: 101)

<400> SEQUENCE: 108

Arg Asp Ser Ser Gln Pro Pro Arg Thr Ile Ala Arg Gln Thr Ala Arg
1 5 10 15

Cys Ala Cys

<210> SEQ ID NO 109
<211> LENGTH: 11
<212> TYPE: PRT
<213> ORGANISM: Artificial Sequence
<220> FEATURE:
<223> OTHER INFORMATION: Peptide Sequence #8 (residues 24-34 of SEQ ID NO: 101)

<400> SEQUENCE: 109

Gln Pro Pro Arg Thr Ile Ala Arg Gln Thr Ala
1 5 10

<210> SEQ ID NO 110
<211> LENGTH: 17
<212> TYPE: PRT
<213> ORGANISM: Artificial Sequence
<220> FEATURE:
<223> OTHER INFORMATION: Peptide Sequence #9 (residues 37-53 of SEQ ID NO: 101)

<400> SEQUENCE: 110

Ala Cys Arg Lys Gly Gln Ile Ala Gly Thr Thr Arg Ala Arg Pro Ala
1 5 10 15

Cys

<210> SEQ ID NO 111
<211> LENGTH: 19
<212> TYPE: PRT
<213> ORGANISM: Artificial Sequence
<220> FEATURE:
<223> OTHER INFORMATION: Peptide Sequence #10 (residues 37-55 of SEQ ID NO: 101)

<400> SEQUENCE: 111

Ala Cys Arg Lys Gly Gln Ile Ala Gly Thr Thr Arg Ala Arg Pro Ala
1 5 10 15

Cys Val Asp

<210> SEQ ID NO 112
<211> LENGTH: 20
<212> TYPE: PRT
<213> ORGANISM: Artificial Sequence
<220> FEATURE:
<223> OTHER INFORMATION: Peptide Sequence #12 (residues 56-65 of SEQ ID NO: 101)

<400> SEQUENCE: 112

Ala Cys Arg Lys Gly Gln Ile Ala Gly Thr Thr Arg Ala Arg Pro Ala
1 5 10 15

Cys Val Asp Ala
20

<210> SEQ ID NO 113
<211> LENGTH: 10
<212> TYPE: PRT
<213> ORGANISM: Artificial Sequence
<220> FEATURE:

<223> OTHER INFORMATION: Peptide Sequence #12 (residues 56-65 of SEQ ID NO: 101)

<400> SEQUENCE: 113

Ala Arg Ile Ile Lys Thr Lys Gln Trp Cys
1 5 10

<210> SEQ ID NO 114
<211> LENGTH: 12
<212> TYPE: PRT
<213> ORGANISM: Artificial Sequence
<220> FEATURE:
<223> OTHER INFORMATION: Peptide Sequence #13 (residues 56-67 of SEQ ID NO: 101)

<400> SEQUENCE: 114

Ala Arg Ile Ile Lys Thr Lys Gln Trp Cys Asp Met
1 5 10

<210> SEQ ID NO 115
<211> LENGTH: 13
<212> TYPE: PRT
<213> ORGANISM: Artificial Sequence
<220> FEATURE:
<223> OTHER INFORMATION: Peptide Sequence #14 (residues 56-68 of SEQ ID NO: 101)

<400> SEQUENCE: 115

Ala Arg Ile Ile Lys Thr Lys Gln Trp Cys Asp Met Leu
1 5 10

<210> SEQ ID NO 116
<211> LENGTH: 16
<212> TYPE: PRT
<213> ORGANISM: Artificial Sequence
<220> FEATURE:
<223> OTHER INFORMATION: Peptide Sequence #15 (residues 56-71 of SEQ ID NO: 101)

<400> SEQUENCE: 116

Ala Arg Ile Ile Lys Thr Lys Gln Trp Cys Asp Met Leu Pro Cys Leu
1 5 10 15

<210> SEQ ID NO 117
<211> LENGTH: 11
<212> TYPE: PRT
<213> ORGANISM: Artificial Sequence
<220> FEATURE:
<223> OTHER INFORMATION: Peptide Sequence #16 (residues 57-67 of SEQ ID NO: 101)

<400> SEQUENCE: 117

Arg Ile Ile Lys Thr Lys Gln Trp Cys Asp Met
1 5 10

<210> SEQ ID NO 118
<211> LENGTH: 12
<212> TYPE: PRT
<213> ORGANISM: Artificial Sequence
<220> FEATURE:
<223> OTHER INFORMATION: Peptide Sequence #17 (residues 57-68 of SEQ ID NO: 101)

<400> SEQUENCE: 118

Arg Ile Ile Lys Thr Lys Gln Trp Cys Asp Met Leu
1 5 10

<210> SEQ ID NO 119
<211> LENGTH: 8
<212> TYPE: PRT
<213> ORGANISM: Artificial Sequence
<220> FEATURE:
<223> OTHER INFORMATION: Peptide Sequence #18 (residues 64-71 of SEQ ID NO: 101)

<400> SEQUENCE: 119

Trp Cys Asp Met Leu Pro Cys Leu
1 5

<210> SEQ ID NO 120
<211> LENGTH: 8
<212> TYPE: PRT
<213> ORGANISM: Artificial Sequence
<220> FEATURE:
<223> OTHER INFORMATION: Peptide Sequence #19 (residues 68-75 of SEQ ID NO: 101)

<400> SEQUENCE: 120

Leu Pro Cys Leu Glu Gly Glu Gly
1 5

<210> SEQ ID NO 121
<211> LENGTH: 7
<212> TYPE: PRT
<213> ORGANISM: Artificial Sequence
<220> FEATURE:
<223> OTHER INFORMATION: Peptide Sequence #20 (residues 69-75 of SEQ ID NO: 101)

<400> SEQUENCE: 121

Pro Cys Leu Glu Gly Glu Gly
1 5

<210> SEQ ID NO 122
<211> LENGTH: 9
<212> TYPE: PRT
<213> ORGANISM: Artificial Sequence
<220> FEATURE:
<223> OTHER INFORMATION: Peptide Sequence #21 (residues 69-77 of SEQ ID NO: 101)

<400> SEQUENCE: 122

Pro Cys Leu Glu Gly Glu Gly Cys Asp
1 5

<210> SEQ ID NO 123
<211> LENGTH: 10
<212> TYPE: PRT
<213> ORGANISM: Artificial Sequence
<220> FEATURE:
<223> OTHER INFORMATION: Peptide Sequence #22 (residues 69-78 of SEQ ID NO: 101)

<400> SEQUENCE: 123

Pro Cys Leu Glu Gly Glu Gly Cys Asp Leu
1 5 10

<210> SEQ ID NO 124
<211> LENGTH: 7
<212> TYPE: PRT
<213> ORGANISM: Artificial Sequence
<220> FEATURE:
<223> OTHER INFORMATION: Peptide Sequence #23 (residues 72-78 of SEQ ID NO: 101)

<400> SEQUENCE: 124

Glu Gly Glu Gly Cys Asp Leu
1 5

<210> SEQ ID NO 125
<211> LENGTH: 8
<212> TYPE: PRT
<213> ORGANISM: Artificial Sequence
<220> FEATURE:
<223> OTHER INFORMATION: Peptide Sequence #24 (residues 72-79 of SEQ ID NO: 101)

<400> SEQUENCE: 125

Glu Gly Glu Gly Cys Asp Leu Leu
1 5

<210> SEQ ID NO 126
<211> LENGTH: 21
<212> TYPE: PRT
<213> ORGANISM: Artificial Sequence
<220> FEATURE:
<223> OTHER INFORMATION: Peptide Sequence #25 (residues 78-98 of SEQ ID NO: 101)

<400> SEQUENCE: 126

Leu Leu Ile Asn Arg Ser Gly Trp Thr Cys Thr Gln Pro Gly Gly Arg
1 5 10 15

Ile Lys Thr Thr Thr
20

<210> SEQ ID NO 127
<211> LENGTH: 20
<212> TYPE: PRT
<213> ORGANISM: Artificial Sequence
<220> FEATURE:
<223> OTHER INFORMATION: Peptide Sequence #26 (residues 79-98 of SEQ ID NO: 101)

<400> SEQUENCE: 127

Leu Ile Asn Arg Ser Gly Trp Thr Cys Thr Gln Pro Gly Gly Arg Ile
1 5 10 15

Lys Thr Thr Thr
20

<210> SEQ ID NO 128
<211> LENGTH: 20
<212> TYPE: PRT
<213> ORGANISM: Artificial Sequence
<220> FEATURE:
<223> OTHER INFORMATION: 2-13D-37-1.5W-41 Ab VH-CDR3

<400> SEQUENCE: 128

Ser Ser Tyr Val Cys Pro Gly Gly Phe Ser Cys Trp Gly Asp Thr Gly
1 5 10 15

Gln Ile Asp Ala
20

<210> SEQ ID NO 129
<211> LENGTH: 20
<212> TYPE: PRT
<213> ORGANISM: Artificial Sequence
<220> FEATURE:
<223> OTHER INFORMATION: 2-13D-37-3W-16 Ab VH-CDR3

<400> SEQUENCE: 129

Ser Asn Tyr Ala Cys Pro Gly Gly Phe Ser Cys Trp Gly Asp Thr Gly 1 5 10 15

Gln Ile Asp Ala
20

<210> SEQ ID NO 130
<211> LENGTH: 129
<212> TYPE: PRT
<213> ORGANISM: Artificial Sequence
<220> FEATURE:
<223> OTHER INFORMATION: 2-13D-37-1.5W-41 Ab VH

<400> SEQUENCE: 130

Ala Val Thr Leu Asp Glu Ser Gly Gly Gly Leu Gln Thr Pro Gly Gly
1 5 10 15

Ala Leu Arg Leu Ser Cys Ser Ala Ser Gly Phe Asp Phe Ser Ser His
20 25 30

Gly Met Phe Trp Val Arg Gln Ala Pro Gly Lys Gly Leu Glu Tyr Val
35 40 45

Ser Glu Ile Thr Asn Asp Gly Ser Gly Thr Asn Tyr Gly Ser Ala Val
50 55 60

Lys Gly Arg Ala Thr Ile Ser Arg Asp Asn Gly Gln Ser Thr Leu Tyr
65 70 75 80

Leu Gln Met Asn Ser Leu Arg Ala Glu Asp Thr Gly Thr Tyr Phe Cys
85 90 95

Ala Arg Ser Ser Tyr Val Cys Pro Gly Gly Phe Ser Cys Trp Gly Asp
100 105 110

Thr Gly Gln Ile Asp Ala Trp Gly His Gly Thr Glu Val Ile Val Ser
115 120 125

Ser

<210> SEQ ID NO 131
<211> LENGTH: 129
<212> TYPE: PRT
<213> ORGANISM: Artificial Sequence
<220> FEATURE:
<223> OTHER INFORMATION: 2-13D-37-3W-16 Ab VH

<400> SEQUENCE: 131

Ala Val Thr Leu Asp Glu Ser Gly Gly Gly Leu Gln Thr Pro Gly Gly
1 5 10 15

Ala Leu Arg Leu Ser Cys Ser Ala Ser Gly Phe Asp Phe Ser Ser His
20 25 30

Gly Met Phe Trp Val Arg Gln Ala Pro Gly Lys Gly Leu Glu Tyr Val
35 40 45

Ser Glu Ile Thr Asn Asp Gly Ser Gly Thr Asn Tyr Gly Ser Ala Val
50 55 60

Lys Gly Arg Ala Thr Ile Ser Arg Asp Asn Gly Gln Ser Thr Leu Tyr
65 70 75 80

Leu Gln Met Asn Ser Leu Arg Ala Glu Asp Thr Gly Thr Tyr Phe Cys
85 90 95

Ala Arg Ser Asn Tyr Ala Cys Pro Gly Gly Phe Ser Cys Trp Gly Asp
100 105 110

Thr Gly Gln Ile Asp Ala Trp Gly His Gly Thr Glu Val Ile Val Ser
115 120 125

Ser

<210> SEQ ID NO 132

<211> LENGTH: 250
<212> TYPE: PRT
<213> ORGANISM: Artificial Sequence
<220> FEATURE:
<223> OTHER INFORMATION: scFv - 2-13D-37-1.5W-41 Ab

<400> SEQUENCE: 132

Ala Leu Thr Gln Pro Ser Ser Val Ser Ala Asn Pro Gly Glu Thr Ala
1 5 10 15

Lys Ile Thr Cys Ser Gly Gly Val Tyr Ser Tyr Gly Trp Phe Gln Gln
20 25 30

Lys Pro Gly Ser Ala Leu Val Thr Val Ile Tyr Trp Asp Asp Glu Arg
35 40 45

Pro Ser Asp Ile Pro Ser Arg Phe Ser Gly Ala Leu Ser Gly Ser Thr
50 55 60

Asn Thr Leu Thr Ile Thr Gly Val Gln Ala Glu Asp Glu Ala Asp Tyr
65 70 75 80

Tyr Cys Gly Thr Glu Asp Ile Ser Gly Thr Ala Gly Val Phe Gly Ala
85 90 95

Gly Thr Thr Leu Thr Val Leu Gly Gln Ser Ser Arg Ser Ser Gly Gly
100 105 110

Gly Gly Ser Ser Gly Gly Gly Gly Ser Ala Val Thr Leu Asp Glu Ser
115 120 125

Gly Gly Gly Leu Gln Thr Pro Gly Gly Ala Leu Arg Leu Ser Cys Ser
130 135 140

Ala Ser Gly Phe Asp Phe Ser Ser His Gly Met Phe Trp Val Arg Gln
145 150 155 160

Ala Pro Gly Lys Gly Leu Glu Tyr Val Ser Glu Ile Thr Asn Asp Gly
165 170 175

Ser Gly Thr Asn Tyr Gly Ser Ala Val Lys Gly Arg Ala Thr Ile Ser
180 185 190

Arg Asp Asn Gly Gln Ser Thr Leu Tyr Leu Gln Met Asn Ser Leu Arg
195 200 205

Ala Glu Asp Thr Gly Thr Tyr Phe Cys Ala Arg Ser Ser Tyr Val Cys
210 215 220

Pro Gly Gly Phe Ser Cys Trp Gly Asp Thr Gly Gln Ile Asp Ala Trp
225 230 235 240

Gly His Gly Thr Glu Val Ile Val Ser Ser
245 250

<210> SEQ ID NO 133
<211> LENGTH: 250
<212> TYPE: PRT
<213> ORGANISM: Artificial Sequence
<220> FEATURE:
<223> OTHER INFORMATION: scFv - 2-13D-37-3W-16 Ab

<400> SEQUENCE: 133

Ala Leu Thr Gln Pro Ser Ser Val Ser Ala Asn Pro Gly Glu Thr Ala
1 5 10 15

Lys Ile Thr Cys Ser Gly Gly Val Tyr Ser Tyr Gly Trp Phe Gln Gln
20 25 30

Lys Pro Gly Ser Ala Leu Val Thr Val Ile Tyr Trp Asp Asp Glu Arg
35 40 45

Pro Ser Asp Ile Pro Ser Arg Phe Ser Gly Ala Leu Ser Gly Ser Thr
50 55 60

Asn Thr Leu Thr Ile Thr Gly Val Gln Ala Glu Asp Glu Ala Asp Tyr

```
65                  70                  75                  80

Tyr Cys Gly Thr Glu Asp Ile Ser Gly Thr Ala Gly Val Phe Gly Ala
                85                  90                  95

Gly Thr Thr Leu Thr Val Leu Gly Gln Ser Ser Arg Ser Ser Gly Gly
            100                 105                 110

Gly Gly Ser Ser Gly Gly Gly Gly Ser Ala Val Thr Leu Asp Glu Ser
        115                 120                 125

Gly Gly Gly Leu Gln Thr Pro Gly Gly Ala Leu Arg Leu Ser Cys Ser
    130                 135                 140

Ala Ser Gly Phe Asp Phe Ser Ser His Gly Met Phe Trp Val Arg Gln
145                 150                 155                 160

Ala Pro Gly Lys Gly Leu Glu Tyr Val Ser Glu Ile Thr Asn Asp Gly
                165                 170                 175

Ser Gly Thr Asn Tyr Gly Ser Ala Val Lys Gly Arg Ala Thr Ile Ser
            180                 185                 190

Arg Asp Asn Gly Gln Ser Thr Leu Tyr Leu Gln Met Asn Ser Leu Arg
        195                 200                 205

Ala Glu Asp Thr Gly Thr Tyr Phe Cys Ala Arg Ser Asn Tyr Ala Cys
    210                 215                 220

Pro Gly Gly Phe Ser Cys Trp Gly Asp Thr Gly Gln Ile Asp Ala Trp
225                 230                 235                 240

Gly His Gly Thr Glu Val Ile Val Ser Ser
                245                 250


<210> SEQ ID NO 134
<211> LENGTH: 387
<212> TYPE: DNA
<213> ORGANISM: Artificial Sequence
<220> FEATURE:
<223> OTHER INFORMATION: 2-13D-37-1.5W-41 Ab VH

<400> SEQUENCE: 134

gccgtgacgt tggacgagtc cgggggcggc ctccagacgc ccggaggagc gctccgcctt     60

agctgcagcg cctccgggtt cgatttcagc agccatggca tgttctgggt gcgacaggcg    120

cccggcaagg ggttggaata tgtctcggag attaccaatg atggtagtgg cacaaactac    180

gggtcggcgg tgaagggccg tgccaccatc tcgagggaca acgggcagag cacactgtat    240

ctgcagatga acagcctcag ggctgaggac accggcacct acttctgcgc cagatcttct    300

tatgtttgtc ctggtggttt tagttgttgg ggtgatactg gtcaaataga cgcatggggc    360

cacgggaccg aagtcatcgt ctcctcc                                        387


<210> SEQ ID NO 135
<211> LENGTH: 387
<212> TYPE: DNA
<213> ORGANISM: Artificial Sequence
<220> FEATURE:
<223> OTHER INFORMATION: 2-13D-37-3W-16 Ab VH

<400> SEQUENCE: 135

gccgtgacgt tggacgagtc cgggggcggc ctccagacgc ccggaggagc gctccgcctt     60

agctgcagcg cctccgggtt cgatttcagc agccatggca tgttctgggt gcgacaggcg    120

cccggcaagg ggttggaata tgtctcggag attaccaatg atggtagtgg cacaaactac    180

gggtcggcgg tgaagggccg tgccaccatc tcgagggaca acgggcagag cacactgtat    240

ctgcagatga acagcctcag ggctgaggac accggcacct acttctgcgc cagatctaat    300
```

tatgcttgtc ctggtggttt tagttgttgg ggtgatactg gtcaaataga cgcatggggc 360
cacgggaccg aagtcatcgt ctcctcc 387

<210> SEQ ID NO 136
<211> LENGTH: 309
<212> TYPE: DNA
<213> ORGANISM: Artificial Sequence
<220> FEATURE:
<223> OTHER INFORMATION: 2-13D-37-1.5W-41 Ab VL

<400> SEQUENCE: 136
gccctgactc agccgtcctc ggtgtcagca aacccaggag aaaccgcgaa gataacctgc 60
tccgggggtg tgtatagcta tggctggttc cagcagaagc ctggcagtgc ccttgtcact 120
gtgatctact gggatgatga gagaccctcg gacatccctt cacgattctc cggtgcccta 180
tccggctcca caaacacatt aaccatcact ggggtccaag ccgaagacga ggctgattat 240
tattgtggga ctgaagacat cagcggcact gctggtgtat ttggggccgg gacaaccctg 300
accgtcctg 309

<210> SEQ ID NO 137
<211> LENGTH: 309
<212> TYPE: DNA
<213> ORGANISM: Artificial Sequence
<220> FEATURE:
<223> OTHER INFORMATION: 2-13D-37-3W-16 Ab VL

<400> SEQUENCE: 137
gccctgactc agccgtcctc ggtgtcagca aacccaggag aaaccgcgaa gataacctgc 60
tccgggggtg tgtatagcta tggctggttc cagcagaagc ctggcagtgc ccttgtcact 120
gtgatctact gggatgatga gagaccctcg gacatccctt cacgattctc cggtgcccta 180
tccggctcca caaacacatt aaccatcact ggggtccaag ccgaagacga ggctgattat 240
tattgtggga ctgaagacat cagcggcact gctggtgtat ttggggccgg gacaaccctg 300
accgtcctg 309

<210> SEQ ID NO 138
<211> LENGTH: 100
<212> TYPE: PRT
<213> ORGANISM: Artificial Sequence
<220> FEATURE:
<223> OTHER INFORMATION: FAM19A5 Protein Mutant

<400> SEQUENCE: 138

Gln Phe Leu Lys Glu Gly Gln Leu Ala Ala Gly Thr Ser Glu Ile Val
1 5 10 15

Thr Leu Asp Arg Asp Ser Ser Gln Pro Arg Arg Thr Ile Ala Arg Gln
20 25 30

Thr Ala Arg Ser Ala Ser Arg Lys Gly Gln Ile Ala Gly Thr Thr Arg
35 40 45

Ala Arg Pro Ala Ser Val Asp Ala Arg Ile Ile Lys Thr Lys Gln Trp
50 55 60

Ser Asp Met Leu Pro Ser Leu Glu Gly Glu Gly Ser Asp Leu Leu Ile
65 70 75 80

Asn Arg Ser Gly Trp Thr Ser Thr Gln Pro Gly Gly Arg Ile Lys Thr
85 90 95

Thr Thr Val Ser
100

<210> SEQ ID NO 139
<211> LENGTH: 25
<212> TYPE: PRT
<213> ORGANISM: Artificial Sequence
<220> FEATURE:
<223> OTHER INFORMATION: F1 Fragment

<400> SEQUENCE: 139

```
Gln Phe Leu Lys Glu Gly Gln Leu Ala Ala Gly Thr Ser Glu Ile Val
1               5                   10                  15

Thr Leu Asp Arg Gly Gly Gly Ser Cys
            20                  25
```

<210> SEQ ID NO 140
<211> LENGTH: 25
<212> TYPE: PRT
<213> ORGANISM: Artificial Sequence
<220> FEATURE:
<223> OTHER INFORMATION: F2 Fragment

<400> SEQUENCE: 140

```
Thr Leu Asp Arg Asp Ser Ser Gln Pro Arg Arg Thr Ile Ala Arg Gln
1               5                   10                  15

Thr Ala Arg Ser Gly Gly Gly Ser Cys
            20                  25
```

<210> SEQ ID NO 141
<211> LENGTH: 25
<212> TYPE: PRT
<213> ORGANISM: Artificial Sequence
<220> FEATURE:
<223> OTHER INFORMATION: F3 Fragment

<400> SEQUENCE: 141

```
Thr Ala Arg Ser Ala Ser Arg Lys Gly Gln Ile Ala Gly Thr Thr Arg
1               5                   10                  15

Ala Arg Pro Ala Gly Gly Gly Ser Cys
            20                  25
```

<210> SEQ ID NO 142
<211> LENGTH: 25
<212> TYPE: PRT
<213> ORGANISM: Artificial Sequence
<220> FEATURE:
<223> OTHER INFORMATION: F4 Fragment

<400> SEQUENCE: 142

```
Ala Arg Pro Ala Ser Val Asp Ala Arg Ile Ile Lys Thr Lys Gln Trp
1               5                   10                  15

Ser Asp Met Leu Gly Gly Gly Ser Cys
            20                  25
```

<210> SEQ ID NO 143
<211> LENGTH: 25
<212> TYPE: PRT
<213> ORGANISM: Artificial Sequence
<220> FEATURE:
<223> OTHER INFORMATION: F5 Fragment

<400> SEQUENCE: 143

```
Ser Asp Met Leu Pro Ser Leu Glu Gly Glu Gly Ser Asp Leu Leu Ile
1               5                   10                  15

Asn Arg Ser Gly Gly Gly Gly Ser Cys
            20                  25
```

<210> SEQ ID NO 144
<211> LENGTH: 25
<212> TYPE: PRT
<213> ORGANISM: Artificial Sequence
<220> FEATURE:
<223> OTHER INFORMATION: F6 Fragment

<400> SEQUENCE: 144

Asn Arg Ser Gly Trp Thr Ser Thr Gln Pro Gly Gly Arg Ile Lys Thr
1 5 10 15

Thr Thr Val Ser Gly Gly Gly Ser Cys
20 25

<210> SEQ ID NO 145
<211> LENGTH: 87
<212> TYPE: PRT
<213> ORGANISM: Artificial Sequence
<220> FEATURE:
<223> OTHER INFORMATION: IGLV1-51*02

<400> SEQUENCE: 145

Val Leu Thr Gln Pro Pro Ser Val Ser Ala Ala Pro Gly Gln Lys Val
1 5 10 15

Thr Ile Ser Cys Ser Gly Ser Ser Ser Asn Ile Gly Asn Asn Tyr Val
20 25 30

Ser Trp Tyr Gln Gln Leu Pro Gly Thr Ala Pro Lys Leu Leu Ile Tyr
35 40 45

Glu Asn Asn Lys Arg Pro Ser Gly Ile Pro Asp Arg Phe Ser Gly Ser
50 55 60

Lys Ser Gly Thr Ser Ala Thr Leu Gly Ile Thr Gly Leu Gln Thr Gly
65 70 75 80

Asp Glu Ala Asp Tyr Tyr Cys
85

<210> SEQ ID NO 146
<211> LENGTH: 10
<212> TYPE: PRT
<213> ORGANISM: Artificial Sequence
<220> FEATURE:
<223> OTHER INFORMATION: IGLJ2*01

<400> SEQUENCE: 146

Phe Gly Gly Gly Thr Lys Leu Thr Val Leu
1 5 10

<210> SEQ ID NO 147
<211> LENGTH: 98
<212> TYPE: PRT
<213> ORGANISM: Artificial Sequence
<220> FEATURE:
<223> OTHER INFORMATION: IGHV3-64*04

<400> SEQUENCE: 147

Gln Val Gln Leu Val Glu Ser Gly Gly Gly Leu Val Gln Pro Gly Gly
1 5 10 15

Ser Leu Arg Leu Ser Cys Ser Ala Ser Gly Phe Thr Phe Ser Ser Tyr
20 25 30

Ala Met His Trp Val Arg Gln Ala Pro Gly Lys Gly Leu Glu Tyr Val
35 40 45

Ser Ala Ile Ser Ser Asn Gly Gly Ser Thr Tyr Tyr Ala Asp Ser Val
50 55 60

```
Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg


<210> SEQ ID NO 148
<211> LENGTH: 11
<212> TYPE: PRT
<213> ORGANISM: Artificial Sequence
<220> FEATURE:
<223> OTHER INFORMATION: IGHJ1*01

<400> SEQUENCE: 148

Trp Gly Gln Gly Thr Leu Val Thr Val Ser Ser
1               5                   10


<210> SEQ ID NO 149
<211> LENGTH: 85
<212> TYPE: PRT
<213> ORGANISM: Artificial Sequence
<220> FEATURE:
<223> OTHER INFORMATION: IGLV3-27*01

<400> SEQUENCE: 149

Glu Leu Thr Gln Pro Ser Ser Val Ser Val Ser Pro Gly Gln Thr Ala
1               5                   10                  15

Arg Ile Thr Cys Ser Gly Asp Val Leu Ala Lys Lys Tyr Ala Arg Trp
            20                  25                  30

Phe Gln Gln Lys Pro Gly Gln Ala Pro Val Leu Val Ile Tyr Lys Asp
        35                  40                  45

Ser Glu Arg Pro Ser Gly Ile Pro Glu Arg Phe Ser Gly Ser Ser Ser
    50                  55                  60

Gly Thr Thr Val Thr Leu Thr Ile Ser Gly Ala Gln Val Glu Asp Glu
65                  70                  75                  80

Ala Asp Tyr Tyr Cys
                85


<210> SEQ ID NO 150
<211> LENGTH: 131
<212> TYPE: PRT
<213> ORGANISM: Artificial Sequence
<220> FEATURE:
<223> OTHER INFORMATION: Fully deimmunized clone 3-2

<400> SEQUENCE: 150

Ala Val Thr Leu Asp Glu Ser Gly Gly Gly Leu Gln Thr Pro Gly Gly
1               5                   10                  15

Ala Leu Arg Leu Ser Cys Lys Ala Ser Gly Phe Thr Phe Ser Ser Tyr
            20                  25                  30

Asn Met Phe Trp Val Arg Gln Ala Pro Gly Lys Gly Leu Glu Tyr Val
        35                  40                  45

Ser Ala Ile Ser Ser Ser Gly Ser Ser Thr Asn Tyr Ala Pro Ala Val
    50                  55                  60

Lys Gly Arg Ala Thr Ile Ser Arg Asp Asn Gly Gln Ser Thr Leu Tyr
65                  70                  75                  80

Leu Gln Met Asn Ser Leu Arg Ala Glu Asp Thr Gly Thr Tyr Tyr Cys
                85                  90                  95

Ala Lys Ser Ser Tyr Asp Cys Pro Tyr Gly His Cys Ser Ser Gly Val
```

```
            100                 105                 110

Asp Ser Ala Gly Glu Ile Asp Ala Trp Gly His Gly Thr Glu Val Ile
        115                 120                 125

Val Ser Ser
    130


<210> SEQ ID NO 151
<211> LENGTH: 129
<212> TYPE: PRT
<213> ORGANISM: Artificial Sequence
<220> FEATURE:
<223> OTHER INFORMATION: Fully deimmunized clone 2-13

<400> SEQUENCE: 151

Ala Val Thr Leu Asp Glu Ser Gly Gly Gly Leu Gln Thr Pro Gly Gly
1               5                   10                  15

Ala Leu Arg Leu Ser Cys Ser Ala Ser Gly Phe Thr Phe Ser Ser His
            20                  25                  30

Gly Met Phe Trp Val Arg Gln Ala Pro Gly Lys Gly Leu Glu Tyr Val
        35                  40                  45

Ser Ala Ile Thr Asn Asp Gly Ser Gly Thr Asn Tyr Gly Ser Ala Val
    50                  55                  60

Lys Gly Arg Ala Thr Ile Ser Arg Asp Asn Gly Gln Ser Thr Leu Tyr
65                  70                  75                  80

Leu Gln Met Asn Ser Leu Arg Ala Glu Asp Thr Gly Thr Tyr Phe Cys
                85                  90                  95

Ala Arg Ser Thr Tyr Glu Cys Pro Gly Gly Phe Ser Cys Trp Gly Asp
            100                 105                 110

Thr Gly Gln Ile Asp Ala Trp Gly His Gly Thr Glu Val Ile Val Ser
        115                 120                 125

Ser


<210> SEQ ID NO 152
<211> LENGTH: 12
<212> TYPE: PRT
<213> ORGANISM: Artificial Sequence
<220> FEATURE:
<223> OTHER INFORMATION: Peptide Sequence #27 (residues 3-14 of SEQ ID
      NO: 101)

<400> SEQUENCE: 152

Leu Lys Glu Gly Gln Leu Ala Ala Gly Thr Cys Glu
1               5                   10


<210> SEQ ID NO 153
<211> LENGTH: 19
<212> TYPE: PRT
<213> ORGANISM: Artificial Sequence
<220> FEATURE:
<223> OTHER INFORMATION: Peptide Sequence #28 (residues 4-22 of SEQ ID
      NO: 101)

<400> SEQUENCE: 153

Lys Glu Gly Gln Leu Ala Ala Gly Thr Cys Glu Ile Val Thr Leu Asp
1               5                   10                  15

Arg Asp Ser


<210> SEQ ID NO 154
<211> LENGTH: 18
<212> TYPE: PRT
<213> ORGANISM: Artificial Sequence
```

<220> FEATURE:
<223> OTHER INFORMATION: Peptide Sequence #29

<400> SEQUENCE: 154

Asp Arg Asp Ser Ser Gln Pro Pro Arg Thr Ile Ala Arg Gln Thr Ala
1               5                   10                  15

Arg Cys

<210> SEQ ID NO 155
<211> LENGTH: 12
<212> TYPE: PRT
<213> ORGANISM: Artificial Sequence
<220> FEATURE:
<223> OTHER INFORMATION: Peptide Sequence #30

<400> SEQUENCE: 155

Pro Arg Thr Ile Ala Arg Gln Thr Ala Arg Cys Ala
1               5                   10

<210> SEQ ID NO 156
<211> LENGTH: 15
<212> TYPE: PRT
<213> ORGANISM: Artificial Sequence
<220> FEATURE:
<223> OTHER INFORMATION: Peptide Sequence #31

<400> SEQUENCE: 156

Pro Arg Thr Ile Ala Arg Gln Thr Ala Arg Cys Ala Cys Arg Lys
1               5                   10                  15

<210> SEQ ID NO 157
<211> LENGTH: 23
<212> TYPE: PRT
<213> ORGANISM: Artificial Sequence
<220> FEATURE:
<223> OTHER INFORMATION: Peptide Sequence #32

<400> SEQUENCE: 157

Thr Ala Arg Cys Ala Cys Arg Lys Gly Gln Ile Ala Gly Thr Thr Arg
1               5                   10                  15

Ala Arg Pro Ala Cys Val Asp
            20

<210> SEQ ID NO 158
<211> LENGTH: 10
<212> TYPE: PRT
<213> ORGANISM: Artificial Sequence
<220> FEATURE:
<223> OTHER INFORMATION: Peptide Sequence #33

<400> SEQUENCE: 158

Ala Arg Cys Ala Cys Arg Lys Gly Gln Ile
1               5                   10

<210> SEQ ID NO 159
<211> LENGTH: 16
<212> TYPE: PRT
<213> ORGANISM: Artificial Sequence
<220> FEATURE:
<223> OTHER INFORMATION: Peptide Sequence #34

<400> SEQUENCE: 159

Cys Arg Lys Gly Gln Ile Ala Gly Thr Thr Arg Ala Arg Pro Ala Cys
1               5                   10                  15

```
<210> SEQ ID NO 160
<211> LENGTH: 17
<212> TYPE: PRT
<213> ORGANISM: Artificial Sequence
<220> FEATURE:
<223> OTHER INFORMATION: Peptide Sequence #35

<400> SEQUENCE: 160

Arg Lys Gly Gln Ile Ala Gly Thr Thr Arg Ala Arg Pro Ala Cys Val
1               5                   10                  15

Asp


<210> SEQ ID NO 161
<211> LENGTH: 10
<212> TYPE: PRT
<213> ORGANISM: Artificial Sequence
<220> FEATURE:
<223> OTHER INFORMATION: Peptide Sequence #36

<400> SEQUENCE: 161

Ile Ala Gly Thr Thr Arg Ala Arg Pro Ala
1               5                   10


<210> SEQ ID NO 162
<211> LENGTH: 12
<212> TYPE: PRT
<213> ORGANISM: Artificial Sequence
<220> FEATURE:
<223> OTHER INFORMATION: Peptide Sequence #37

<400> SEQUENCE: 162

Gly Thr Thr Arg Ala Arg Pro Ala Cys Val Asp Ala
1               5                   10


<210> SEQ ID NO 163
<211> LENGTH: 14
<212> TYPE: PRT
<213> ORGANISM: Artificial Sequence
<220> FEATURE:
<223> OTHER INFORMATION: Peptide Sequence #38

<400> SEQUENCE: 163

Val Asp Ala Arg Ile Ile Lys Thr Lys Gln Trp Cys Asp Met
1               5                   10


<210> SEQ ID NO 164
<211> LENGTH: 10
<212> TYPE: PRT
<213> ORGANISM: Artificial Sequence
<220> FEATURE:
<223> OTHER INFORMATION: Peptide Sequence #39

<400> SEQUENCE: 164

Ile Lys Thr Lys Gln Trp Cys Asp Met Leu
1               5                   10


<210> SEQ ID NO 165
<211> LENGTH: 25
<212> TYPE: PRT
<213> ORGANISM: Artificial Sequence
<220> FEATURE:
<223> OTHER INFORMATION: Peptide Sequence #40

<400> SEQUENCE: 165

Pro Cys Leu Glu Gly Glu Gly Cys Asp Leu Leu Ile Asn Arg Ser Gly
1               5                   10                  15
```

Trp Thr Cys Thr Gln Pro Gly Gly Arg
20 25

<210> SEQ ID NO 166
<211> LENGTH: 19
<212> TYPE: PRT
<213> ORGANISM: Artificial Sequence
<220> FEATURE:
<223> OTHER INFORMATION: Peptide Sequence #41

<400> SEQUENCE: 166

Ile Asn Arg Ser Gly Trp Thr Cys Thr Gln Pro Gly Gly Arg Ile Lys
1 5 10 15

Thr Thr Thr

<210> SEQ ID NO 167
<211> LENGTH: 18
<212> TYPE: PRT
<213> ORGANISM: Artificial Sequence
<220> FEATURE:
<223> OTHER INFORMATION: Peptide Sequence #42

<400> SEQUENCE: 167

Asn Arg Ser Gly Trp Thr Cys Thr Gln Pro Gly Gly Arg Ile Lys Thr
1 5 10 15

Thr Thr

<210> SEQ ID NO 168
<211> LENGTH: 13
<212> TYPE: PRT
<213> ORGANISM: Artificial Sequence
<220> FEATURE:
<223> OTHER INFORMATION: Peptide Sequence #43

<400> SEQUENCE: 168

Thr Cys Thr Gln Pro Gly Gly Arg Ile Lys Thr Thr Thr
1 5 10

<210> SEQ ID NO 169
<211> LENGTH: 11
<212> TYPE: PRT
<213> ORGANISM: Artificial Sequence
<220> FEATURE:
<223> OTHER INFORMATION: Peptide Sequence #44

<400> SEQUENCE: 169

Thr Gln Pro Gly Gly Arg Ile Lys Thr Thr Thr
1 5 10

<210> SEQ ID NO 170
<211> LENGTH: 13
<212> TYPE: PRT
<213> ORGANISM: Artificial Sequence
<220> FEATURE:
<223> OTHER INFORMATION: Peptide Sequence #45

<400> SEQUENCE: 170

Cys Arg Lys Gly Gln Ile Ala Gly Thr Thr Arg Ala Arg
1 5 10

<210> SEQ ID NO 171
<211> LENGTH: 9
<212> TYPE: PRT
<213> ORGANISM: Artificial Sequence
<220> FEATURE:
<223> OTHER INFORMATION: Synthetic Construct

<400> SEQUENCE: 171

Ile Tyr Tyr Cys Gly Ser Trp Asp Ser
1 5

<210> SEQ ID NO 172
<211> LENGTH: 9
<212> TYPE: PRT
<213> ORGANISM: artificial sequence
<220> FEATURE:
<223> OTHER INFORMATION: Synthetic Construct

<400> SEQUENCE: 172

Val Arg Gly Arg Ala Thr Ile Ser Arg
1 5

<210> SEQ ID NO 173
<211> LENGTH: 9
<212> TYPE: PRT
<213> ORGANISM: artificial sequence
<220> FEATURE:
<223> OTHER INFORMATION: Synthetic Construct

<400> SEQUENCE: 173

Val Arg Leu Gln Leu Asn Asn Pro Gly
1 5

<210> SEQ ID NO 174
<211> LENGTH: 9
<212> TYPE: PRT
<213> ORGANISM: artificial sequence
<220> FEATURE:
<223> OTHER INFORMATION: Synthetic Construct

<400> SEQUENCE: 174

Val Lys Ile Thr Cys Ser Gly Gly Gly
1 5

<210> SEQ ID NO 175
<211> LENGTH: 9
<212> TYPE: PRT
<213> ORGANISM: artificial sequence
<220> FEATURE:
<223> OTHER INFORMATION: Synthetic Construct

<400> SEQUENCE: 175

Ile Tyr Glu Ser Asn Lys Arg Pro Ser
1 5

<210> SEQ ID NO 176
<211> LENGTH: 9
<212> TYPE: PRT
<213> ORGANISM: artificial sequence
<220> FEATURE:
<223> OTHER INFORMATION: Synthetic Construct

<400> SEQUENCE: 176

Leu Ser Leu Val Cys Lys Ala Ser Gly
1 5

<210> SEQ ID NO 177
<211> LENGTH: 9
<212> TYPE: PRT
<213> ORGANISM: artificial sequence
<220> FEATURE:
<223> OTHER INFORMATION: Synthetic Construct

<400> SEQUENCE: 177

Ser Leu Val Cys Lys Ala Ser Gly Phe
1 5

<210> SEQ ID NO 178
<211> LENGTH: 9
<212> TYPE: PRT
<213> ORGANISM: artificial sequence
<220> FEATURE:
<223> OTHER INFORMATION: Synthetic Construct

<400> SEQUENCE: 178

Phe Asn Met Phe Trp Val Arg Gln Ala
1 5

<210> SEQ ID NO 179
<211> LENGTH: 9
<212> TYPE: PRT
<213> ORGANISM: artificial sequence
<220> FEATURE:
<223> OTHER INFORMATION: Synthetic Construct

<400> SEQUENCE: 179

Leu Glu Tyr Val Ala Gln Ile Ser Ser
1 5

<210> SEQ ID NO 180
<211> LENGTH: 9
<212> TYPE: PRT
<213> ORGANISM: artificial sequence
<220> FEATURE:
<223> OTHER INFORMATION: Synthetic Construct

<400> SEQUENCE: 180

Val Ala Gln Ile Ser Ser Ser Gly Ser
1 5

<210> SEQ ID NO 181
<211> LENGTH: 9
<212> TYPE: PRT
<213> ORGANISM: artificial sequence
<220> FEATURE:
<223> OTHER INFORMATION: Synthetic Construct

<400> SEQUENCE: 181

Leu Gln Leu Asn Asn Pro Gly Ala Glu
1 5

<210> SEQ ID NO 182
<211> LENGTH: 9
<212> TYPE: PRT
<213> ORGANISM: artificial sequence
<220> FEATURE:
<223> OTHER INFORMATION: Synthetic Construct

<400> SEQUENCE: 182

Val Lys Ile Thr Cys Ser Gly Gly Ser
1 5

<210> SEQ ID NO 183
<211> LENGTH: 9
<212> TYPE: PRT
<213> ORGANISM: artificial sequence
<220> FEATURE:
<223> OTHER INFORMATION: Synthetic Construct

<400> SEQUENCE: 183

Val Tyr Phe Cys Gly Thr Glu Asp Ile
1 5

<210> SEQ ID NO 184
<211> LENGTH: 9
<212> TYPE: PRT
<213> ORGANISM: artificial sequence
<220> FEATURE:
<223> OTHER INFORMATION: Synthetic Construct

<400> SEQUENCE: 184

Val Arg Leu Gln Leu Asn Asn Leu Arg
1 5

<210> SEQ ID NO 185
<211> LENGTH: 9
<212> TYPE: PRT
<213> ORGANISM: artificial sequence
<220> FEATURE:
<223> OTHER INFORMATION: Synthetic Construct

<400> SEQUENCE: 185

Leu Val Cys Lys Ala Ser Gly Phe Thr
1 5

<210> SEQ ID NO 186
<211> LENGTH: 9
<212> TYPE: PRT
<213> ORGANISM: artificial sequence
<220> FEATURE:
<223> OTHER INFORMATION: Synthetic Construct

<400> SEQUENCE: 186

Trp Val Arg Gln Thr Pro Gly Lys Gly
1 5

<210> SEQ ID NO 187
<211> LENGTH: 9
<212> TYPE: PRT
<213> ORGANISM: artificial sequence
<220> FEATURE:
<223> OTHER INFORMATION: Synthetic Construct

<400> SEQUENCE: 187

Tyr Val Ala Glu Ile Thr Asn Asp Gly
1 5

<210> SEQ ID NO 188
<211> LENGTH: 9
<212> TYPE: PRT
<213> ORGANISM: artificial sequence
<220> FEATURE:
<223> OTHER INFORMATION: Synthetic Construct

<400> SEQUENCE: 188

Val Lys Gly Arg Ala Thr Ile Ser Arg
1 5

<210> SEQ ID NO 189
<211> LENGTH: 9
<212> TYPE: PRT
<213> ORGANISM: artificial sequence
<220> FEATURE:
<223> OTHER INFORMATION: Synthetic Construct

<400> SEQUENCE: 189

-continued

```
Leu Gln Leu Asn Asn Leu Arg Ala Glu
1               5


<210> SEQ ID NO 190
<211> LENGTH: 9
<212> TYPE: PRT
<213> ORGANISM: artificial sequence
<220> FEATURE:
<223> OTHER INFORMATION: Synthetic Construct

<400> SEQUENCE: 190

Leu Arg Ala Glu Asp Thr Gly Thr Tyr
1               5
```

ANTI-FAMILY WITH SEQUENCE SIMILARITY 19, MEMBER A5 ANTIBODIES AND METHOD OF USE THEREOF

CROSS-REFERENCE TO RELATED APPLICATIONS

This PCT application claims the priority benefit of U.S. Provisional Application Nos. 62/787,711, filed Jan. 2, 2019, and 62/838,190, filed Apr. 24, 2019, each of which is incorporated herein by reference in its entirety.

STATEMENT OF GOVERNMENT SUPPORT

This work was supported by the Industrial Technology Innovation Program (10081300, Development of new therapeutic monoclonal antibody drug via inhibitory mechanism of glial scar formation for ischemic stroke) funded By the Ministry of Trade, Industry & Energy (MOTIE, Korea).

REFERENCE TO SEQUENCE LISTING SUBMITTED ELECTRONICALLY

The content of the electronically submitted sequence listing in ASCII text file (Name: 3763.0160002_SequenceListing_ST25.txt; Size: 107,433 bytes; and Date of Creation: Jan. 31, 2025) filed with the application is incorporated herein by reference in its entirety.

FIELD OF THE DISCLOSURE

The present disclosure provides antibodies (e.g., de-immunized or affinity matured) that specifically bind to family with sequence similarity 19, member A5 (FAM19A5), compositions comprising such antibodies, and method of using such antibodies for preventing or treating disorders or diseases, such as those resulting from a central nervous system damage in a subject.

BACKGROUND OF THE DISCLOSURE

FAM19A5 is a member of the TAFA subfamily of proteins which is composed of five highly homologous small proteins. Tang T. Y. et al., *Genomics* 83(4):727-34 (2004). These proteins contain conserved cysteine residues at fixed positions, and are distantly related to macrophage inflammatory protein 1-alpha (MIP-1-alpha), a member of the CC-chemokine family. The TAFA proteins are predominantly expressed in specific regions of the brain and the spinal cord. These proteins are believed to be generated and secreted by adult neural stem cells in neurogenesis processes.

FAM19A5 is predominantly expressed in the brain of vertebrates and is believed that FAM19A5 is important in the development, differentiation, formation of a complete central nervous system, and can be used in the prevention or treatment of central nervous system injuries and/or diseases. U.S. Patent Publication No. 2015/0118230.

While inhibiting FAM19A5 can play an important role in treating the central nervous system, there is still a need to develop antibodies that specifically bind to FAM19A5 and that are capable of modulating FAM19A5 activity, especially those antibodies that can be used in human subjects without adverse effects.

BRIEF SUMMARY OF THE DISCLOSURE

Provided herein is an isolated antibody, or antigen binding portion thereof, which specifically binds a human family with sequence similarity 19, member A5 (FAM19A5) protein ("anti-FAM19A5 antibody"), comprising a heavy chain CDR1, CDR2, and CDR3 and a light chain CDR1, CDR2, and CDR3, wherein the heavy chain CDR1, CDR2, and CDR3 comprises the amino acid sequences set forth in SEQ ID NOs: 5, 6, and 7, respectively, each of which optionally comprising one, two, three, four, or five mutations, wherein the light chain CDR1, CDR2, and CDR3 comprise the amino acid sequences set forth in SEQ ID NOs: 8, 9, and 10, respectively, wherein at least one of the light chain CDR1, CDR2, and CDR3 comprising one, two, three, four, or five mutations, and wherein the antibody has a reduced immunogenicity in human compared to a reference antibody comprising the VH set forth in SEQ ID NO: 11 and the VL set forth in SEQ ID NO: 12.

In some embodiments, the heavy chain CDR3 of an anti-FAM19A5 antibody disclosed herein comprises the amino acid sequence set forth in SEQ ID NO: 7.

In some embodiments, the heavy chain CDR1 of an anti-FAM19A5 antibody comprises the amino acid sequence set forth in SEQ ID NO: 5, with one or two mutations. In certain embodiments, the mutations comprise a substitution of Threonine at amino acid 3 of SEQ ID NO: 5 to an acidic amino acid. In further embodiments, the mutations comprise a substitution of Serine at amino acid 5 of SEQ ID NO: 5 to an acidic amino acid. In certain embodiments, the acidic amino acid comprises Aspartic Acid or Glutamic Acid.

In some embodiments, the heavy chain CDR2 of an anti-FAM19A5 antibody comprises the amino acid sequence set forth in SEQ ID NO: 6, with one, two, three, four, or five mutations. In some embodiments, the mutations comprise a substitution of Arginine at amino acid 16 of SEQ ID NO: 6 to a basic amino acid. In certain embodiments, the basic amino acid comprises Lysine. In further embodiments, the mutations comprise one or more of the following: (a) a substitution of Glycine at amino acid 6 of SEQ ID NO: 6 to an acidic amino acid; (b) a substitution of Serine at amino acid 7 of SEQ ID NO: 6 to an acidic amino acid; (c) a substitution of Serine at amino acid 8 of SEQ ID NO: 6 to an acidic amino acid; (d) a substitution of Threonine at amino acid 9 of SEQ ID NO: 6 to an acidic amino acid; and (e) a substitution of Arginine at amino acid 16 of SEQ ID NO: 6 to a basic amino acid. In certain embodiments, the acidic amino acid comprises Aspartic Acid or Glutamic Acid. In certain embodiments, the basic amino acid comprises Lysine.

In some embodiments, the light chain CDR3 of an anti-FAM19A5 antibody disclosed herein comprises the amino acid sequence set forth in SEQ ID NO: 10, with one, two, three, four, or five mutations. In some embodiments, the mutations comprise one or more of the following: (a) a substitution of Serine at amino acid 6 of SEQ ID NO: 10 to an acidic amino acid or to an aliphatic amino acid; (b) a substitution of Asparagine at amino acid 7 of SEQ ID NO: 10 to an acidic amino acid or to a hydroxyl or sulfur/selenium-containing amino acid; (c) a substitution of Glycine at amino acid 8 of SEQ ID NO: 10 to an acidic amino acid or to a hydroxyl or sulfur/selenium-containing amino acid; (d) a substitution of Glycine at amino acid 9 of SEQ ID NO: 10 to an acidic amino acid or to a hydroxyl or sulfur/selenium-containing amino acid; and (e) a substitution of Isoleucine at amino acid 10 of SEQ ID NO: 10 to a basic amino acid. In certain embodiments, the acidic amino acid comprises Aspartic Acid or Glutamic Acid. In some embodiments, the hydroxyl or sulfur/selenium-containing amino acid comprises Serine. In further embodiments, the basic amino acid comprises Histidine.

In some embodiments, the light chain CDR1 of an anti-FAM19A5 antibody of the present disclosure comprises the amino acid sequence set forth in SEQ ID NO: 8, with one, two, three, or four mutations. In certain embodiments, the mutations comprise one or more of the following: (a) a substitution of Tyrosine at amino acid 6 of SEQ ID NO: 8 to an acidic amino acid; (b) a substitution of Arginine at amino acid 7 of SEQ ID NO: 8 to an acidic amino acid; (c) a substitution of Glycine at amino acid 8 of SEQ ID NO: 8 to an acidic amino acid; and (d) a substitution of Serine at amino acid 9 of SEQ ID NO: 8 to an acidic amino acid. In some embodiments, the acidic amino acid comprises Glutamic Acid or Glutamine.

In some embodiments, the light chain CDR2 comprises the amino acid sequence set forth in SEQ ID NO: 9, with one, two, three, or four mutations. In some embodiments, the mutations comprise one or more of the following: (a) a substitution of Glutamic Acid at amino acid 1 of SEQ ID NO: 9 to an acidic amino acid; (b) a substitution of Serine at amino acid 2 of SEQ ID NO: 9 to an acidic amino acid; (c) a substitution of Asparagine at amino acid 3 of SEQ ID NO: 9 to an acidic amino acid, to a basic amino acid, or to an aliphatic amino acid; and (d) a substitution of Lysine at amino acid 4 of SEQ ID NO: 9 to an acidic amino acid or to an aliphatic amino acid. In certain embodiments, the acidic amino acid comprises Glutamine, Asparagine, Aspartic Acid, or Glutamic Acid. In some embodiments, the basic amino acid comprises Histidine. In further embodiments, the aliphatic amino acid comprises Leucine. In certain embodiments, the mutations comprise a substitution of Serine at amino acid 2 of SEQ ID NO: 9 to an acidic amino acid. In some embodiments, the acidic amino acid comprises Aspartate, Glutamate, Asparagine, Glutamine, or combinations thereof. In certain embodiments, the acidic amino acid is Asparagine.

Also provided herein is an isolated antibody, or antigen binding portion thereof, which specifically binds to a human FAM19A5 protein, comprising a heavy chain CDR1, CDR2, and CDR3 and a light chain CDR1, CDR2, and CDR3, wherein: (i) the heavy chain CDR1 comprises the amino acid sequence set forth in SEQ ID NO: 5; (ii) the heavy chain CDR2 comprises the amino acid sequence set forth in SEQ ID NO: 13; (iii) the heavy chain CDR3 comprises the amino acid sequence set forth in SEQ ID NO: 7; (iv) the light chain CDR1 comprises the amino acid sequence set forth in SEQ ID NO: 8; (v) the light chain CDR2 comprises the amino acid sequence set forth in SEQ ID NO: 20; and (vi) the light chain CDR3 comprises the amino acid sequence set forth in SEQ ID NO: 10.

Provided herein is an isolated antibody, or antigen binding portion thereof, which specifically binds to a human FAM19A5 protein, comprising a heavy chain CDR1, CDR2, and CDR3 and a light chain CDR1, CDR2, and CDR3, wherein: (i) the heavy chain CDR1 comprises the amino acid sequence set forth in SEQ ID NO: 14; (ii) the heavy chain CDR2 comprises the amino acid sequence set forth in SEQ ID NO: 15; (iii) the heavy chain CDR3 comprises the amino acid sequence set forth in SEQ ID NO: 7; (iv) the light chain CDR1 comprises the amino acid sequence set forth in SEQ ID NO: 21; (v) the light chain CDR2 comprises the amino acid sequence set forth in SEQ ID NO: 22; and (vi) the light chain CDR3 comprises the amino acid sequence set forth in SEQ ID NO: 23.

Provided herein is an isolated antibody, or antigen binding portion thereof, which specifically binds to a human FAM19A5 protein, comprising a heavy chain CDR1, CDR2, and CDR3 and a light chain CDR1, CDR2, and CDR3, wherein: (i) the heavy chain CDR1 comprises the amino acid sequence set forth in SEQ ID NO: 14; (ii) the heavy chain CDR2 comprises the amino acid sequence set forth in SEQ ID NO: 15; (iii) the heavy chain CDR3 comprises the amino acid sequence set forth in SEQ ID NO: 7; (iv) the light chain CDR1 comprises the amino acid sequence set forth in SEQ ID NO: 21; (v) the light chain CDR2 comprises the amino acid sequence set forth in SEQ ID NO: 24; and (vi) the light chain CDR3 comprises the amino acid sequence set forth in SEQ ID NO: 23.

Provided herein is an isolated antibody, or antigen binding portion thereof, which specifically binds to a human FAM19A5 protein, comprising a heavy chain CDR1, CDR2, and CDR3 and a light chain CDR1, CDR2, and CDR3, wherein: (i) the heavy chain CDR1 comprises the amino acid sequence set forth in SEQ ID NO: 14; (ii) the heavy chain CDR2 comprises the amino acid sequence set forth in SEQ ID NO: 15; (iii) the heavy chain CDR3 comprises the amino acid sequence set forth in SEQ ID NO: 7; (iv) the light chain CDR1 comprises the amino acid sequence set forth in SEQ ID NO: 8; (v) the light chain CDR2 comprises the amino acid sequence set forth in SEQ ID NO: 25; and (vi) the light chain CDR3 comprises the amino acid sequence set forth in SEQ ID NO: 23.

Provided herein is an isolated antibody, or antigen binding portion thereof, which specifically binds to a human FAM19A5 protein, comprising a heavy chain CDR1, CDR2, and CDR3 and a light chain CDR1, CDR2, and CDR3, wherein: (i) the heavy chain CDR1 comprises the amino acid sequence set forth in SEQ ID NO: 14; (ii) the heavy chain CDR2 comprises the amino acid sequence set forth in SEQ ID NO: 15; (iii) the heavy chain CDR3 comprises the amino acid sequence set forth in SEQ ID NO: 7; (iv) the light chain CDR1 comprises the amino acid sequence set forth in SEQ ID NO: 8; (v) the light chain CDR2 comprises the amino acid sequence set forth in SEQ ID NO: 24; and (vi) the light chain CDR3 comprises the amino acid sequence set forth in SEQ ID NO: 23.

Provided herein is an isolated antibody, or antigen binding portion thereof, which specifically binds to a human FAM19A5 protein, comprising a heavy chain CDR1, CDR2, and CDR3 and a light chain CDR1, CDR2, and CDR3, wherein: (i) the heavy chain CDR1 comprises the amino acid sequence set forth in SEQ ID NO: 14; (ii) the heavy chain CDR2 comprises the amino acid sequence set forth in SEQ ID NO: 15; (iii) the heavy chain CDR3 comprises the amino acid sequence set forth in SEQ ID NO: 7; (iv) the light chain CDR1 comprises the amino acid sequence set forth in SEQ ID NO: 8; (v) the light chain CDR2 comprises the amino acid sequence set forth in SEQ ID NO: 26; and (vi) the light chain CDR3 comprises the amino acid sequence set forth in SEQ ID NO: 27.

Provided herein is an isolated antibody, or antigen binding portion thereof, which specifically binds to a human FAM19A5 protein, comprising a heavy chain CDR1, CDR2, and CDR3 and a light chain CDR1, CDR2, and CDR3, wherein: (i) the heavy chain CDR1 comprises the amino acid sequence set forth in SEQ ID NO: 14; (ii) the heavy chain CDR2 comprises the amino acid sequence set forth in SEQ ID NO: 15; (iii) the heavy chain CDR3 comprises the amino acid sequence set forth in SEQ ID NO: 7; (iv) the light chain CDR1 comprises the amino acid sequence set forth in SEQ ID NO: 8; (v) the light chain CDR2 comprises the amino acid sequence set forth in SEQ ID NO: 28; and (vi) the light chain CDR3 comprises the amino acid sequence set forth in SEQ ID NO: 29.

In some embodiments, an anti-FAM19A5 antibody disclosed herein comprises a heavy chain variable region (VH) and a light chain variable region (VL), wherein the VH comprises an amino acid sequence which is at least about 80%, at least about 85%, at least about 90%, at least about 95%, at least about 96%, at least about 97%, at least about 98%, at least about 99%, or about 100% identical to the amino acid sequence set forth in SEQ ID NO: 11 and/or wherein the VL comprises an amino acid sequence which is at least about 80%, at least about 85%, at least about 90%, at least about 95%, at least about 96%, at least about 97%, at least about 98%, at least about 99%, or about 100% identical to the amino acid sequence set forth in SEQ ID NO: 12.

In some embodiments, an anti-FAM19A5 antibody cross-competes with a reference antibody, which comprises a heavy chain variable region (VH) and a light chain variable region (VL), wherein: (a) the VH comprises the amino acid sequence set forth in SEQ ID NO: 33, and the VL comprises the amino acid sequence set forth in SEQ ID NO: 38; (b) the VH comprises the amino acid sequence set forth in SEQ ID NO: 34, and the VL comprises the amino acid sequence set forth in SEQ ID NO: 39; (c) the VH comprises the amino acid sequence set forth in SEQ ID NO: 34, and the VL comprises the amino acid sequence set forth in SEQ ID NO: 41; (d) the VH comprises the amino acid sequence set forth in SEQ ID NO: 34, and the VL comprises the amino acid sequence set forth in SEQ ID NO: 40; (e) the VH comprises the amino acid sequence set forth in SEQ ID NO: 34, and the VL comprises the amino acid sequence set forth in SEQ ID NO: 42; (f) the VH comprises the amino acid sequence set forth in SEQ ID NO: 34, and the VL comprises the amino acid sequence set forth in SEQ ID NO: 43; or (g) the VH comprises the amino acid sequence set forth in SEQ ID NO: 34, and the VL comprises the amino acid sequence set forth in SEQ ID NO: 44.

In some embodiments, an anti-FAM19A5 antibody disclosed herein binds to the same human FAM19A5 epitope as a reference antibody, which comprises a heavy chain variable region (VH) and a light chain variable region (VL), wherein: (a) the VH comprises the amino acid sequence set forth in SEQ ID NO: 33, and the VL comprises the amino acid sequence set forth in SEQ ID NO: 38; (b) the VH comprises the amino acid sequence set forth in SEQ ID NO: 34, and the VL comprises the amino acid sequence set forth in SEQ ID NO: 39; (c) the VH comprises the amino acid sequence set forth in SEQ ID NO: 34, and the VL comprises the amino acid sequence set forth in SEQ ID NO: 41; (d) the VH comprises the amino acid sequence set forth in SEQ ID NO: 34, and the VL comprises the amino acid sequence set forth in SEQ ID NO: 40; (e) the VH comprises the amino acid sequence set forth in SEQ ID NO: 34, and the VL comprises the amino acid sequence set forth in SEQ ID NO: 42; (f) the VH comprises the amino acid sequence set forth in SEQ ID NO: 34, and the VL comprises the amino acid sequence set forth in SEQ ID NO: 43; or (g) the VH comprises the amino acid sequence set forth in SEQ ID NO: 34, and the VL comprises the amino acid sequence set forth in SEQ ID NO: 44.

In some embodiments, the human FAM19A5 epitope comprises the amino acid sequence set forth in SEQ ID NO: 90, 91, or 92.

The present disclosure further provides an isolated antibody, or antigen binding portion thereof, which specifically binds a human family with sequence similarity 19, member A5 (FAM19A5) protein ("anti-FAM19A5 antibody"), comprising a heavy chain CDR1, CDR2, and CDR3 and a light chain CDR1, CDR2, and CDR3, wherein the heavy chain CDR1, CDR2, and CDR3 comprises the amino acid sequences set forth in SEQ ID NOs: 16, 17, and 18, respectively, each of which optionally comprising one, two, or three mutations, wherein the light chain CDR1, CDR2, and CDR3 comprise the amino acid sequences set forth in SEQ ID NOs: 30, 31, and 32, respectively, wherein at least one of the light chain CDR1, CDR2, and CDR3 comprises one, two, or three mutations, and wherein the antibody has a reduced immunogenicity in human and/or higher binding affinity to human FAM19A5 protein compared to a reference antibody comprising the VH set forth in SEQ ID NO: 35 and the VL set forth in SEQ ID NO: 45.

In some embodiments, the heavy chain CDR3 of an anti-FAM19A5 antibody comprises the amino acid sequence set forth in SEQ ID NO: 18, 128, or 129.

In some embodiments, the heavy chain CDR1 of an anti-FAM19A5 antibody comprises the amino acid sequence set forth in SEQ ID NO: 16. In other embodiments, the heavy chain CDR1 comprises the amino acid sequence set forth in SEQ ID NO: 19.

In some embodiments, the heavy chain CDR2 of an anti-FAM19A5 antibody comprises the amino acid sequence set forth in SEQ ID NO: 18.

In some embodiments, the light chain CDR3 of an anti-FAM19A5 antibody comprises the amino acid sequence set forth in SEQ ID NO: 32.

In some embodiments, the light chain CDR2 of an anti-FAM19A5 antibody comprises the amino acid sequence set forth in SEQ ID NO: 31.

In some embodiments, the light chain CDR1 of an anti-FAM19A5 antibody disclosed herein comprises the amino acid sequence set forth in SEQ ID NO: 30, with one mutation. In certain embodiments, the mutation comprises a substitution of Serine at amino acid 4 of SEQ ID NO: 30 to an aliphatic amino acid. In some embodiments, the aliphatic amino acid comprises Valine.

In some embodiments, an anti-FAM19A5 antibody disclosed herein comprises a heavy chain variable region (VH) and a light chain variable region (VL), wherein the VH comprises an amino acid sequence which is at least about 80%, at least about 85%, at least about 90%, at least about 95%, at least about 96%, at least about 97%, at least about 98%, at least about 99%, or about 100% identical to the amino acid sequence set forth in SEQ ID NO: 35 and/or wherein the VL comprises an amino acid sequence which is at least about 80%, at least about 85%, at least about 90%, at least about 95%, at least about 96%, at least about 97%, at least about 98%, at least about 99%, or about 100% identical to the amino acid sequence set forth in SEQ ID NO: 45.

In some embodiments, an anti-FAM19A5 antibody cross-competes with a reference antibody, which comprises a heavy chain variable region (VH) and a light chain variable region (VL), wherein the VH comprises the amino acid sequence set forth in SEQ ID NO: 36, and the VL comprises the amino acid sequence set forth in SEQ ID NO: 46. In other embodiments, an anti-FAM19A5 antibody cross-competes with a reference antibody, which comprises a heavy chain variable region (VH) and a light chain variable region (VL), wherein the VH comprises the amino acid sequence set forth in SEQ ID NO: 37, and the VL comprises the amino acid sequence set forth in SEQ ID NO: 46. In further embodiments, an anti-FAM19A5 antibody cross-competes with a reference antibody, which comprises a heavy chain variable region (VH) and a light chain variable region (VL), wherein the VH comprises the amino acid sequence set forth in SEQ ID NO: 130, and the VL comprises the amino acid sequence set forth in SEQ ID NO: 46. In some embodiments, an anti-FAM19A5 antibody cross-competes with a reference antibody, which comprises a heavy chain variable region (VH) and a light chain variable region (VL), wherein the VH comprises the amino acid sequence set forth in SEQ ID NO: 131, and the VL comprises the amino acid sequence set forth in SEQ ID NO: 46.

In some embodiments, an anti-FAM19A5 antibody is selected from the group consisting of an IgG1, IgG2, IgG3, IgG4, a variant thereof, and any combination thereof. In certain embodiments, an anti-FAM19A5 antibody is a chimeric antibody, a human antibody, or a humanized antibody. In some embodiments, an anti-FAM19A5 antibody comprises a Fab, a Fab', a F(ab')2, a Fv, or a single chain Fv (scFv).

In some embodiments, an anti-FAM19A5 antibody disclosed herein is a scFv. In certain embodiments, the scFv comprises a VH and a VL, wherein: (a) the VH comprises the amino acid sequence set forth in SEQ ID NO: 33, and the VL comprises the amino acid sequence set forth in SEQ ID NO: 38; (b) the VH comprises the amino acid sequence set forth in SEQ ID NO: 34, and the VL comprises the amino acid sequence set forth in SEQ ID NO: 39; (c) the VH comprises the amino acid sequence set forth in SEQ ID NO: 34, and the VL comprises the amino acid sequence set forth in SEQ ID NO: 41; (d) the VH comprises the amino acid sequence set forth in SEQ ID NO: 34, and the VL comprises the amino acid sequence set forth in SEQ ID NO: 40; (e) the VH comprises the amino acid sequence set forth in SEQ ID NO: 34, and the VL comprises the amino acid sequence set forth in SEQ ID NO: 42; (f) the VH comprises the amino acid sequence set forth in SEQ ID NO: 34, and the VL comprises the amino acid sequence set forth in SEQ ID NO: 43; (g) the VH comprises the amino acid sequence set forth in SEQ ID NO: 34, and the VL comprises the amino acid sequence set forth in SEQ ID NO: 44; (h) the VH comprises the amino acid sequence set forth in SEQ ID NO: 36, and the VL comprises the amino acid sequence set forth in SEQ ID NO: 46; (i) the VH comprises the amino acid sequence set forth in SEQ ID NO: 37, and the VL comprises the amino acid sequence set forth in SEQ ID NO: 46; (j) the VH comprises the amino acid sequence set forth in SEQ ID NO: 130, and the VL comprises the amino acid sequence set forth in SEQ ID NO: 46; or (k) the VH comprises the amino acid sequence set forth in SEQ ID NO: 131, and the VL comprises the amino acid sequence set forth in SEQ ID NO: 46.

In some embodiments, an anti-FAM19A5 antibody exhibits one or more of the following properties: (a) binds to soluble human FAM19A5 with a KD of 10 nM or less as measured by enzyme-linked immunosorbent assay (ELISA); (b) binds to membrane bound human FAM19A5 with a KD of 10 nM or less as measured by ELISA; (c) reduces, reverses, delays, and/or prevents an onset of reactive gliosis; (d) suppresses an excessive proliferation of reactive astrocytes; (e) decreases expression of chondroitin sulfate proteoglycans including neurocan and neuron-glial antigen 2 (NG2); (f) increases expression of c-fos and pERK in the nucleus of neurons; (g) promotes survival of neurons; (h) increases expression of GAP43 in neurons; (i) promotes regrowth of an axon; (j) induces normalization of blood vessels, e.g., in a tumor; (k) suppresses growth of a tumor; (1) enhances infiltration of immune cells into a tumor; (m) enhances infiltration of neuronal cells into a tumor; (n) enhances phagocytic activity of a macrophage or a microglia; (o) increases a mitochondrial membrane potential of a macrophage or a microglia; (p) reduces recruitment of myeloid-derive suppressor cells (MDSCs) to a tumor; (q) reduces necrosis and edema in a tumor; (r) reduces tissue permeability of a tumor; and (s) increases a blood flow rate in a tumor.

Also provided herein are nucleic acids encoding the anti-FAM19A5 antibodies disclosed herein, vectors comprising the nucleic acid, cells comprising the vector, and immunoconjugates comprising the anti-FAM19A5 antibodies of the present disclosure. Compositions comprising the anti-FAM19A5 antibodies, the nucleic acids, the vectors, the cells, or the immunoconjugates of the present disclosure, and a carrier are also disclosed herein. The present disclosure also provides kits comprising anti-FAM19A5 antibodies, the nucleic acids, the vectors, the cells, or the immunoconjugates of the present disclosure, and an instruction for use.

Provided herein is also a method of producing an antibody which specifically binds to a human FAM19A5 protein, comprising culturing the cells disclosed herein under suitable conditions and isolating the antibody.

The present disclosure further provides a method of treating a disease or condition in a subject in need thereof, comprising administering the anti-FAM19A5 antibody, the nucleic acid, the vector, the cell, or the immunoconjugate described herein. In some embodiments, the disease or condition comprises a tumor, a fibrosis, a glaucoma, a mood disorder, a retinopathy, an age-related macular degeneration, or a neuropathic pain. In certain embodiments, the disease or condition is a tumor.

In some embodiments, the tumor comprises a melanoma, pancreatic cancer, glioma, breast cancer, lymphoma, lung cancer, kidney cancer, prostate cancer, fibrosarcoma, colon adenocarcinoma, liver cancer, or ovarian cancer. In certain embodiments, the glioma is glioblastoma multiforme (GBM).

In some embodiments, the anti-FAM19A5 antibody, the nucleic acid, the vector, the cell, or the immunoconjugate of the present disclosure induces a normalization of blood vessels. In certain embodiments, the normalization of blood vessels is accompanied by changes in properties of the blood vessels comprising increased connectivity, increased wall thickness, reduced vessel diameter, more regular vessel direction and distribution pattern, increased vessel number, reduction of leakage and permeability, increased pericyte coverage and proximity on the blood vessels, increased oxygenation, or combinations thereof.

In some embodiments, the anti-FAM19A5 antibody, the nucleic acid, the vector, the cell, or the immunoconjugate of the present disclosure suppresses growth of the tumor. In some embodiments, the anti-FAM19A5 antibody, the nucleic acid, the vector, the cell, or the immunoconjugate disclosed herein enhances infiltration of immune cells into the tumor. In certain embodiments, the immune cells comprise macrophages, dendritic cells, T lymphocytes, B lymphocytes, natural killer (NK) cells, or combinations thereof. In some embodiments, the immune cells further display hypertrophy. In some embodiments, the enhanced infiltration of immune cells into the tumor is accompanied by increased infiltration of neuronal cells into the tumor. In certain embodiments, the neuronal cells comprise astrocytes, glial cells, or combinations thereof.

In some embodiments, the anti-FAM19A5 antibody, the nucleic acid, the vector, the cell, or the immunoconjugate enhances phagocytic activity of a macrophage or a microglia. In some embodiments, the anti-FAM19A5 antibody, the nucleic acid, the vector, the cell, or the immunoconjugate increases a mitochondrial membrane potential of a macrophage or microglia.

In some embodiments, the anti-FAM19A5 antibody, the nucleic acid, the vector, the cell, or the immunoconjugate disclosed herein reduces recruitment of myeloid-derived suppressor cells (MDSCs) to the tumor. In some embodiments, the anti-FAM19A5 antibody, the nucleic acid, the vector, the cell, or the immunoconjugate reduces necrosis and edema in the tumor. In some embodiments, the anti-FAM19A5 antibody, the nucleic acid, the vector, the cell, or the immunoconjugate reduces tissue permeability of the tumor. In some embodiments, the anti-FAM19A5 antibody, the nucleic acid, the vector, the cell, or the immunoconjugate increases blood flow rate in the tumor.

In some embodiments, the method of treating a disease or disorder further comprises administering an additional therapeutic agent. In certain embodiments, the additional therapeutic agent comprises a chemotherapy, immunotherapy, radiotherapy, or combinations thereof.

BRIEF DESCRIPTION OF THE DRAWINGS

FIGS. 1A, 1B, and 1C show the analysis of 96 clones from the 4$^{th}$ round, 5$^{th}$ round, or 5$^{th}$ round biopanning derived from the first chicken, the second chicken, and the third chicken, respectively. For each of the clones shown in FIGS. 1A, 1B, and 1C, the vertical bars correspond to FAM19A5 protein, negative control protein, hemagglutinin protein, and BSA (going from left to right). In each of FIGS. 1A, 1B, and 1C, the boxed clones are those 8 clones that were selected for further analysis (see Example 4).

In FIG. 2B, for each of the antibodies shown, the bar on the left represent binding of the antibodies to FAM19A5 protein. The bar on the right represents the negative control (measured binding in the presence of the blocking buffer alone, i.e., no recombinant FAM19A5 protein). The column labeled as "2$^{nd}$ only" represents another negative control to show background level of the assay (measured binding in the absence of the primary anti-FAM19A5 antibodies).

FIG. 4 provides the amino acid sequences of epitopes F1-F6 (conjugated to BSA) and their location on the human FAM19A5 polypeptide. The top amino acid sequence shown is the wild-type FAM19A5 isoform 2 (without the signal peptide) (SEQ ID NO: 101). The second amino acid sequence shown is the same sequence but the cysteine residues were mutated to serine to reduce nonspecific activity during peptide synthesis (SEQ ID NO: 138). The different epitope fragments shown include: F1 (SEQ ID NO: 139), F2 (SEQ ID NO: 140), F3 (SEQ ID NO: 141), F4 (SEQ ID NO: 142), F5 (SEQ ID NO: 143), and F6 (SEQ ID NO: 144).

FIGS. 6A, 6B, 6C, and 6D show the results for the following antibodies generated in HEK293F cells: (A) wild-type 3-2 antibody, (B) 1-30 antibody, (C) 1-32 antibody, and (D) 6-10 antibody, respectively. FIGS. 6E, 6F, 6G, 6H, 6I, and 6J show the results for the following antibodies generated in CHO cells: (E) 1-17 antibody, (F) 1-30 antibody, (G) 1-32 antibody, (H) 4-11 antibody, (I) 6-10 antibody, and (J) low-PI antibody, respectively. As discussed in Example 7, mutant peptides were generated, wherein each of the mutant peptide had an alanine substitution at a single amino acid residue within the epitope fragment F2. Binding of the antibodies to the different mutant peptides was measured using ELISA.

FIG. 9A provides a schematic showing where the different amino acid mutations were made to de-immunize the 3-2 antibody. FIG. 9B provides a sequence comparison of the light chain variable region (VL) and heavy chain variable region (VH) among the following: (i) wild-type 3-2 antibody ("clone 3-2") (VL=SEQ ID NO: 12; VH=SEQ ID NO: 11), (ii) completely de-immunized 3-2 antibody ("fully de-immunized clone 3-2") (VL=SEQ ID NO: 38; VH=SEQ ID NO: 150), and (iii) de-immunized except at one amino acid within the heavy chain CDR2) antibody ("de-immunized clone 3-2") (VL=SEQ ID NO: 38; VH=SEQ ID NO: 33). Additional sequences shown in FIG. 9B include: (a) immunoglobulin lambda variable 1-51 (IGLV1-51*02) (SEQ ID NO: 145), (b) immunoglobulin lambda joining 2 (IGLJ2*01) (SEQ ID NO: 146), (c) immunoglobulin heavy variable 3-64 (IGHV3-64*04) (SEQ ID NO: 147), and (d) immunoglobulin heavy joining 1 (IGHJ1*01) (SEQ ID NO: 148). Amino acid residues with high and moderate immunogenicity potential, as determined by ITOPE™ analysis, are boxed and indicated with "1" and "2," respectively. FIG. 9C shows a comparison of the binding of the (i) wild-type 3-2 antibody, (ii) completely de-immunized 3-2 antibody, and (iii) de-immunized except at one amino acid with the heavy chain CDR2 ("deimmunized clone-3-2") antibody to FAM19A5 protein, as measured by ELISA. Each single chain variable fragment (scFv) displaying phage was added to the wells of a microtiter plate coated with FAM19A5 (■) or anti-HA antibody (□). The background signal was measured in control wells that were coated with BSA. The wells were probed with HRP-conjugated anti-M13 antibody. Absorbance at 405 nm was measured. The results are shown as the mean f SD acquired from experiments conducted in quadruplicate.

FIG. 10A provides a comparison of the light chain variable region (VL) (top three rows) and heavy chain variable region (VH) (bottom three rows) for the two de-immunized 2-13 antibodies to wild-type 2-13 antibody ("clone 2-13"). The sequences provided in FIG. 10A are as follows: (a) clone 2-13 VL (SEQ ID NO: 45), (b) immunoglobulin lambda variable 3-27 (IGLV3-27*01) (SEQ ID NO: 149), (c) immunoglobulin lambda joining 2 (IGLJ2*01) (SEQ ID NO: 146), (d) fully de-immunized clone 2-13 VL (SEQ ID NO: 46), (e) de-immunized clone 2-13 VL (SEQ ID NO: 46), (f) clone 2-13 VH (SEQ ID NO: 35), (g) immunoglobulin heavy variable 3-64 (IGHV3-64*04) (SEQ ID NO: 147), (h) immunoglobulin heavy joining 1 (IGHJ1*01) (SEQ ID NO: 148), (i) fully de-immunized clone 2-13 VH (SEQ ID NO: 151), and (j) de-immunized clone 2-13 VH (SEQ ID NO: 36). Amino acid residues with high and moderate immunogenicity potential, as determined by ITOPE™ analysis, are boxed and indicated with "1" and "2," respectively. FIG. 10B shows a comparison of the binding of the (i) wild-type 2-13 antibody, (ii) completely de-immunized 2-13 antibody, and (iii) de-immunized except at one amino acid with the heavy chain CDR2 (deimmunized clone 2-13) antibody to FAM19A5 protein, as measured by ELISA. Each single chain variable fragment (scFv) displaying phage was added to the wells of a microtiter plate coated with FAM19A5 (■) or anti-HA antibody (□). The background signal was measured in control wells that were coated with BSA. The wells were probed with HRP-conjugated anti-M13 antibody. Absorbance at 405 nm was measured. The results are shown as the mean±SD acquired from experiments conducted in quadruplicate.

1-30, (iv) 1-32, (v) 4-11, and (vi) 6-10. FIG. 13A shows the binding analysis of the antibodies to FAM19A5 protein. The results are shown as the mean f SD. FIG. 13B shows the solubility (CamSol score) and hydrophobicity (GRAVY score) data.

FIGS. 16A and 16B show the results using SDS-PAGE for the antibodies from cultured media and purified protein. FIG. 16C shows the results using Western Blot. In each of FIGS. 16A, 16B, and 16C, lanes "1" and "2" correspond to antibodies 2-13D-37-1.5W-41 and 2-13D-37-3W-16, respectively. Within lanes "1" and "2," "A" and "B" correspond to before centrifugation and after centrifugation, respectively. In FIG. 16B, the left panel shows a reducing SDS-PAGE and the right panel shows a non-reducing SDS-PAGE.

FIG. 17A shows the amino acid sequence alignment of the light chain variable region (top three boxes) and the heavy chain variable region (bottom three boxes) for the following antibodies: deimmunized clone 2-13D-37, deimmunized clone 2-13D-37-1.5W-41, and deimmunized clone 2-13D-37-3W-16. The specific VL and VH sequences for the following antibodies are provided: (a) clone 2-13D-37 (SEQ ID NOs: 46 and 37, respectively), (b) clone 2-13D-37-1.5W-41 (SEQ ID NOs: 46 and 130, respectively), and (c) clone 2-13D-37-3W-16 (SEQ ID NOs: 46 and 131, respectively). Amino acid residues with high and moderate immunogenicity potential, as determined by ITOPE™ analysis, are boxed and indicated with "1" and "2," respectively. Other amino acid residues of interest are also noted: "3"=potential tryptophan or methionine oxidation; "4"=potential asparagine deamidation; "5"=potential aspartate isomerization; and "6"=non-canonical cysteine pair. Such amino acid residues can lead to product variants during natural cellular processing and degradation events. FIG. 17B shows the binding analysis of deimmunized clone 2-13D-37, deimmunized clone 2-13D-37-1.5W-41 and deimmunized clone 2-13D-37-3W-16 to FAM19A5 protein. Each single chain variable fragment (scFv) displaying phage was added to the wells of a microtiter plate coated with FAM19A5 (■) or anti-HA antibody (□). The background signal was measured in control wells that were coated with BSA. The wells were probed with HRP-conjugated anti-M13 antibody. Absorbance at 405 nm was measured.

FIG. 19 provides a table summarizing the percent coverage achieved with different experimental conditions tested for the HDX-MS assay described in Example 11. One or more of the following parameters were adjusted: (i) sample concentration, (ii) quench condition, (iii) pepsin concentration and/or duration of digestion, and (v) quench hold time (minutes). Depending on the analysis, C18 or C8 pepsin immobilized columns were used with either on-line (on) or off-line (off) digestion, as indicated in FIG. 19.

FIGS. 20A and 20B provide the results of pepsin digestion of FAM19A5 protein using the optimized conditions described in Example 11. FIG. 20A shows the percent coverage and redundancy of the 44 peptides that were identified relative to the mature FAM19A5 protein (SEQ ID NO: 101, i.e., SEQ ID NO: 2 minus the signal peptide, which corresponds to the first 25 amino acids). Each of the horizontal bars represents an individual peptide. FIG. 20B provides the amino acid sequences of the 44 peptides, including their start and end site relative to SEQ ID NO: 101, single ion mass (MHP), and retention time (RT). The sequences of the 44 peptides are as follows: (1) FLKEGQL (SEQ ID NO: 102), (2) FLKEGQLAAGTCE (SEQ ID NO: 103), (3) LKEGQLAAG (SEQ ID NO: 104), (4) LKEGQLAAGTCE (SEQ ID NO: 152), (5) LKEGQLAAGTCEI (SEQ ID NO: 105), (6) LKEGQLAAGTCEIVTL (SEQ ID NO: 106), (7) KEGQLAAGTCEIVTLDRDS (SEQ ID NO:

153), (8) AAGTCEI (SEQ ID NO: 107), (9) DRDSSQPPRTIARQTARC (SEQ ID NO: 154), (10) RDSSQPPRTIARQTARCAC (SEQ ID NO: 108), (11) QPPRTIARQTA (SEQ ID NO: 109), (12) PRTIARQTARCA (SEQ ID NO: 155), (13) PRTIARQTARCACRK (SEQ ID NO: 156), (14) TARCACRKGQIAGTTRARPACVD (SEQ ID NO: 157), (15) ARCACRKGQI (SEQ ID NO: 158), (16) ACRKGQIAGTTRARPAC (SEQ ID NO: 110), (17) ACRKGQIAGTTRARPACVD (SEQ ID NO: 111), (18) ACRKGQIAGTTRARPACVDA (SEQ ID NO: 112), (19) CRKGQIAGTTRARPAC (SEQ ID NO: 159), (20) RKGQIAGTTRARPACVD (SEQ ID NO: 160), (21) IAGTTRARPA (SEQ ID NO: 161), (22) GTTRARPACVDA (SEQ ID NO: 162), (23) VDARIIKTKQWCDM (SEQ ID NO: 163), (24) ARIIKTKQWC (SEQ ID NO: 113), (25) ARIIKTKQWCDM (SEQ ID NO: 114), (26) ARIIKTKQWCDML (SEQ ID NO: 115), (27) ARIIKTKQWCDMLPCL (SEQ ID NO: 116), (28) RIIKTKQWCDM (SEQ ID NO: 117), (29) RIIKTKQWCDML (SEQ ID NO: 118), (30) IKTKQWCDML (SEQ ID NO: 164), (31) WCDMLPCL (SEQ ID NO: 119), (32) LPCLEGEG (SEQ ID NO: 120), (33) PCLEGEG (SEQ ID NO: 121), (34) PCLEGEGCD (SEQ ID NO: 122), (35) PCLEGEGCDL (SEQ ID NO: 123), (36) PCLEGEGCDLLINRSGWTCTQPGGR (SEQ ID NO: 165), (37) EGEGCDL (SEQ ID NO: 124), (38) EGEGCDLL (SEQ ID NO: 125), (39) LLINRSGWTCTQPGGRIKTTT (SEQ ID NO: 126), (40) LINRSGWTCTQPGGRIKTTT (SEQ ID NO: 127), (41) INRSGWTCTQPGGRIKTTT (SEQ ID NO: 166), (42) NRSGWTCTQPGGRIKTTT (SEQ ID NO: 167), (43) TCTQPGGRIKTTT (SEQ ID NO: 168), and (44) TQPGGRIKTTT (SEQ ID NO: 169).

Figure 21:
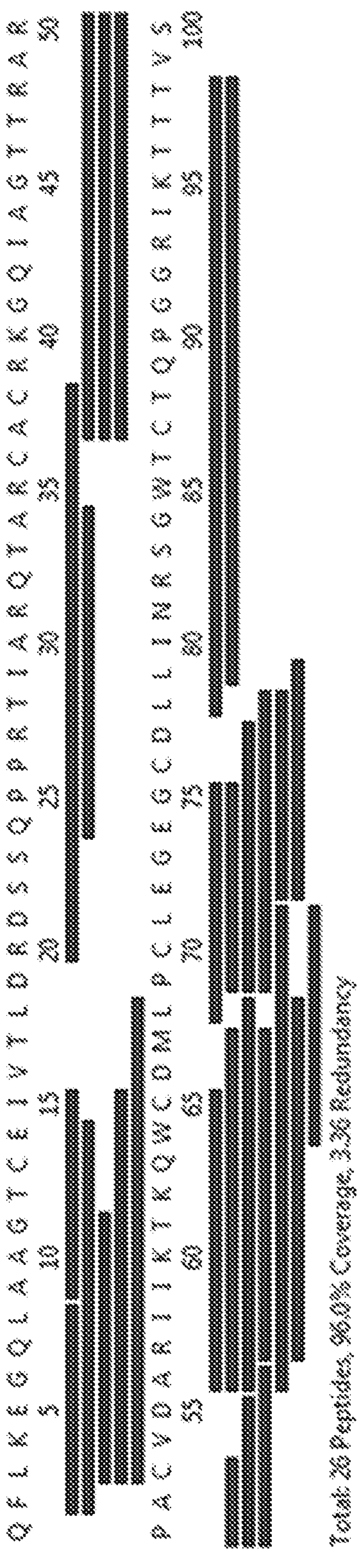

FIG. 21 shows the percent coverage and redundancy of the 22 peptides that were identified with pepsin digestion of FAM19A5 protein after deuterium labeling, as described in Example 11. Each of the horizontal bars represents an individual peptide. Total peptides shown include: (1) FLKEGQL (SEQ ID NO: 102), (2) AAGTCEI (SEQ ID NO: 107), (3) FLKEGQLAAGTCE (SEQ ID NO: 103), (4) LKEGQLAAG (SEQ ID NO: 104), (5) LKEGQLAAGTCEI (SEQ ID NO: 105), (6) LKEGQLAAGTCEIVTL (SEQ ID NO: 106), (7) RDSSQPPRTIARQTARCAC (SEQ ID NO: 108), (8) QPPRTIARQTA (SEQ ID NO: 109), (9) ACRKGQIAGTTRARPAC (SEQ ID NO: 110), (10) ACRKGQIAGTTRARPACVD (SEQ ID NO: 111), (11) ACRKGQIAGTTRARPACVDA (SEQ ID NO: 112), (12) ARIIKTKQWC (SEQ ID NO: 113), (13) ARIIKTKQWCDM (SEQ ID NO: 114), (14) ARIIKTKQWCDML (SEQ ID NO: 115), (15) RIIKTKQWCDM (SEQ ID NO: 117), (16) ARIIKTKQWCDMLPCL (SEQ ID NO: 116), (17) RIIKTKQWCDML (SEQ ID NO: 118), (18) WCDMLPCL (SEQ ID NO: 119), (19) LPCLEGEG (SEQ ID NO: 120), (20) PCLEGEG (SEQ ID NO: 121), (21) PCLEGEGCD (SEQ ID NO: 122), (22) PCLEGEGCDL (SEQ ID NO: 123), (23) EGEGCDL (SEQ ID NO: 124), (24) EGEGCDLL (SEQ ID NO: 125), (25) LLINRSGWTCTQPGGRIKTTT (SEQ ID NO: 126), and (26) LINRSGWTCTQPGGRIKTTT (SEQ ID NO: 127).

Figure 22A:
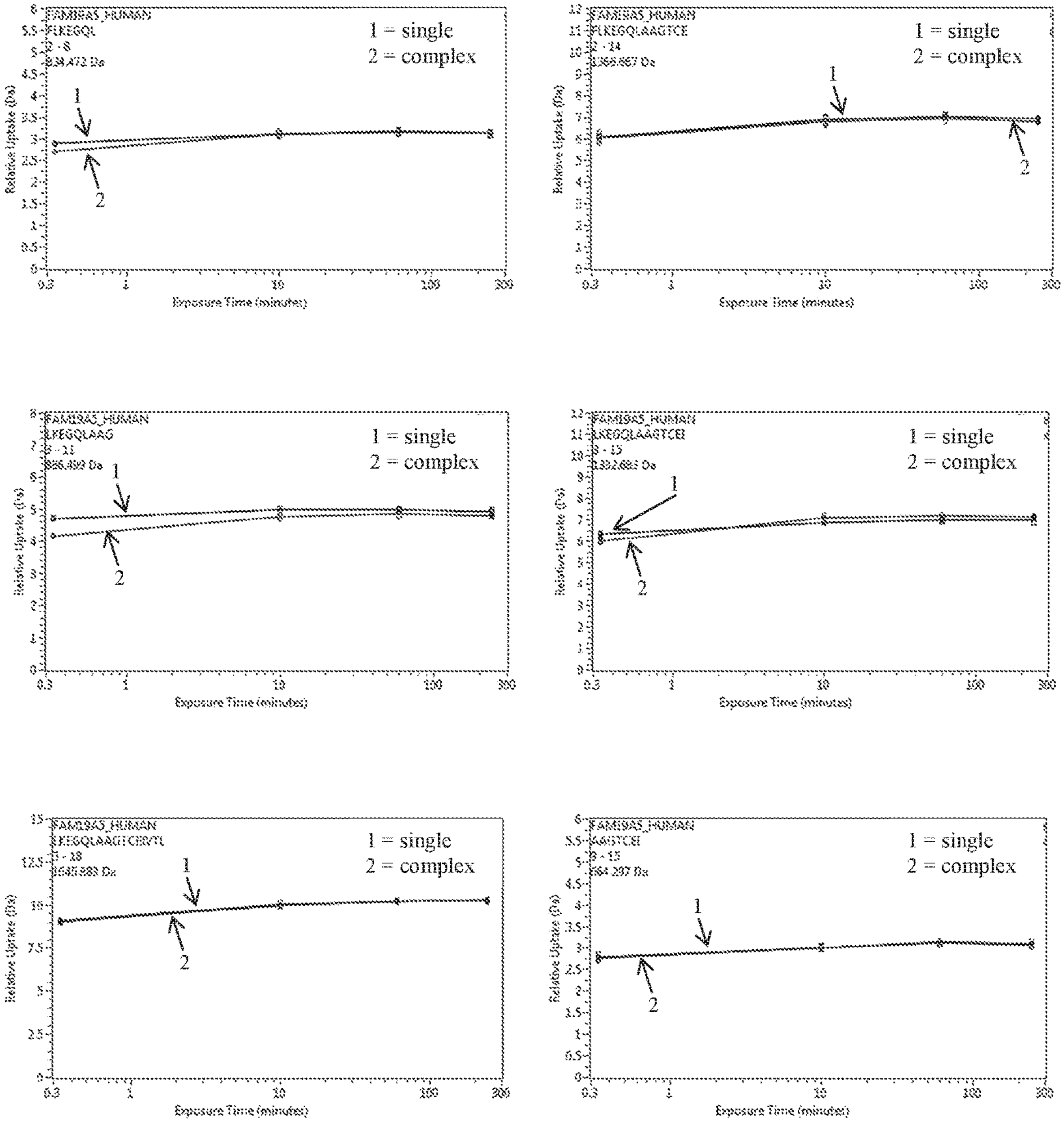
Figure 22B:
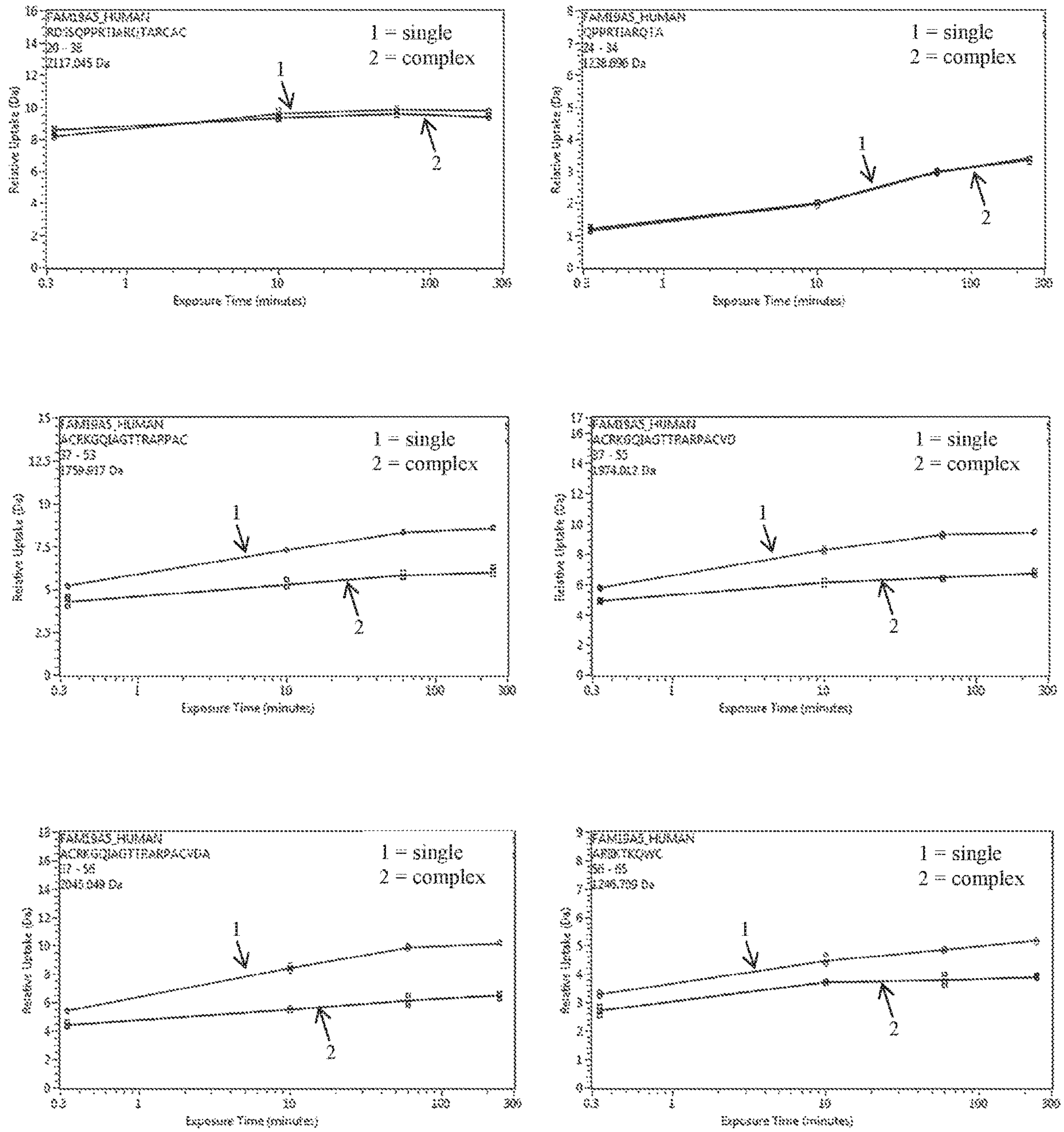
Figure 22C:
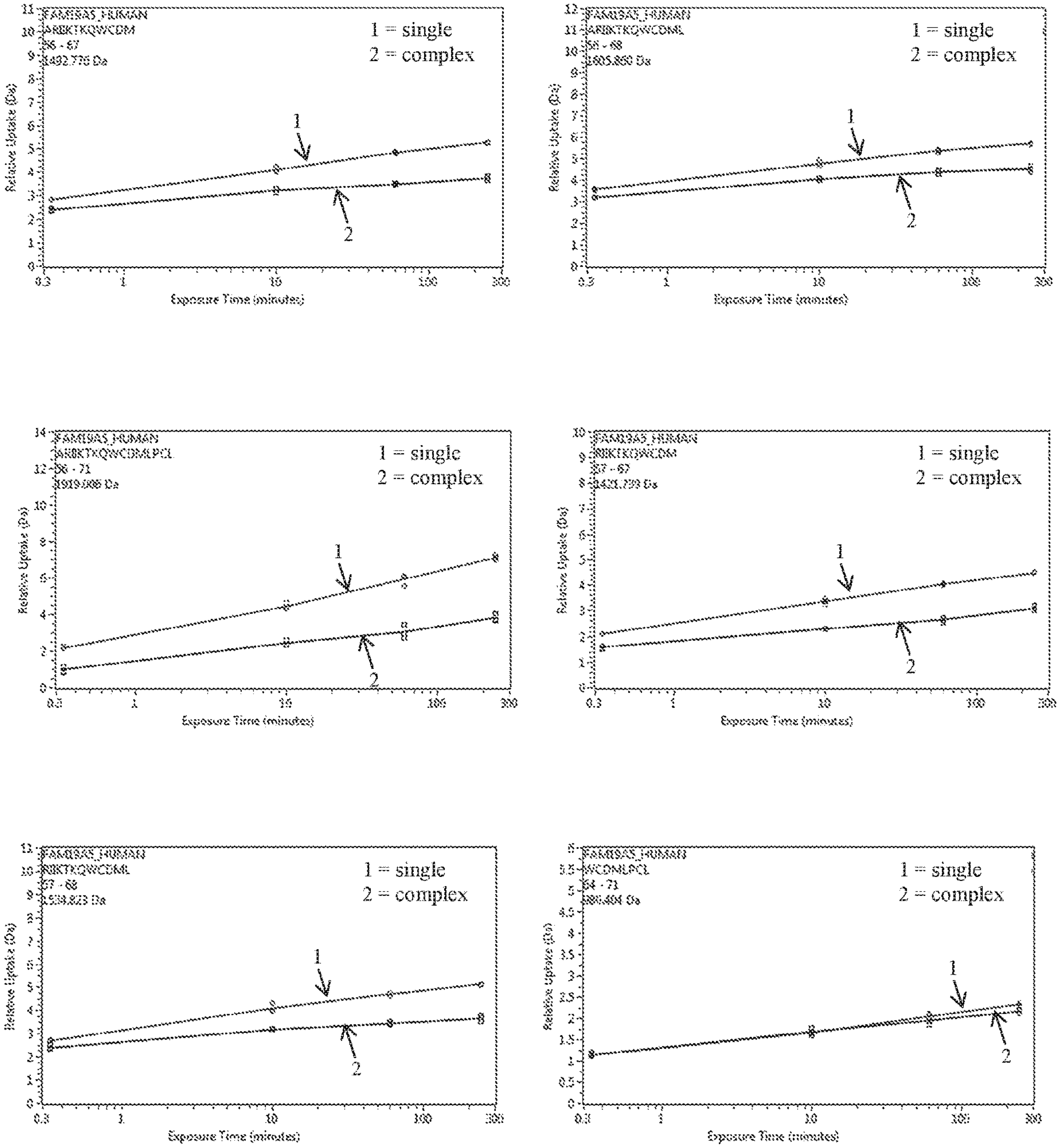
Figure 22D:
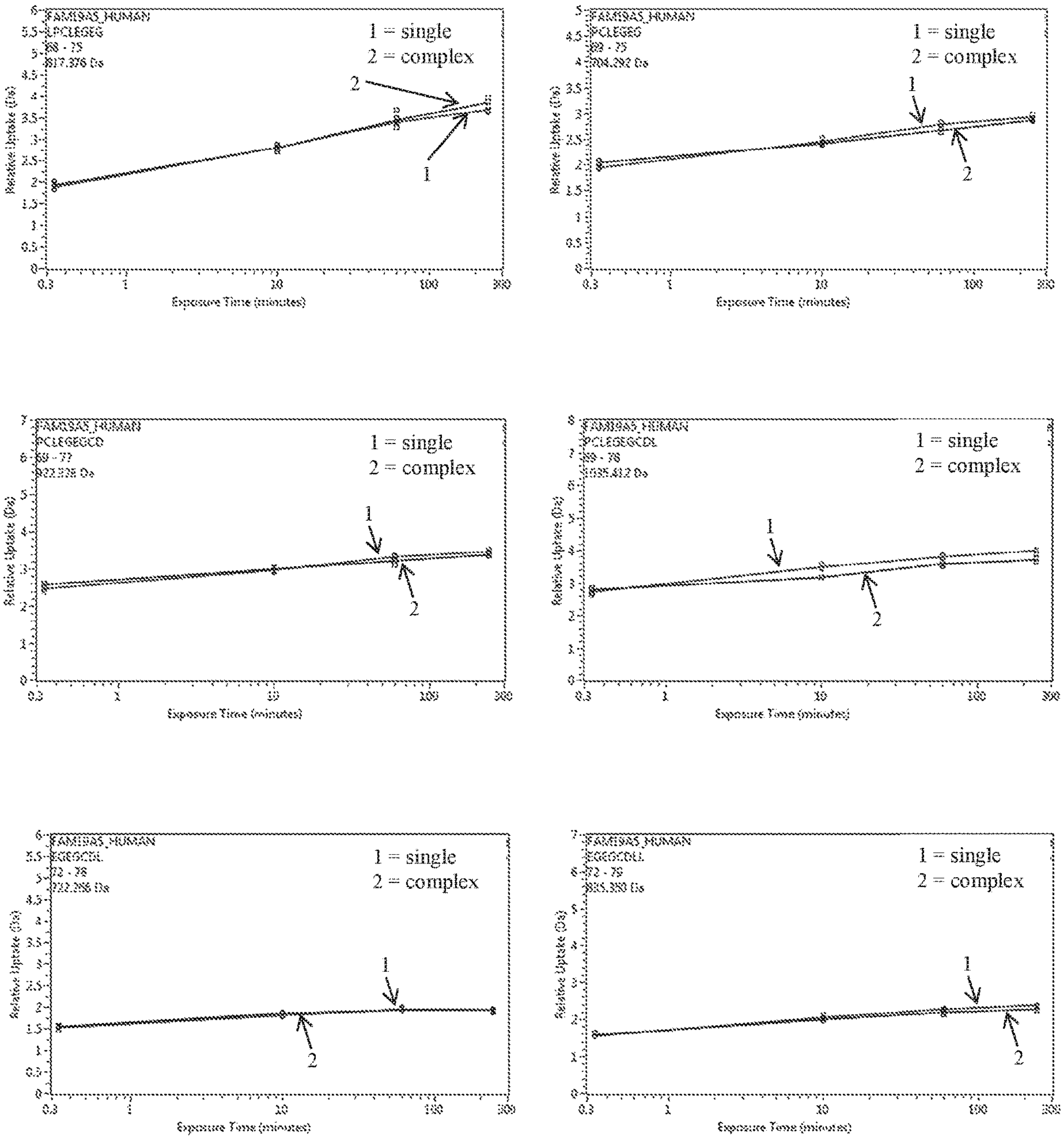
Figure 22E:
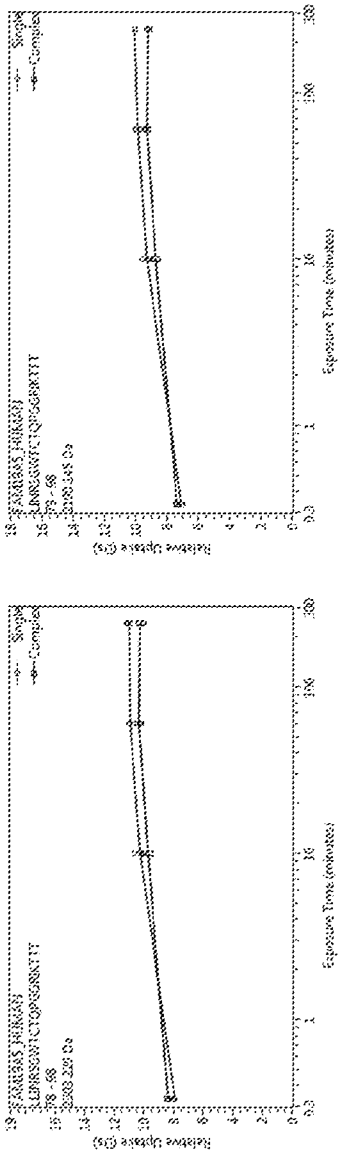

FIGS. 22A, 22B, 22C, 22D, and 22E provides comparison of deuterium uptake between single (antigen alone, "1") and antigen-antibody (2-13) complex ("2") as a function of time. The y-axis shows the maximum deuterium uptake (if the peptide contained Proline, the maximum value was [(number of amino acids−1)−(number of proline)]). The x-axis provides the duration of the deuterium labeling. FIG. 22A provides data for the following peptides: (i) FLKEGQL (SEQ ID NO: 102) (upper left graph), (ii) FLKEGQLAAGTCE (SEQ ID NO: 103) (upper right graph), (iii) LKEGQLAAG (SEQ ID NO: 104) (middle left graph), (iv) LKEGQLAAGTCEI (SEQ ID NO: 105) (middle right graph), (v) LKEGQLAAGTCEIVTL (SEQ ID NO: 106) (bottom left graph), and (vi) AAGTCEI (SEQ ID NO: 107) (bottom right graph). FIG. 22B provides data for the following peptides: (i) RDSSQPPRTIARQTARCAC (SEQ ID NO: 108) (upper left graph), (ii) QPPRTIARQTA (SEQ ID NO: 109) (upper right graph), (iii) ACRKGQIAGTTRARPAC (SEQ ID NO: 110) (middle left graph), (iv) ACRKGQIAGTTRARPACVD (SEQ ID NO: 111) (middle right graph), (v) ACRKGQIAGTTRARPACVDA (SEQ ID NO: 112) (bottom left graph), and (vi) ARIIKTKQWC (SEQ ID NO: 113) (bottom right graph). FIG. 22C provides data for the following peptides: (i) ARIIKTKQWCDM (SEQ ID NO: 114) (upper left graph), (ii) ARIIKTKQWCDML (SEQ ID NO: 115) (upper right graph), (iii) ARIIKTKQWCDMLPCL (SEQ ID NO: 116) (middle left graph), (iv) RIIKTKQWCDM (SEQ ID NO: 117) (middle right graph), (v) RIIKTKQWCDML (SEQ ID NO: 118) (bottom left graph), and (vi) WCDMLPCL (SEQ ID NO: 119) (bottom right graph). FIG. 22D provides data for the following peptides: (i) LPCLEGEG (SEQ ID NO: 120) (upper left graph), (ii) PCLEGEG (SEQ ID NO: 121) (upper right graph), (iii) PCLEGEGCD (SEQ ID NO: 122) (middle left graph), (iv) PCLEGEGCDL (SEQ ID NO: 123) (middle right graph), (v) EGEGCDL (SEQ ID NO: 124) (bottom left graph), and (vi) EGEGCDLL (SEQ ID NO: 125) (bottom right graph). FIG. 22E provides data for the following peptides: (i) LLINRSGWTCTQPGGRIKTTT (SEQ ID NO: 126) (left graph) and (ii) LINRSGWTCTQPGGRIKTTT (SEQ ID NO: 127) (right graph). In each of the graphs, additional information regarding the peptides (i.e., start and end site (of SEQ ID NO: 101, i.e., SEQ ID NO: 2 minus the signal peptide, which corresponds to the first 25 amino acids) and size) are provided in the upper corner of each graph.

Figure 23A:
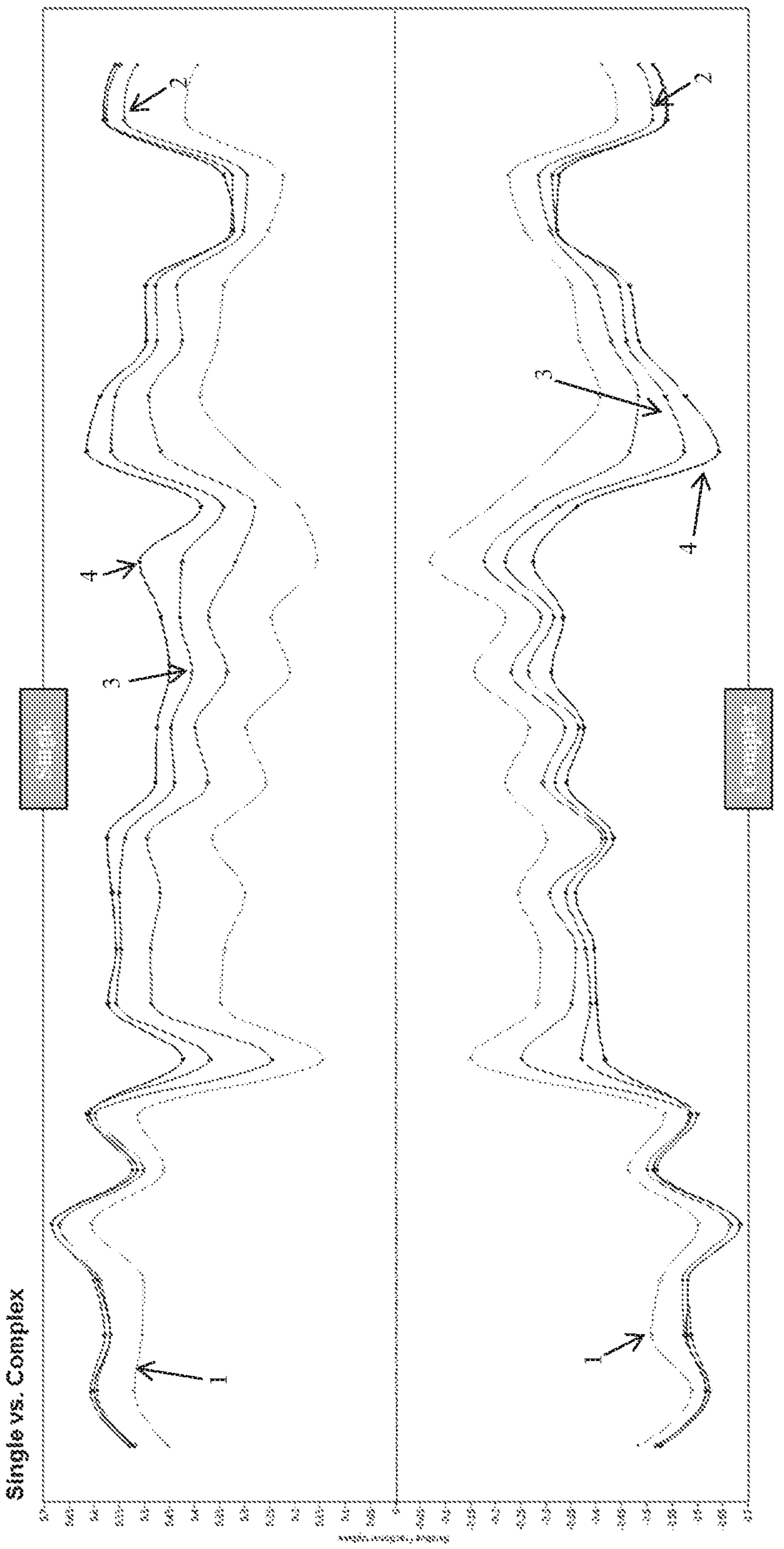
Figure 23B:
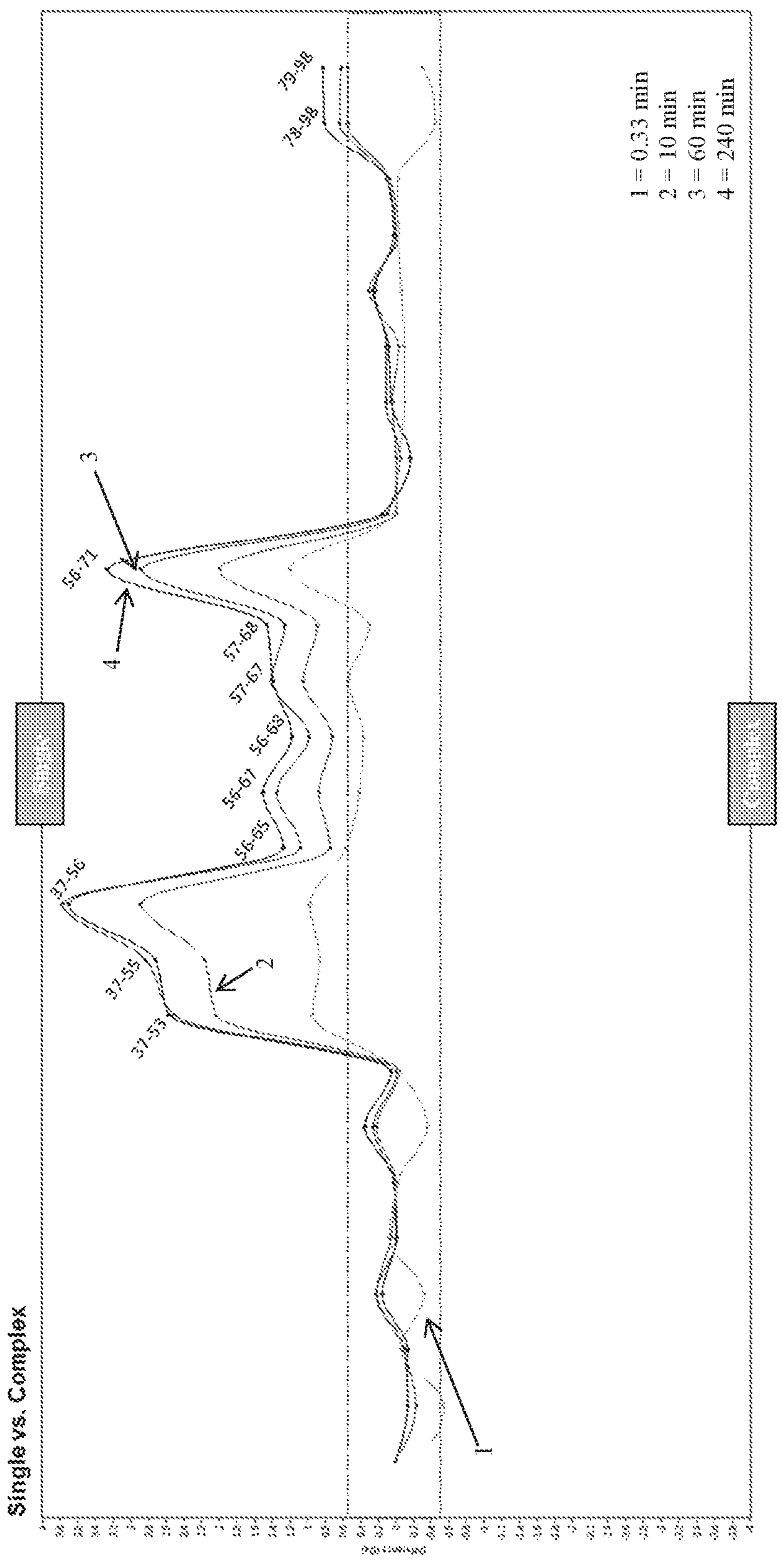
Figure 23C:
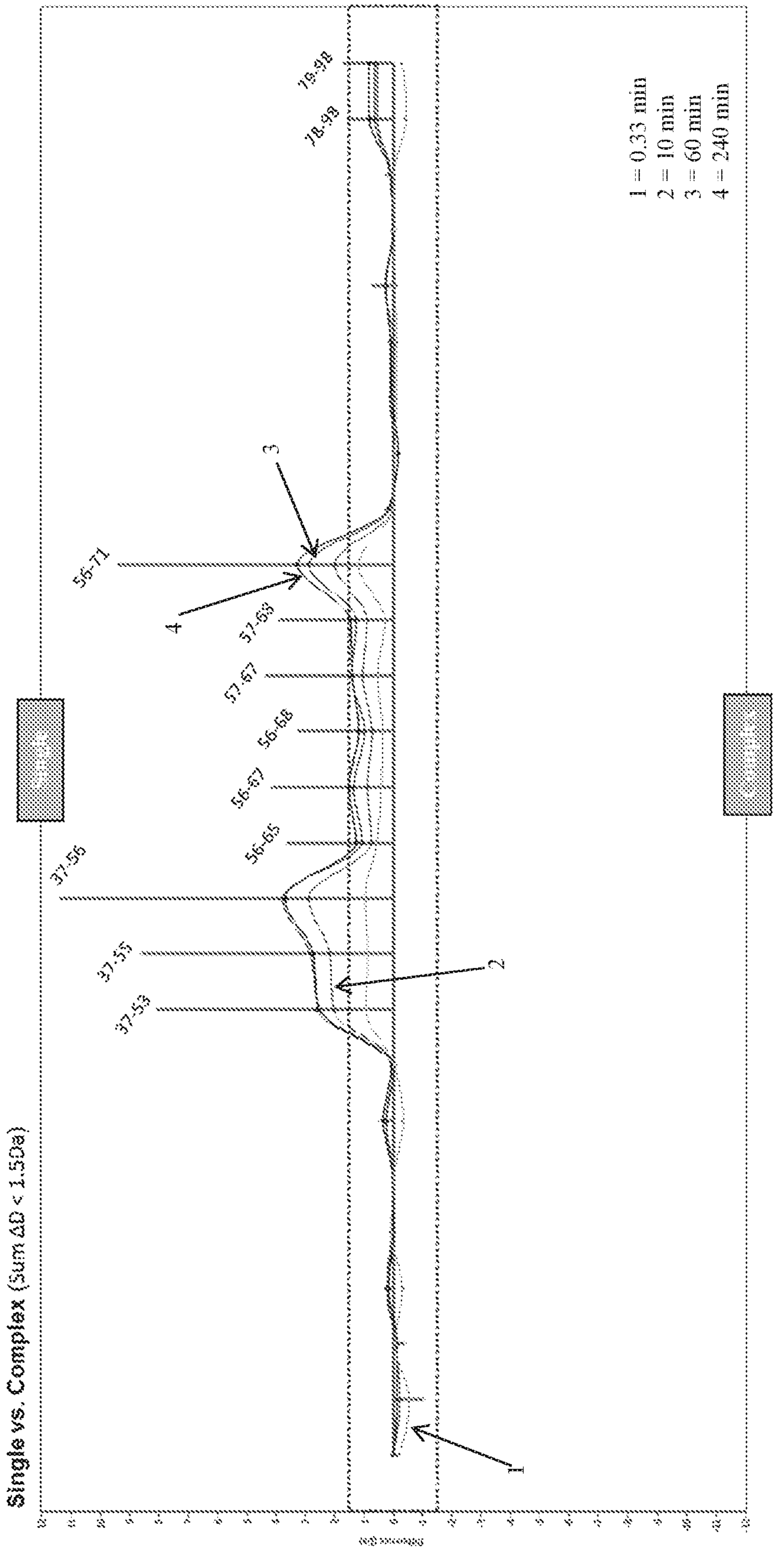

FIGS. 23A, 23B, and 23C show key amino acid residues along the FAM19A5 protein with significant differences in deuterium uptake (i.e., greater than 0.5 Da) between single and complex samples. FIG. 23A provides a Butterfly map analysis of the deuterium uptake of single (antigen alone, top graph) and antigen-antibody (2-13) complex (bottom graph). FIG. 23B provides plot of the difference in deuterium uptake between single and complex samples. FIG. 23C shows the data as a sum of the difference of deuterium uptake less than 1.5 Da. In FIGS. 23A, 23B, and 23C, each of the lines represents a different duration of deuterium labeling: (i) "1" (0.33 minutes or 20 seconds), (ii) "2" (10 minutes), (iii) "3" (60 minutes), and (iv) "4" (240 minutes). Also, each point corresponds to an individual peptide. In FIGS. 23B and 23C, the start and end site (of SEQ ID NO: 101) of peptides with differences in deuterium uptake of greater than ±0.5 Da between the single (antigen alone) and antigen-peptide complex are shown. The dotted box in FIGS. 23B and 23C show differences in deuterium uptake of less than ±0.5 Da.

Figure 24:
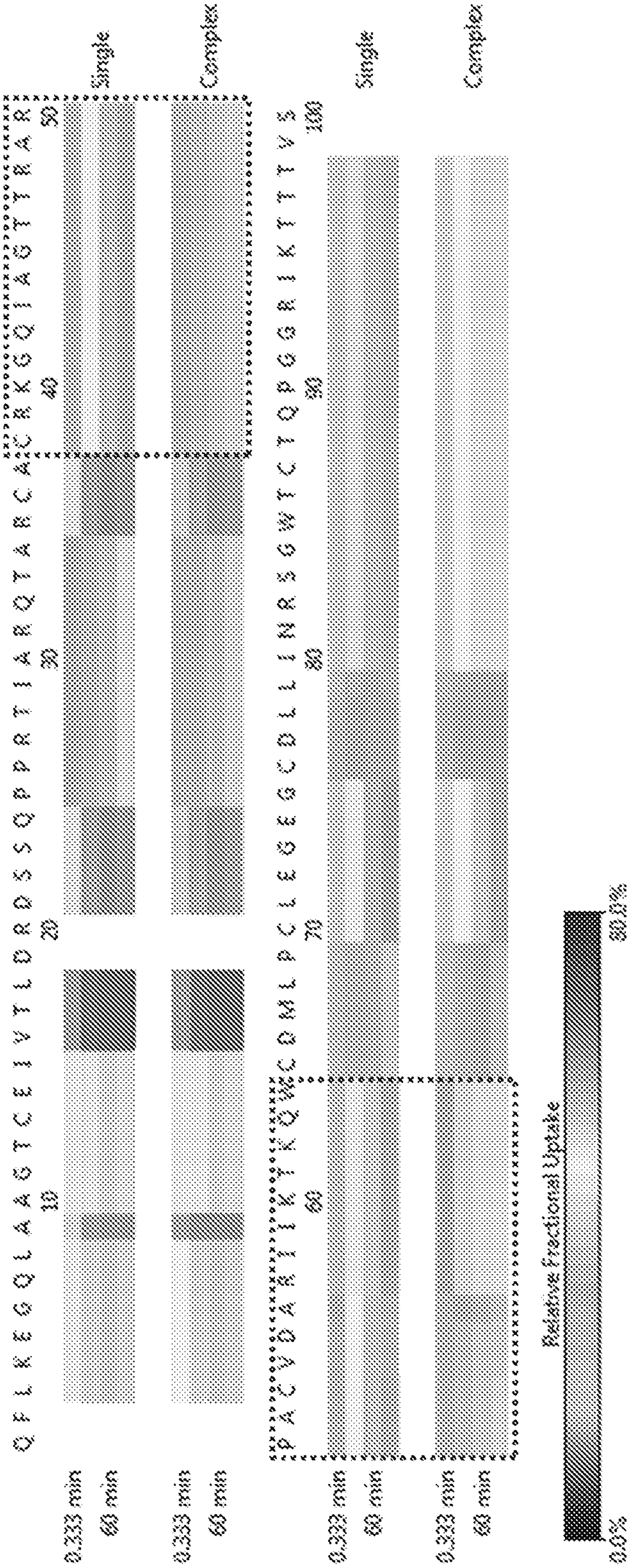

FIG. 24 provides a heat map analysis showing regions of the FAM19A5 protein with significant differences in deuterium uptake between single (antigen alone) and antigen-antibody (2-13) complex samples. The residues boxed in dotted red line represent the key amino acid residues: (i) CRKGQIAGTTRAR (amino acid residues 38-50 of SEQ ID NO: 101 or amino acid residues 63-75 of SEQ ID NO: 2) (SEQ ID NO: 170) and (ii) PACVDARIIKTKQW (amino acid residues 51-64 of SEQ ID NO: 101 or amino acid residues 76-85 of SEQ ID NO: 2) (SEQ ID NO: 97).

Figure 25:
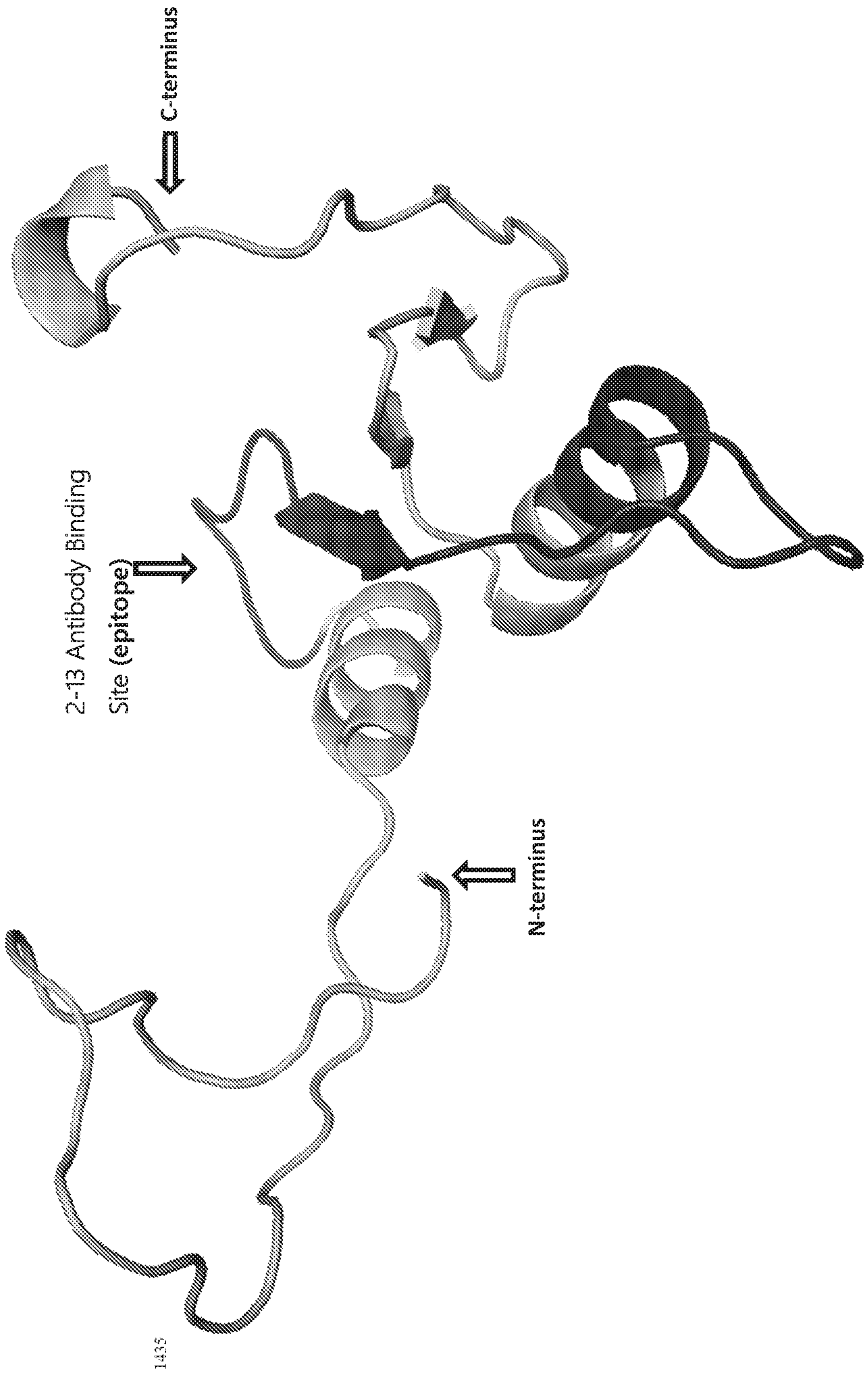

FIG. 25 provides a 3-dimensional structure of the FAM19A5 protein and the location of the key binding epitope for the 2-13 antibody.

DETAILED DESCRIPTION OF THE DISCLOSURE

Disclosed herein is an isolated monoclonal antibody, or antigen binding portion thereof, which specifically binds to human family with sequence similarity 19, member A5 (FAM19A5) protein ("anti-FAM19A5 antibody") and exhibits one or more of the properties disclosed herein. Specifically, the anti-FAM19A5 antibody has been de-immunized to reduce immunogenicity in a human subject.

To facilitate an understanding of the disclosure disclosed herein, a number of terms and phrases are defined. Additional definitions are set forth throughout the detailed description.

I. Definitions

Throughout this disclosure, the term "a" or "an" entity refers to one or more of that entity; for example, "an antibody," is understood to represent one or more antibodies. As such, the terms "a" (or "an"), "one or more," and "at least one" can be used interchangeably herein.

Furthermore, "and/or" where used herein is to be taken as specific disclosure of each of the two specified features or components with or without the other. Thus, the term "and/or" as used in a phrase such as "A and/or B" herein is intended to include "A and B," "A or B," "A" (alone), and "B" (alone). Likewise, the term "and/or" as used in a phrase such as "A, B, and/or C" is intended to encompass each of the following aspects: A, B, and C; A, B, or C; A or C; A or B; B or C; A and C; A and B; B and C; A (alone); B (alone); and C (alone).

It is understood that wherever aspects are described herein with the language "comprising," otherwise analogous aspects described in terms of "consisting of" and/or "consisting essentially of" are also provided.

Unless defined otherwise, all technical and scientific terms used herein have the same meaning as commonly understood by one of ordinary skill in the art to which this disclosure is related. For example, the Concise Dictionary of Biomedicine and Molecular Biology, Juo, Pei-Show, 2nd ed., 2002, CRC Press; The Dictionary of Cell and Molecular Biology, 3rd ed., 1999, Academic Press; and the Oxford Dictionary Of Biochemistry And Molecular Biology, Revised, 2000, Oxford University Press, provide one of skill with a general dictionary of many of the terms used in this disclosure.

Units, prefixes, and symbols are denoted in their Système International de Unites (SI) accepted form. Numeric ranges are inclusive of the numbers defining the range. Unless otherwise indicated, amino acid sequences are written left to right in amino to carboxy orientation. The headings provided herein are not limitations of the various aspects of the disclosure, which can be had by reference to the specification as a whole. Accordingly, the terms defined immediately below are more fully defined by reference to the specification in its entirety.

The term "about" is used herein to mean approximately, roughly, around, or in the regions of. When the term "about" is used in conjunction with a numerical range, it modifies that range by extending the boundaries above and below the numerical values set forth. In general, the term "about" can modify a numerical value above and below the stated value by a variance of, e.g., 10 percent, up or down (higher or lower).

The term "family with sequence similarity 19, member A5" or "FAM19A5" refers to a protein that belongs to the TAFA family (also known as FAM19 family) of five highly homologous proteins and is predominantly expressed in brain and the spinal cord. FAM19A5 is also known as TAFA5 or Chemokine-like protein TAFA-5.

In humans, the gene encoding FAM19A5 is located on chromosome 22. There are multiple human FAM19A5 (UniProt: Q7Z5A7) isoforms, which are believed to be produced by alternative splicing: isoform 1 (UniProt: Q7Z5A7-1), which consists of 132 amino acids, isoform 2 (UniProt: Q7Z5A7-2), which consists of 125 amino acids, and isoform 3 (UniProt: Q7Z5A7-3), which consists of 53 amino acids. Human FAM19A5 protein is believed to exist as both membrane bound and soluble (secreted) forms. Isoform 1 is believed to be a membrane protein with one transmembrane region. Isoform 2, which was reported in Tang T. Y. et al., Genomics 83(4):727-34 (2004) as a secreted protein (soluble), contains a signal peptide at amino acid positions 1-25. Isoform 1 is believed to be a membrane protein and predicted based on EST data. Below are the amino acid sequences of the three known human FAM19A5 isoforms.

(I) Isoform 1 (UniProt: Q7Z5A7-1, transmembrane protein): this isoform has been chosen as the canonical sequence. MAPSPRTGSR QDATALPSMS STFWAFMILA SLLIAYCSQL AAGTCEIVTL DRDSSQPRRT IARQTARCAC RKGQIAGTTR ARPACVDARI IKTKQWCDML PCLEGEGCDL LINRSGWTCT QPGGRIKTTT VS (SEQ ID NO: 1)

(II) Isoform 2 (UniProt: Q7Z5A7-2, soluble protein): MQLLKALWAL AGAALCCFLV LVIHAQFLKE GQLAAGTCEI VTLDRDSSQP RRTIARQTAR CACRKGQIAG TTRARPACVD ARIIKTKQWC DMLPCLEGEG CDLLINRSGW TCTQPGGRIK TTTVS (SEQ ID NO: 2)

(III) Isoform 3 (UniProt: Q7Z5A7-3): MYHHREWPAR IIKTKQWCDM LPCLEGEGCD LLINRSGWTC TQPGGRIKTT TVS (SEQ ID NO: 3)

The term "FAM19A5" includes any variants or isoforms of FAM19A5 which are naturally expressed by cells. Accordingly, antibodies described herein can cross-react with different isoforms in the same species (e.g., different isoforms of human FAM19A5), or cross-react with FAM19A5 from species other than human (e.g., mouse FAM19A5). Alternatively, the antibodies can be specific for human FAM19A5 and cannot exhibit any cross-reactivity with other species. FAM19A5 or any variants and isoforms thereof, can either be isolated from cells or tissues which naturally express them or be recombinantly produced. The polynucleotide encoding human FAMB9A5 has the GenBank Accession No. BC039396 and the following sequence:

TABLE 1A

Polynucleotide sequence of human FAM19A5

| | Polynucleotide sequence (SEQ ID NO: 4) |
|---|---|
| FAM19A5 | ggcggcggag gatggcgcgc gcggggcccg cacgtggagg ccggcgcggg |
| (GenBank | ggcgcgggca gggccggctg ctgagacgcg ctgctgcccc ccgcgcgggc |
| Accession No. | gccgcggctt caatggcgcc atcgcccagg accggcagcc ggcaagatgc |
| BC039396) | gaccgccctg cccagcatgt cctcaacttt ctgggcgttc atgatcctgg |
| | ccagcctgct catcgcctac tgcagtcagc tggccgccgg cacctgtgag |
| | attgtgacct tggaccggga cagcagccag cctcggagga cgatcgcccg |
| | gcagaccgcc cgctgtgcgt gtagaaaggg gcagatcgcc ggcaccacga |
| | gagcccggcc cgcctgtgtg gacgcaagaa tcatcaagac caagcagtgg |
| | tgtgacatgc ttccgtgtct ggaggggGaa ggctgcgact tgttaatcaa |
| | ccggtcaggc tggacgtgca cgcagcccgg cgggaggata aagaccacca |
| | cggtctcctg acaaacacag cccctgaggg ggccccggga gtggccttgg |
| | ctccctggag agcccacgtc tcagccacag ttctccactc gcctcggact |
| | tcacccgttc tctgccgccc gcccactccg tttccctgtg gtccgtgaag |
| | gacggcctca ggccttggca tcctgagctt cggtctgtcc agccgacccg |
| | aggaggccgg actcagacac ataggcgggg ggcggcacct ggcatcagca |
| | atacgcagtc tgtgggagcc cggccgcgcc cagcccccgc cgaccgtggc |
| | gttggccctg ctgtcctcag aggaggagga ggaggaggca gctccggcag |
| | ccacagaagg ctgcagccca gcccgcctga gacacgacgc ctgccccagg |
| | ggactgtcag gcacagaagc ggcctcctcc cgtgccccag actgtccgaa |
| | ttgcttttat tttcttatac tttcagtata ctccatagac caaagagcaa |
| | aatctatctg aacctggacg caccctcact gtcagggtcc ctggggtcgc |
| | ttgtgcgggc gggagggcaa tggtggcaga gacatgctgg tggccccggc |
| | ggagcggaga gggcggccgt ggtggaggcc tccaccccag gagcaccccg |
| | cacaccctcg gaggacgggc ttcggctgcg cggaggccgt ggcacacctg |
| | cgggaggcag cgacggcccc cacgcagacg ccgggaacgc aggccgcttt |
| | attcctctgt acttagatca acttgaccgt actaaaatcc ctttctgttt |
| | taaccagtta aacatgcctc ttctacagct ccatttttga tagttggata |
| | atccagtatc tgccaagagc atgttgggtc tcccgtgact gctgcctcat |
| | cgatacccca tttagctcca gaaagcaaag aaaactcgag taacacttgt |
| | ttgaaagaga tcattaaatg tattttgcaa agcccaaaaa aaaaaaaaaa a |

The terms "antibody" and "antibodies" are terms of art and can be used interchangeably herein and refer to a molecule with an antigen binding site that specifically binds an antigen. The terms as used to herein include whole antibodies and any antigen binding fragments (i.e., "antigen-binding portions") or single chains thereof. An "antibody" refers, in one embodiment, to a glycoprotein comprising at least two heavy (H) chains and two light (L) chains inter-connected by disulfide bonds, or an antigen binding portion thereof. In another embodiment, an "antibody" refers to a single chain antibody comprising a single variable domain, e.g., VHH domain. Each heavy chain is comprised of a heavy chain variable region (abbreviated herein as VH) and a heavy chain constant region. In certain naturally-occurring antibodies, the heavy chain constant region is comprised of three domains, CH1, CH2 and CH3. In certain naturally-occurring antibodies, each light chain is comprised of a light chain variable region (abbreviated herein as VL) and a light chain constant region. The light chain constant region is comprised of one domain, CL.

The VH and VL regions can be further subdivided into regions of hypervariability, termed complementarity determining regions (CDR), interspersed with regions that are more conserved, termed framework regions (FR). Each VH and VL is composed of three CDRs and four FRs, arranged from amino-terminus to carboxy-terminus in the following order: FR1, CDR1, FR2, CDR2, FR3, CDR3, and FR4. The variable regions of the heavy and light chains contain a binding domain that interacts with an antigen. The constant regions of the antibodies can mediate the binding of the immunoglobulin to host tissues or factors, including various cells of the immune system (e.g., effector cells) and the first component (C1q) of the classical complement system.

The term "Kabat numbering" and like terms are recognized in the art and refer to a system of numbering amino acid residues in the heavy and light chain variable regions of an antibody, or an antigen-binding portion thereof. In certain aspects, the CDRs of an antibody can be determined according to the Kabat numbering system (see, e.g., Kabat E A & Wu T T (1971) Ann NY Acad Sci 190: 382-391 and Kabat E A et al., (1991) Sequences of Proteins of Immunological Interest, Fifth Edition, U.S. Department of Health and Human Services, NIH Publication No. 91-3242). Using the Kabat numbering system, CDRs within an antibody heavy chain molecule are typically present at amino acid positions 31 to 35, which optionally can include one or two additional amino acids, following 35 (referred to in the Kabat numbering scheme as 35A and 35B) (CDR1), amino acid positions 50 to 65 (CDR2), and amino acid positions 95 to 102 (CDR3). Using the Kabat numbering system, CDRs within an antibody light chain molecule are typically present at amino acid positions 24 to 34 (CDR1), amino acid positions 50 to 56 (CDR2), and amino acid positions 89 to 97 (CDR3). In a specific embodiment, the CDRs of the antibodies described herein have been determined according to the Kabat numbering scheme.

The phrases "amino acid position numbering as in Kabat," "Kabat position," and grammatical variants thereof refer to the numbering system used for heavy chain variable domains or light chain variable domains of the compilation of antibodies in Kabat et al., Sequences of Proteins of Immunological Interest, 5th Ed. Public Health Service, National Institutes of Health, Bethesda, Md. (1991). Using this numbering system, the actual linear amino acid sequence can contain fewer or additional amino acids corresponding to a shortening of, or insertion into, a FW or CDR of the variable domain. For example, a heavy chain variable domain can include a single amino acid insert (residue 52a according to Kabat) after residue 52 of H2 and inserted residues (e.g., residues 82a, 82b, and 82c, etc. according to Kabat) after heavy chain FW residue 82. See TABLE 1B.

TABLE 1B

| Loop | Kabat | AbM | Chothia |
|---|---|---|---|
| L1 | L24-L34 | L24-L34 | L24-L34 |
| L2 | L50-L56 | L50-L56 | L50-L56 |
| L3 | L89-L97 | L89-L97 | L89-L97 |
| H1 | H31-H35B | H26-H35B | H26-H32 . . . 34 |
| | | (Kabat Numbering) | |
| H1 | H31-H35 | H26-H35 | H26-H32 |
| | | (Chothia Numbering) | |
| H2 | H50-H65 | H50-H58 | H52-H56 |
| H3 | H95-H102 | H95-H102 | H95-H102 |

The Kabat numbering of residues can be determined for a given antibody by alignment at regions of homology of the sequence of the antibody with a "standard" Kabat numbered sequence. Chothia refers instead to the location of the structural loops (Chothia and Lesk, *J. Mol. Biol.* 196:901-917 (1987)). The end of the Chothia CDR-H1 loop when numbered using the Kabat numbering convention varies between H32 and H34 depending on the length of the loop (this is because the Kabat numbering scheme places the insertions at H35A and H35B; if neither 35A nor 35B is present, the loop ends at 32; if only 35A is present, the loop ends at 33; if both 35A and 35B are present, the loop ends at 34). The AbM hypervariable regions represent a compromise between the Kabat CDRs and Chothia structural loops, and are used by Oxford Molecular's AbM antibody modeling software.

IMGT (ImMunoGeneTics) also provides a numbering system for the immunoglobulin variable regions, including the CDRs. See e.g., Lefranc, M. P. et al., *Dev. Comp. Immunol.* 27: 55-77(2003), which is herein incorporated by reference. The IMGT numbering system was based on an alignment of more than 5,000 sequences, structural data, and characterization of hypervariable loops and allows for easy comparison of the variable and CDR regions for all species. According to the IMGT numbering schema VH-CDR1 is at positions 26 to 35, VH-CDR2 is at positions 51 to 57, VH-CDR3 is at positions 93 to 102, VL-CDR1 is at positions 27 to 32, VL-CDR2 is at positions 50 to 52, and VL-CDR3 is at positions 89 to 97.

For all heavy chain constant region amino acid positions discussed in the present disclosure, numbering is according to the EU index first described in Edelman et al., 1969*, Proc. Natl. Acad. Sci. USA* 63(1):78-85, describing the amino acid sequence of myeloma protein EU, which is the first human IgG1 sequenced. The EU index of Edelman et al. is also set forth in Kabat et al., 1991, Sequences of Proteins of Immunological Interest, 5th Ed., United States Public Health Service, National Institutes of Health, Bethesda. Thus, the phrases "EU index as set forth in Kabat" or "EU index of Kabat" and "position . . . according to the EU index as set forth in Kabat," and grammatical variants thereof refer to the residue numbering system based on the human IgG1 EU antibody of Edelman et al. as set forth in Kabat 1991.

The numbering system used for the variable domains (both heavy chain and light chain) and light chain constant region amino acid sequence is that set forth in Kabat 1991.

Antibodies can be of any type (e.g., IgG, IgE, IgM, IgD, IgA or IgY), any class (e.g., IgD, IgG2, IgG3, IgG4, IgA1 or IgA2), or any subclass (e.g., IgG1, IgG2, IgG3 and IgG4 in humans, and IgG1, IgG2a, IgG2b and IgG3 in mice) of immunoglobulin molecule. Immunoglobulins, e.g., IgG1, exist in several allotypes, which differ from each other in at most a few amino acids. An antibody disclosed herein can be from any of the commonly known isotypes, classes, subclasses, or allotypes. In certain embodiments, the antibodies described herein are of the IgG1, IgG2, IgG3 or IgG4 subclass or any hybrid thereof. In certain embodiments, the antibodies are of the IgG2, IgG4 or IgG2/IgG4 subclass.

"Antibody" includes, by way of example, both naturally-occurring and non-naturally-occurring antibodies; monoclonal and polyclonal antibodies; chimeric and humanized antibodies; human and nonhuman antibodies; wholly synthetic antibodies; single chain antibodies; monospecific antibodies; multispecific antibodies (including bispecific antibodies); tetrameric antibodies comprising two heavy chain and two light chain molecules; an antibody light chain monomer; an antibody heavy chain monomer; an antibody light chain dimer, an antibody heavy chain dimer; an antibody light chain-antibody heavy chain pair; intrabodies; heteroconjugate antibodies; monovalent antibodies; single chain antibodies; camelized antibodies; affybodies; anti-idiotypic (anti-Id) antibodies. (including, e.g., anti- anti-Id antibodies), and single-domain antibodies (sdAbs), which include binding molecules consisting of a single monomeric variable antibody domain that are fully capable of antigen binding (e.g., a VH domain or a VL domain). Harmen M. M. and Haard H. J. *Appl Microbiol Biotechnol.* 77(1): 13-22 (2007)).

The term "antigen-binding portion" of an antibody, as used herein, refers to one or more fragments of an antibody that retain the ability to specifically bind to an antigen (e.g., human FAM19A5). Such "fragments" are, for example between about 8 and about 1500 amino acids in length, suitably between about 8 and about 745 amino acids in length, suitably about 8 to about 300, for example about 8 to about 200 amino acids, or about 10 to about 50 or 100 amino acids in length. It has been shown that the antigen-binding function of an antibody can be performed by fragments of a full-length antibody. Examples of binding fragments encompassed within the term "antigen-binding portion" of an antibody, e.g., an anti-FAM19A5 antibody described herein, include (i) a Fab fragment, a monovalent fragment consisting of the VL, VH, CL, and CH1 domains; (ii) a F(ab')2 fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, and disulfide-linked Fvs (sdFv) (v) a dAb fragment (Ward et al., (1989) Nature 341:544-546), which consists of a VH domain; and (vi) an isolated complementarity determining region (CDR) or (vii) a combination of two or more isolated CDRs which can optionally be joined by a synthetic linker. Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv); see, e.g., Bird et al., (1988) *Science* 242:423-426; and Huston et al., (1988) *Proc. Natl. Acad. Sci. USA* 85:5879-5883). Such single chain antibodies are also intended to be encompassed within the term "antigen-binding portion" of an antibody. These antibody fragments are obtained using conventional techniques known to those with skill in the art, and the fragments are screened for utility in the same manner as are intact antibodies. Antigen-binding portions can be produced by recombinant DNA techniques, or by enzymatic or chemical cleavage of intact immunoglobulins.

As used herein, the terms "variable region" and "variable domain" are used interchangeably and are common in the art. The variable region typically refers to a portion of an antibody, generally, a portion of a light or heavy chain, typically about the amino-terminal 110 to 120 amino acids in the mature heavy chain and about 90 to 115 amino acids in the mature light chain, which differ extensively in sequence among antibodies and are used in the binding and specificity of a particular antibody for its particular antigen. The variability in sequence is concentrated in those regions called complementarity determining regions (CDRs) while the more highly conserved regions in the variable domain are called framework regions (FR).

Without wishing to be bound by any particular mechanism or theory, it is believed that the CDRs of the light and heavy chains are primarily responsible for the interaction and specificity of the antibody with antigen. In certain embodiments, the variable region is a human variable region. In certain embodiments, the variable region comprises rodent or murine CDRs and human framework regions (FRs). In particular embodiments, the variable region is a primate (e.g., non-human primate) variable region. In certain embodiments, the variable region comprises rodent or murine CDRs and primate (e.g., non-human primate) framework regions (FRs).

As used herein, the term "heavy chain" (HC) when used in reference to an antibody can refer to any distinct type, e.g., alpha (α), delta (δ), epsilon (ε), gamma (γ) and mu (μ), based on the amino acid sequence of the constant domain, which give rise to IgA, IgD, IgE, IgG and IgM classes of antibodies, respectively, including subclasses of IgG, e.g., IgG1, IgG2, IgG3 and IgG4.

As used herein, the term "light chain" (LC) when used in reference to an antibody can refer to any distinct type, e.g., kappa (κ) or lambda (λ) based on the amino acid sequence of the constant domains. Light chain amino acid sequences are well known in the art. In specific embodiments, the light chain is a human light chain.

The terms "VL" and "VL domain" are used interchangeably to refer to the light chain variable region of an antibody.

The terms "VH" and "VH domain" are used interchangeably to refer to the heavy chain variable region of an antibody.

As used herein, the terms "constant region" and "constant domain" are interchangeable and have its meaning common in the art. The constant region is an antibody portion, e.g., a carboxyl terminal portion of a light and/or heavy chain which is not directly involved in binding of an antibody to antigen but which can exhibit various effector functions, such as interaction with the Fe receptor. The constant region of an immunoglobulin molecule generally has a more conserved amino acid sequence relative to an immunoglobulin variable domain.

An "Fc region" (fragment crystallizable region) or "Fc domain" or "Fc" refers to the C-terminal region of the heavy chain of an antibody that mediates the binding of the immunoglobulin to host tissues or factors, including binding to Fc receptors located on various cells of the immune system (e.g., effector cells) or to the first component (C1q) of the classical complement system. Thus, a Fc region comprises the constant region of an antibody excluding the first constant region immunoglobulin domain (e.g., CH1 or CL). In IgG, IgA and IgD antibody isotypes, the Fc region comprises two identical protein fragments, derived from the second (CH2) and third (CH3) constant domains of the antibody's two heavy chains; IgM and IgE Fc regions comprise three heavy chain constant domains (CH domains 2-4) in each polypeptide chain. For IgG, the Fc region comprises immunoglobulin domains Cγ2 and Cγ3 and the hinge between Cγ1 and Cγ2. Although the boundaries of the Fc region of an immunoglobulin heavy chain might vary, the human IgG heavy chain Fc region is usually defined to stretch from an amino acid residue at position C226 or P230 (or amino acid between these two amino acids) to the carboxy-terminus of the heavy chain, wherein the numbering is according to the EU index as in Kabat. The CH2 domain of a human IgG Fc region extends from about amino acid 231 to about amino acid 340, whereas the CH3 domain is positioned on C-terminal side of a Cm domain in a Fc region, i.e., it extends from about amino acid 341 to about amino acid 447 of an IgG. As used herein, the Fc region can be a native sequence Fc, including any allotypic variant, or a variant Fc (e.g., a non-naturally-occurring Fc). Fc can also refer to this region in isolation or in the context of a Fe-comprising protein polypeptide such as a "binding protein comprising a Fc region," also referred to as an "Fc fusion protein" (e.g., an antibody or immunoadhesion).

A "native sequence Fc region" or "native sequence Fc" comprises an amino acid sequence that is identical to the amino acid sequence of a Fc region found in nature. Native sequence human Fc regions include a native sequence human IgG1 Fc region; native sequence human IgG2 Fc region; native sequence human IgG3 Fc region; and native sequence human IgG4 Fc region as well as naturally-occurring variants thereof. Native sequence Fc includes the various allotypes of Fes (see, e.g., Jefferis et al., (2009) mAbs 1:1; Vidarsson G. et al., *Front Immunol.* 5:520 (published online Oct. 20, 2014)).

An "Fc receptor" or "FcR" is a receptor that binds to the Fc region of an immunoglobulin. FcRs that bind to an IgG antibody comprise receptors of the FcγR family, including allelic variants and alternatively spliced forms of these receptors. The FcγR family consists of three activating (FcγRI, FcγRIII, and FcγRIV in mice; FcγRIA, FcγRIIA, and FcγRIIIA in humans) and one inhibitory (FcγRIIB) receptor. Human IgG1 binds to most human Fc receptors and elicits the strongest Fc effector functions. It is considered equivalent to murine IgG2a with respect to the types of activating Fc receptors that it binds to. Conversely, human IgG4 elicits the least Fc effector functions. Vidarsson G. et al., *Front Immunol.* 5:520 (published online Oct. 20, 2014).

The constant region can be manipulated, e.g., by recombinant technology, to eliminate one or more effector functions. An "effector function" refers to the interaction of an antibody Fc region with a Fc receptor or ligand, or a biochemical event that results therefrom. Exemplary "effector functions" include C1q binding, complement dependent cytotoxicity (CDC), Fc receptor binding, FcγR-mediated effector functions such as ADCC and antibody dependent cell-mediated phagocytosis (ADCP), and down regulation of a cell surface receptor (e.g., the B cell receptor; BCR). Such effector functions generally require the Fc region to be combined with a binding domain (e.g., an antibody variable domain). Accordingly, the term "a constant region without the Fc function" include constant regions with reduced or without one or more effector functions mediated by Fc region.

Effector functions of an antibody can be reduced or avoided by different approaches. Effector functions of an antibody can be reduced or avoided by using antibody fragments lacking the Fc region (e.g., such as a Fab, F(ab')2, single chain Fv (scFv), or a sdAb consisting of a monomeric VH or VL domain). Alternatively, the so-called aglycosylated antibodies can be generated by removing sugars that are linked to particular residues in the Fc region to reduce the effector functions of an antibody while retaining other valuable attributes of the Fc region (e.g., prolonged half-life and heterodimerization). Aglycosylated antibodies can be generated by, for example, deleting or altering the residue the sugar is attached to, removing the sugars enzymatically, producing the antibody in cells cultured in the presence of a glycosylation inhibitor, or by expressing the antibody in cells unable to glycosylate proteins (e.g., bacterial host cells). See, e.g., U.S. Pub. No. 20120100140. Another approach is to employ Fc regions from an IgG subclass that have reduced effector function, for example, IgG2 and IgG4 antibodies are characterized by having lower levels of Fc effector functions than IgG1 and IgG3. The residues most proximal to the hinge region in the CH2 domain of the Fc part are responsible for effector functions of antibodies as it contains a largely overlapping binding site for C1q (complement) and IgG-Fc receptors (FcγR) on effector cells of the innate immune system. Vidarsson G. et al., *Front Immunol.* 5:520 (published online Oct. 20, 2014). Accordingly, antibodies with reduced or without Fc effector functions can be prepared by generating, e.g., a chimeric Fc region which comprises a CH2 domain from an IgG antibody of the IgG4 isotype and a CH3 domain from an IgG antibody of the IgG1 isotype, or a chimeric Fc region which comprises hinge region from IgG2 and CH2 region from IgG4 (see, e.g., Lau C. et al., *J. Immunol.* 191:4769-4777 (2013)), or a Fc region with mutations that result in altered Fc effector functions, e.g., reduced or no Fc functions. Such Fc regions with mutations are known in the art. See, e.g., U.S. Pub. No. 20120100140 and U.S. and PCT applications cited therein and An et al., *mAbs* 1:6, 572-579 (2009); the disclosure of which are incorporated by reference to their entirety.

A "hinge", "hinge domain" or "hinge region" or "antibody hinge region" refers to the domain of a heavy chain constant region that joins the CH1 domain to the CH2 domain and includes the upper, middle, and lower portions of the hinge (Roux et al., *J. Immunol.* 1998 161:4083). The hinge provides varying levels of flexibility between the binding and effector regions of an antibody and also provides sites for intermolecular disulfide bonding between the two heavy chain constant regions. As used herein, a hinge starts at Glu216 and ends at Gly237 for all IgG isotypes (Roux et al., 1998 *J Immunol* 161:4083). The sequences of wild-type IgG1, IgG2, IgG3 and IgG4 hinges are known in the art. See, e.g., Kabat E A et al., (1991) Sequences of Proteins of Immunological Interest, Fifth Edition, U.S. Department of Health and Human Services, NIH Publication No. 91-3242; Vidarsson G. et al., *Front Immunol.* 5:520 (published online Oct. 20, 2014).

The term "CH1 domain" refers to the heavy chain constant region linking the variable domain to the hinge in a heavy chain constant domain. As used herein, a CH1 domain starts at A118 and ends at V215. The term "CH1 domain" includes wildtype CH1 domains, as well as naturally existing variants thereof (e.g., allotypes). CH1 domain sequences of IgG1, IgG2, IgG3, and IgG4 (including wildtype and allotypes) are known in the art. See, e.g., Kabat E A et al., (1991) supra and Vidarsson G. et al., *Front Immunol.* 5:520 (published online Oct. 20, 2014). Exemplary CH1 domains include CH1 domains with mutations that modify a biological activity of an antibody, e.g., half-life, e.g., described in U.S. Pub. No. 20120100140 and U.S. patents and publications and PCT publications cited therein.

The term "CH2 domain" refers to the heavy chain constant region linking the hinge to the CH3 domain in a heavy chain constant domain. As used herein, a CH2 domain starts at P238 and ends at K340. The term "CH2 domain" includes wildtype CH2 domains, as well as naturally existing variants thereof (e.g., allotypes). CH2 domain sequences of IgG1, IgG2, IgG3, and IgG4 (including wildtype and allotypes) are known in the art. See, e.g., Kabat E A et al., (1991) supra and Vidarsson G. et al., *Front Immunol.* 5:520 (published online Oct. 20, 2014). Exemplary CH2 domains include CH2 domains with mutations that modify a biological activity of an antibody, e.g., half-life and/or reduced Fc effector function, e.g., described in U.S. Pub. No. 20120100140 and U.S. patents and publications and PCT publications cited therein.

The term "CH3 domain" refers to the heavy chain constant region that is C-terminal to the CH2 domain in a heavy chain constant domain. As used herein, a CH3 domain starts at G341 and ends at K447. The term "CH3 domain" includes wildtype CH3 domains, as well as naturally existing variants thereof (e.g., allotypes). CH3 domain sequences of IgG1, IgG2, IgG3, and IgG4 (including wildtype and allotypes) are known in the art. See, e.g., Kabat E A et al., (1991) supra and Vidarsson G. et al., *Front Immunol.* 5:520 (published online Oct. 20, 2014). Exemplary CH3 domains include CH3 domains with mutations that modify a biological activity of an antibody, e.g., half-life, e.g., described in U.S. Pub. No. 20120100140 and U.S. patents and publications and PCT publications cited therein.

As used herein, "isotype" refers to the antibody class (e.g., IgG1, IgG2, IgG3, IgG4, IgM, IgA1 IgA2, IgD, and IgE antibody) that is encoded by the heavy chain constant region genes.

"Allotype" refers to naturally-occurring variants within a specific isotype group, which variants differ in a few amino acids (see, e.g., Jefferis et al., (2009) *mAbs* 1:1). Antibodies described herein can be of any allotype. Allotypes of IgG1, IgG2, IgG3, and IgG4 are known in the art. See, e.g., Kabat E A et al., (1991) supra; Vidarsson G. et al., *Front Immunol.* 5:520 (published online Oct. 20, 2014); and Lefranc M P, *mAbs* 1:4, 1-7(2009).

The phrases "an antibody recognizing an antigen" and "an antibody specific for an antigen" are used interchangeably herein with the term "an antibody which binds specifically to an antigen."

An "isolated antibody," as used herein, is intended to refer to an antibody which is substantially free of other antibodies having different antigenic specificities (e.g., an isolated antibody that specifically binds to FAM19A5 is substantially free of antibodies that specifically bind antigens other than FAM19A5). An isolated antibody that specifically binds to an epitope of FAM19A5 can, however, have cross-reactivity to other FAM19A5 proteins from different species.

"Binding affinity" generally refers to the strength of the sum total of non-covalent interactions between a single binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a molecule X for its partner Y can generally be represented by the dissociation constant ($K_D$). Affinity can be measured and/or expressed in a number of ways known in the art, including, but not limited to, equilibrium dissociation constant ($K_D$), and equilibrium association constant ($K_A$). The $K_D$ is calculated from the quotient of $k_{off}/k_{on}$ and is expressed as a molar concentration (M), whereas $K_A$ is calculated from the quotient of $k_{on}/k_{off}$. $k_{on}$ refers to the association rate constant of, e.g., an antibody to an antigen, and $k_{off}$ refers to the dissociation of, e.g., an antibody to an antigen. The $k_{on}$ and $k_{off}$ can be determined by techniques known to one of ordinary skill in the art, such as immunoassays (e.g., enzyme-linked immunosorbent assay (ELISA)), BIACORE® or kinetic exclusion assay (KinExA).

As used herein, the terms "specifically binds," "specifically recognizes," "specific binding," "selective binding," and "selectively binds," are analogous terms in the context of antibodies and refer to molecules (e.g., antibodies) that bind to an antigen (e.g., epitope or immune complex) as such binding is understood by one skilled in the art. For example, a molecule that specifically binds to an antigen can bind to other peptides or polypeptides, generally with lower affinity as determined by, e.g., immunoassays, BIACORE®, KinExA 3000 instrument (Sapidyne Instruments, Boise, ID), or other assays known in the art. In a specific embodiment, molecules that specifically bind to an antigen bind to the antigen with a $K_A$ that is at least 2 logs, 2.5 logs, 3 logs, 4 logs or greater than the $K_A$ when the molecules bind to another antigen.

Antibodies typically bind specifically to their cognate antigen with high affinity, reflected by a dissociation constant ($K_D$) of $10^{-5}$ to $10^{-11}$ M or less. Any $K_D$ greater than about $10^{-4}$ M is generally considered to indicate nonspecific binding. As used herein, an antibody that "binds specifically" to an antigen refers to an antibody that binds to the antigen and substantially identical antigens with high affinity, which means having a $K_D$ of $10^{-7}$ M or less, preferably $10^{-8}$ M or less, even more preferably $10^{-9}$ M or less, and most preferably between $10^{-8}$ M and $10^{-10}$ M or less, when determined by, e.g., immunoassays (e.g., ELISA) or surface plasmon resonance (SPR) technology in a BIACORE 2000 instrument using the predetermined antigen, but does not bind with high affinity to unrelated antigens.

As used herein, the term "antigen" refers to any natural or synthetic immunogenic substance, such as a protein, peptide, or hapten. An antigen can be FAM19A5 or a fragment thereof.

As used herein, an "epitope" is a term in the art and refers to a localized region of an antigen to which an antibody can specifically bind. An epitope can be, for example, contiguous amino acids of a polypeptide (linear or contiguous epitope) or an epitope can, for example, come together from two or more non-contiguous regions of a polypeptide or polypeptides (conformational, non-linear, discontinuous, or non-contiguous epitope). Epitopes formed from contiguous amino acids are typically, but not always, retained on exposure to denaturing solvents, whereas epitopes formed by tertiary folding are typically lost on treatment with denaturing solvents. An epitope typically includes at least 3, 4, 5, 6, 7, 8, 9, 10, 11, 12, 13, 14, 15, or 20 amino acids in a unique spatial conformation. Methods for determining what epitopes are bound by a given antibody (i.e., epitope mapping) are well known in the art and include, for example, immunoblotting and immunoprecipitation assays, wherein overlapping or contiguous peptides from (e.g., from FAM19A5) are tested for reactivity with a given antibody (e.g., anti-FAM19A5 antibody). Methods of determining spatial conformation of epitopes include techniques in the art and those described herein, for example, x-ray crystallography, 2-dimensional nuclear magnetic resonance and HDX-MS (see, e.g., Epitope Mapping Protocols in Methods in Molecular Biology, Vol. 66, G. E. Morris, Ed. (1996)).

In certain embodiments, the epitope to which an antibody binds can be determined by, e.g., NMR spectroscopy, X-ray diffraction crystallography studies, ELISA assays, hydrogen/deuterium exchange coupled with mass spectrometry (e.g., liquid chromatography electrospray mass spectrometry), array-based oligo-peptide scanning assays, and/or mutagenesis mapping (e.g., site-directed mutagenesis mapping). For X-ray crystallography, crystallization can be accomplished using any of the known methods in the art (e.g., Giege R et al., (1994) *Acta Crystallogr D Biol Crystallogr* 50(Pt 4): 339-350; McPherson A (1990) *Eur J Biochem* 189: 1-23; Chayen N E (1997) *Structure* 5: 1269-1274; McPherson A (1976) *J Biol Chem* 251: 6300-6303). Antibody:antigen crystals can be studied using well known X-ray diffraction techniques and can be refined using computer software such as X-PLOR (Yale University, 1992, distributed by Molecular Simulations, Inc.; see, e.g., Meth Enzymol (1985) volumes 114 & 115, eds Wyckoff H W et al.; U.S. 2004/0014194), and BUSTER (Bricogne G (1993) *Acta Crystallogr D Biol Crystallogr* 49(Pt 1): 37-60; Bricogne G (1997) *Meth Enzymol* 276A: 361-423, ed Carter C W; Roversi P et al., (2000) *Acta Crystallogr D Biol Crystallogr* 56(Pt 10): 1316-1323). Mutagenesis mapping studies can be accomplished using any method known to one of skill in the art. See, e.g., Champe M et al., (1995) *J Biol Chem* 270: 1388-1394 and Cunningham B C & Wells J A (1989) *Science* 244: 1081-1085 for a description of mutagenesis techniques, including alanine scanning mutagenesis techniques.

The term "epitope mapping" refers to the process of identification of the molecular determinants for antibody-antigen recognition.

The term "binds to the same epitope" with reference to two or more antibodies means that the antibodies bind to the same segment of amino acid residues, as determined by a given method. Techniques for determining whether antibodies bind to the "same epitope on FAM19A5" with the antibodies described herein include, for example, epitope mapping methods, such as, x-ray analyses of crystals of antigen:antibody complexes which provides atomic resolution of the epitope and hydrogen/deuterium exchange mass spectrometry (HDX-MS). Other methods monitor the binding of the antibody to antigen fragments or mutated variations of the antigen where loss of binding due to a modification of an amino acid residue within the antigen sequence is often considered an indication of an epitope component. In addition, computational combinatorial methods for epitope mapping can also be used. These methods rely on the ability of the antibody of interest to affinity isolate specific short peptides from combinatorial phage display peptide libraries. Antibodies having the same VH and VL or the same CDR1, 2 and 3 sequences are expected to bind to the same epitope.

Antibodies that "compete with another antibody for binding to a target" refer to antibodies that inhibit (partially or completely) the binding of the other antibody to the target. Whether two antibodies compete with each other for binding to a target, i.e., whether and to what extent one antibody inhibits the binding of the other antibody to a target, can be determined using known competition experiments. In certain embodiments, an antibody competes with, and inhibits binding of another antibody to a target by at least 10%, 20%, 30%, 40%, 50%, 60%, 70%, 80%, 90% or 100%. The level of inhibition or competition can be different depending on which antibody is the "blocking antibody" (i.e., the cold antibody that is incubated first with the target). Competition assays can be conducted as described, for example, in Ed Harlow and David Lane, Cold Spring Harb Protoc; 2006; doi: 10.1101/pdb.prot4277 or in Chapter 11 of "Using Antibodies" by Ed Harlow and David Lane, Cold Spring Harbor Laboratory Press, Cold Spring Harbor, NY, USA 1999. Competing antibodies bind to the same epitope, an overlapping epitope or to adjacent epitopes (e.g., as evidenced by steric hindrance).

Other competitive binding assays include: solid phase direct or indirect radioimmunoassay (RIA), solid phase direct or indirect enzyme immunoassay (EIA), sandwich competition assay (see Stahli et al., *Methods in Enzymology* 9:242 (1983)); solid phase direct biotin-avidin EIA (see Kirkland et al., *J. Immunol.* 137:3614 (1986)); solid phase direct labeled assay, solid phase direct labeled sandwich assay (see Harlow and Lane, Antibodies: A Laboratory Manual, Cold Spring Harbor Press (1988)); solid phase direct label RIA using 1-125 label (see Morel et al., *Mol. Immunol.* 25(1):7 (1988)); solid phase direct biotin-avidin EIA (Cheung et al., *Virology* 176:546 (1990)); and direct labeled RIA. (Moldenhauer et al., *Scand. J. Immunol.* 32:77 (1990)).

A "bispecific" or "bifunctional antibody" is an artificial hybrid antibody having two different heavy/light chain pairs and two different binding sites. Bispecific antibodies can be produced by a variety of methods including fusion of hybridomas or linking of Fab' fragments. See, e.g., Songsivilai & Lachmann, *Clin. Exp. Immunol.* 79:315-321 (1990); Kostelny et al., *J. Immunol.* 148, 1547-1553 (1992).

The term "monoclonal antibody," as used herein, refers to an antibody that displays a single binding specificity and affinity for a particular epitope or a composition of antibodies in which all antibodies display a single binding specificity and affinity for a particular epitope. Accordingly, the term "human monoclonal antibody" refers to an antibody or antibody composition that display(s) a single binding specificity and which has variable and optional constant regions derived from human germline immunoglobulin sequences. In one embodiment, human monoclonal antibodies are produced by a hybridoma which includes a B cell obtained from a transgenic non-human animal, e.g., a transgenic mouse, having a genome comprising a human heavy chain transgene and a light chain transgene fused to an immortalized cell.

The term "recombinant human antibody," as used herein, includes all human antibodies that are prepared, expressed, created or isolated by recombinant means, such as (a) antibodies isolated from an animal (e.g., a mouse) that is transgenic or transchromosomal for human immunoglobulin genes or a hybridoma prepared therefrom, (b) antibodies isolated from a host cell transformed to express the antibody, e.g., from a transfectoma, (c) antibodies isolated from a recombinant, combinatorial human antibody library, and (d) antibodies prepared, expressed, created or isolated by any other means that involve splicing of human immunoglobulin gene sequences to other DNA sequences. Such recombinant human antibodies comprise variable and constant regions that utilize particular human germline immunoglobulin sequences are encoded by the germline genes, but include subsequent rearrangements and mutations which occur, for example, during antibody maturation. As known in the art (see, e.g., Lonberg (2005) *Nature Biotech.* 23(9): 1117-1125), the variable region contains the antigen binding domain, which is encoded by various genes that rearrange to form an antibody specific for a foreign antigen. In addition to rearrangement, the variable region can be further modified by multiple single amino acid changes (referred to as somatic mutation or hypermutation) to increase the affinity of the antibody to the foreign antigen. The constant region will change in further response to an antigen (i.e., isotype switch). Therefore, the rearranged and somatically mutated nucleic acid molecules that encode the light chain and heavy chain immunoglobulin polypeptides in response to an antigen cannot have sequence identity with the original nucleic acid molecules, but instead will be substantially identical or similar (i.e., have at least 80% identity).

A "human" antibody (HuMAb) refers to an antibody having variable regions in which both the framework and CDR regions are derived from human germline immunoglobulin sequences. Furthermore, if the antibody contains a constant region, the constant region also is derived from human germline immunoglobulin sequences. The antibodies described herein can include amino acid residues not encoded by human germline immunoglobulin sequences (e.g., mutations introduced by random or site-specific mutagenesis in vitro or by somatic mutation in vivo). However, the term "human antibody", as used herein, is not intended to include antibodies in which CDR sequences derived from the germline of another mammalian species, such as a mouse, have been grafted onto human framework sequences. The terms "human" antibodies and "fully human" antibodies and are used synonymously.

A "humanized" antibody refers to an antibody in which some, most or all of the amino acids outside the CDR domains of a non-human antibody are replaced with corresponding amino acids derived from human immunoglobulins. In one embodiment of a humanized form of an antibody, some, most or all of the amino acids outside the CDR domains have been replaced with amino acids from human immunoglobulins, whereas some, most or all amino acids within one or more CDR regions are unchanged. Small additions, deletions, insertions, substitutions or modifications of amino acids are permissible as long as they do not abrogate the ability of the antibody to bind to a particular antigen. A "humanized" antibody retains an antigenic specificity similar to that of the original antibody.

As used herein, the term "de-immunized" or "de-immunization" refers to a process in which an antibody, or an antigen binding portion thereof, is modified to reduce its immunogenicity, e.g., in a human subject. For example, the heavy chain variable region (VH) and the light chain variable region (VL) sequences from the original antibody can be analyzed and a human T cell epitope "map" can be generated from each V region showing the location of epitopes in relation to complementarity-determining regions (CDRs) and other key residues within the sequence. Individual T cell epitopes from the T cell epitope map are analyzed in order to identify alternative amino acid substitutions with a low risk of altering activity of the final antibody. A range of alternative VH and VL sequences are designed comprising combinations of amino acid substitutions and these sequences are subsequently incorporated into a range of FAM19A5-specific antibodies, or antigen binding portion thereof, for use in the diagnostic and treatment methods disclosed herein, which are then tested for function. Complete heavy and light chain genes comprising modified V and human C regions are then cloned into expression vectors and the subsequent plasmids introduced into cell lines for the production of whole antibody. The antibodies are then compared in appropriate biochemical and biological assays, and the optimal variant is identified. An antibody can be de-immunized by using methods described herein or by any other methods known in the art. See, e.g., WO 98/52976 or WO 00/34317.

A "chimeric antibody" refers to an antibody in which the variable regions are derived from one species and the constant regions are derived from another species, such as an antibody in which the variable regions are derived from a mouse antibody and the constant regions are derived from a human antibody.

The term "cross-reacts," as used herein, refers to the ability of an antibody described herein to bind to FAM19A5 from a different species. For example, an antibody described herein that binds human FAM19A5 can also bind another species of FAM19A5 (e.g., mouse FAM19A5). As used herein, cross-reactivity can be measured by detecting a specific reactivity with purified antigen in binding assays (e.g., SPR, ELISA) or binding to, or otherwise functionally interacting with, cells physiologically expressing FAM19A5. Methods for determining cross-reactivity include standard binding assays as described herein, for example, by BIACORE® surface plasmon resonance (SPR) analysis using a BIACORE® 2000 SPR instrument (Biacore AB, Uppsala, Sweden), or flow cytometric techniques.

The term "naturally-occurring" as used herein as applied to an object refers to the fact that an object can be found in nature. For example, a polypeptide or polynucleotide sequence that is present in an organism (including viruses) that can be isolated from a source in nature and which has not been intentionally modified by man in the laboratory is naturally-occurring.

A "polypeptide" refers to a chain comprising at least two consecutively linked amino acid residues, with no upper limit on the length of the chain. One or more amino acid residues in the protein can contain a modification such as, but not limited to, glycosylation, phosphorylation or disulfide bond formation. A "protein" can comprise one or more polypeptides.

The term "nucleic acid molecule," as used herein, is intended to include DNA molecules and RNA molecules. A nucleic acid molecule can be single-stranded or double-stranded, and can be cDNA.

The term "vector," as used herein, is intended to refer to a nucleic acid molecule capable of transporting another nucleic acid to which it has been linked. One type of vector is a "plasmid," which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" (or simply, "expression vectors") In general, expression vectors of utility in recombinant DNA techniques are often in the form of plasmids. In the present specification, "plasmid" and "vector" can be used interchangeably as the plasmid is the most commonly used form of vector. However, also included are other forms of expression vectors, such as viral vectors (e.g., replication defective retroviruses, adenoviruses and adeno-associated viruses), which serve equivalent functions.

The term "recombinant host cell" (or simply "host cell"), as used herein, is intended to refer to a cell that comprises a nucleic acid that is not naturally present in the cell, and can be a cell into which a recombinant expression vector has been introduced. It should be understood that such terms are intended to refer not only to the particular subject cell but to the progeny of such a cell. Because certain modifications can occur in succeeding generations due to either mutation or environmental influences, such progeny cannot, in fact, be identical to the parent cell, but are still included within the scope of the term "host cell" as used herein.

As used herein, the term "linked" refers to the association of two or more molecules. The linkage can be covalent or non-covalent. The linkage also can be genetic (i.e., recombinantly fused). Such linkages can be achieved using a wide variety of art recognized techniques, such as chemical conjugation and recombinant protein production.

As used herein, "administering" refers to the physical introduction of a therapeutic agent or a composition comprising a therapeutic agent to a subject, using any of the various methods and delivery systems known to those skilled in the art. Preferred routes of administration for antibodies described herein include intravenous, intraperitoneal, intramuscular, subcutaneous, spinal or other parenteral routes of administration, for example by injection or infusion. The phrase "parenteral administration" as used herein means modes of administration other than enteral and topical administration, usually by injection, and includes, without limitation, intravenous, intraperitoneal, intramuscular, intraarterial, intrathecal, intralymphatic, intralesional, intracapsular, intraorbital, intracardiac, intradermal, transtracheal, subcutaneous, subcuticular, intraarticular, subcapsular, subarachnoid, intraspinal, epidural and intrasternal injection and infusion, as well as in vivo electroporation. Alternatively, an antibody described herein can be administered via a non-parenteral route, such as a topical, epidermal or mucosal route of administration, for example, intranasally, orally, vaginally, rectally, sublingually or topically. Administering can also be performed, for example, once, a plurality of times, and/or over one or more extended periods.

The terms "treat," "treating," and "treatment," as used herein, refer to any type of intervention or process performed on, or administering an active agent to, the subject with the objective of reversing, alleviating, ameliorating, inhibiting, or slowing down or preventing the progression, development, severity or recurrence of a symptom, complication, condition or biochemical indicia associated with a disease. Treatment can be of a subject having a disease or a subject who does not have a disease (e.g., for prophylaxis).

As used herein, the term "subject" includes any human or non-human animal. The term "non-human animal" includes all vertebrates, e.g., mammals and non-mammals, such as non-human primates, sheep, dog, cow, chickens, amphibians, reptiles, etc.

As used herein, the term "onset of gliosis" or "onset of reactive gliosis" includes the beginning or initiation of gliosis. Gliosis is a nonspecific reactive change of glial cells in the central nervous system (CNS, e.g., brain and/or the spinal cord) in response to injury or damage from e.g., trauma, cerebrospinal damage, brain tumor, infection, ischemia, stroke, autoimmune responses, and/or neurodegenerative diseases, and includes the proliferation or hypertrophy of several different types of glial cells, including astrocytes, microglia, and oligodendrocytes. Onset of gliosis can lead to scar formation, which inhibits axonal regeneration in the part of the CNS that has been traumatized or injured. Detrimental effects of an onset of gliosis include irreversible or permanent damage to the neurons and/or prevention of the surrounding neurons from recovering. Accordingly, the terms "delay an onset of gliosis" and "delay an onset of reactive gliosis" include inhibit, slow down, suppress, or prevent the beginning or initiation of gliosis and its associated detrimental effects of the CNS.

As used herein, the term "excessive proliferation of reactive astrocytes" includes an abnormal increase in the number of astrocytes due to the destruction of nearby neurons from e.g., CNS damage, trauma, injury, cerebrospinal damage, brain tumor, infection, ischemia, stroke, autoimmune responses, and/or neurodegenerative disease. Excessive proliferation of reactive astrocytes can lead to detrimental effects in the CNS including scar formation, which inhibits axonal regeneration in the part of the CNS that has been traumatized or injured, exacerbation of inflammation, production and release of neurotoxic levels of reactive oxygen species, release of potentially excitotoxic glutamate, the potential contribution to seizure genesis, compromise of blood-brain barrier function, cytotoxic edema during trauma and stroke, potential for chronic cytokine activation of astrocytes to contribute to chronic pain, and secondary degeneration after CNS injury. Sofroniew, Michael V. (2009) *Trends in Neurosciences,* 32(12):638-47; McGraw, J. et al. (2001) *Journal of Neuroscience Research* 63(2):109-15; and Sofroniew, M. V. (2005) *The Neuroscientist* 11(5): 400-7. Accordingly, the terms "suppress excessive proliferation of reactive astrocytes" includes inhibit, slowing down, suppress, curb, or prevent excessive or abnormal proliferation of reactive astrocytes and its associated detrimental effects of the CNS.

As used herein, the term "chondroitin sulfate proteoglycans" includes proteoglycans composed of a protein core and a chondroitin sulfate. Chondroitin sulfate proteoglycans, also known as CSPGs, are extracellular matrix molecules widely expressed throughout the developing and adult CNS. CSGPs play key roles in neural development and glial scar formation, and they inhibit axon regeneration after injury in the CNS. Known CSPGs include aggrecan (CSPG1), versican (CSPG2), neurocan (CSPG3), CSPG4 (or neuron-glial antigen 2 (NG2)), CSPG5, SMC3 (CSPG6, structural maintenance of chromosomes 3), brevican (CSPG7), and CD44 (CSPG8, cluster of differentiation 44), phosphacanneurocan (CSPG3). Rhodes, K. E. and Fawcett, J. W. (2004) *Journal of Anatom.* 204(1):33-48. Thus, the term "decrease expression of chondroitin sulfate proteoglycans" includes decrease, inhibit, reduce the level of one or more CSGPs, or reduce the activity of or render inactive one or more CSGPs. In certain embodiments, the term includes decrease, inhibit, reduce the level of neurocan, NG2, or both, or reduce the activity of or render inactive neurocan, NG2, or both.

As used herein, the term "neuron" includes electrically excitable cells that process and transmit information through electrical and chemical signals. Neurons are the major components of the brain and spinal cord of the CNS, and of the ganglia of the peripheral nervous system (PNS), and can connect to each other to form neural networks. A typical neuron is composed of a cell body (soma), dendrites, and an axon. The soma (the cell body) of a neuron contains the nucleus. The dendrites of a neuron are cellular extensions with many branches, where the majority of input to the neuron occurs. The axon is a finer, cable-like projection extending from the soma and carries nerve signals away from the soma and certain types of information back to the soma. The term "promote regrowth of neuron" includes stimulating, promoting, increasing, or activating growth of neurons, preferably after injury or damage.

As used herein, the term "c-fos" includes the protooncogene c-fos, which is rapidly induced by stimulation of a neurotransmitter. c-fos exists in many species including mouse and human. The c-fos gene and protein are known and characterized. See Curran, T, The c-fos proto-oncogene, pp 307-327 (The Oncogene Handbook, Reddy E P et al., (eds.) Elsevier)(1988). The expression of c-fos can be determined by methods known in the art, e.g., Northern blot, quantitative PCR, or immunohistochemistry. The term "increases expression of c-fos" includes increase the level of c-fos mRNA, c-fos protein, or c-fos protein activity.

As used herein, the term "pERK" includes phosphorylated extracellular signal-regulated kinase. Extracellular signal-regulated kinase or ERK, includes ERK1 and ERK2, is a member of mitogen-activated protein kinase (MAPK) family. ERK is activated via phosphorylation by its upstream kinase to form pERK, which then activates down-stream targets. ERK is involved in neural and synaptic plasticity underlying learning, and memory and pain hypersensitivity. Ji R. R. et al., *Nat Neurosci* (1999) 2:1114-1119. The ERK gene, protein, phosphorylation, and activation are known and characterized, and the expression of ERK and pERK can be determined by methods known in the art (e.g., Northern blot, quantitative PCR, or immunohistochemistry). See Gao Y. J. and Ji R. R., *Open Pain J.* (2009) 2:11-17. The term "increase expression of pERK" includes increase the level of ERK mRNA, ERK protein, or pERK activity.

As used herein, the term "GAP43," also known as "growth Associated Protein 43," is a nervous tissue-specific protein that promotes neurite formation, regeneration, and plasticity. Benowitz L. I. and Routtenberg A. (1997) *Trends in Neurosciences* 20 (2): 84-91; Aarts L. H. et al., (1998) *Advances in Experimental Medicine and Biology* 446: 85-106. The human GAP43 is encoded by the GAP43 gene. Human GAP43 polypeptide sequence (UniProt: KB-P17677) and the cDNA sequence encoding the polypeptide are known in the art. Kosik K. S. et al., (1988) *Neuron* 1(2):127-32; Ng S. C. et al., (1988) *Neuron* 1(2): 133-9. The expression of GAP43 can be determined by methods known in the art (e.g., Northern blot, quantitative PCR, or immunohistochemistry). The term "increase GAP43 in neurons" includes enhancing or increasing the level of GAP43 mRNA, GAP43 protein, or increasing the activity of GAP43 protein.

The term "therapeutically effective amount" as used herein refers to an amount of a drug, alone or in combination with another therapeutic agent, effective to "treat" a disease or disorder in a subject or reduce the risk, potential, possibility or occurrence of a disease or disorder (e.g., a central nervous system damage). A "therapeutically effective amount" includes an amount of a drug or a therapeutic agent that provides some improvement or benefit to a subject having or at risk of having a disease or disorder (e.g., a central nervous system damage such as a traumatic brain injury or other disease disclosed herein). Thus, a "therapeutically effective" amount is an amount that reduces the risk, potential, possibility or occurrence of a disease or provides disorder or some alleviation, mitigation, and/or reduces at least one indicator (e.g., an onset of reactive gliosis), and/or decrease in at least one clinical symptom of a disease or disorder.

II. Anti-FAM19A5 Antibodies

Disclosed herein are antibodies, e.g., monoclonal antibodies, which are characterized by particular functional features or properties. For example, the antibodies, which specifically bind human FAM19A5, have been mutated (e.g., substituted or deleted) by removing and/or modifying regions or residues that are highly immunogenic in humans (i.e., de-immunized). Accordingly, the antibodies disclosed herein, i.e., anti-FAM19A5 antibody, have reduced immunogenicity when administered to a human subject, compared to a reference antibody (e.g., a corresponding antibody that has not been de-immunized, e.g., 3-2 or 2-13 antibody).

In addition, the antibodies described herein exhibit one or more of the following functional properties:

(a) binds to soluble human FAM19A5 with a $K_D$ of 10 nM or less;

(b) binds to membrane bound human FAM19A5 with a $K_D$ of 10 nM or less;

(c) reduces, reverses, delays, and/or prevents an onset of reactive gliosis;

(d) suppresses an excessive proliferation of reactive astrocytes (e) decreases expression of chondroitin sulfate proteoglycans including neurocan and neuron-glial antigen 2 (NG2);

(f) increases expression of c-fos and pERK in the nucleus of neurons;

(g) promotes survival of neurons.

(h) increases expression of GAP43 in neurons; and (i) promotes regrowth of an axon.

In some embodiments, the anti-FAM19A5 antibody has been de-immunized such that the antibody is less immunogenic when administered to a human subject, compared to a reference antibody (e.g., a corresponding antibody which has not been de-immunized, e.g., antibody 3-2 or 2-13). In some embodiments, the immunogenicity of the antibody has been reduced by at least about 5%, at least about 10%, at least about 15%, at least about 20%, at least about 25%, at least about 30%, at least about 35%, at least about 40%, at least about 45%, at least about 50%, at least about 60%, at least about 70%, at least about 80%, at least about 90%, or at least about 100%, compared to a reference antibody (e.g., a corresponding antibody which has not been de-immunized, e.g., antibody 3-2 or 2-13). In some embodiments, the de-immunization process does not alter the binding affinity of the antibody.

In some embodiments, the anti-FAM19A5 antibody disclosed herein has undergone affinity maturation, such that the antibody binds to FAM19A5 protein with greater affinity, compared to a reference antibody (e.g., a corresponding antibody which has not undergone affinity maturation, e.g., antibody 2-13). In certain embodiments, the binding affinity of the antibody has been increased by at least about 5%, at least about 10%, at least about 15%, at least about 20%, at least about 25%, at least about 30%, at least about 35%, at least about 40%, at least about 45%, at least about 50%, at least about 60%, at least about 70%, at least about 80%, at least about 90%, or at least about 100% or more, compared to a reference antibody (e.g., a corresponding antibody which has not undergone affinity maturation, e.g., antibody 2-13). In some embodiments, the affinity maturation process does not alter the immunogenicity of the antibody.

In some embodiments, the anti-FAM19A5 antibody disclosed herein has both been de-immunized and undergone affinity maturation, such that, when compared to a reference antibody (e.g., a corresponding antibody which has not been de-immunized or undergone affinity maturation, e.g., antibody 3-2 or 2-13), the antibody is not only less immunogenic when administered to a human subject, but also binds to FAM19A5 protein with greater affinity. In some embodiments, the immunogenicity of the antibody has been reduced by at least about 5%, at least about 10%, at least about 15%, at least about 20%, at least about 25%, at least about 30%, at least about 35%, at least about 40%, at least about 45%, at least about 50%, at least about 60%, at least about 70%, at least about 80%, at least about 90%, or at least about 100%, compared to a reference antibody. In some embodiments, the binding affinity of the antibody has been increased by at least about 5%, at least about 10%, at least about 15%, at least about 20%, at least about 25%, at least about 30%, at least about 35%, at least about 40%, at least about 45%, at least about 50%, at least about 60%, at least about 70%, at least about 80%, at least about 90%, or at least about 100% or more, compared to a reference antibody.

In some embodiments, the anti-FAM19A5 antibody specifically binds to soluble human FAM19A5 or membrane-bound human with high affinity, for example, with a $K_D$ of $10^{-7}$ M or less, $10^{-8}$ M (10 nM) or less, $10^{-9}$ M (1 nM) or less, $10^{-10}$ M (0.1 nM) or less, $10^{-11}$ M or less, or $10^{-12}$ M or less, e.g., $10^{-12}$ M to $10^{-7}$ M, $10^{-11}$ M to $10^{-7}$ M, $10^{-10}$ M to $10^{-7}$ M, or $10^{-9}$ M to $10^{-7}$ M, e.g., $10^{-12}$ M, $5\times10^{-12}$ M, $10^{-11}$ M, $5\times10^{-11}$ M, $10^{-10}$ M, $5\times10^{-10}$ M, $10^{-9}$ M, $5\times10^{-9}$ M, $10^{-8}$ M, $5\times10^{-8}$ M, $10^{-7}$ M, or $5\times10^{-7}$ M. Standard assays to evaluate the binding ability of the antibody toward human FAM19A5 of various species are known in the art, including for example, ELISAs, Western blots, and RIAs. Suitable assays are described in detail in the Examples. The binding kinetics (e.g., binding affinity) of the antibodies also can be assessed by standard assays known in the art, such as by ELISA, BIACORE® analysis or KinExA. Assays to evaluate the effects of the antibodies on functional properties of FAM19A5 (e.g., ligand binding) are described in further detail infra and in the Examples.

In some embodiments, the anti-FAM19A5 antibody specifically binds to soluble human FAM19A5 with a $K_D$, e.g., as determined by ELISA, of $10^{-7}$ M or less, $10^{-8}$ M (10 nM) or less, $10^{-9}$ M (1 nM) or less, $10^{-10}$ M or less, $10^{-2}$ M to $10^{-7}$ M, $10^{-11}$ M to $10^{-7}$ M, $10^{-10}$ M to $10^{-7}$ M, $10^{-9}$ M to $10^{-7}$ M, or $10^{-8}$ M to $10^{-7}$ M. In some embodiments, the anti-FAM19A5 antibody specifically binds to soluble FAM19A5 with a $K_D$ of 10 nM or less, e.g., between 0.1 and 10 nM, between 0.1 and 5 nM, between 0.1 and 1 nM, between 0.5 and 10 nM, between 0.5 and 5 nM, between 0.5 and 1 nM, between 1 and 10 nM, between 1 and 5 nM, or between 5 and 10 nM. In some embodiments, the anti-FAM19A5 antibody specifically binds to soluble human FAM19A5 with a $K_D$ of about 1 pM, about 2 pM, about 3 pM, about 4 pM, about 5 pM, about 6 pM, about 7 pM, about 8 pM, about 9 pM, about 10 pM, about 20 pM, about 30 pM, about 40 pM, about 50 pM, about 60 pM, about 70 pM, about 80 pM, about 90 pM, about 100 pM, about 200 pM, about 300 pM, about 400 pM, about 500 pM, about 600 pM, about 700 pM, about 800 pM, or about 900 pM, or about 1 nM, about 2 nM, about 3 nM, about 4 nM, about 5 nM, about 6 nM, about 7 nM, about 8 nM, or about 9 nM, or about 10 nM, about 20 nM, about 30 nM, about 40 nM, about 50 nM, about 60 nM, about 70 nM, about 80 nM, or about 90 nM, as determined by as determined by ELISA.

In some embodiments, the anti-FAM19A5 antibody specifically binds to membrane-bound human with a $K_D$, e.g., as determined by ELISA, of $10^{-7}$ M or less, $10^{-8}$ M (10 nM) or less, $10^{-9}$ M (1 nM) or less, $10^{-10}$ M or less, $10^{-12}$M to $10^{-7}$M, $10^{-11}$ M to $10^{-7}$M, $10^{-0}$ M to $10^{-7}$ M, $10^{-9}$ M to $10^{-7}$ M, or $10^{-8}$ M to $10^{-7}$ M. In certain embodiments, the anti-FAM19A5 antibody specifically binds to membrane-bound human FAM19A5 with a $K_D$ of 10 nM or less as determined by ELISA, e.g., between 0.1 and 10 nM, between 0.1 and 5 nM, between 0.1 and 1 nM, between 0.5 and 10 nM, between 0.5 and 5 nM, between 0.5 and 1 nM, between 1 and 10 nM, between 1 and 5 nM, or between 5 and 10 nM. In some embodiments, the anti-FAM19A5 antibody specifically binds to membrane-bound human FAM19A5 with a $K_D$ of about 1 pM, about 2 pM, about 3 pM, about 4 pM, about 5 pM, about 6 pM, about 7 pM, about 8 pM, about 9 pM, about 10 pM, about 20 pM, about 30 pM, about 40 pM, about 50 pM, about 60 pM, about 70 pM, about 80 pM, about 90 pM, about 100 pM, about 200 pM, about 300 pM, about 400 pM, about 500 pM, about 600 pM, about 700 pM, about 800 pM, or about 900 pM, or about 1 nM, about 2 nM, about 3 nM, about 4 nM, about 5 nM, about 6 nM, about 7 nM, about 8 nM, or about 9 nM, or about 10 nM, about 20 nM, about 30 nM, about 40 nM, about 50 nM, about 60 nM, about 70 nM, about 80 nM, or about 90 nM, as determined by as determined by ELISA.

An anti-FAM19A5 antibody of the present disclosure can delay or inhibit an onset of gliosis, e.g., delay, slow down or suppress an onset or beginning of a nonspecific reactive change of glial cells in the central nervous system (CNS, e.g., brain and/or the spinal cord) in response to injury or damage from, e.g., trauma, cerebrospinal damage, brain tumor, infection, ischemia, stroke, autoimmune responses, and/or neurodegenerative disease.

An anti-FAM19A5 antibody of the present disclosure can delay, inhibit, slow down, suppress, curb, or prevent excessive or abnormal proliferation of reactive astrocytes and its associated detrimental effects of the CNS. For example, an anti-FAM19A5 antibody of the present disclosure can inhibit or prevent abnormal increase in the number of astrocytes due to the destruction of neurons from e.g., CNS damage, trauma, injury, cerebrospinal damage, brain tumor, infection, ischemia, stroke, autoimmune responses, and/or neurodegenerative disease, inhibit or prevent scar formation in the CNS, inhibit or reduce the release of neurotoxic levels of reactive oxygen species or release of potentially excitotoxic glutamate, reduce or inhibit seizure, pain, and/or secondary degeneration after CNS injury. An anti-FAM19A5 antibody of the present disclosure can promote, stimulate, increase, or activate regrowth of neurons and/or axon, preferably after CNS injury or damage.

An anti-FAM19A5 antibody of the present disclosure can inhibit expression of chondroitin sulfate proteoglycans including proteoglycans composed of a protein core and a chondroitin sulfate (CSGPs), such as aggrecan (CSPG1), versican (CSPG2), neurocan (CSPG3), CSPG4 (or neuron-glial antigen 2 (NG2)), CSPG5, SMC3 (CSPG6, structural maintenance of chromosomes 3), brevican (CSPG7), CD44 (CSPG8, cluster of differentiation 44), and phosphacanneurocan (CSPG3). In some embodiments, the anti-FAM19A5 antibody of the present disclosure inhibits, decreases, or reduces the level of neurocan and/or NG2, or the activities of neurocan and/or NG2.

An anti-FAM19A5 antibody of the present disclosure can increase expression of c-fos and pERK in the nucleus of neurons, e.g., increase the mRNA, protein, and/or protein activity of c-fos and pERK. An anti-FAM19A5 antibody of the present disclosure can also increase or enhance the level of expression of GAP43 mRNA, GAP43 protein or increase or enhance the GAP43 protein activities.

In some embodiments, an anti-FAM19A5 antibody of the present disclosure comprises a heavy chain CDR1, CDR2, and CDR3 and a light chain CDR1, CDR2, and CDR3, wherein the heavy chain CDR1, CDR2, and CDR3 comprises the amino acid sequences set forth in SEQ ID NOs: 5, 6, and 7, respectively, each of which optionally comprising one, two, three, four, or five mutations, wherein the light chain CDR1, CDR2, and CDR3 comprise the amino acid sequences set forth in SEQ ID NOs: 8, 9, and 10, respectively, wherein at least one of the light chain CDR1, CDR2, and CDR3 comprising one, two, three, four, or five mutations, and wherein the antibody has a reduced immunogenicity in human compared to a reference antibody comprising the VH set forth in SEQ ID NO: 11 and the VL set forth in SEQ ID NO: 12.

In some embodiments, the mutations that are included in the antibody are substitution, deletion, and/or insertion. In one embodiment, the mutation is a substitution, e.g., conservative substitution. "Conservative substitution" (also referred to as conservative replacement) as used herein means an amino acid replacement that changes a given amino acid to a different amino acid with similar biochemical properties (e.g., charge, hydrophobicity and size). Although there are many ways to classify amino acids, they are often sorted into six main groups on the basis of their structure and the general chemical characteristics of their R groups.

TABLE 2

| Amino Acid Classes | |
|---|---|
| Class | Amino Acids |
| Aliphatic | Glycine, Alanine, Valine, Leucine, Isoleucine |
| Hydroxyl or sulfur/selenium-containing | Serine, Cysteine, Selenocysteine, Threonine, Methionine |
| Cyclic | Proline |
| Aromatic | Phenylalanine, Tyrosine, Tryptophan |
| Basic | Histidine, Lysine, Arginine |
| Acidic and their amides | Aspartate, Glutamate, Asparagine, Glutamine |

Conversely, a radical replacement, or radical substitution, is an amino acid replacement that exchanges an initial amino acid by a final amino acid with different physicochemical properties. In certain embodiments, the amino acid mutation at the FAM19A5 antibody is a radical substitution. In other embodiments, the amino acid mutation at the FAM19A5 antibody is a combination of a conservative substitution and a radical substitution.

In some embodiments, the heavy chain CDR3 comprises the amino acid sequence set forth in SEQ ID NO: 7. In certain embodiments, the heavy chain CDR3 comprises the amino acid sequence set forth in SEQ ID NO: 7, with one, two, or three mutations.

In some embodiments, the heavy chain CDR1 comprises the amino acid sequence set forth in SEQ ID NO: 5, optionally with one or two mutations. In certain embodiments, the mutations comprise a substitution of Threonine at amino acid 3 of SEQ ID NO: 5 to an acidic amino acid. In further embodiments, the mutations comprise a substitution of Serine at amino acid 5 of SEQ ID NO: 5 to an acidic amino acid. In some embodiments, the acidic amino acid comprises Aspartic Acid or Glutamic Acid.

In some embodiments, the heavy chain CDR2 comprises the amino acid sequence set forth in SEQ ID NO: 6, optionally with one, two, three, four, or five mutations. In certain embodiments, the mutations comprise a substitution of Arginine at amino acid 16 of SEQ ID NO: 6 to a basic amino acid. In some embodiments, the basic amino acid comprises Lysine. In some embodiments, the mutations comprise one or more of the following:

(a) a substitution of Glycine at amino acid 6 of SEQ ID NO: 6 to an acidic amino acid;
(b) a substitution of Serine at amino acid 7 of SEQ ID NO: 6 to an acidic amino acid;
(c) a substitution of Serine at amino acid 8 of SEQ ID NO: 6 to an acidic amino acid;
(d) a substitution of Threonine at amino acid 9 of SEQ ID NO: 6 to an acidic amino acid; and
(e) a substitution of Arginine at amino acid 16 of SEQ ID NO: 6 to a basic amino acid.

In certain embodiments, the acidic amino acid comprises Aspartic Acid or Glutamic Acid. In some embodiments, the basic amino acid comprises Lysine.

In some embodiments, the light chain CDR3 comprises the amino acid sequence set forth in SEQ ID NO: 10, optionally with one, two, three, four, or five mutations. In certain embodiments, the mutations comprise one or more of the following:

(a) a substitution of Serine at amino acid 6 of SEQ ID NO: 10 to an acidic amino acid or to an aliphatic amino acid;
(b) a substitution of Asparagine at amino acid 7 of SEQ ID NO: 10 to an acidic amino acid or to a hydroxyl or sulfur/selenium-containing amino acid;
(c) a substitution of Glycine at amino acid 8 of SEQ ID NO: 10 to an acidic amino acid or to a hydroxyl or sulfur/selenium-containing amino acid;
(d) a substitution of Glycine at amino acid 9 of SEQ ID NO: 10 to an acidic amino acid or to a hydroxyl or sulfur/selenium-containing amino acid; and
(e) a substitution of Isoleucine at amino acid 10 of SEQ ID NO: 10 to a basic amino acid.

In some embodiments, the acidic amino acid comprises Aspartic Acid or Glutamic Acid. In certain embodiments, the hydroxyl or sulfur/selenium-containing amino acid comprises Serine. In further embodiments, the basic amino acid comprises Histidine.

In some embodiments, the light chain CDR1 comprises the amino acid sequence set forth in SEQ ID NO: 8, with one, two, three, or four mutations. In certain embodiments, the mutations comprise one or more of the following:

(a) a substitution of Tyrosine at amino acid 6 of SEQ ID NO: 8 to an acidic amino acid;
(b) a substitution of Arginine at amino acid 7 of SEQ ID NO: 8 to an acidic amino acid;
(c) a substitution of Glycine at amino acid 8 of SEQ ID NO: 8 to an acidic amino acid; and
(d) a substitution of Serine at amino acid 9 of SEQ ID NO: 8 to an acidic amino acid.

In some embodiments, the acidic amino acid comprises Glutamic Acid or Glutamine.

In some embodiments, the light chain CDR2 comprises the amino acid sequence set forth in SEQ ID NO: 9, with one, two, three, or four mutations. In certain embodiments, the mutations comprise one or more of the following:

(a) a substitution of Glutamic Acid at amino acid 1 of SEQ ID NO: 9 to an acidic amino acid;
(b) a substitution of Serine at amino acid 2 of SEQ ID NO: 9 to an acidic amino acid;
(c) a substitution of Asparagine at amino acid 3 of SEQ ID NO: 9 to an acidic amino acid, to a basic amino acid, or to an aliphatic amino acid; and
(d) a substitution of Lysine at amino acid 4 of SEQ ID NO: 9 to an acidic amino acid or to an aliphatic amino acid.

In some embodiments, the acidic amino acid comprises Glutamine, Asparagine, Aspartic Acid, or Glutamic Acid. In certain embodiments, the basic amino acid comprises Histidine. In further embodiments, the aliphatic amino acid comprises Leucine.

In some embodiments, the mutations comprise a substitution of Serine at amino acid 2 of SEQ ID NO: 9 to an acidic amino acid. In certain embodiments, the acidic amino acid comprises Aspartate, Glutamate, Asparagine, Glutamine, or combinations thereof. In further embodiments, the acidic amino acid is Asparagine.

In some embodiments, an anti-FAM19A5 antibody disclosed herein comprises a heavy chain CDR1, CDR2, and CDR3 and a light chain CDR1, CDR2, and CDR3, wherein: (i) the heavy chain CDR1 comprises the amino acid sequence set forth in SEQ ID NO: 5; (ii) the heavy chain CDR2 comprises the amino acid sequence set forth in SEQ ID NO: 13; (iii) the heavy chain CDR3 comprises the amino acid sequence set forth in SEQ ID NO: 7; (iv) the light chain CDR1 comprises the amino acid sequence set forth in SEQ ID NO: 8; (v) the light chain CDR2 comprises the amino acid sequence set forth in SEQ ID NO: 20; and (vi) the light chain CDR3 comprises the amino acid sequence set forth in SEQ ID NO: 10.

In some embodiments, an anti-FAM19A5 antibody comprises a heavy chain CDR1, CDR2, and CDR3 and a light chain CDR1, CDR2, and CDR3, wherein: (i) the heavy chain CDR1 comprises the amino acid sequence set forth in SEQ ID NO: 14; (ii) the heavy chain CDR2 comprises the amino acid sequence set forth in SEQ ID NO: 15; (iii) the heavy chain CDR3 comprises the amino acid sequence set forth in SEQ ID NO: 7; (iv) the light chain CDR1 comprises the amino acid sequence set forth in SEQ ID NO: 21; (v) the light chain CDR2 comprises the amino acid sequence set forth in SEQ ID NO: 22; and (vi) the light chain CDR3 comprises the amino acid sequence set forth in SEQ ID NO: 23.

In some embodiments, an anti-FAM19A5 antibody of the present disclosure comprises a heavy chain CDR1, CDR2, and CDR3 and a light chain CDR1, CDR2, and CDR3, wherein: (i) the heavy chain CDR1 comprises the amino acid sequence set forth in SEQ ID NO: 14; (ii) the heavy chain CDR2 comprises the amino acid sequence set forth in SEQ ID NO: 15; (iii) the heavy chain CDR3 comprises the amino acid sequence set forth in SEQ ID NO: 7; (iv) the light chain CDR1 comprises the amino acid sequence set forth in SEQ ID NO: 21; (v) the light chain CDR2 comprises the amino acid sequence set forth in SEQ ID NO: 24; and (vi) the light chain CDR3 comprises the amino acid sequence set forth in SEQ ID NO: 23.

In some embodiments, an anti-FAM19A5 antibody comprises a heavy chain CDR1, CDR2, and CDR3 and a light chain CDR1, CDR2, and CDR3, wherein: (i) the heavy chain CDR1 comprises the amino acid sequence set forth in SEQ ID NO: 14; (ii) the heavy chain CDR2 comprises the amino acid sequence set forth in SEQ ID NO: 15; (iii) the heavy chain CDR3 comprises the amino acid sequence set forth in SEQ ID NO: 7; (iv) the light chain CDR1 comprises the amino acid sequence set forth in SEQ ID NO: 8; (v) the light chain CDR2 comprises the amino acid sequence set forth in SEQ ID NO: 25; and (vi) the light chain CDR3 comprises the amino acid sequence set forth in SEQ ID NO: 23.

In some embodiments, an anti-FAM19A5 antibody disclosed herein comprises a heavy chain CDR1, CDR2, and CDR3 and a light chain CDR1, CDR2, and CDR3, wherein: (i) the heavy chain CDR1 comprises the amino acid sequence set forth in SEQ ID NO: 14; (ii) the heavy chain CDR2 comprises the amino acid sequence set forth in SEQ ID NO: 15; (iii) the heavy chain CDR3 comprises the amino acid sequence set forth in SEQ ID NO: 7; (iv) the light chain CDR1 comprises the amino acid sequence set forth in SEQ ID NO: 8; (v) the light chain CDR2 comprises the amino acid sequence set forth in SEQ ID NO: 24; and (vi) the light chain CDR3 comprises the amino acid sequence set forth in SEQ ID NO: 23.

In some embodiments, an anti-FAM19A5 antibody comprises a heavy chain CDR1, CDR2, and CDR3 and a light chain CDR1, CDR2, and CDR3, wherein: (i) the heavy chain CDR1 comprises the amino acid sequence set forth in SEQ ID NO: 14; (ii) the heavy chain CDR2 comprises the amino acid sequence set forth in SEQ ID NO: 15; (iii) the heavy chain CDR3 comprises the amino acid sequence set forth in SEQ ID NO: 7; (iv) the light chain CDR1 comprises the amino acid sequence set forth in SEQ ID NO: 8; (v) the light chain CDR2 comprises the amino acid sequence set forth in SEQ ID NO: 26; and (vi) the light chain CDR3 comprises the amino acid sequence set forth in SEQ ID NO: 27.

In some embodiments, an anti-FAM19A5 antibody comprises a heavy chain CDR1, CDR2, and CDR3 and a light chain CDR1, CDR2, and CDR3, wherein: (i) the heavy chain CDR1 comprises the amino acid sequence set forth in SEQ ID NO: 14; (ii) the heavy chain CDR2 comprises the amino acid sequence set forth in SEQ ID NO: 15; (iii) the heavy chain CDR3 comprises the amino acid sequence set forth in SEQ ID NO: 7; (iv) the light chain CDR1 comprises the amino acid sequence set forth in SEQ ID NO: 8; (v) the light chain CDR2 comprises the amino acid sequence set forth in SEQ ID NO: 28; and (vi) the light chain CDR3 comprises the amino acid sequence set forth in SEQ ID NO: 29.

In some embodiments, an anti-FAM19A5 antibody of the present disclosure is humanized. In other embodiments, the humanized anti-FAM19A5 comprises a framework region of a human antibody. In certain embodiments, an anti-FAM19A5 antibody comprises one or more (e.g., one, two, three, four, five, six, seven or more) mutations within a framework region (i.e., FR1, FR2, FR3, and FR4 of VH and/or FR1, FR2, FR3, and FR4 of VL) of the antibody.

In some embodiments, an anti-FAM19A5 antibody comprises a mutation within FR1 of VH. In certain embodiments, the mutation comprises an amino acid substitution at residue 19 (e.g., Serine to a basic amino acid, e.g., Arginine) and/or at residue 21 (e.g., Valine to a hydroxyl or sulfur/selenium-containing amino acid, e.g., Serine) of SEQ ID NO: 11.

In some embodiments, an anti-FAM19A5 antibody disclosed herein comprises a mutation within FR2 of VH. In certain embodiments, the mutation comprises an amino acid substitution at residue 49 (e.g., Alanine to a hydroxyl or sulfur/selenium-containing amino acid, e.g., Serine) of SEQ ID NO: 11.

In some embodiments, an anti-FAM19A5 antibody of the present disclosure comprises a mutation within FR3 of VH. In certain embodiments, the mutation comprises an amino acid substitution at residue 79 (e.g., Valine to an aliphatic amino acid, e.g., Leucine), residue 80 (e.g., Arginine to an aromatic amino acid, e.g., Tyrosine), residue 83 (e.g., Leucine to a hydroxyl or sulfur/selenium-containing amino acid, e.g., Methionine), residue 85 (e.g., Asparagine to a hydroxyl or sulfur/selenium-containing amino acid, e.g., Serine), residue 86 (e.g., Proline to an aliphatic amino acid, e.g., Leucine), and/or residue 87 (e.g., Glycine to a basic amino acid, e.g., Arginine) of SEQ ID NO: 11.

In some embodiments, an anti-FAM19A5 antibody comprises a mutation within FR2 of VL. In certain embodiments, the mutation comprises a deletion of amino acid residue 39 of SEQ ID NO: 12.

In some embodiments, an anti-FAM19A5 antibody disclosed herein comprises a mutation within FR3 of VL. In some embodiments, the mutation comprises an amino acid substitution at residue 81 (e.g., Aspartic Acid to an aliphatic amino acid, e.g., Glycine) and/or residue 85 (e.g., Isoleucine to an acidic amino acid, e.g., Aspartic Acid) of SEQ ID NO: 12.

In some embodiments, an anti-FAM19A5 antibody of the present disclosure comprises a heavy chain variable region (VH) and a light chain variable region (VL), wherein the VH comprises an amino acid sequence which is at least about 80%, at least about 85%, at least about 90%, at least about 95%, at least about 96%, at least about 97%, at least about 98%, at least about 99%, or about 100% identical to the amino acid sequence set forth as SEQ ID NO: 11, and/or wherein the VL comprises an amino acid sequence which is at least about 80%, at least about 85%, at least about 90%, at least about 95%, at least about 96%, at least about 97%, at least about 98%, at least about 99%, or about 100% identical to the amino acid sequence set forth as SEQ ID NO: 12, wherein the antibody has reduced immunogenicity compared to a reference antibody comprising the VH set forth as SEQ ID NO: 11 and the VL set forth as SEQ ID NO: 12.

In some embodiments, an anti-FAM19A5 antibody disclosed herein cross-competes with a reference antibody, which comprises a heavy chain variable region (VH) and a light chain variable region (VL), wherein:

(a) the VH comprises the amino acid sequence set forth in SEQ ID NO: 33, and the VL comprises the amino acid sequence set forth in SEQ ID NO: 38;
(b) the VH comprises the amino acid sequence set forth in SEQ ID NO: 34, and the VL comprises the amino acid sequence set forth in SEQ ID NO: 39;
(c) the VH comprises the amino acid sequence set forth in SEQ ID NO: 34, and the VL comprises the amino acid sequence set forth in SEQ ID NO: 41;
(d) the VH comprises the amino acid sequence set forth in SEQ ID NO: 34, and the VL comprises the amino acid sequence set forth in SEQ ID NO: 40;
(e) the VH comprises the amino acid sequence set forth in SEQ ID NO: 34, and the VL comprises the amino acid sequence set forth in SEQ ID NO: 42;
(f) the VH comprises the amino acid sequence set forth in SEQ ID NO: 34, and the VL comprises the amino acid sequence set forth in SEQ ID NO: 43; or
(g) the VH comprises the amino acid sequence set forth in SEQ ID NO: 34, and the VL comprises the amino acid sequence set forth in SEQ ID NO: 44.

In some embodiments, an anti-FAM19A5 antibody binds to the same human FAM19A5 epitope as a reference antibody, which comprises a heavy chain variable region (VH) and a light chain variable region (VL), wherein:

(a) the VH comprises the amino acid sequence set forth in SEQ ID NO: 33, and the VL comprises the amino acid sequence set forth in SEQ ID NO: 38;

(b) the VH comprises the amino acid sequence set forth in SEQ ID NO: 34, and the VL comprises the amino acid sequence set forth in SEQ ID NO: 39;

(c) the VH comprises the amino acid sequence set forth in SEQ ID NO: 34, and the VL comprises the amino acid sequence set forth in SEQ ID NO: 41;

(d) the VH comprises the amino acid sequence set forth in SEQ ID NO: 34, and the VL comprises the amino acid sequence set forth in SEQ ID NO: 40;

(e) the VH comprises the amino acid sequence set forth in SEQ ID NO: 34, and the VL comprises the amino acid sequence set forth in SEQ ID NO: 42;

(f) the VH comprises the amino acid sequence set forth in SEQ ID NO: 34, and the VL comprises the amino acid sequence set forth in SEQ ID NO: 43; or (g) the VH comprises the amino acid sequence set forth in SEQ ID NO: 34, and the VL comprises the amino acid sequence set forth in SEQ ID NO: 44.

In some embodiments, an anti-FAM19A5 antibody disclosed herein comprises a heavy chain CDR1, CDR2, and CDR3 and a light chain CDR1, CDR2, and CDR3, wherein the heavy chain CDR1, CDR2, and CDR3 comprises the amino acid sequences set forth in SEQ ID NOs: 16, 17, and 18, respectively, each of which optionally comprising one, two, or three mutations, wherein the light chain CDR1, CDR2, and CDR3 comprise the amino acid sequences set forth in SEQ ID NOs: 30, 31, and 32, respectively, wherein at least one of the light chain CDR1, CDR2, and CDR3 comprises one, two, or three mutations, and wherein the antibody has a reduced immunogenicity in human and/or higher binding affinity to human FAM19A5 protein compared to a reference antibody comprising the VH set forth in SEQ ID NO: 35 and the VL set forth in SEQ ID NO: 45.

In some embodiments, the heavy chain CDR3 comprises the amino acid sequence set forth in SEQ ID NO: 18. In certain embodiments, the heavy chain CDR3 comprises the amino acid sequence set forth in SEQ ID NO: 18, optionally with one or two mutations. In some embodiments, the mutation comprises one or more of the following: (a) a substitution of Threonine at amino acid 2 of SEQ ID NO: 18 to a hydroxyl or sulfur/selenium-containing amino acid; and (b) a substitution of Glutamic Acid at amino acid 4 of SEQ ID NO: 18 to an aliphatic amino acid. In certain embodiments, the hydroxyl or sulfur/selenium-containing amino acid comprises Serine. In some embodiments, the aliphatic amino acid comprises Valine. In some embodiments, the mutation comprises one or more of the following: (a) a substitution of Threonine at amino acid 2 of SEQ ID NO: 18 to an acidic acid; and (b) a substitution of Glutamic Acid at amino acid 4 of SEQ ID NO: 18 to an aliphatic amino acid. In certain embodiments, the acidic acid comprises Asparagine. In certain embodiments, the aliphatic amino acid comprises Alanine.

In some embodiments, the heavy chain CDR1 comprises the amino acid sequence set forth in SEQ ID NO: 16. In certain embodiments, the heavy chain CDR1 comprises the amino acid sequence set forth in SEQ ID NO: 16, optionally with one mutation. In some embodiments, the mutation comprises a substitution of Threonine at amino acid 3 of SEQ ID NO: 16 to an acidic amino acid. In certain embodiments, the acidic amino acid comprises Aspartic Acid.

In some embodiments, the heavy chain CDR2 comprises the amino acid sequence set forth in SEQ ID NO: 17.

In some embodiments, the light chain CDR3 comprises the amino acid sequence set forth in SEQ ID NO: 32. In certain embodiments, the light chain CDR2 comprises the amino acid sequence set forth in SEQ ID NO: 31. In some embodiments, the light chain CDR2 comprises the amino acid sequence set forth in SEQ ID NO: 31, with one, two, or three mutations.

In further embodiments, the light chain CDR1 comprises the amino acid sequence set forth in SEQ ID NO: 30, optionally with one mutation. In certain embodiments, the mutation comprises a substitution of Serine at amino acid 4 of SEQ ID NO: 30 to an aliphatic amino acid. In some embodiments, the aliphatic amino acid comprises Valine.

In some embodiments, an anti-FAM19A5 antibody disclosed herein comprises a heavy chain CDR1, CDR2, and CDR3 and a light chain CDR1, CDR2, and CDR3, wherein: (i) the heavy chain CDR1 comprises the amino acid sequence set forth in SEQ ID NO: 16; (ii) the heavy chain CDR2 comprises the amino acid sequence set forth in SEQ ID NO: 17; (iii) the heavy chain CDR3 comprises the amino acid sequence set forth in SEQ ID NO: 18; (iv) the light chain CDR1 comprises the amino acid sequence set forth in SEQ ID NO: 80; (v) the light chain CDR2 comprises the amino acid sequence set forth in SEQ ID NO: 31; and (vi) the light chain CDR3 comprises the amino acid sequence set forth in SEQ ID NO: 32.

In some embodiments, an anti-FAM19A5 antibody disclosed herein comprises a heavy chain CDR1, CDR2, and CDR3 and a light chain CDR1, CDR2, and CDR3, wherein: (i) the heavy chain CDR1 comprises the amino acid sequence set forth in SEQ ID NO: 19; (ii) the heavy chain CDR2 comprises the amino acid sequence set forth in SEQ ID NO: 17; (iii) the heavy chain CDR3 comprises the amino acid sequence set forth in SEQ ID NO: 18; (iv) the light chain CDR1 comprises the amino acid sequence set forth in SEQ ID NO: 80; (v) the light chain CDR2 comprises the amino acid sequence set forth in SEQ ID NO: 31; and (vi) the light chain CDR3 comprises the amino acid sequence set forth in SEQ ID NO: 32.

In some embodiments, an anti-FAM19A5 antibody disclosed herein comprises a heavy chain CDR1, CDR2, and CDR3 and a light chain CDR1, CDR2, and CDR3, wherein: (i) the heavy chain CDR1 comprises the amino acid sequence set forth in SEQ ID NO: 19; (ii) the heavy chain CDR2 comprises the amino acid sequence set forth in SEQ ID NO: 17; (iii) the heavy chain CDR3 comprises the amino acid sequence set forth in SEQ ID NO: 128; (iv) the light chain CDR1 comprises the amino acid sequence set forth in SEQ ID NO: 80; (v) the light chain CDR2 comprises the amino acid sequence set forth in SEQ ID NO: 31; and (vi) the light chain CDR3 comprises the amino acid sequence set forth in SEQ ID NO: 32.

In some embodiments, an anti-FAM19A5 antibody disclosed herein comprises a heavy chain CDR1, CDR2, and CDR3 and a light chain CDR1, CDR2, and CDR3, wherein: (i) the heavy chain CDR1 comprises the amino acid sequence set forth in SEQ ID NO: 19; (ii) the heavy chain CDR2 comprises the amino acid sequence set forth in SEQ ID NO: 17; (iii) the heavy chain CDR3 comprises the amino acid sequence set forth in SEQ ID NO: 129; (iv) the light chain CDR1 comprises the amino acid sequence set forth in SEQ ID NO: 80; (v) the light chain CDR2 comprises the amino acid sequence set forth in SEQ ID NO: 31; and (vi) the light chain CDR3 comprises the amino acid sequence set forth in SEQ ID NO: 32.

In some embodiments, an anti-FAM19A5 antibody of the present disclosure is humanized. In other embodiments, the humanized anti-FAM19A5 comprises a framework region of a human antibody. In certain embodiments, an anti-FAM19A5 antibody comprises one or more (e.g., one, two, three, four, five, six, seven or more) mutations within a framework region (i.e., FR1, FR2, FR3, and FR4 of VH and/or FR1, FR2, FR3, and FR4 of VL) of the antibody.

In some embodiments, an anti-FAM19A5 antibody disclosed herein comprises a mutation within FR1 of VH. In certain embodiments, the mutation comprises an amino acid substitution at residue 19 (e.g., Serine to a basic amino acid, e.g., Arginine), residue 21 (e.g., Valine to a hydroxyl or sulfur/selenium-containing amino acid, e.g., Serine), and/or residue 23 (e.g., Lysine to a hydroxyl or sulfur/selenium-containing amino acid, e.g., Serine) of SEQ ID NO: 35.

In some embodiments, an anti-FAM19A5 antibody comprises a mutation within FR2 of VH. In certain embodiments, the mutation comprises an amino acid substitution at residue 40 (e.g., Tyrosine to an aliphatic amino acid, e.g., Alanine) and/or residue 49 (e.g., Alanine to a hydroxyl or sulfur/selenium-containing amino acid, e.g., Serine) of SEQ ID NO: 35.

In some embodiments, an anti-FAM19A5 antibody comprises a mutation within FR3 of VH. In certain embodiments, the mutation comprises an amino acid substitution at residue 79 (e.g., Valine to an aliphatic amino acid, e.g., Leucine), residue 80 (e.g., Arginine to an aromatic amino acid, e.g., Tyrosine), residue 83 (e.g., Leucine to a hydroxyl or sulfur/selenium-containing amino acid, e.g., Methionine), and/or residue 85 (e.g., Asparagine to a hydroxyl or sulfur/selenium-containing amino acid, e.g., Serine) of SEQ ID NO: 35.

In some embodiments, an anti-FAM19A5 antibody comprises a mutation within FR1 of VL. In certain embodiments, the mutation comprises an amino acid substitution at residue 16 (e.g., Valine to an aliphatic amino acid, e.g., Alanine) of SEQ ID NO: 45.

In some embodiments, an anti-FAM19A5 antibody comprises a mutation within FR2 of VL. In certain embodiments, the mutation comprises a deletion of amino acid residue 34 of SEQ ID NO: 45.

In some embodiments, an anti-FAM19A5 antibody disclosed herein comprises a mutation within FR3 of VL. In some embodiments, the mutation comprises an amino acid substitution at residue 76 (e.g., Aspartic Acid to an acidic amino acid, e.g., Glutamic Acid), residue 80 (e.g., Valine to an acidic amino acid, e.g., Aspartic Acid), and/or residue 82 (e.g., Phenylalanine to an aromatic amino acid, e.g., Tyrosine) of SEQ ID NO: 45.

In some embodiments, an anti-FAM19A5 antibody disclosed herein comprises a heavy chain variable region (VH) and a light chain variable region (VL), wherein the VH comprises an amino acid sequence which is at least about 80%, at least about 85%, at least about 90%, at least about 95%, at least about 96%, at least about 97%, at least about 98%, at least about 99%, or about 100% identical to the amino acid sequence set forth in SEQ ID NO: 35 and/or wherein the VL comprises an amino acid sequence which is at least about 80%, at least about 85%, at least about 90%, at least about 95%, at least about 96%, at least about 97%, at least about 98%, at least about 99%, or about 100% identical to the amino acid sequence set forth in SEQ ID NO: 45.

In some embodiments, an anti-FAM19A5 antibody of the present disclosure cross-competes with a reference antibody, which comprises a heavy chain variable region (VH) and a light chain variable region (VL), wherein (i) the VH comprises the amino acid sequence set forth in SEQ ID NO: 36, and the VL comprises the amino acid sequence set forth in SEQ ID NO: 46; (ii) the VH comprises the amino acid sequence set forth in SEQ ID NO: 37, and the VL comprises the amino acid sequence set forth in SEQ ID NO: 46; (iii) the VH comprises the amino acid sequence set forth in SEQ ID NO: 130, and the VL comprises the amino acid sequence set forth in SEQ ID NO: 46; or (iv) the VH comprises the amino acid sequence set forth in SEQ ID NO: 131, and the VL comprises the amino acid sequence set forth in SEQ ID NO: 46.

In some embodiments, an anti-FAM19A5 antibody disclosed herein binds to the same human FAM19A5 epitope as a reference antibody, which comprises a heavy chain variable region (VH) and a light chain variable region (VL), wherein (i) the VH comprises the amino acid sequence set forth in SEQ ID NO: 36, and the VL comprises the amino acid sequence set forth in SEQ ID NO: 46; (ii) the VH comprises the amino acid sequence set forth in SEQ ID NO: 37, and the VL comprises the amino acid sequence set forth in SEQ ID NO: 46; (iii) the VH comprises the amino acid sequence set forth in SEQ ID NO: 130, and the VL comprises the amino acid sequence set forth in SEQ ID NO: 46; or (iv) the VH comprises the amino acid sequence set forth in SEQ ID NO: 131, and the VL comprises the amino acid sequence set forth in SEQ ID NO: 46.

In some embodiments, an anti-FAM19A5 antibody of the present disclosure cross-competes for binding to (or inhibits binding of) a human FAM19A5 epitope with a reference antibody (e.g., 3-2 or 2-13 antibody).

In some embodiments, an anti-FAM19A5 antibody inhibits binding of such a reference antibody (e.g., 3-2 or 2-13 antibody) to human FAM19A5 by at least about 10%, at least about 20%, at least about 30%, at least about 40%, at least about 50%, at least about 60%, at least about 70%, at least about 80%, at least about 90% or by at least about 100%. Competing antibodies bind to the same epitope, an overlapping epitope or to adjacent epitopes (e.g., as evidenced by steric hindrance). Whether two antibodies compete with each other for binding to a target can be determined using competition experiments known in the art such as RIA and EIA.

Techniques for determining whether two antibodies bind to the same epitope include, e.g., epitope mapping methods, such as, x-ray analyses of crystals of antigen:antibody complexes which provides atomic resolution of the epitope and hydrogen/deuterium exchange mass spectrometry (HDX-MS), methods monitoring the binding of the antibody to antigen fragments or mutated variations of the antigen, where loss of binding due to a modification of an amino acid residue within the antigen sequence is often considered an indication of an epitope component, computational combinatorial methods for epitope mapping.

An anti-FAM19A5 antibody that would be useful in the methods disclosed herewith can bind to at least one epitope of mature human FAM19A5, as determined, e.g., by binding of the antibodies to fragments of human FAM19A5. In some embodiments, an anti-FAM19A5 antibody binds to at least one epitope, which has the amino acid sequence of TLDRDSSQPRRTIARQTARC (SEQ ID NO: 90 or amino acid residues 42 to 61 of SEQ ID NO: 2), or bind to a fragment located within the amino acid sequence of SEQ ID NO: 90, e.g., an epitope having at least 1, 2, 3, 4, 5, 6, 7, 8, 9, 10, 11, 12, 13, 14, 15, 16, 17, 18, 19, or 20 amino acids of SEQ ID NO: 90. In some embodiments, an anti-FAM19A5 antibody disclosed herein binds to one or more amino acids corresponding to amino acid residues 44 to52 (i.e., DRDSSQPRR) of SEQ ID NO: 2, e.g., amino acid residues 45, 46, 50, 51, and 52 (RD---PRR), e.g., amino acid residues 45, 50, 51, and 52 (i.e., R----PRR), e.g., amino acid residues 43, 50, and 51 (i.e., R----PR).

In some embodiments, an anti-FAM19A5 antibody binds to at least one epitope, which has the amino acid sequence of TARCACRKGQIAGTTRARPA (SEQ ID NO: 91 or amino acid residues 58 to 77 of SEQ ID NO: 2), or bind to a fragment located within the amino acid sequence of SEQ ID NO: 91, e.g., an epitope having at least 1, 2, 3, 4, 5, 6, 7, 8, 9, 10, 11, 12, 13, 14, 15, 16, 17, 18, 19, or 20 amino acids of SEQ ID NO: 91. In some embodiments, an anti-FAM19A5 antibody binds to at one or more amino acids corresponding to amino acid residue 63 to 75 (i.e., CRKGQIAGTTRAR) of SEQ ID NO: 2. In some embodiments, an anti-FAM19A5 antibody binds to at least one epitope, which has the amino acid sequence of ARPACVDARIIKTKQWCDML (SEQ ID NO: 92 or amino acid residues 74 to 93 of SEQ ID NO: 2), or bind to a fragment located within the amino acid sequence of SEQ ID NO: 92, e.g., an epitope having at least 1, 2, 3, 4, 5, 6, 7, 8, 9, 10, 11, 12, 13, 14, 15, 16, 17, 18, 19, or 20 amino acids of SEQ ID NO: 92. In some embodiments, an anti-FAM19A5 antibody binds to at one or more amino acids corresponding to amino acid residue 76 to 89 (i.e., PACVDARIIKTKQW) of SEQ ID NO: 2.

In some embodiments, the at least one epitope has the amino acid sequence that is at least 90%, at least about 95%, at least about 96%, at least about 97%, at least about 98%, at least about 99%, or about 100% identical to SEQ ID NO: 90, 91, or 92.

In some embodiments, the anti-FAM19A5 antibody or antigen-binding portion thereof binds to a human FAM19A5 epitope only, which is SEQ ID NO: 89, 90, 91, 92, 93, or 94, or a fragment located within the amino acid sequence of SEQ ID NO: 89, 90, 91, 92, 93, or 94, e.g., an epitope having 1, 2, 3, 4, 5, 6, 7, 8, 9, 10, 11, 12, 13, 14, 15, 16, 17, 18, 19, or 20 amino acids of SEQ ID NO: 89, 90, 91, 92, 93, or 94.

In some embodiments, an anti-FAM19A5 antibody of the present disclosure binds to SEQ ID NO: 90 or a fragment thereof in its native conformation (i.e., un-denatured). In some embodiments, the anti-FAM19A5 antibody or antigen-binding portion thereof binds to both glycosylated and unglycosylated human FAM19A5.

In some embodiments, an anti-FAM19A5 antibody binds to one or more additional FAM19A5 epitopes. In some embodiments, the one or more additional FAM19A5 epitopes are selected from QLAAGTCEIVTLDR (SEQ ID NO: 89, epitope F1), TLDRDSSQPRRTIARQTARC (SEQ ID NO: 90, epitope F2), TARCACRKGQIAGTTRARPA (SEQ ID NO: 91, epitope F3), ARPACVDARIIKTKQWCDML (SEQ ID NO: 92, epitope F4), CDMLPCLEGEGCDLLINRSG (SEQ ID NO: 93, epitope F5), or NRSGWTCTQPGGRIKTTTVS (SEQ ID NO: 94, epitope F6), or a fragment located within the amino acid sequence of SEQ ID NO: 89, SEQ ID NO: 90, SEQ ID NO: 91, SEQ ID NO: 92, SEQ ID NO: 93, or SEQ ID NO: 94, or any combination thereof. A fragment located within the amino acid sequence of SEQ ID NO: 89, SEQ ID NO: 90, SEQ ID NO: 91, SEQ ID NO: 92, SEQ ID NO: 93, or SEQ ID NO: 94, includes a fragment having 1, 2, 3, 4, 5, 6, 7, 8, 9, 10, 11, 12, 13, 14, 15, 16, 17, 18, 19, or 20 amino acids of any of SEQ ID NO: 89, SEQ ID NO: 90, SEQ ID NO: 91, SEQ ID NO: 92, SEQ ID NO: 93, or SEQ ID NO: 94. In some embodiments, the one or more additional FAM19A5 epitopes are selected from SEQ ID NO: 89, 90, 91, 92, 93, or 94, or a fragment located within the amino acid sequence of SEQ ID NO: 89, 90, 91, 92, 93, or 94, e.g., a fragment having 1, 2, 3, 4, 5, 6, 7, 8, 9, 10, 11, 12, 13, 14, 15, 16, 17, 18, 19, or 20 amino acids of SEQ ID NO: 89, 90, 91, 92, 93, or 94, or any combination thereof. In some embodiments, the anti-FAM19A5 antibody or antigen-binding portion thereof of the disclosure binds to any of the one or more additional epitopes in their native conformation (i.e., un-denatured). In some embodiments, the anti-FAM19A5 antibody or antigen-binding portion thereof binds to both glycosylated and unglycosylated of the one or more additional FAM19A5 epitopes.

In some embodiments, provided herein is an antibody, or antigen-binding fragment thereof, that binds to FAM19A5 (e.g., human FAM19A5) with a 20%, 25%, 30%, 35%, 40%, 45%, 50%, 55%, 60%, 65%, 70%, 75%, 80%, 85%, 90%, 95% or higher affinity than to another protein in the FAM19A family as measured by, e.g., a immunoassay (e.g., ELISA), surface plasmon resonance, or kinetic exclusion assay. In a certain embodiments, the anti-FAM19A5 antibody, or antigen-binding fragment thereof, binds to FAM19A5 (e.g., human FAM19A5) with no cross reactivity with another protein in the FAM19A family as measured by, e.g., an immunoassay.

In some embodiments, the anti-FAM19A5 antibodies of the present disclosure are not native antibodies or are not naturally-occurring antibodies. For example, in some embodiments, the anti-FAM19A5 antibodies have post-translational modifications that are different from those of antibodies that are naturally-occurring, such as by having more, less or a different type of post-translational modification.

The amino acid sequences of the VH and VL CDRs of exemplary antibodies of the present disclosure are provided in Tables 3 and 4, respectively. The VH and VL amino acid sequences are provided in Tables 5 and 6, respectively.

TABLE 3

Variable heavy chain CDR amino acid sequences (identified using IMGT)

| Antibody | VH-CDR1 | VH-CDR2 | VH-CDR3 |
|---|---|---|---|
| Reference anti-FAM19A5 Antibody ("3-2") | GFTFSSFNMF (SEQ ID NO: 5) | QISSSGSSTNYAPAVRG (SEQ ID NO: 6) | SSYDCPYGHCSSGVDSAGEIDA (SEQ ID NO: 7) |
| 1-7A-IT | GFTFSSFNMF (SEQ ID NO: 5) | QISSSGSSTNYAPAVKG (SEQ ID NO: 13) | SSYDCPYGHCSSGVDSAGEIDA (SEQ ID NO: 7) |
| Low-PI | GFDFESFNMF (SEQ ID NO: 14) | QISSSEEDENYAPAVKG (SEQ ID NO: 15) | SSYDCPYGHCSSGVDSAGEIDA (SEQ ID NO: 7) |

TABLE 3-continued

| Variable heavy chain CDR amino acid sequences (identified using IMGT) | | | |
|---|---|---|---|
| Antibody | VH-CDR1 | VH-CDR2 | VH-CDR3 |
| 1-30 | GFDFESFNMF (SEQ ID NO: 14) | QISSSEEDENYAPAVKG (SEQ ID NO: 15) | SSYDCPYGHCSSGVDSAGEIDA (SEQ ID NO: 7) |
| 1-17 | GFDFESFNMF (SEQ ID NO: 14) | QISSSEEDENYAPAVKG (SEQ ID NO: 15) | SSYDCPYGHCSSGVDSAGEIDA (SEQ ID NO: 7) |
| 1-32 | GFDFESFNMF (SEQ ID NO: 14) | QISSSEEDENYAPAVKG (SEQ ID NO: 15) | SSYDCPYGHCSSGVDSAGEIDA (SEQ ID NO: 7) |
| 4-11 | GFDFESFNMF (SEQ ID NO: 14) | QISSSEEDENYAPAVKG (SEQ ID NO: 15) | SSYDCPYGHCSSGVDSAGEIDA (SEQ ID NO: 7) |
| 6-10 | GFDFESFNMF (SEQ ID NO: 14) | QISSSEEDENYAPAVKG (SEQ ID NO: 15) | SSYDCPYGHCSSGVDSAGEIDA (SEQ ID NO: 7) |
| Reference anti-FAM19A5 Antibody ("2-13") | GFTFSSHGMF (SEQ ID NO: 16) | EITNDGSGTNYGSAVKG (SEQ ID NO: 17) | STYECPGGFSCWGDTGQIDA (SEQ ID NO: 18) |
| 2-13D | GFTFSSHGMF (SEQ ID NO: 16) | EITNDGSGTNYGSAVKG (SEQ ID NO: 17) | STYECPGGFSCWGDTGQIDA (SEQ ID NO: 18) |
| 2-13D-37 | GFDFSSHGMF (SEQ ID NO: 19) | EITNDGSGTNYGSAVKG (SEQ ID NO: 17) | STYECPGGFSCWGDTGQIDA (SEQ ID NO: 18) |
| 2-13D-37-1.5W-41 | GFDFSSHGMF (SEQ ID NO: 19) | EITNDGSGTNYGSAVKG (SEQ ID NO: 17) | SSYVCPGGFSCWGDTGQIDA (SEQ ID NO: 128) |
| 2-13D-37-3W-16 | GFDFSSHGMF (SEQ ID NO: 19) | EITNDGSGTNYGSAVKG (SEQ ID NO: 17) | SNYACPGGFSCWGDTGQIDA (SEQ ID NO: 129) |

TABLE 4

| Variable light chain CDR amino acid sequences (identified using IMGT) | | | |
|---|---|---|---|
| Antibody | VL-CDR1 | VL-CDR2 | VL-CDR3 |
| Reference anti-FAM19A5 Antibody ("3-2") | SGGGSYAGSYYYG (SEQ ID NO: 8) | ESNKRPS (SEQ ID NO: 9) | GSWDSSNGGI (SEQ ID NO: 10) |
| 1-7A-IT | SGGGSYAGSYYYG (SEQ ID NO: 8) | ENNKRPS (SEQ ID NO: 20) | GSWDSSNGGI (SEQ ID NO: 10) |
| Low-PI | SGGGSEEEQYYYG (SEQ ID NO: 21) | EDEERPS (SEQ ID NO: 22) | GSWDSEDEDH (SEQ ID NO: 23) |
| 1-30 | SGGGSEEEQYYYG (SEQ ID NO: 21) | QDEERPS (SEQ ID NO: 24) | GSWDSEDEDH (SEQ ID NO: 23) |
| 1-17 | SGGGSYAGSYYYG (SEQ ID NO: 8) | EDEQRPS (SEQ ID NO: 25) | GSWDSEDEDH (SEQ ID NO: 23) |
| 1-32 | SGGGSYAGSYYYG (SEQ ID NO: 8) | QDEERPS (SEQ ID NO: 24) | GSWDSEDEDH (SEQ ID NO: 23) |
| 4-11 | SGGGSYAGSYYYG (SEQ ID NO: 8) | EDHERPS (SEQ ID NO: 26) | GSWDSSDEDH (SEQ ID NO: 27) |
| 6-10 | SGGGSYAGSYYYG (SEQ ID NO: 8) | QDLLRPS (SEQ ID NO: 28) | GSWDSLSSSH (SEQ ID NO: 29) |
| Reference anti-FAM19A5 Antibody ("2-13") | SGGSYSYG (SEQ ID NO: 30) | WDDERPS (SEQ ID NO: 31) | GTEDISGTAGV (SEQ ID NO: 32) |

TABLE 4-continued

| Variable light chain CDR amino acid sequences (identified using IMGT) | | | |
|---|---|---|---|
| Antibody | VL-CDR1 | VL-CDR2 | VL-CDR3 |
| 2-13D | SGGVYSYG (SEQ ID NO: 80) | WDDERPS (SEQ ID NO: 31) | GTEDISGTAGV (SEQ ID NO: 32) |
| 2-13D-37 | SGGVYSYG (SEQ ID NO: 80) | WDDERPS (SEQ ID NO: 31) | GTEDISGTAGV (SEQ ID NO: 32) |
| 2-13D-37-1.5W-41 | SGGVYSYG (SEQ ID NO: 80) | WDDERPS (SEQ ID NO: 31) | GTEDISGTAGV (SEQ ID NO: 32) |
| 2-13D-37-3W-16 | SGGVYSYG (SEQ ID NO: 80) | WDDERPS (SEQ ID NO: 31) | GTEDISGTAGV (SEQ ID NO: 32) |

TABLE 5

| Variable heavy chain amino acid sequence | |
|---|---|
| Antibody | VH Amino Acid Sequence (SEQ ID NO) |
| Reference anti-FAM19A5 Antibody ("3-2") | AVTLDESGGGLQTPGGALSLVCKASGFTFSSFNMFWVRQAPGKGLEYVAQISSSGSSTNYAPAVRGRATISRDNGQSTVRLQLNNPGAEDTGTYYCAKSSYDCPYGHCSSGVDSAGEIDAWGHGTEVIVSS (SEQ ID NO: 11) |
| 1-7A-IT | AVTLDESGGGLQTPGGALRLSCKASGFTFSSFNMFWVRQAPGKGLEYVSQISSSGSSTNYAPAVKGRATISRDNGQSTLYLQMNSLRAEDTGTYYCAKSSYDCPYGHCSSGVDSAGEIDAWGHGTEVIVSS (SEQ ID NO: 33) |
| Low-PI | AVTLDESGGGLQTPGGALRLSCKASGFDFESFNMFWVRQAPGKGLEYVSQISSSEEDENYAPAVKGRATISRDNGQSTLYLQMNSLRAEDTGTYYCAKSSYDCPYGHCSSGVDSAGEIDAWGHGTEVIVSS (SEQ ID NO: 34) |
| 1-30 | AVTLDESGGGLQTPGGALRLSCKASGFDFESFNMFWVRQAPGKGLEYVSQISSSEEDENYAPAVKGRATISRDNGQSTLYLQMNSLRAEDTGTYYCAKSSYDCPYGHCSSGVDSAGEIDAWGHGTEVIVSS (SEQ ID NO: 34) |
| 1-17 | AVTLDESGGGLQTPGGALRLSCKASGFDFESFNMFWVRQAPGKGLEYVSQISSSEEDENYAPAVKGRATISRDNGQSTLYLQMNSLRAEDTGTYYCAKSSYDCPYGHCSSGVDSAGEIDAWGHGTEVIVSS (SEQ ID NO: 34) |
| 1-32 | AVTLDESGGGLQTPGGALRLSCKASGFDFESFNMFWVRQAPGKGLEYVSQISSSEEDENYAPAVKGRATISRDNGQSTLYLQMNSLRAEDTGTYYCAKSSYDCPYGHCSSGVDSAGEIDAWGHGTEVIVSS (SEQ ID NO: 34) |
| 4-11 | AVTLDESGGGLQTPGGALRLSCKASGFDFESFNMFWVRQAPGKGLEYVSQISSSEEDENYAPAVKGRATISRDNGQSTLYLQMNSLRAEDTGTYYCAKSSYDCPYGHCSSGVDSAGEIDAWGHGTEVIVSS (SEQ ID NO: 34) |
| 6-10 | AVTLDESGGGLQTPGGALRLSCKASGFDFESFNMFWVRQAPGKGLEYVSQISSSEEDENYAPAVKGRATISRDNGQSTLYLQMNSLRAEDTGTYYCAKSSYDCPYGHCSSGVDSAGEIDAWGHGTEVIVSS (SEQ ID NO: 34) |
| Reference anti-FAM19A5 Antibody ("2-13") | AVTLDESGGGLQTPGGALSLVCKASGFTFSSHGMFWVRQTPGKGLEYVAEITNDGSGTNYGSAVKGRATISRDNGQSTVRLQLNNLRAEDTGTYFCARSTYECPGGFSCWGDTGQIDAWGHGTEVIVSS (SEQ ID NO: 35) |
| 2-13D | AVTLDESGGGLQTPGGALRLSCSASGFTFSSHGMFWVRQAPGKGLEYVSEITNDGSGTNYGSAVKGRATISRDNGQSTLYLQMNSLRAEDTGTYFCARSTYECPGGFSCWGDTGQIDAWGHGTEVIVSS (SEQ ID NO: 36) |
| 2-13D-37 | AVTLDESGGGLQTPGGALRLSCSASGFDFSSHGMFWVRQAPGKGLEYVSEITNDGSGTNYGSAVKGRATISRDNGQSTLYLQMNSLRAEDTGTYFCARSTYECPGGFSCWGDTGQIDAWGHGTEVIVSS (SEQ ID NO: 37) |
| 2-13D-37-1.5W-41 | AVTLDESGGGLQTPGGALRLSCSASGFDFSSHGMFWVRQAPGKGLEYVSEITNDGSGTNYGSAVKGRATISRDNGQSTLYLQMNSLRAEDTGTYFCARSSYVCPGGFSCWGDTGQIDAWGHGTEVIVSS (SEQ ID NO: 130) |

TABLE 5-continued

| Variable heavy chain amino acid sequence | |
|---|---|
| Antibody | VH Amino Acid Sequence (SEQ ID NO) |
| 2-13D-37-3W-16 | AVTLDESGGGLQTPGGALRLSCSASGFDFSSHGMFWVRQAPGKGLEYVSEITNDGSGTNYGSAVKGRATISRDNGQSTLYLQMNSLRAEDTGTYFCARSNYACPGGFSCWGDTGQIDAWGHGTEVIVSS (SEQ ID NO: 131) |

TABLE 6

| Variable light chain amino acid sequence | |
|---|---|
| Antibody | VL Amino Acid Sequence (SEQ ID NO) |
| Reference anti-FAM19A5 Antibody ("3-2") | ALTQPSSVSANPGETVKITCSGGGSYAGSYYYGWYQQKAPGSAPVTLIYESNKRPSDIPSRFSGSTSGSTATLTITGVQADDEAIYYCGSWDSSNGGIFGAGTTLTVL (SEQ ID NO: 12) |
| 1-7A-IT | ALTQPSSVSANPGETVKITCSGGGSYAGSYYYGWYQQKPGSAPVTLIYENNKRPSDIPSRFSGSTSGSTATLTITGVQAGDEADYYCGSWDSSNGGIFGAGTTLTVL (SEQ ID NO: 38) |
| Low-PI | ALTQPSSVSANPGETVKITCSGGGSEEEQYYYGWYQQKPGSAPVTLIYEDEERPSDIPSRFSGSTSGSTATLTITGVQAGDEADYYCGSWDSEDEDHFGAGTTLTVL (SEQ ID NO: 39) |
| 1-30 | ALTQPSSVSANPGETVKITCSGGGSEEEQYYYGWYQQKPGSAPVTLIYQDEERPSDIPSRFSGSTSGSTATLTITGVQAGDEADYYCGSWDSEDEDHFGAGTTLTVL (SEQ ID NO: 40) |
| 1-17 | ALTQPSSVSANPGETVKITCSGGGSYAGSYYYGWYQQKPGSAPVTLIYEDEQRPSDIPSRFSGSTSGSTATLTITGVQAGDEADYYCGSWDSEDEDHFGAGTTLTVL (SEQ ID NO: 41) |
| 1-32 | ALTQPSSVSANPGETVKITCSGGGSYAGSYYYGWYQQKPGSAPVTLIYQDEERPSDIPSRFSGSTSGSTATLTITGVQAGDEADYYCGSWDSEDEDHFGAGTTLTVL (SEQ ID NO: 42) |
| 4-11 | ALTQPSSVSANPGETVKITCSGGGSYAGSYYYGWYQQKPGSAPVTLIYEDHERPSDIPSRFSGSTSGSTATLTITGVQAGDEADYYCGSWDSSDEDHFGAGTTLTVL (SEQ ID NO: 43) |
| 6-10 | ALTQPSSVSANPGETVKITCSGGGSYAGSYYYGWYQQKPGSAPVTLIYQDLLRPSDIPSRFSGSTSGSTATLTITGVQAGDEADYYCGSWDSLSSSHFGAGTTLTVL (SEQ ID NO: 44) |
| Reference anti-FAM19A5 Antibody ("2-13") | ALTQPSSVSANPGETVKITCSGGSYSYGWFQQKSPGSALVTVIYWDDERPSDIPSRFSGALSGSTNTLTITGVQADDEAVYFCGTEDISGTAGVFGAGTTLTVL (SEQ ID NO: 45) |
| 2-13D | ALTQPSSVSANPGETAKITCSGGVYSYGWFQQKPGSALVTVIYWDDERPSDIPSRFSGALSGSTNTLTITGVQAEDEADYYCGTEDISGTAGVFGAGTTLTVL (SEQ ID NO: 46) |
| 2-13D-37 | ALTQPSSVSANPGETAKITCSGGVYSYGWFQQKPGSALVTVIYWDDERPSDIPSRFSGALSGSTNTLTITGVQAEDEADYYCGTEDISGTAGVFGAGTTLTVL (SEQ ID NO: 46) |
| 2-13D-37-1.5W-41 | ALTQPSSVSANPGETAKITCSGGVYSYGWFQQKPGSALVTVIYWDDERPSDIPSRFSGALSGSTNTLTITGVQAEDEADYYCGTEDISGTAGVFGAGTTLTVL (SEQ ID NO: 46) |
| 2-13D-37-3W-16 | ALTQPSSVSANPGETAKITCSGGVYSYGWFQQKPGSALVTVIYWDDERPSDIPSRFSGALSGSTNTLTITGVQAEDEADYYCGTEDISGTAGVFGAGTTLTVL (SEQ ID NO: 46) |

In some embodiments, an anti-FAM19A5 antibody of the present disclosure comprises heavy and light chain variable regions, wherein the heavy chain variable region (VH) comprises the heavy chain CDR1, CDR2, and CDR3 of SEQ ID NO: 33 and/or the light chain variable region (VL) comprises the light chain CDR1, CDR2, and CDR3 of SEQ ID NO: 38. In other embodiments, the anti-FAM19A5 antibody comprises a VH and VL, wherein the VH comprises the amino acid sequence set forth in SEQ ID NO: 33, and/or the VL comprises the amino acid sequence set forth in SEQ ID NO: 38.

In some embodiments, an anti-FAM19A5 antibody of the present disclosure comprises heavy and light chain variable regions, wherein the heavy chain variable region (VH) comprises the heavy chain CDR1, CDR2, and CDR3 of SEQ ID NO: 34 and/or the light chain variable region (VL) comprises the light chain CDR1, CDR2, and CDR3 of SEQ ID NO: 39. In other embodiments, the anti-FAM19A5 antibody comprises a VH and VL, wherein the VH comprises the amino acid sequence set forth in SEQ ID NO: 34, and/or the VL comprises the amino acid sequence set forth in SEQ ID NO: 39.

In some embodiments, an anti-FAM19A5 antibody of the present disclosure comprises heavy and light chain variable regions, wherein the heavy chain variable region (VH) comprises the heavy chain CDR1, CDR2, and CDR3 of SEQ ID NO: 34 and/or the light chain variable region (VL) comprises the light chain CDR1, CDR2, and CDR3 of SEQ ID NO: 41. In other embodiments, the anti-FAM19A5 antibody comprises a VH and VL, wherein the VH comprises the amino acid sequence set forth in SEQ ID NO: 34, and/or the VL comprises the amino acid sequence set forth in SEQ ID NO: 41.

In some embodiments, an anti-FAM19A5 antibody of the present disclosure comprises heavy and light chain variable regions, wherein the heavy chain variable region (VH) comprises the heavy chain CDR1, CDR2, and CDR3 of SEQ ID NO: 34 and/or the light chain variable region (VL) comprises the light chain CDR1, CDR2, and CDR3 of SEQ ID NO: 40. In other embodiments, the anti-FAM19A5 antibody comprises a VH and VL, wherein the VH comprises the amino acid sequence set forth in SEQ ID NO: 34, and/or the VL comprises the amino acid sequence set forth in SEQ ID NO: 40.

In some embodiments, an anti-FAM19A5 antibody of the present disclosure comprises heavy and light chain variable regions, wherein the heavy chain variable region (VH) comprises the heavy chain CDR1, CDR2, and CDR3 of SEQ ID NO: 34 and/or the light chain variable region (VL) comprises the light chain CDR1, CDR2, and CDR3 of SEQ ID NO: 42. In other embodiments, the anti-FAM19A5 antibody comprises a VH and VL, wherein the VH comprises the amino acid sequence set forth in SEQ ID NO: 34, and/or the VL comprises the amino acid sequence set forth in SEQ ID NO: 42.

In some embodiments, an anti-FAM19A5 antibody of the present disclosure comprises heavy and light chain variable regions, wherein the heavy chain variable region (VH) comprises the heavy chain CDR1, CDR2, and CDR3 of SEQ ID NO: 34 and/or the light chain variable region (VL) comprises the light chain CDR1, CDR2, and CDR3 of SEQ ID NO: 43. In other embodiments, the anti-FAM19A5 antibody comprises a VH and VL, wherein the VH comprises the amino acid sequence set forth in SEQ ID NO: 34, and/or the VL comprises the amino acid sequence set forth in SEQ ID NO: 43.

In some embodiments, an anti-FAM19A5 antibody of the present disclosure comprises heavy and light chain variable regions, wherein the heavy chain variable region (VH) comprises the heavy chain CDR1, CDR2, and CDR3 of SEQ ID NO: 34 and/or the light chain variable region (VL) comprises the light chain CDR1, CDR2, and CDR3 of SEQ ID NO: 44. In other embodiments, the anti-FAM19A5 antibody comprises a VH and VL, wherein the VH comprises the amino acid sequence set forth in SEQ ID NO: 34, and/or the VL comprises the amino acid sequence set forth in SEQ ID NO: 44.

In some embodiments, an anti-FAM19A5 antibody of the present disclosure comprises heavy and light chain variable regions, wherein the heavy chain variable region (VH) comprises the heavy chain CDR1, CDR2, and CDR3 of SEQ ID NO: 36 and/or the light chain variable region (VL) comprises the light chain CDR1, CDR2, and CDR3 of SEQ ID NO: 46. In other embodiments, the anti-FAM19A5 antibody comprises a VH and VL, wherein the VH comprises the amino acid sequence set forth in SEQ ID NO: 36, and/or the VL comprises the amino acid sequence set forth in SEQ ID NO: 46.

In some embodiments, an anti-FAM19A5 antibody of the present disclosure comprises heavy and light chain variable regions, wherein the heavy chain variable region (VH) comprises the heavy chain CDR1, CDR2, and CDR3 of SEQ ID NO: 37 and/or the light chain variable region (VL) comprises the light chain CDR1, CDR2, and CDR3 of SEQ ID NO: 46. In other embodiments, the anti-FAM19A5 antibody comprises a VH and VL, wherein the VH comprises the amino acid sequence set forth in SEQ ID NO: 37, and/or the VL comprises the amino acid sequence set forth in SEQ ID NO: 46.

In some embodiments, an anti-FAM19A5 antibody of the present disclosure comprises heavy and light chain variable regions, wherein the heavy chain variable region (VH) comprises the heavy chain CDR1, CDR2, and CDR3 of SEQ ID NO: 130 and/or the light chain variable region (VL) comprises the light chain CDR1, CDR2, and CDR3 of SEQ ID NO: 46. In other embodiments, the anti-FAM19A5 antibody comprises a VH and VL, wherein the VH comprises the amino acid sequence set forth in SEQ ID NO: 37, and/or the VL comprises the amino acid sequence set forth in SEQ ID NO: 46.

some embodiments, an anti-FAM19A5 antibody of the present disclosure comprises heavy and light chain variable regions, wherein the heavy chain variable region (VH) comprises the heavy chain CDR1, CDR2, and CDR3 of SEQ ID NO: 131 and/or the light chain variable region (VL) comprises the light chain CDR1, CDR2, and CDR3 of SEQ ID NO: 46. In other embodiments, the anti-FAM19A5 antibody comprises a VH and VL, wherein the VH comprises the amino acid sequence set forth in SEQ ID NO: 37, and/or the VL comprises the amino acid sequence set forth in SEQ ID NO: 46.

In some embodiments, an anti-FAM19A5 antibody of the present disclosure comprises a VH and a VL, wherein the VH comprises an amino acid sequence which is at least about 80%, at least about 85%, at least about 90%, at least about 95%, at least about 96/o, at least about 97%, at least about 98%, at least about 99%, or about 100% identical to the amino acid sequence set forth in SEQ ID NOs: 33, 34, 36, 37, 130, or 131.

In some embodiments, an anti-FAM19A5 antibody of the present disclosure comprises a VH and a VL, wherein the VL comprises an amino acid sequence which is at least about 80%, at least about 85%, at least about 90%, at least about 95%, at least about 96%, at least about 97%, at least about 98%, at least about 99%, or about 100% identical to the amino acid sequence set forth in SEQ ID NOs: 38, 39, 40, 41, 42, 43, 44, or 46.

In some embodiments, an anti-FAM19A5 antibody of the present disclosure comprises a VH and a VL, wherein:

(a) the VH comprises the amino acid sequence set forth in SEQ ID NO: 33, and the VL comprises the amino acid sequence set forth in SEQ ID NO: 38;

(b) the VH comprises the amino acid sequence set forth in SEQ ID NO: 34, and the VL comprises the amino acid sequence set forth in SEQ ID NO: 39;

(c) the VH comprises the amino acid sequence set forth in SEQ ID NO: 34, and the VL comprises the amino acid sequence set forth in SEQ ID NO: 41;

(d) the VH comprises the amino acid sequence set forth in SEQ ID NO: 34, and the VL comprises the amino acid sequence set forth in SEQ ID NO: 40;

(e) the VH comprises the amino acid sequence set forth in SEQ ID NO: 34, and the VL comprises the amino acid sequence set forth in SEQ ID NO: 42;
(f) the VH comprises the amino acid sequence set forth in SEQ ID NO: 34, and the VL comprises the amino acid sequence set forth in SEQ ID NO: 43;
(g) the VH comprises the amino acid sequence set forth in SEQ ID NO: 34, and the VL comprises the amino acid sequence set forth in SEQ ID NO: 44;
(h) the VH comprises the amino acid sequence set forth in SEQ ID NO: 36, and the VL comprises the amino acid sequence set forth in SEQ ID NO: 46;
(i) the VH comprises the amino acid sequence set forth in SEQ ID NO: 37, and the VL comprises the amino acid sequence set forth in SEQ ID NO: 46;
(j) the VH comprises the amino acid sequence set forth in SEQ ID NO: 130, and the VL comprises the amino acid sequence set forth in SEQ ID NO: 46; or
(k) the VH comprises the amino acid sequence set forth in SEQ ID NO: 131, and the VL comprises the amino acid sequence set forth in SEQ ID NO: 46.

A VH domain, or one or more CDRs thereof, described herein can be linked to a constant domain for forming a heavy chain, e.g., a full length heavy chain. Similarly, a VL domain, or one or more CDRs thereof, described herein can be linked to a constant domain for forming a light chain, e.g., a full length light chain. A full length heavy chain and full length light chain combine to form a full length antibody.

Accordingly, in specific embodiments, provided herein is an antibody comprising an antibody light chain and heavy chain, e.g., a separate light chain and heavy chain. With respect to the light chain, in a specific embodiment, the light chain of an antibody described herein is a kappa light chain. In another specific embodiment, the light chain of an antibody described herein is a lambda light chain. In yet another specific embodiment, the light chain of an antibody described herein is a human kappa light chain or a human lambda light chain. In a particular embodiment, an antibody described herein, which specifically binds to a FAM19A5 polypeptide (e.g., human FAM19A5) comprises a light chain which comprises any VL or VL CDR amino acid sequences described herein, and wherein the constant region of the light chain comprises the amino acid sequence of a human kappa light chain constant region. In a particular embodiment, an antibody described herein, which specifically binds to a FAM19A5 polypeptide (e.g., human FAM19A5) comprises a light chain which comprises a VL or VL CDR amino acid sequences described herein, and wherein the constant region of the light chain comprises the amino acid sequence of a human lambda light chain constant region. Non-limiting examples of human constant region sequences have been described in the art, e.g., see U.S. Pat. No. 5,693,780 and Kabat E A et al., (1991) supra.

With respect to the heavy chain, in some embodiments, the heavy chain of an antibody described herein can be an alpha (α), delta (δ), epsilon (ε), gamma (γ) or mu (μ) heavy chain. In another specific embodiment, the heavy chain of an antibody described can comprise a human alpha (α), delta (δ), epsilon (ε), gamma (γ) or mu (μ) heavy chain. In one embodiment, an antibody described herein, which specifically binds to FAM19A5 (e.g., human FAM19A5), comprises a heavy chain which comprises a VH or VH CDR amino acid sequence described herein, and wherein the constant region of the heavy chain comprises the amino acid sequence of a human gamma (γ) heavy chain constant region. In another embodiment, an antibody described herein, which specifically binds to FAM19A5 (e.g., human FAM19A5), comprises a heavy chain which comprises a VH or VH CDR amino acid sequence disclosed herein, and wherein the constant region of the heavy chain comprises the amino acid of a human heavy chain described herein or known in the art. Non-limiting examples of human constant region sequences have been described in the art, e.g., see U.S. Pat. No. 5,693,780 and Kabat E A et al., (1991) supra.

In some embodiments, an antibody described herein, which specifically binds to FAM19A5 (e.g., human FAM19A5) comprises a VL domain and a VH domain comprising the VH or VH CDRs and VL and VL CDRs described herein, and wherein the constant regions comprise the amino acid sequences of the constant regions of an IgG, IgE, IgM, IgD, IgA or IgY immunoglobulin molecule, or a human IgG, IgE, IgM, IgD, IgA or IgY immunoglobulin molecule. In another specific embodiment, an antibody described herein, which specifically binds to FAM19A5 (e.g., human FAM19A5) comprises a VL domain and a VH domain comprising any amino acid sequences described herein, and wherein the constant regions comprise the amino acid sequences of the constant regions of an IgG, IgE, IgM, IgD, IgA or IgY immunoglobulin molecule, any subclass (e.g., IgG1, IgG2, IgG3, IgG4, IgA1 and IgA2) of immunoglobulin molecule. In some embodiments, the constant regions comprise the amino acid sequences of the constant regions of a human IgG, which are naturally-occurring, including subclasses (e.g., IgG1, IgG2, IgG3 or IgG4), and allotypes (e.g., G1m, G2m, G3m, and nG4m) and variants thereof. See, e.g., Vidarsson G. et al. Front Immunol. 5:520 (published online Oct. 20, 2014) and Jefferis R. and Lefranc M P, mAbs 1:4, 1-7(2009). In some embodiments, the constant regions comprise the amino acid sequences of the constant regions of a human IgG1, IgG2, IgG3, or IgG4, or variants thereof.

In certain embodiments, the anti-FAM19A5 antibody disclosed herein does not have Fc effector functions, e.g., complement-dependent cytotoxicity (CDC) and/or antibody-dependent cellular phagocytosis (ADCP). Effector functions are mediated by the Fc region and the residues most proximal to the hinge region in the CH2 domain of the Fc region are responsible for effector functions of antibodies as it contains a largely overlapping binding site for C1q (complement) and IgG-Fc receptors (FcγR) on effector cells of the innate immune system. Also, IgG2 and IgG4 antibodies have lower levels of Fc effector functions than IgG1 and IgG3 antibodies. Effector functions of an antibody can be reduced or avoided by different approaches known in the art, including (1) using antibody fragments lacking the Fc region (e.g., such as a Fab, $F(ab')_2$, single chain Fv (scFv), or a sdAb consisting of a monomeric VH or VL domain); (2) generating aglycosylated antibodies, which can be generated by, for example, deleting or altering the residue the sugar is attached to, removing the sugars enzymatically, producing the antibody in cells cultured in the presence of a glycosylation inhibitor, or by expressing the antibody in cells unable to glycosylate proteins (e.g., bacterial host cells, see e.g., U.S. Pub. No. 20120100140); (3) employing Fc regions from an IgG subclass that have reduced effector function (e.g., a Fc region from IgG2 or IgG4 antibodies or a chimeric Fc region comprising a CH2 domain from IgG2 or IgG4 antibodies, see, e.g., U.S. Pub. No. 20120100140 and Lau C. et al., *J. Immunol.* 191:4769-4777 (2013)); and (4) generating a Fc region with mutations that result in reduced or no Fc functions. See, e.g., U.S. Pub. No. 20120100140 and U.S. and PCT applications cited therein and An et al., *mAbs* 1:6, 572-579 (2009).

Thus, in some embodiments, the anti-FAM19A5 antibody disclosed herein is a Fab, a Fab', a F(ab')2, a Fv, a single chain Fv (scFv), or a sdAb consisting of a monomeric VH or VL domain. Such antibody fragments are well known in the art and are described supra.

In some embodiments, the anti-FAM19A5 antibody is a single chain Fv. The amino acid sequences of exemplary anti-FAM19A5 scFv are provided in Table 7 below.

TABLE 7

| Amino acid sequences of anti-FAM19A5 scFv | |
|---|---|
| ScFv Antibody | VL Amino Acid Sequence (SEQ ID NO) |
| Reference anti-FAM19A5 Antibody ("3-2") | ALTQPSSVSANPGETVKITCSGGGSYAGSYYYGWYQQKAPGSAPVTLIYESNKRPSDIPS RFSGSTSGSTATLTITGVQADDEAIYYCGSWDSSNGGIFGAGTTLTVLGQSSRSSGGGGS SGGGGSAVTLDESGGGLQTPGGALSLVCKASGFTFSSFNMFWVRQAPGKGLEYVAQISSS GSSTNYAPAVRGRATISRDNGQSTVRLQLNNPGAEDTGTYYCAKSSYDCPYGHCSSGVDS AGEIDAWGHGTEVIVSS (SEQ ID NO: 47) |
| 1-7A-IT | ALTQPSSVSANPGETVKITCSGGGSYAGSYYYGWYQQKPGSAPVTLIYENNKRPSDIPSR FSGSTSGSTATLTITGVQAGDEADYYCGSWDSSNGGIFGAGTTLTVLGQSSRSSGGGGSS GGGGSAVTLDESGGGLQTPGGALRLSCKASGFTFSSFNMFWVRQAPGKGLEYVSQISSSG SSTNYAPAVKGRATISRDNGQSTLYLQMNSLRAEDTGTYYCAKSSYDCPYGHCSSGVDSA GEIDAWGHGTEVIVSS (SEQ ID NO: 48) |
| Low-PI | ALTQPSSVSANPGETVKITCSGGGSEEEQYYYGWYQQKPGSAPVTLIYEDEERPSDIPSR FSGSTSGSTATLTITGVQAGDEADYYCGSWDSEDEDHFGAGTTLTVLGQSSRSSGGGGSS GGGGSAVTLDESGGGLQTPGGALRLSCKASGFDFESFNMFWVRQAPGKGLEYVSQISSSE EDENYAPAVKGRATISRDNGQSTLYLQMNSLRAEDTGTYYCAKSSYDCPYGHCSSGVDSA GEIDAWGHGTEVIVSS (SEQ ID NO: 49) |
| 1-30 | ALTQPSSVSANPGETVKITCSGGGSEEEQYYYGWYQQKPGSAPVTLIYQDEERPSDIPSR FSGSTSGSTATLTITGVQAGDEADYYCGSWDSEDEDHFGAGTTLTVLGQSSRSSGGGGSS GGGGSAVTLDESGGGLQTPGGALRLSCKASGFDFESFNMFWVRQAPGKGLEYVSQISSSE EDENYAPAVKGRATISRDNGQSTLYLQMNSLRAEDTGTYYCAKSSYDCPYGHCSSGVDSA GEIDAWGHGTEVIVSS (SEQ ID NO: 50) |
| 1-17 | ALTQPSSVSANPGETVKITCSGGGSYAGSYYYGWYQQKPGSAPVTLIYEDEQRPSDIPSR FSGSTSGSTATLTITGVQAGDEADYYCGSWDSEDEDHFGAGTTLTVLGQSSRSSGGGGSS GGGGSAVTLDESGGGLQTPGGALRLSCKASGFDFESFNMFWVRQAPGKGLEYVSQISSSE EDENYAPAVKGRATISRDNGQSTLYLQMNSLRAEDTGTYYCAKSSYDCPYGHCSSGVDSA GEIDAWGHGTEVIVSS (SEQ ID NO: 51) |
| 1-32 | ALTQPSSVSANPGETVKITCSGGGSYAGSYYYGWYQQKPGSAPVTLIYQDEERPSDIPSR FSGSTSGSTATLTITGVQAGDEADYYCGSWDSEDEDHFGAGTTLTVLGQSSRSSGGGGSS GGGGSAVTLDESGSGLQTPGGALRLSCKASGFDFESFNMFWVRQAPGKGLEYVSQISSSE EDENYAPAVKGRATISRDNGQSTLYLQMNSLRAEDTGTYYCAKSSYDCPYGHCSSGVDSA GEIDAWGHGTEVIVSS (SEQ ID NO: 52) |
| 4-11 | ALTQPSSVSANPGETVKITCSGGGSYAGSYYYGWYQQKPGSAPVTLIYEDHERPSDIPSR FSGSTSGSTATLTITGVQAGDEADYYCGSWDSSDEDHFGAGTTLTVLGQSSRSSGGGGSS GGGGSAVTLDESGGGLQTPGGALRLSCKASGFDFESFNMFWVRQAPGKGLEYVSQISSSE EDENYAPAVKGRATISRDNGQSTLYLQMNSLRAEDTGTYYCAKSSYDCPYGHCSSCVDSA GEIDAWGHGTEVIVSS (SEQ ID NO: 53) |
| 6-10 | ALTQPSSVSANPGETVKITCSGGCSYAGSYYYGWYQQKPCSAPVTLIYQDLLRPSDIPSR FSGSTSGSTATLTITGVQAGDEADYYCGSWDSLSSSHFGAGTTLTVLGQSSRSSGGGGSS GGGGSAVTLDESGGGLQTPGGALRLSCKASGFDFESFNMFWVRQAPGKGLEYVSQISSSE EDENYAPAVKGRATISRDNGQSTLYLQMNSLRAEDTGTYYCAKSSYDCPYGHCSSGVDSA GEIDAWGHGTEVIVSS (SEQ ID NO: 54) |
| Reference anti-FAM19A5 Antibody ("2-13") | ALTQPSSVSANPGETVKITCSGGSYSYGWFQQKSPGSALVTVIYWDDERPSDIPSRFSGA LSGSTNTLTITGVQADDEAVYFCGTEDISGTAGVFGAGTTLTVLGQSSRSSGGGGSSGGG GSAVTLDESGGGLQTPGGALSLVCKASGFTFSSHGMFWVRQTPGKGLEYVAEITNDGSGT NYGSAVKGRATISRDNGQSTVRLQLNNLRAEDTGTYFCARSTYECPGGFSCWGDTGQIDA WGHGTEVIVSS (SEQ ID NO: 55) |
| 2-13D | ALTQPSSVSANPGETAKITCSGGVYSYGWFQQKPGSALVTVIYWDDERPSDIPSRFSGAL SGSTNTLTITGVQAEDEADYYCGTEDISGTAGVFGAGTTLTVLGQSSRSSGGGGSSGGGG SAVTLDESGGGLQTPGGALRLSCSASGFTFSSHGMFWVRQAPGKGLEYVSEITNDGSGTN YGSAVKGRATISRDNGQSTLYLQMNSLRAEDTGTYFCARSTYECPGGFSCWGDTGQIDAW GHGTEVIVSS (SEQ ID NO: 56) |
| 2-13D-37 | ALTQPSSVSANPGETAKITCSGGVYSYGWFQQKPGSALVTVIYWDDERPSDIPSRFSGAL SGSTNTLTITGVQAEDEADYYCGTEDISGTAGVFGAGTTLTVLGQSSRSSGGGGSSGGGG SAVTLDESGGGLQTPGGALRLSCSASGFDFSSHGMFWVRQAPGKGLEYVSEITNDGSGTN YGSAVKGRATISRDNGQSTLYLQMNSLRAEDTGTYFCARSTYECPGGFSCWGDTGQIDAW GHGTEVIVSS (SEQ ID NO: 57) |
| 2-13D-37-1.5W-41 | ALTQPSSVSANPGETAKITCSGGVYSYGWFQQKPGSALVTVIYWDDERPSDIPSRFSGAL SGSTNTLTITGVQAEDEADYYCGTEDISGTAGVFGAGTTLTVLGQSSRSSGGGGSSGGGG SAVTLDESGGGLQTPGGALRLSCSASGFDFSSHGMFWVRQAPGKGLEYVSEITNDGSGTN |

TABLE 7-continued

| Amino acid sequences of anti-FAM19A5 scFv | |
|---|---|
| ScFv Antibody | VL Amino Acid Sequence (SEQ ID NO) |
| | YGSAVKGRATISRDNGQSTLYLQMNSLRAEDTGTYFCARSSYVCPGGFSCWGDTGQIDAW GHGTEVIVSS (SEQ ID NO: 132) |
| 2-13D-37-3W-16 | ALTQPSSVSANPGETAKITCSGGVYSYGWFQQKPGSALVTVIYWDDERPSDIPSRFSGAL SGSTNTLTITGVQAEDEADYYCGTEDISGTAGVFGAGTTLTVLGQSSRSSGGGGSSGGGG SAVTLDESGGGLQTPGGALRLSCSASGFDFSSHGMFWVRQAPGKGLEYVSEITNDGSGTN YGSAVKGRATISRDNGQSTLYLQMNSLRAEDTGTYFCARSNYACPGGFSCWGDTGQIDAW GHGTEVIVSS (SEQ ID NO: 133) |

In some embodiments, the anti-FAM19A5 antibody disclosed herein comprises a Fe region with reduced or no Fc effector function. In some embodiments, the constant regions comprise the amino acid sequences of the Fe region of a human IgG2 or IgG4, in some embodiments, the anti-FAM19A5 antibody is of an IgG2/IgG4 isotype. In some embodiments, the anti-FAM19A5 antibody comprises a chimeric Fc region which comprises a CH2 domain from an IgG antibody of the IgG4 isotype and a CH3 domain from an IgG antibody of the IgG1 isotype, or a chimeric Fc region which comprises a hinge region from IgG2 and a CH2 region from IgG4, or a Fc region with mutations that result in reduced or no Fc functions. Fc regions with reduced or no Fe effector function include those known in the art. See, e.g., Lau C. et al., *J. Immunol.* 191:4769-4777 (2013); An et al., mAbs 1:6, 572-579 (2009); and U.S. Pub. No. 20120100140 and the U.S. patents and publications and PCT publications cited therein. Also Fc regions with reduced or no Fc effector function can be readily made by a person of ordinary skill in the art.

III. Nucleic Acid Molecules

Another aspect described herein pertains to one or more nucleic acid molecules that encode any one of the antibodies described herein. The nucleic acids can be present in whole cells, in a cell lysate, or in a partially purified or substantially pure form. A nucleic acid is "isolated" or "rendered substantially pure" when purified away from other cellular components or other contaminants, e.g., other cellular nucleic acids (e.g., other chromosomal DNA, e.g., the chromosomal DNA that is linked to the isolated DNA in nature) or proteins, by standard techniques, including alkaline/SDS treatment, CsCl banding, column chromatography, restriction enzymes, agarose gel electrophoresis and others well known in the art. See, F. Ausubel, et al., ed. (1987) Current Protocols in Molecular Biology, Greene Publishing and Wiley Interscience, New York. A nucleic acid described herein can be, for example, DNA or RNA and can or cannot contain intronic sequences. In a certain embodiments, the nucleic acid is a cDNA molecule.

Nucleic acids described herein can be obtained using standard molecular biology techniques. For antibodies expressed by hybridomas (e.g., hybridomas prepared from transgenic mice carrying human immunoglobulin genes as described further below), cDNAs encoding the light and heavy chains of the antibody made by the hybridoma can be obtained by standard PCR amplification or cDNA cloning techniques. For antibodies obtained from an immunoglobulin gene library (e.g., using phage display techniques), nucleic acid encoding the antibody can be recovered from the library.

Certain nucleic acids molecules described herein are those encoding the VH and VL sequences of the various anti-FAM19A5 antibodies of the present disclosure. Exemplary DNA sequences encoding the VH and VL sequence of such antibodies are set forth in Tables 8 and 9, respectively.

TABLE 8

| Variable heavy chain polynucleotide sequence | |
|---|---|
| Antibody | Variable Heavy Chain Polynucleotide Sequence (SEQ ID NO) |
| Reference anti-FAM19A5 Antibody ("3-2") | GCCGTGACGTTGGACGAGTCCGGGGGCGGCCTCCAGACGCCCGGAGGAGCGCTCAGCCTC GTCTGCAAGGCCTCCGGGTTCACCTTCAGCAGCTTCAACATGTTCTGGGTGCGACAGGCG CCCGGCAAGGGGCTGGAATACGTCGCTCAAATTAGCAGCAGTGGTAGTAGCACAAACTAC GCACCCGCGGTGAGGGGCCGTGCCACCATCTCGAGGGACAACGGGCAGAGCACAGTGAGG CTGCAGCTGAACAACCCCGGGGCTGAAGACACCGGCACCTACTACTGCGCCAAAAGTAGT TATGACTGTCCTTACGGTCATTGTAGTAGTGGTGTTGATAGTGCTGGTGAGATCGACGCA TGGGGCCACGGGACCGAAGTCATCGTCTCCTCC (SEQ ID NO: 58) |
| 1-7A-IT | GCCGTGACGTTGGATGAATCCGGGGGCGGCCTCCAGACGCCCGGAGGAGCGCTCCGCCTC AGCTGCAAGGCCTCTGGGTTCACCTTCAGCAGCTTCAACATGTTCTGGGTGCGACAGGCG CCCGGCAAGGGGCTGGAATACGTCTCGCAGATTAGCAGCAGTGGTAGTAGCACAAACTAC GCACCCGCGGTGAAAGGCCGTGCCACCATCTCGAGGGACAACGGGCAGAGCACACTGTAT CTGCAGATGAACAGCCTGCGCGCTGAAGACACCGGCACCTACTACTGCGCCAAAAGTAGT TATGACTGTCCTTACGGTCATTGTAGTAGTGGTGTTGATAGTGCTGGTGAGATCGACGCA TGGGGCCACGGGACCGAAGTCATCGTCTCCTCC (SEQ ID NO: 59) |
| Low-PI | GCCGTGACGTTGGATGAATCCGGGGGCGGCCTCCAGACGCCCGGAGGAGCGCTCCGCCTC AGCTGCAAGGCCTCTGGGTTCACCTTCAGCAGCTTCAACATGTTCTGGGTGCGACAGGCG CCCGGCAAGGGGCTGGAATACGTCTCGCAGATTAGCAGCAGTGGTAGTAGCACAAACTAC GCACCCGCGGTGAAAGGCCGTGCCACCATCTCGAGGGACAACGGGCAGAGCACACTGTAT CTGCAGATGAACAGCCTGCGCGCTGAAGACACCGGCACCTACTACTGCGCCAAAAGTAGT |

TABLE 8-continued

Variable heavy chain polynucleotide sequence

| Antibody | Variable Heavy Chain Polynucleotide Sequence (SEQ ID NO) |
|---|---|
| | TATGACTGTCCTTACGGTCATTGTAGTAGTGGTGTTGATAGTGCTGGTGAGATCGACGCA<br>TGGGGCCACGGGACCGAAGTCATCGTCTCCTCC (SEQ ID NO: 60) |
| 1-30 | GCCGTGACGTTGGATGAATCCGGGGGCGGCCTCCAGACGCCCGGAGGAGCGCTCCGCCTC<br>AGCTGCAAGGCCTCTGGCTTTGATTTTGAAAGCTTCAACATGTTCTGGGTGCGACAGGCG<br>CCCGGCAAGGGGCTGGAATACGTCTCGCAGATTAGCAGCAGTGAAGAAGATGAAAACTAC<br>GCACCCGCGGTGAAAGGCCGTGCCACCATCTCGAGGGACAACGGGCAGAGCACACTGTAT<br>CTGCAGATGAACAGCCTGCGCGCTGAAGACACCGGCACCTACTACTGCGCCAAAAGTAGT<br>TATGACTGTCCTTACGGTCATTGTAGTAGTGGTGTTGATAGTGCTGGTGAGATCGACGCA<br>TGGGGCCACGGGACCGAAGTCATCGTCTCCTCC (SEQ ID NO: 61) |
| 1-17 | GCCGTGACGTTGGATGAATCCGGGGGCGGCCTCCAGACGCCCGGAGGAGCGCTCCGCCTC<br>AGCTGCAAGGCCTCTGGCTTTGATTTTGAAAGCTTCAACATGTTCTGGGTGCGACAGGCG<br>CCCGGCAAGGGGCTGGAATACGTCTCGCAGATTAGCAGCAGTGAAGAAGATGAAAACTAC<br>GCACCCGCGGTGAAAGGCCGTGCCACCATCTCGAGGGACAACGGGCAGAGCACACTGTAT<br>CTGCAGATGAACAGCCTGCGCGCTGAAGACACCGGCACCTACTACTGCGCCAAAAGTAGT<br>TATGACTGTCCTTACGGTCATTGTAGTAGTGGTGTTGATAGTGCTGGTGAGATCGACGCA<br>TGGGGCCACGGGACCGAAGTCATCGTCTCCTCC (SEQ ID NO: 62) |
| 1-32 | GCCGTGACGTTGGATGAATCCGGGGGCGGCCTCCAGACGCCCGGAGGAGCGCTCCGCCTC<br>AGCTGCAAGGCCTCTGGCTTTGATTTTGAAAGCTTCAACATGTTCTGGGTGCGACAGGCG<br>CCCGGCAAGGGGCTGGAATACGTCTCGCAGATTAGCAGCAGTGAAGAAGATGAAAACTAC<br>GCACCCGCGGTGAAAGGCCGTGCCACCATCTCGAGGGACAACGGGCAGAGCACACTGTAT<br>CTGCAGATGAACAGCCTGCGCGCTGAAGACACCGGCACCTACTACTGCGCCAAAAGTAGT<br>TATGACTGTCCTTACGGTCATTGTAGTAGTGGTGTTGATAGTGCTGGTGAGATCGACGCA<br>TGGGGCCACGGGACCGAAGTCATCGTCTCCTCC (SEQ ID NO: 63) |
| 4-11 | GCCGTGACGTTGGATGAATCCGGGGGCGGCCTCCAGACGCCCGGAGGAGCGCTCCGCCTC<br>AGCTGCAAGGCCTCTGGCTTTGATTTTGAAAGCTTCAACATGTTCTGGGTGCGACAGGCG<br>CCCGGCAAGGGGCTGGAATACGTCTCGCAGATTAGCAGCAGTGAAGAAGATGAAAACTAC<br>GCACCCGCGGTGAAAGGCCGTGCCACCATCTCGAGGGACAACGGGCAGAGCACACTGTAT<br>CTGCAGATGAACAGCCTGCGCGCTGAAGACACCGGCACCTACTACTGCGCCAAAAGTAGT<br>TATGACTGTCCTTACGGTCATTGTAGTAGTGGTGTTGATAGTGCTGGTGAGATCGACGCA<br>TGGGGCCACGGGACCGAAGTCATCGTCTCCTCC (SEQ ID NO: 64) |
| 6-10 | GCCGTGACGTTGGATGAATCCGGGGGCGGCCTCCAGACGCCCGGAGGAGCGCTCCGCCTC<br>AGCTGCAAGGCCTCTGGCTTTGATTTTGAAAGCTTCAACATGTTCTGGGTGCGACAGGCG<br>CCCGGCAAGGGGCTGGAATACGTCTCGCAGATTAGCAGCAGTGAAGAAGATGAAAACTAC<br>GCACCCGCGGTGAAAGGCCGTGCCACCATCTCGAGGGACAACGGGCAGAGCACACTGTAT<br>CTGCAGATGAACAGCCTGCGCGCTGAAGACACCGGCACCTACTACTGCGCCAAAAGTAGT<br>TATGACTGTCCTTACGGTCATTGTAGTAGTGGTGTTGATAGTGCTGGTGAGATCGACGCA<br>TGGGGCCACGGGACCGAAGTCATCGTCTCCTCC (SEQ ID NO: 65) |
| Reference<br>anti-FAM19A5<br>Antibody<br>("2-13") | GCCGTGACGTTGGACGAGTCCGGGGGCGGCCTCCAGACGCCCGGAGGAGCGCTCAGCCTC<br>GTCTGCAAGGCCTCCGGGTTCACCTTCAGCAGCCATGGCATGTTCTGGGTGCGACAGACG<br>CCCGGCAAGGGGTTGGAATATGTCGCTGAAATTACCAATGATGGTAGTGGCACAAACTAC<br>GGGTCGGCGGTGAAGGGCCGTGCCACCATCTCGAGGGACAACGGGCAGAGCACAGTGAGG<br>CTGCAGCTGAACAACCTCAGGGCTGAGGACACCGGCACCTACTTCTGCGCCAGATCTACT<br>TATGAATGTCCTGGTGGTTTTAGTTGTTGGGGTGATACTGGTCAAATAGACGCATGGGGC<br>CACGGGACCGAAGTCATCGTCTCCTCC (SEQ ID NO: 66) |
| 2-13D | GCCGTGACGTTGGACGAGTCCGGGGGCGGCCTCCAGACGCCCGGAGGAGCGCTCCGCCTT<br>AGCTGCAGCGCCTCCGGGTTCACCTTCAGCAGCCATGGCATGTTCTGGGTGCGACAGGCG<br>CCCGGCAAGGGGTTGGAATATGTCTCGGAGATTACCAATGATGGTAGTGGCACAAACTAC<br>GGGTCGGCGGTGAAGGGCCGTGCCACCATCTCGAGGGACAACGGGCAGAGCACACTGTAT<br>CTGCAGATGAACAGCCTCAGGGCTGAGGACACCGGCACCTACTTCTGCGCCAGATCTACT<br>TATGAATGTCCTGGTGGTTTTAGTTGTTGGGGTGATACTGGTCAAATAGACGCATGGGGC<br>CACGGGACCGAAGTCATCGTCTCCTCC (SEQ ID NO: 67) |
| 2-13D-37 | GCCGTGACGTTGGACGAGTCCGGGGGCGGCCTCCAGACGCCCGGAGGAGCGCTCCGCCTT<br>AGCTGCAGCGCCTCCGGGTTCGATTTCAGCAGCCATGGCATGTTCTGGGTGCGACAGGCG<br>CCCGGCAAGGGGTTGGAATATGTCTCGGAGATTACCAATGATGGTAGTGGCACAAACTAC<br>GGGTCGGCGGTGAAGGGCCGTGCCACCATCTCGAGGGACAACGGGCAGAGCACACTGTAT<br>CTGCAGATGAACAGCCTCAGGGCTGAGGACACCGGCACCTACTTCTGCGCCAGATCTACT<br>TATGAATGTCCTGGTGGTTTTAGTTGTTGGGGTGATACTGGTCAAATAGACGCATGGGGC<br>CACGGGACCGAAGTCATCGTCTCCTCC (SEQ ID NO: 68) |
| 2-13D-37-1.5W-41 | GCCGTGACGTTGGACGAGTCCGGGGGCGGCCTCCAGACGCCCGGAGGAGCGCTCCGCCTT<br>AGCTGCAGCGCCTCCGGGTTCGATTTCAGCAGCCATGGCATGTTCTGGGTGCGACAGGCG<br>CCCGGCAAGGGGTTGGAATATGTCTCGGAGATTACCAATGATGGTAGTGGCACAAACTAC<br>GGGTCGGCGGTGAAGGGCCGTGCCACCATCTCGAGGGACAACGGGCAGAGCACACTGTAT<br>CTGCAGATGAACAGCCTCAGGGCTGAGGACACCGGCACCTACTTCTGCGCCAGATCTTCT<br>TATGTTTGTCCTGGTGGTTTTAGTTGTTGGGGTGATACTGGTCAAATAGACGCATGGGGC<br>CACGGGACCGAAGTCATCGTCTCCTCC (SEQ ID NO: 134) |

TABLE 8-continued

| Variable heavy chain polynucleotide sequence | |
|---|---|
| Antibody | Variable Heavy Chain Polynucleotide Sequence (SEQ ID NO) |
| 2-13D-37-3W-16 | GCCGTGACGTTGGACGAGTCCGGGGGCGGCCTCCAGACGCCCGGAGGAGCGCTCCGCCTT AGCTGCAGCGCCTCCGGGTTCGATTTCAGCAGCCATGGCATGTTCTGGGTGCGACAGGCG CCCGGCAAGGGGTTGGAATATGTCTCGGAGATTACCAATGATGGTAGTGGCACAAACTAC GGGTCGGCGGTGAAGGGCCGTGCCACCATCTCGAGGGACAACGGGCAGAGCACACTGTAT CTGCAGATGAACAGCCTCAGGGCTGAGGACACCGGCACCTACTTCTGCGCCAGATCTAAT TATGCTTGTCCTGGTGGTTTTAGTTGTTGGGGTGATACTGGTCAAATAGACGCATGGGGC CACGGGACCGAAGTCATCGTCTCCTCC (SEQ ID NO: 135) |

TABLE 9

| Variable light chain polynucleotide sequence | |
|---|---|
| Antibody | Variable Light Chain Polynucleotide Sequence (SEQ ID NO) |
| Reference anti-FAM19A5 Antibody ("3-2") | GCCCTGACTCAGCCGTCCTCGGTGTCAGCAAACCCAGGAGAAACCGTCAAGATCACCTGC TCCGGGGGTGGCAGCTATGCTGGAAGTTACTATTATGGCTGGTACCAGCAGAAGGCACCT GGCAGTGCCCCTGTCACTCTGATCTATGAAAGCAACAAGAGACCCTCGGACATCCCTTCA CGATTCTCCGGTTCCACATCTGGCTCCACAGCCACACTAACCATCACTGGGGTCCAAGCC GATGACGAGGCTATCTATTACTGTGGGAGCTGGGACAGTAGCAATGGTGGTATATTTGGG GCCGGGACAACCCTGACCGTCCTA (SEQ ID NO: 69) |
| 1-7A-IT | GCCCTGACTCAGCCGTCCTCGGTGTCAGCAAACCCAGGAGAAACCGTCAAGATCACCTGC TCCGGGGGTGGCAGCTATGCTGGAAGTTACTATTATGGCTGGTATCAGCAGAAGCCTGGC AGTGCCCCTGTCACTCTGATCTATGAAAACAACAAGAGACCCTCGGACATCCCTTCACGA TTCTCCGGTTCCACATCTGGCTCCACAGCCACACTAACCATCACTGGGGTCCAAGCCGGC GACGAGGCTGATTATTACTGTGGGAGCTGGGACAGTAGCAATGGTGGTATATTTGGGGCC GGGACAACCCTGACCGTCCTA (SEQ ID NO: 70) |
| Low-PI | GCCCTGACTCAGCCGTCCTCGGTGTCAGCAAACCCAGGAGAAACCGTCAAGATCACCTGC TCCGGGGGTGGCAGCTATGCTGGAAGTTACTATTATGGCTGGTATCAGCAGAAGCCTGGC AGTGCCCCTGTCACTCTGATCTATGAAAACAACAAGAGACCCTCGGACATCCCTTCACGA TTCTCCGGTTCCACATCTGGCTCCACAGCCACACTAACCATCACTGGGGTCCAAGCCGGC GACGAGGCTGATTATTACTGTGGGAGCTGGGACAGTAGCAATGGTGGTATATTTGGGGCC GGGACAACCCTGACCGTCCTA (SEQ ID NO: 71) |
| 1-30 | GCCCTGACTCAGCCGTCCTCGGTGTCAGCAAACCCAGGAGAAACCGTCAAGATCACCTGC TCCGGGGGTGGCAGCGAAGAAGAACAGTACTATTATGGCTGGTATCAGCAGAAGCCTGGC AGTGCCCCTGTCACTCTGATCTATCAGGATGAAGAAAGACCCTCGGACATCCCTTCACGA TTCTCCGGTTCCACATCTGGCTCCACAGCCACACTAACCATCACTGGGGTCCAAGCCGGC GACGAGGCTGATTATTACTGTGGGAGCTGGGACAGTGAAGATGAAGATCATTTTGGGGCC GGGACAACCCTGACCGTCCTA (SEQ ID NO: 72) |
| 1-17 | GCCCTGACTCAGCCGTCCTCGGTGTCAGCAAACCCAGGAGAAACCGTCAAGATCACCTGC TCCGGGGGTGGCAGCTATGCTGGAAGTTACTATTATGGCTGGTATCAGCAGAAGCCTGGC AGTGCCCCTGTCACTCTGATCTATGAAGATGAACAGAGACCCTCGGACATCCCTTCACGA TTCTCCGGTTCCACATCTGGCTCCACAGCCACACTAACCATCACTGGGGTCCAAGCCGGC GACGAGGCTGATTATTACTGTGGGAGCTGGGACAGTGAAGATGAAGATCATTTTGGGGCC GGGACAACCCTGACCGTCCTA (SEQ ID NO: 73) |
| 1-32 | GCCCTGACTCAGCCGTCCTCGGTGTCAGCAAACCCAGGAGAAACCGTCAAGATCACCTGC TCCGGGGGTGGCAGCTATGCTGGAAGTTACTATTATGGCTGGTATCAGCAGAAGCCTGGC AGTGCCCCTGTCACTCTGATCTATCAGGATGAAGAAAGACCCTCGGACATCCCTTCACGA TTCTCCGGTTCCACATCTGGCTCCACAGCCACACTAACCATCACTGGGGTCCAAGCCGGC GACGAGGCTGATTATTACTGTGGGAGCTGGGACAGTGAAGATGAAGATCATTTTGGGGCC GGGACAACCCTGACCGTCCTA (SEQ ID NO: 74) |
| 4-11 | GCCCTGACTCAGCCGTCCTCGGTGTCAGCAAACCCAGGAGAAACCGTCAAGATCACCTGC TCCGGGGGTGGCAGCTATGCTGGAAGTTACTATTATGGCTGGTATCAGCAGAAGCCTGGC AGTGCCCCTGTCACTCTGATCTATGAAGACCACGAGAGACCCTCGGACATCCCTTCACGA TTCTCCGGTTCCACATCTGGCTCCACAGCCACACTAACCATCACTGGGGTCCAAGCCGGC GACGAGGCTGATTATTACTGTGGGAGCTGGGACAGTAGCGATGAAGATCATTTTGGGGCC GGGACAACCCTGACCGTCCTA (SEQ ID NO: 75) |
| 6-10 | GCCCTGACTCAGCCGTCCTCGGTGTCAGCAAACCCAGGAGAAACCGTCAAGATCACCTGC TCCGGGGGTGGCAGCTATGCTGGAAGTTACTATTATGGCTGGTATCAGCAGAAGCCTGGC AGTGCCCCTGTCACTCTGATCTATCAGGATCTGCTGAGACCCTCGGACATCCCTTCACGA TTCTCCGGTTCCACATCTGGCTCCACAGCCACACTAACCATCACTGGGGTCCAAGCCGGC GACGAGGCTGATTATTACTGTGGGAGCTGGGACAGTCTGAGCAGCAGCCATTTTGGGGCC GGGACAACCCTGACCGTCCTA (SEQ ID NO: 76) |
| Reference anti-FAM19A5 Antibody | GCCCTGACTCAGCCGTCCTCGGTGTCAGCAAACCCAGGAGAAACCGTCAAGATAACCTGC TCCGGGGGTAGCTATAGCTATGGCTGGTTCCAGCAGAAGTCTCCTGGCAGTGCCCTTGTC ACTGTGATCTACTGGGATGATGAGAGACCCTCGGACATCCCTTCACGATTCTCCGGTGCC |

TABLE 9-continued

Variable light chain polynucleotide sequence

| Antibody | Variable Light Chain Polynucleotide Sequence (SEQ ID NO) |
|---|---|
| ("2-13") | CTATCCGGCTCCACAAACACATTAACCATCACTGGGGTCCAAGCCGACGACGAGGCTGTC TATTTCTGTGGGACTGAAGACATCAGCGGCACTGCTGGTGTATTTGGGGCCGGGACAACC CTGACCGTCCTG (SEQ ID NO: 77) |
| 2-13D | GCCCTGACTCAGCCGTCCTCGGTGTCAGCAAACCCAGGAGAAACCGCGAAGATAACCTGC TCCGGGGGTGTGTATAGCTATGGCTGGTTCCAGCAGAAGCCTGGCAGTGCCCTTGTCACT GTGATCTACTGGGATGATGAGAGACCCTCGGACATCCCTTCACGATTCTCCGGTGCCCTA TCCGGCTCCACAAACACATTAACCATCACTGGGGTCCAAGCCGAAGACGAGGCTGATTAT TATTGTGGGACTGAAGACATCAGCGGCACTGCTGGTGTATTTGGGGCCGGGACAACCCTG ACCGTCCTG (SEQ ID NO: 78) |
| 2-13D-37 | GCCCTGACTCAGCCGTCCTCGGTGTCAGCAAACCCAGGAGAAACCGCGAAGATAACCTGC TCCGGGGGTGTGTATAGCTATGGCTGGTTCCAGCAGAAGCCTGGCAGTGCCCTTGTCACT GTGATCTACTGGGATGATGAGAGACCCTCGGACATCCCTTCACGATTCTCCGGTGCCCTA TCCGGCTCCACAAACACATTAACCATCACTGGGGTCCAAGCCGAAGACGAGGCTGATTAT TATTGTGGGACTGAAGACATCAGCGGCACTGCTGGTGTATTTGGGGCCGGGACAACCCTG ACCGTCCTG (SEQ ID NO: 79) |
| 2-13D-37-1.5W-41 | GCCCTGACTCAGCCGTCCTCGGTGTCAGCAAACCCAGGAGAAACCGCGAAGATAACCTGC TCCGGGGGTGTGTATAGCTATGGCTGGTTCCAGCAGAAGCCTGGCAGTGCCCTTGTCACT GTGATCTACTGGGATGATGAGAGACCCTCGGACATCCCTTCACGATTCTCCGGTGCCCTA TCCGGCTCCACAAACACATTAACCATCACTGGGGTCCAAGCCGAAGACGAGGCTGATTAT TATTGTGGGACTGAAGACATCAGCGGCACTGCTGGTGTATTTGGGGCCGGGACAACCCTG ACCGTCCTG (SEQ ID NO: 136) |
| 2-13D-37-3W-16 | GCCCTGACTCAGCCGTCCTCGGTGTCAGCAAACCCAGGAGAAACCGCGAAGATAACCTGC TCCGGGGGTGTGTATAGCTATGGCTGGTTCCAGCAGAAGCCTGGCAGTGCCCTTGTCACT GTGATCTACTGGGATGATGAGAGACCCTCGGACATCCCTTCACGATTCTCCGGTGCCCTA TCCGGCTCCACAAACACATTAACCATCACTGGGGTCCAAGCCGAAGACGAGGCTGATTAT TATTGTGGGACTGAAGACATCAGCGGCACTGCTGGTGTATTTGGGGCCGGGACAACCCTG ACCGTCCTG (SEQ ID NO: 137) |

A method for making an anti-FAM19A5 antibody as disclosed herein can comprise expressing the heavy chain and the light chains in a cell line comprising the nucleotide sequences encoding the heavy and light chains with a signal peptide. Host cells comprising these nucleotide sequences are encompassed herein.

Once DNA fragments encoding VH and VL segments are obtained, these DNA fragments can be further manipulated by standard recombinant DNA techniques, for example to convert the variable region genes to full-length antibody chain genes, to Fab fragment genes or to a scFv gene. In these manipulations, a VL- or VH-encoding DNA fragment is operatively linked to another DNA fragment encoding another protein, such as an antibody constant region or a flexible linker. The term "operatively linked", as used in this context, is intended to mean that the two DNA fragments are joined such that the amino acid sequences encoded by the two DNA fragments remain in-frame.

The isolated DNA encoding the VH region can be converted to a full-length heavy chain gene by operatively linking the VH-encoding DNA to another DNA molecule encoding heavy chain constant regions (hinge, CH1, CH2 and/or CH3). The sequences of human heavy chain constant region genes are known in the art (see e.g., Kabat, E. A., et al. (1991) Sequences of Proteins of Immunological Interest, Fifth Edition, U.S. Department of Health and Human Services, NIH Publication No. 91-3242) and DNA fragments encompassing these regions can be obtained by standard PCR amplification. The heavy chain constant region can be an IgG1, IgG2, IgG3, IgG4, IgA, IgE, IgM or IgD constant region, for example, an IgG2 and/or IgG 4 constant region. For a Fab fragment heavy chain gene, the VH-encoding DNA can be operatively linked to another DNA molecule encoding only the heavy chain CH1 constant region.

The isolated DNA encoding the VL region can be converted to a full-length light chain gene (as well as a Fab light chain gene) by operatively linking the VL-encoding DNA to another DNA molecule encoding the light chain constant region, CL. The sequences of human light chain constant region genes are known in the art (see, e.g., Kabat, E. A., et al. (1991) Sequences of Proteins of Immunological Interest, Fifth Edition, U.S. Department of Health and Human Services, NIH Publication No. 91-3242) and DNA fragments encompassing these regions can be obtained by standard PCR amplification. The light chain constant region can be a kappa or lambda constant region.

To create a scFv gene, the VH- and VL-encoding DNA fragments are operatively linked to another fragment encoding a flexible linker, e.g., encoding the amino acid sequence (Gly4-Ser)3, such that the VH and VL sequences can be expressed as a contiguous single-chain protein, with the VL and VH regions joined by the flexible linker (see, e.g., Bird et al. (1988) *Science* 242:423-426; Huston et al. (1988) *Proc. Natl. Acad. Sci. USA* 85:5879-5883; McCafferty et al. (1990) *Nature* 348:552-554). The amino acid sequences of exemplary anti-FAM19A5 scFv are provided in Tables 7.

In some embodiments, the present disclosure provides a vector comprising an isolated nucleic acid molecule comprising a nucleotide sequence encoding an antibody. In other embodiments, the vectors can be used for gene therapy.

Suitable vectors for the disclosure include expression vectors, viral vectors, and plasmid vectors. In one embodiment, the vector is a viral vector.

As used herein, an expression vector refers to any nucleic acid construct which contains the necessary elements for the transcription and translation of an inserted coding sequence, or in the case of an RNA viral vector, the necessary elements for replication and translation, when introduced into an appropriate host cell. Expression vectors can include plasmids, phagemids, viruses, and derivatives thereof.

Expression vectors of the disclosure can include polynucleotides encoding the antibody or described herein. In one embodiment, the coding sequences for the antibody are operably linked to an expression control sequence. As used herein, two nucleic acid sequences are operably linked when they are covalently linked in such a way as to permit each component nucleic acid sequence to retain its functionality. A coding sequence and a gene expression control sequence are said to be operably linked when they are covalently linked in such a way as to place the expression or transcription and/or translation of the coding sequence under the influence or control of the gene expression control sequence. Two DNA sequences are said to be operably linked if induction of a promoter in the 5' gene expression sequence results in the transcription of the coding sequence and if the nature of the linkage between the two DNA sequences does not (1) result in the introduction of a frame-shift mutation, (2) interfere with the ability of the promoter region to direct the transcription of the coding sequence, or (3) interfere with the ability of the corresponding RNA transcript to be translated into a protein. Thus, a gene expression sequence would be operably linked to a coding nucleic acid sequence if the gene expression sequence were capable of effecting transcription of that coding nucleic acid sequence such that the resulting transcript is translated into the desired antibody.

Viral vectors include, but are not limited to, nucleic acid sequences from the following viruses: retrovirus, such as Moloney murine leukemia virus, Harvey murine sarcoma virus, murine mammary tumor virus, and Rous sarcoma virus; lentivirus; adenovirus; adeno-associated virus; SV40-type viruses; polyomaviruses; Epstein-Barr viruses; papilloma viruses; herpes virus; vaccinia virus; polio virus; and RNA virus such as a retrovirus. One can readily employ other vectors well-known in the art. Certain viral vectors are based on non-cytopathic eukaryotic viruses in which non-essential genes have been replaced with the gene of interest. Non-cytopathic viruses include retroviruses, the life cycle of which involves reverse transcription of genomic viral RNA into DNA with subsequent proviral integration into host cellular DNA. Retroviruses have been approved for human gene therapy trials. Most useful are those retroviruses that are replication-deficient (i.e., capable of directing synthesis of the desired proteins, but incapable of manufacturing an infectious particle). Such genetically altered retroviral expression vectors have general utility for the high efficiency transduction of genes in vivo. Standard protocols for producing replication-deficient retroviruses (including the steps of incorporation of exogenous genetic material into a plasmid, transfection of a packaging cell line with plasmid, production of recombinant retroviruses by the packaging cell line, collection of viral particles from tissue culture media, and infection of the target cells with viral particles) are provided in Kriegler, M., Gene Transfer and Expression, A Laboratory Manual, W.H. Freeman Co., New York (1990) and Murry, E. J., Methods in Molecular Biology, Vol. 7, Humana Press, Inc., Cliffton, N.J. (1991).

In one embodiment, the virus is an adeno-associated virus, a double-stranded DNA virus. The adeno-associated virus can be engineered to be replication-deficient and is capable of infecting a wide range of cell types and species. It further has advantages such as heat and lipid solvent stability; high transduction frequencies in cells of diverse lineages, including hematopoietic cells; and lack of superinfection inhibition thus allowing multiple series of transductions. Reportedly, the adeno-associated virus can integrate into human cellular DNA in a site-specific manner, thereby minimizing the possibility of insertional mutagenesis and variability of inserted gene expression characteristic of retroviral infection. In addition, wild-type adeno-associated virus infections have been followed in tissue culture for greater than 100 passages in the absence of selective pressure, implying that the adeno-associated virus genomic integration is a relatively stable event. The adeno-associated virus can also function in an extrachromosomal fashion.

In other embodiments, the vector is derived from lentivirus. In certain embodiments, the vector is a vector of a recombinant lentivirus capable of infecting non-dividing cells.

The lentiviral genome and the proviral DNA typically have the three genes found in retroviruses: gag, pol and env, which are flanked by two long terminal repeat (LTR) sequences. The gag gene encodes the internal structural (matrix, capsid and nucleocapsid) proteins; the pol gene encodes the RNA-directed DNA polymerase (reverse transcriptase), a protease and an integrase; and the env gene encodes viral envelope glycoproteins. The 5' and 3' LTR's serve to promote transcription and polyadenylation of the virion RNA's. The LTR contains all other cis-acting sequences necessary for viral replication. Lentiviruses have additional genes including vif, vpr, tat, rev, vpu, nef and vpx (in HIV-1, HIV-2 and/or SIV).

Adjacent to the 5' LTR are sequences necessary for reverse transcription of the genome (the tRNA primer binding site) and for efficient encapsidation of viral RNA into particles (the Psi site). If the sequences necessary for encapsidation (or packaging of retroviral RNA into infectious virions) are missing from the viral genome, the cis defect prevents encapsidation of genomic RNA.

However, the resulting mutant remains capable of directing the synthesis of all virion proteins. The disclosure provides a method of producing a recombinant lentivirus capable of infecting a non-dividing cell comprising transfecting a suitable host cell with two or more vectors carrying the packaging functions, namely gag, pol and env, as well as rev and tat. As will be disclosed herein below, vectors lacking a functional tat gene are desirable for certain applications. Thus, for example, a first vector can provide a nucleic acid encoding a viral gag and a viral pol and another vector can provide a nucleic acid encoding a viral env to produce a packaging cell. Introducing a vector providing a heterologous gene, herein identified as a transfer vector, into that packaging cell yields a producer cell which releases infectious viral particles carrying the foreign gene of interest.

According to the above-indicated configuration of vectors and foreign genes, the second vector can provide a nucleic acid encoding a viral envelope (env) gene. The env gene can be derived from nearly any suitable virus, including retroviruses. In some embodiments, the env protein is an amphotropic envelope protein which allows transduction of cells of human and other species.

Examples of retroviral-derived env genes include, but are not limited to: Moloney murine leukemia virus (MoMuLV or MMLV), Harvey murine sarcoma virus (HaMuSV or HSV), murine mammary tumor virus (MuMTV or MMTV), gibbon ape leukemia virus (GaLV or GALV), human immunodeficiency virus (HIV) and Rous sarcoma virus (RSV). Other env genes such as Vesicular stomatitis virus (VSV) protein G (VSV G), that of hepatitis viruses and of influenza also can be used.

The vector providing the viral env nucleic acid sequence is associated operably with regulatory sequences described elsewhere herein.

In certain embodiments, the vector includes a lentiviral vector in which the HIV virulence genes env, vif, vpr, vpu and nef were deleted without compromising the ability of the vector to transduce non-dividing cells.

In some embodiments, the vector includes a lentiviral vector which comprises a deletion of the U3 region of the 3' LTR. The deletion of the U3 region can be the complete deletion or a partial deletion.

In some embodiments, the lentiviral vector of the disclosure comprising the FVIII nucleotide sequence described herein can be transfected in a cell with (a) a first nucleotide sequence comprising a gag, a pol, or gag and pol genes and (b) a second nucleotide sequence comprising a heterologous env gene; wherein the lentiviral vector lacks a functional tat gene. In other embodiments, the cell is further transfected with a fourth nucleotide sequence comprising a rev gene. In certain embodiments, the lentiviral vector lacks functional genes selected from vif, vpr, vpu, vpx and nef, or a combination thereof.

In certain embodiments, a lentiviral vector comprises one or more nucleotide sequences encoding a gag protein, a Rev-response element, a central polypurine track (cPPT), or any combination thereof.

Examples of the lentiviral vectors are disclosed in WO9931251, W09712622, W09817815, W09817816, and WO9818934, which are incorporated herein by reference in their entireties.

Other vectors include plasmid vectors. Plasmid vectors have been extensively described in the art and are well-known to those of skill in the art. See, e.g., Sambrook et al., Molecular Cloning: A Laboratory Manual, Second Edition, Cold Spring Harbor Laboratory Press, 1989. In the last few years, plasmid vectors have been found to be particularly advantageous for delivering genes to cells in vivo because of their inability to replicate within and integrate into a host genome. These plasmids, however, having a promoter compatible with the host cell, can express a peptide from a gene operably encoded within the plasmid. Some commonly used plasmids available from commercial suppliers include pBR322, pUC18, pUC19, various pcDNA plasmids, pRC/CMV, various pCMV plasmids, pSV40, and pBlueScript. Additional examples of specific plasmids include pcDNA3.1, catalog number V79020; pcDNA3.1/hygro, catalog number V87020; pcDNA4/myc-His, catalog number V86320; and pBudCE4.1, catalog number V53220, all from Invitrogen (Carlsbad, CA.). Other plasmids are well-known to those of ordinary skill in the art. Additionally, plasmids can be custom designed using standard molecular biology techniques to remove and/or add specific fragments of DNA.

IV. Antibody Production

Antibodies or fragments thereof that immunospecifically bind to FAM19A5 (e.g., human FAM19A5) can be produced by any method known in the art for the synthesis of antibodies, for example, by chemical synthesis or by recombinant expression techniques. The methods described herein employs, unless otherwise indicated, conventional techniques in molecular biology, microbiology, genetic analysis, recombinant DNA, organic chemistry, biochemistry, PCR, oligonucleotide synthesis and modification, nucleic acid hybridization, and related fields within the skill of the art. These techniques are described, for example, in the references cited herein and are fully explained in the literature. See, e.g., Maniatis T et al., (1982) Molecular Cloning: A Laboratory Manual, Cold Spring Harbor Laboratory Press; Sambrook J et al., (1989), Molecular Cloning: A Laboratory Manual, Second Edition, Cold Spring Harbor Laboratory Press; Sambrook J et al., (2001) Molecular Cloning: A Laboratory Manual, Cold Spring Harbor Laboratory Press, Cold Spring Harbor, NY; Ausubel F M et al., Current Protocols in Molecular Biology, John Wiley & Sons (1987 and annual updates); Current Protocols in Immunology, John Wiley & Sons (1987 and annual updates) Gait (ed.) (1984) Oligonucleotide Synthesis: A Practical Approach, IRL Press; Eckstein (ed.) (1991) Oligonucleotides and Analogues: A Practical Approach, IRL Press; Birren B et al., (eds.) (1999) Genome Analysis: A Laboratory Manual, Cold Spring Harbor Laboratory Press.

In a specific embodiment, an antibody described herein is an antibody (e.g., recombinant antibody) prepared, expressed, created or isolated by any means that involves creation, e.g., via synthesis, genetic engineering of DNA sequences. In certain embodiments, such antibody comprises sequences (e.g., DNA sequences or amino acid sequences) that do not naturally exist within the antibody germline repertoire of an animal or mammal (e.g., human) in vivo. In some embodiments, the anti-FAM19A5 antibodies disclosed herein have been de-immunized.

As described in the Examples (e.g., Example 2), the anti-FAM19A5 antibodies were initially generated by immunizing chickens with a synthetic FAM19A5 peptide. Therefore, to minimize the risk of immunogenicity when administered to human subjects, the anti-FAM19A5 antibodies (e.g., 3-2 and 2-13) have been modified to more closely resemble the immunogenic sequences of human antibodies. In some embodiments, the de-immunized anti-FAM19A5 antibodies disclosed herein have similar binding affinity to human FAM19A5, compared to their corresponding counterpart antibodies that have not been de-immunized. In some embodiments, anti-FAM19A5 antibodies disclosed herein have also undergone affinity maturation. The methods for de-immunizing an antibody are disclosed herein and also known in the art.

In a certain aspect, provided herein is a method of making an antibody or an antigen-binding fragment thereof which immunospecifically binds to FAM19A5 (e.g., human FAM19A5) comprising culturing a cell or host cell described herein. In a certain aspect, provided herein is a method of making an antibody or an antigen-binding fragment thereof which immunospecifically binds to FAM19A5 (e.g., human FAM19A5) comprising expressing (e.g., recombinantly expressing) the antibody or antigen-binding fragment thereof using a cell or host cell described herein (e.g., a cell or a host cell comprising polynucleotides encoding an antibody described herein). In a particular embodiment, the cell is an isolated cell. In a particular embodiment, the exogenous polynucleotides have been introduced into the cell. In a particular embodiment, the method further comprises the step of purifying the antibody or antigen-binding fragment thereof obtained from the cell or host cell.

Methods for producing polyclonal antibodies are known in the art (see, for example, Chapter 11 in: Short Protocols in Molecular Biology, (2002) 5th Ed., Ausubel F M et al., eds., John Wiley and Sons, New York).

Monoclonal antibodies can be prepared using a wide variety of techniques known in the art including the use of hybridoma, recombinant, and phage display technologies, or a combination thereof. For example, monoclonal antibodies can be produced using hybridoma techniques including those known in the art and taught, for example, in Harlow E & Lane D, Antibodies: A Laboratory Manual, (Cold Spring Harbor Laboratory Press, 2nd ed. 1988); Hammerling G J et al., in: Monoclonal Antibodies and T-Cell Hybridomas 563 681 (Elsevier, N.Y., 1981). The term "monoclonal antibody" as used herein is not limited to antibodies produced through hybridoma technology. For example, monoclonal antibodies can be produced recombinantly from host cells exogenously expressing an antibody described herein or a fragment thereof, for example, light chain and/or heavy chain of such antibody.

In specific embodiments, a "monoclonal antibody," as used herein, is an antibody produced by a single cell (e.g., hybridoma or host cell producing a recombinant antibody), wherein the antibody immunospecifically binds to FAM19A5 (e.g., human FAM19A5) as determined, e.g., by ELISA or other antigen-binding or competitive binding assay known in the art or in the Examples provided herein. In particular embodiments, a monoclonal antibody can be a chimeric antibody or a humanized antibody. In certain embodiments, a monoclonal antibody is a monovalent antibody or multivalent (e.g., bivalent) antibody. In particular embodiments, a monoclonal antibody is a monospecific or multispecific antibody (e.g., bispecific antibody). Monoclonal antibodies described herein can, for example, be made by the hybridoma method as described in Kohler G & Milstein C (1975) *Nature* 256: 495 or can, e.g., be isolated from phage libraries using the techniques as described herein, for example. Other methods for the preparation of clonal cell lines and of monoclonal antibodies expressed thereby are well known in the art (see, for example, Chapter 11 in: Short Protocols in Molecular Biology, (2002) 5th Ed., Ausubel F M et al, supra).

Methods for producing and screening for specific antibodies using hybridoma technology are routine and well known in the art. For example, in the hybridoma method, a mouse or other appropriate host animal, such as a sheep, goat, rabbit, rat, hamster or macaque monkey, is immunized to elicit lymphocytes that produce or are capable of producing antibodies that will specifically bind to the protein (e.g., human FAM19A5) used for immunization. Alternatively, lymphocytes can be immunized in vitro. Lymphocytes then are fused with myeloma cells using a suitable fusing agent, such as polyethylene glycol, to form a hybridoma cell (Goding J W (Ed), Monoclonal Antibodies: Principles and Practice, pp. 59-103 (Academic Press, 1986)). Additionally, a RIMMS (repetitive immunization multiple sites) technique can be used to immunize an animal (Kilpatrick K E et al., (1997) *Hybridoma* 16:381-9, incorporated by reference in its entirety).

In some embodiments, mice (or other animals, such as chickens, rats, monkeys, donkeys, pigs, sheep, hamster, or dogs) can be immunized with an antigen (e.g., FAM19A5 such as human FAM19A5) and once an immune response is detected, e.g., antibodies specific for the antigen are detected in the mouse serum, the mouse spleen is harvested and splenocytes isolated. The splenocytes are then fused by well-known techniques to any suitable myeloma cells, for example cells from cell line SP20 available from the American Type Culture Collection (ATCC®) (Manassas, VA), to form hybridomas. Hybridomas are selected and cloned by limited dilution. In certain embodiments, lymph nodes of the immunized mice are harvested and fused with NSO myeloma cells.

The hybridoma cells thus prepared are seeded and grown in a suitable culture medium that preferably contains one or more substances that inhibit the growth or survival of the unfused, parental myeloma cells. For example, if the parental myeloma cells lack the enzyme hypoxanthine guanine phosphoribosyl transferase (HGPRT or HPRT), the culture medium for the hybridomas typically will include hypoxanthine, aminopterin, and thymidine (HAT medium), which substances prevent the growth of HGPRT-deficient cells.

Specific embodiments employ myeloma cells that fuse efficiently, support stable high-level production of antibody by the selected antibody-producing cells, and are sensitive to a medium such as HAT medium. Among these myeloma, cell lines are murine myeloma lines, such as NSO cell line or those derived from MOPC-21 and MPC-11 mouse tumors available from the Salk Institute Cell Distribution Center, San Diego, CA, USA, and SP-2 or X63-Ag8.653 cells available from the American Type Culture Collection, Rockville, MD, USA. Human myeloma and mouse-human heteromyeloma cell lines also have been described for the production of human monoclonal antibodies (Kozbor D (1984) *J Immunol* 133: 3001-5; Brodeur et al., Monoclonal Antibody Production Techniques and Applications, pp. 51-63 (Marcel Dekker, Inc., New York, 1987)).

Culture medium in which hybridoma cells are growing is assayed for production of monoclonal antibodies directed against FAM19A5 (e.g., human FAM19A5). The binding specificity of monoclonal antibodies produced by hybridoma cells is determined by methods known in the art, for example, immunoprecipitation or by an in vitro binding assay, such as radioimmunoassay (RIA) or enzyme-linked immunoabsorbent assay (ELISA).

After hybridoma cells are identified that produce antibodies of the desired specificity, affinity, and/or activity, the clones can be subcloned by limiting dilution procedures and grown by standard methods (Goding J W (Ed), Monoclonal Antibodies: Principles and Practice, supra). Suitable culture media for this purpose include, for example, D-MEM or RPMI 1640 medium. In addition, the hybridoma cells can be grown in vivo as ascites tumors in an animal.

The monoclonal antibodies secreted by the subclones are suitably separated from the culture medium, ascites fluid, or serum by conventional immunoglobulin purification procedures such as, for example, protein A-Sepharose, hydroxylapatite chromatography, gel electrophoresis, dialysis, or affinity chromatography.

Antibodies described herein include antibody fragments which recognize specific FAM19A5 (e.g., human FAM19A5) and can be generated by any technique known to those of skill in the art. For example, Fab and F(ab')2 fragments described herein can be produced by proteolytic cleavage of immunoglobulin molecules, using enzymes such as papain (to produce Fab fragments) or pepsin (to produce F(ab')2 fragments). A Fab fragment corresponds to one of the two identical arms of an antibody molecule and contains the complete light chain paired with the VH and CH1 domains of the heavy chain. A F(ab')2 fragment contains the two antigen-binding arms of an antibody molecule linked by disulfide bonds in the hinge region.

Further, the antibodies described herein or antigen-binding fragments thereof can also be generated using various phage display methods known in the art. In phage display methods, functional antibody domains are displayed on the surface of phage particles which carry the polynucleotide sequences encoding them. In particular, DNA sequences encoding VH and VL domains are amplified from animal cDNA libraries (e.g., human or non-human such as murine or chicken cDNA libraries of affected tissues). The DNAs encoding the VH and VL domains are recombined together with a scFv linker by PCR and cloned into a phagemid vector. The vector is electroporated in *E. coli* and the *E. coli* is infected with helper phage. Phage used in these methods are typically filamentous phage including fd and M13, and the VH and VL domains are usually recombinantly fused to either the phage gene III or gene VIII. Phage expressing an antigen binding domain that binds to a particular antigen can be selected or identified with antigen, e.g., using labeled antigen or antigen bound or captured to a solid surface or bead. Examples of phage display methods that can be used to make the antibodies described herein include those disclosed in Brinkman U et al., (1995) *J Immunol Methods* 182: 41-50; Ames R S et al., (1995) *J Immunol Methods* 184: 177-186; Kettleborough C A et al., (1994) *Eur J Immunol* 24: 952-958; Persic L et al., (1997) *Gene* 187: 9-18; Burton D R & Barbas C F (1994) *Advan Immunol* 57: 191-280; PCT Application No. PCT/GB91/001134; International Publication Nos. WO 90/02809, WO 91/10737, WO 92/01047, WO 92/18619, WO 93/11236, WO 95/15982, WO 95/20401, and WO 97/13844; and U.S. Pat. Nos. 5,698,426, 5,223,409, 5,403,484, 5,580,717, 5,427,908, 5,750,753, 5,821,047, 5,571,698, 5,427,908, 5,516,637, 5,780,225, 5,658,727, 5,733,743 and 5,969,108.

As described in the above references, after phage selection, the antibody coding regions from the phage can be isolated and used to generate whole antibodies, including human antibodies, or any other desired antigen binding fragment, and expressed in any desired host, including mammalian cells, insect cells, plant cells, yeast, and bacteria, e.g., as described below. Techniques to recombinantly produce antibody fragments such as Fab, Fab' and F(ab')2 fragments can also be employed using methods known in the art such as those disclosed in PCT publication No. WO 92/22324; Mullinax R L et al., (1992) *BioTechniques* 12(6): 864-9; Sawai H et al., (1995) *Am J Reprod Immunol* 34: 26-34; and Better M et al., (1988) Science 240: 1041-1043.

In one aspect, to generate whole antibodies, PCR primers including VH or VL nucleotide sequences, a restriction site, and a flanking sequence to protect the restriction site can be used to amplify the VH or VL sequences from a template, e.g., scFv clones. Utilizing cloning techniques known to those of skill in the art, the PCR amplified VH domains can be cloned into vectors expressing a VH constant region, and the PCR amplified VL domains can be cloned into vectors expressing a VL constant region, e.g., human kappa or lambda constant regions. The VH and VL domains can also be cloned into one vector expressing the necessary constant regions. The heavy chain conversion vectors and light chain conversion vectors are then co-transfected into cell lines to generate stable or transient cell lines that express full-length antibodies, e.g., IgG, using techniques known to those of skill in the art.

A chimeric antibody is a molecule in which different portions of the antibody are derived from different immunoglobulin molecules. For example, a chimeric antibody can contain a variable region of a non-human animal (e.g., mouse, rat or chicken) monoclonal antibody fused to a constant region of a human antibody. Methods for producing chimeric antibodies are known in the art. See, e.g., Morrison S L (1985) *Science* 229: 1202-7; Oi V T & Morrison S L (1986) *BioTechniques* 4: 214-221; Gillies S D et al., (1989) *J Immunol Methods* 125: 191-202; and U.S. Pat. Nos. 5,807,715, 4,816,567, 4,816,397, and 6,331,415.

A humanized antibody is capable of binding to a predetermined antigen and which comprises a framework region having substantially the amino acid sequence of a human immunoglobulin and CDRs having substantially the amino acid sequence of a non-human immunoglobulin (e.g., a murind or a chicken immunoglobulin). In particular embodiments, a humanized antibody also comprises at least a portion of an immunoglobulin constant region (Fc), typically that of a human immunoglobulin. The antibody also can include the CH1, hinge, CH2, CH3, and CH4 regions of the heavy chain. A humanized antibody can be selected from any class of immunoglobulins, including IgM, IgG, IgD, IgA and IgE, and any isotype, including IgG1, IgG2, IgG3 and IgG4. Humanized antibodies can be produced using a variety of techniques known in the art, including but not limited to, CDR-grafting (European Patent No. EP 239400; International Publication No. WO 91/09967; and U.S. Pat. Nos. 5,225,539, 5,530,101, and 5,585,089), veneering or resurfacing (European Patent Nos. EP 592106 and EP 519596; Padlan E A (1991) *Mol Immunol* 28(4/5): 489-498; Studnicka G M et al., (1994) *Prot Engineering* 7(6): 805-814; and Roguska M A et al., (1994) *PNAS* 91: 969-973), chain shuffling (U.S. Pat. No. 5,565,332), and techniques disclosed in, e.g., U.S. Pat. Nos. 6,407,213, 5,766,886, International Publication No. WO 93/17105; Tan P et al., (2002) *J Immunol* 169: 1119-25; Caldas C et al., (2000) *Protein Eng.* 13(5): 353-60; Morea V et al., (2000) *Methods* 20(3): 267-79; Baca M et al., (1997) *J Biol Chem* 272(16): 10678-84; Roguska M A et al., (1996) *Protein Eng* 9(10): 895 904; Couto J R et al., (1995) *Cancer Res.* 55 (23 Supp): 5973s-5977s; Couto J R et al., (1995) *Cancer Res* 55(8): 1717-22; Sandhu J S (1994) *Gene* 150(2): 409-10 and Pedersen J T et al., (1994) *J Mol Biol* 235(3): 959-73. See also U.S. Application Publication No. US 2005/0042664 A1 (Feb. 24, 2005), which is incorporated by reference herein in its entirety.

Methods for making multispecific (e.g., bispecific antibodies) have been described, see, for example, U.S. Pat. Nos. 7,951,917; 7,183,076; 8,227,577; 5,837,242; 5,989,830; 5,869,620; 6,132,992 and 8,586,713.

Single domain antibodies, for example, antibodies lacking the light chains, can be produced by methods well known in the art. See Riechmann L & Muyldermans S (1999) *J Immunol* 231: 25-38; Nuttall S D et al., (2000) *Curr Pharm Biotechnol* 1(3): 253-263; Muyldermans S, (2001) *J Biotechnol*74(4): 277-302; U.S. Pat. No. 6,005,079; and International Publication Nos. WO 94/04678, WO 94/25591 and WO 01/44301.

Further, antibodies that immunospecifically bind to a FAM19A5 antigen can, in turn, be utilized to generate anti-idiotype antibodies that "mimic" an antigen using techniques well known to those skilled in the art. (See, e.g., Greenspan N S & Bona C A (1989) *FASEB J* 7(5): 437-444; and Nissinoff A (1991) *J Immunol* 147(8): 2429-2438).

In particular embodiments, an antibody described herein, which binds to the same epitope of FAM19A5 (e.g., human FAM19A5) as an anti-FAM19A5 antibody described herein, is a human antibody or an antigen-binding fragment thereof. In particular embodiments, an antibody described herein, which competitively blocks (e.g., in a dose-dependent manner) antibodies described herein from binding to FAM19A5 (e.g., human FAM19A5), is a human antibody or an antigen-binding fragment thereof.

Human antibodies can be produced using any method known in the art. For example, transgenic mice which are incapable of expressing functional endogenous immunoglobulins, but which can express human immunoglobulin genes, can be used. In particular, the human heavy and light chain immunoglobulin gene complexes can be introduced randomly or by homologous recombination into mouse embryonic stem cells. Alternatively, the human variable region, constant region, and diversity region can be introduced into mouse embryonic stem cells in addition to the human heavy and light chain genes. The mouse heavy and light chain immunoglobulin genes can be rendered non-functional separately or simultaneously with the introduction of human immunoglobulin loci by homologous recombination. In particular, homozygous deletion of the JH region prevents endogenous antibody production. The modified embryonic stem cells are expanded and microinjected into blastocysts to produce chimeric mice. The chimeric mice are then bred to produce homozygous offspring which express human antibodies. The transgenic mice are immunized in the normal fashion with a selected antigen, e.g., all or a portion of an antigen (e.g., FAM19A5). Monoclonal antibodies directed against the antigen can be obtained from the immunized, transgenic mice using conventional hybridoma technology. The human immunoglobulin transgenes harbored by the transgenic mice rearrange during B cell differentiation, and subsequently undergo class switching and somatic mutation. Thus, using such a technique, it is possible to produce therapeutically useful IgG, IgA, IgM and IgE antibodies. For an overview of this technology for producing human antibodies, see Lonberg N & Huszar D (1995) Int Rev Immunol 13: 65-93. For a detailed discussion of this technology for producing human antibodies and human monoclonal antibodies and protocols for producing such antibodies, see, e.g., International Publication Nos. WO 98/24893, WO 96/34096 and WO 96/33735; and U.S. Pat. Nos. 5,413,923, 5,625,126, 5,633,425, 5,569,825, 5,661,016, 5,545,806, 5,814,318 and 5,939,598. Examples of mice capable of producing human antibodies include the XENOMOUSE™ (Abgenix, Inc.; U.S. Pat. Nos. 6,075,181 and 6,150,184), the HUAB-MOUSE™ (Mederex, Inc./Gen Pharm; U.S. Pat. Nos. 5,545,806 and 5,569,825), the TRANS CHROMO MOUSE™ (Kirin), and the KM MOUSE™ (Medarex/Kirin).

Human antibodies which specifically bind to FAM19A5 (e.g., human FAM19A5) can be made by a variety of methods known in the art including phage display methods described above using antibody libraries derived from human immunoglobulin sequences. See also U.S. Pat. Nos. 4,444,887, 4,716,111, and 5,885,793; and International Publication Nos. WO 98/46645, WO 98/50433, WO 98/24893, WO 98/16654, WO 96/34096, WO 96/33735, and WO 91/10741.

In some embodiments, human antibodies can be produced using mouse-human hybridomas. For example, human peripheral blood lymphocytes transformed with Epstein-Barr virus (EBV) can be fused with mouse myeloma cells to produce mouse-human hybridomas secreting human monoclonal antibodies, and these mouse-human hybridomas can be screened to determine ones which secrete human monoclonal antibodies that immunospecifically bind to a target antigen (e.g., FAM19A5 such as human FAM19A5)). Such methods are known and are described in the art, see, e.g., Shinmoto H et al., (2004) *Cytotechnology* 46: 19-23; Naganawa Y et al., (2005) *Human Antibodies* 14: 27-31.

V. Methods of Engineering Antibodies

As discussed above, the anti-FAM19A5 antibody having VH and VL sequences disclosed herein can be used to create new anti-FAM19A5 antibody by modifying the VH and/or VL sequences, or the constant region(s) attached thereto. Thus, in another aspect described herein, the structural features of an anti-FAM19A5 antibody described herein is used to create structurally related anti-FAM19A5 antibodies that retain at least one functional property of the antibodies described herein, such as binding to human FAM19A5. For example, the starting material for the engineering method is VH and/or VL sequences provided herein, or one or more CDR regions thereof. To create the engineered antibody, it is not necessary to actually prepare (i.e., express as a protein) an antibody having one or more of the VH and/or VL sequences provided herein, or one, or more CDR regions thereof. Rather, the information contained in the sequence(s) is used as the starting material to create a "second generation" sequence(s) derived from the original sequence(s) and then the "second generation" sequence(s) is prepared and expressed as a protein.

Accordingly, provided herein are methods for preparing an anti-FAM19A5 antibody comprising:

(a) providing: (i) a heavy chain variable region sequence comprising a CDR1, CDR2, and/or CDR3 sequence as set forth in Table 3 or a CDR1, CDR2, and/or CDR3 of the heavy chain variable region as set forth in Table 5; and (ii) a light chain variable region sequence comprising a CDR1, CDR2, and/or CDR3 sequence as set forth in Table 4 or a CDR1, CDR2, and/or CDR3 of the heavy chain variable region as set forth in Table 6;

(b) altering at least one amino acid residue within the heavy chain variable region sequence and/or the light chain variable region sequence to create at least one altered antibody sequence; and (c) expressing the altered antibody sequence as a protein.

Standard molecular biology techniques can be used to prepare and express the altered antibody sequence.

In some embodiments, the antibody encoded by the altered antibody sequence(s) is one that retains one, some or all of the functional properties of the anti-FAM19A5 antibodies described herein, which include, (1) reduced immunogenicity in human subjects;

(2) binding to soluble human FAM19A5, e.g., with a $K_D$ of 10 nM or less (e.g., 0.01 nM to 10 nM), e.g., as measured by Biacore;

(3) binding to membrane bound human FAM19A5, e.g., with a $K_D$ of 10 nM or less (e.g., 0.01 nM to 1 nM), e.g., as measured by ELISA;

(4) binding to membrane bound human FAM19A5, e.g., with an EC50 of 1 nM or less (e.g., 0.01 nM to 1 nM), e.g., as measured by ELISA;

(5) reduces, reverses, delays, and/or prevents an onset of reactive gliosis;

(6) suppresses an excessive proliferation of reactive astrocytes;

(7) decreases expression of chondroitin sulfate proteoglycans including neurocan and neuron-glial antigen 2 (NG2);

(8) increases expression of c-fos and pERK in the nucleus of neurons;

(9) promotes survival of neurons;

(10) increases expression of GAP43 in neurons;

(11) promotes regrowth of an axon; and

(12) competing in either direction or both directions for binding to human FAM19A5 with an anti-FAM19A5 antibody disclosed herein.

The altered antibody can exhibit one or more, two or more, three or more, four or more, five or more, six or more, seven or more, eight or more, nine or more, ten or more, eleven, or all of the functional properties set forth as (1) through (12) above. The functional properties of the altered antibodies can be assessed using standard assays available in the art and/or described herein, such as those set forth in the Examples (e.g., ELISAs, FACS).

In certain embodiments of the methods of engineering antibodies described herein, mutations can be introduced randomly or selectively along all or part of an anti-FAM19A5 antibody coding sequence and the resulting modified anti-FAM19A5 antibodies can be screened for binding activity and/or other functional properties as described herein. Mutational methods have been described in the art. For example, PCT Publication WO 02/092780 by Short describes methods for creating and screening antibody mutations using saturation mutagenesis, synthetic ligation assembly, or a combination thereof. Alternatively, PCT Publication WO 03/074679 by Lazar et al. describes methods of using computational screening methods to optimize physiochemical properties of antibodies.

VI. Cells and Vectors

In certain aspects, provided herein are cells (e.g., host cells) expressing (e.g., recombinantly) antibodies described herein (or an antigen-binding fragment thereof) which specifically bind to FAM19A5 (e.g., human FAM19A5) and related polynucleotides and expression vectors. Provided herein are vectors (e.g., expression vectors) comprising polynucleotides comprising nucleotide sequences encoding anti-FAM19A5 antibodies or a fragment for recombinant expression in host cells, e.g., in mammalian cells. Also provided herein are host cells comprising such vectors for recombinantly expressing anti-FAM19A5 antibodies described herein (e.g., human or humanized antibody). In a particular aspect, provided herein are methods for producing an antibody described herein, comprising expressing such antibody from a host cell.

Recombinant expression of an antibody described herein (e.g., a full-length antibody, heavy and/or light chain of an antibody, or a single chain antibody described herein) that specifically binds to FAM19A5 (e.g., human FAM19A5) involves construction of an expression vector containing a polynucleotide that encodes the antibody. Once a polynucleotide encoding an antibody molecule, heavy and/or light chain of an antibody, or a fragment thereof (e.g., heavy and/or light chain variable domains) described herein has been obtained, the vector for the production of the antibody molecule can be produced by recombinant DNA technology using techniques well known in the art. Thus, methods for preparing a protein by expressing a polynucleotide containing an antibody or antibody fragment (e.g., light chain or heavy chain) encoding nucleotide sequence are described herein. Methods which are well known to those skilled in the art can be used to construct expression vectors containing antibody or antibody fragment (e.g., light chain or heavy chain) coding sequences and appropriate transcriptional and translational control signals. These methods include, for example, in vitro recombinant DNA techniques, synthetic techniques, and in vivo genetic recombination. Also provided are replicable vectors comprising a nucleotide sequence encoding an antibody molecule described herein, a heavy or light chain of an antibody, a heavy or light chain variable domain of an antibody or a fragment thereof, or a heavy or light chain CDR, operably linked to a promoter. Such vectors can, for example, include the nucleotide sequence encoding the constant region of the antibody molecule (see, e.g., International Publication Nos. WO 86/05807 and WO 89/01036; and U.S. Pat. No. 5,122,464) and variable domains of the antibody can be cloned into such a vector for expression of the entire heavy, the entire light chain, or both the entire heavy and light chains.

An expression vector can be transferred to a cell (e.g., host cell) by conventional techniques and the resulting cells can then be cultured by conventional techniques to produce an antibody described herein (e.g., an antibody comprising the VH and/or VL, or one or more of the VH and/or VL CDRs, of an anti-FAM19A5 antibody of the present disclosure) or a fragment thereof. Thus, provided herein are host cells containing a polynucleotide encoding an antibody described herein or fragments thereof, or a heavy or light chain thereof, or fragment thereof, or a single chain antibody described herein, operably linked to a promoter for expression of such sequences in the host cell. In certain embodiments, for the expression of double-chained antibodies, vectors encoding both the heavy and light chains, individually, can be co-expressed in the host cell for expression of the entire immunoglobulin molecule, as detailed below. In certain embodiments, a host cell contains a vector comprising a polynucleotide encoding both the heavy chain and light chain of an antibody described herein, or a fragment thereof. In specific embodiments, a host cell contains two different vectors, a first vector comprising a polynucleotide encoding a heavy chain or a heavy chain variable region of an antibody described herein, or a fragment thereof, and a second vector comprising a polynucleotide encoding a light chain or a light chain variable region of an antibody described herein, or a fragment thereof. In other embodiments, a first host cell comprises a first vector comprising a polynucleotide encoding a heavy chain or a heavy chain variable region of an antibody described herein, or a fragment thereof, and a second host cell comprises a second vector comprising a polynucleotide encoding a light chain or a light chain variable region of an antibody described herein. In specific embodiments, a heavy chain/heavy chain variable region expressed by a first cell associated with a light chain/light chain variable region of a second cell to form an anti-FAM19A5 antibody described herein or an antigen-binding fragment thereof. In certain embodiments, provided herein is a population of host cells comprising such first host cell and such second host cell.

In a particular embodiment, provided herein is a population of vectors comprising a first vector comprising a polynucleotide encoding a light chain/light chain variable region of an anti-FAM19A5 antibody described herein, and a second vector comprising a polynucleotide encoding a heavy chain/heavy chain variable region of an anti-FAM19A5 antibody described herein.

A variety of host-expression vector systems can be utilized to express antibody molecules described herein. Such host-expression systems represent vehicles by which the coding sequences of interest can be produced and subsequently purified, but also represent cells which can, when transformed or transfected with the appropriate nucleotide coding sequences, express an antibody molecule described herein in situ. These include but are not limited to microorganisms such as bacteria (e.g., *E. coli* and *B. subtilis*) transformed with recombinant bacteriophage DNA, plasmid DNA or cosmid DNA expression vectors containing antibody coding sequences; yeast (e.g., *Saccharomyces Pichia*) transformed with recombinant yeast expression vectors containing antibody coding sequences; insect cell systems infected with recombinant virus expression vectors (e.g., baculovirus) containing antibody coding sequences; plant cell systems (e.g., green algae such as *Chlamydomonas reinhardtii*) infected with recombinant virus expression vectors (e.g., cauliflower mosaic virus, CaMV; tobacco mosaic virus, TMV) or transformed with recombinant plasmid expression vectors (e.g., Ti plasmid) containing antibody coding sequences; or mammalian cell systems (e.g., COS (e.g., COS1 or COS), CHO, BHK, MDCK, HEK 293, NSO, PER.C6, VERO, CRL7030, HsS78Bst, HeLa, and NIH 3T3, HEK-293T, HepG2, SP210, R1.1, B-W, L-M, BSCl, BSC40, YB/20 and BMT10 cells) harboring recombinant expression constructs containing promoters derived from the genome of mammalian cells (e.g., metallothionein promoter) or from mammalian viruses (e.g., the adenovirus late promoter; the vaccinia virus 7.5K promoter). In a specific embodiment, cells for expressing antibodies described herein or an antigen-binding fragment thereof are CHO cells, for example CHO cells from the CHO GS SYSTEM™ (Lonza). In a particular embodiment, cells for expressing antibodies described herein are human cells, e.g., human cell lines. In a specific embodiment, a mammalian expression vector is POPTIVEC™ or pcDNA3.3. In a particular embodiment, bacterial cells such as *Escherichia coli*, or eukaryotic cells (e.g., mammalian cells), especially for the expression of whole recombinant antibody molecule, are used for the expression of a recombinant antibody molecule. For example, mammalian cells such as Chinese hamster ovary (CHO) cells, in conjunction with a vector such as the major intermediate early gene promoter element from human cytomegalovirus is an effective expression system for antibodies (Foecking M K & Hofstetter H (1986) *Gene* 45: 101-5; and Cockett M I et al., (1990) *Biotechnology* 8(7): 662-7). In certain embodiments, antibodies described herein are produced by CHO cells or NSO cells. In a specific embodiment, the expression of nucleotide sequences encoding antibodies described herein which immunospecifically bind FAM19A5 (e.g., human FAM19A5) is regulated by a constitutive promoter, inducible promoter or tissue specific promoter.

In bacterial systems, a number of expression vectors can be advantageously selected depending upon the use intended for the antibody molecule being expressed. For example, when a large quantity of such an antibody is to be produced, for the generation of pharmaceutical compositions of an antibody molecule, vectors which direct the expression of high levels of fusion protein products that are readily purified can be desirable. Such vectors include, but are not limited to, the *E. coli* expression vector pUR278 (Ruether U & Mueller-Hill B (1983) *EMBO J* 2: 1791-1794), in which the antibody coding sequence can be ligated individually into the vector in frame with the lac Z coding region so that a fusion protein is produced; pIN vectors (Inouye S & Inouye M (1985) *Nuc Acids Res* 13: 3101-3109; Van Heeke G & Schuster S M (1989) *J Biol Chem* 24: 5503-5509); and the like. For example, pGEX vectors can also be used to express foreign polypeptides as fusion proteins with glutathione 5-transferase (GST). In general, such fusion proteins are soluble and can easily be purified from lysed cells by adsorption and binding to matrix glutathione agarose beads followed by elution in the presence of free glutathione. The pGEX vectors are designed to include thrombin or factor Xa protease cleavage sites so that the cloned target gene product can be released from the GST moiety.

In an insect system, *Autographa californica* nuclear polyhedrosis virus (AcNPV), for example, can be used as a vector to express foreign genes. The virus grows in *Spodoptera frugiperda* cells. The antibody coding sequence can be cloned individually into non-essential regions (for example the polyhedrin gene) of the virus and placed under control of an AcNPV promoter (for example the polyhedrin promoter).

In mammalian host cells, a number of viral-based expression systems can be utilized. In cases where an adenovirus is used as an expression vector, the antibody coding sequence of interest can be ligated to an adenovirus transcription/translation control complex, e.g., the late promoter and tripartite leader sequence. This chimeric gene can then be inserted in the adenovirus genome by in vitro or in vivo recombination. Insertion in a non-essential region of the viral genome (e.g., region E1 or E3) will result in a recombinant virus that is viable and capable of expressing the antibody molecule in infected hosts (see, e.g., Logan J & Shenk T (1984) *PNAS* 81(12): 3655-9). Specific initiation signals can also be required for efficient translation of inserted antibody coding sequences. These signals include the ATG initiation codon and adjacent sequences. Furthermore, the initiation codon must be in phase with the reading frame of the desired coding sequence to ensure translation of the entire insert. These exogenous translational control signals and initiation codons can be of a variety of origins, both natural and synthetic. The efficiency of expression can be enhanced by the inclusion of appropriate transcription enhancer elements, transcription terminators, etc. (see, e.g., Bitter G et al., (1987) *Methods Enzymol.* 153: 516-544).

In addition, a host cell strain can be chosen which modulates the expression of the inserted sequences, or modifies and processes the gene product in the specific fashion desired. Such modifications (e.g., glycosylation) and processing (e.g., cleavage) of protein products can be important for the function of the protein. Different host cells have characteristic and specific mechanisms for the post-translational processing and modification of proteins and gene products. Appropriate cell lines or host systems can be chosen to ensure the correct modification and processing of the foreign protein expressed. To this end, eukaryotic host cells which possess the cellular machinery for proper processing of the primary transcript, glycosylation, and phosphorylation of the gene product can be used. Such mammalian host cells include but are not limited to CHO, VERO, BHK, Hela, MDCK, HEK 293, NIH 3T3, W138, BT483, Hs578T, HTB2, BT20 and T47D, NSO (a murine myeloma cell line that does not endogenously produce any immunoglobulin chains), CRL7030, COS (e.g., COS 1 or COS), PER.C6, VERO, HsS78Bst, HEK-293T, HepG2, SP210, R1.1, B-W, L-M, BSC 1, BSC40, YB/20, BMT10 and HsS78Bst cells. In certain embodiments, anti-FAM19A5 antibodies described herein are produced in mammalian cells, such as CHO cells.

In a specific embodiment, the antibodies described herein or antigen-binding portions thereof have reduced fucose content or no fucose content. Such antibodies can be produced using techniques known one skilled in the art. For example, the antibodies can be expressed in cells deficient or lacking the ability of to fucosylate. In a specific example, cell lines with a knockout of both alleles of 1,6-fucosyltransferase can be used to produce antibodies or antigen-binding portions thereof with reduced fucose content. The POTELLIGENT© system (Lonza) is an example of such a system that can be used to produce antibodies or antigen-binding portions thereof with reduced fucose content.

For long-term, high-yield production of recombinant proteins, stable expression cells can be generated. For example, cell lines which stably express an anti-FAM19A5 antibody described herein an antigen-binding portion thereof can be engineered. In specific embodiments, a cell provided herein stably expresses a light chain/light chain variable domain and a heavy chain/heavy chain variable domain which associate to form an antibody described herein or an antigen-binding portion thereof.

In certain aspects, rather than using expression vectors which contain viral origins of replication, host cells can be transformed with DNA controlled by appropriate expression control elements (e.g., promoter, enhancer, sequences, transcription terminators, polyadenylation sites, etc.) and a selectable marker. Following the introduction of the foreign DNA/polynucleotide, engineered cells can be allowed to grow for 1-2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines. This method can advantageously be used to engineer cell lines which express an anti-FAM19A5 antibody described herein or an antibody binding portion thereof. Such engineered cell lines can be particularly useful in screening and evaluation of compositions that interact directly or indirectly with the antibody molecule.

A number of selection systems can be used, including but not limited to, the herpes simplex virus thymidine kinase (Wigler M et al., (1977) *Cell* 11(1): 223-32), hypoxanthine-guanine phosphoribosyltransferase (Szybalska E H & Szybalski W (1962) *PNAS* 48(12): 2026-2034) and adenine phosphoribosyltransferase (Lowy I et al., (1980) *Cell* 22(3): 817-23) genes can be employed in tk-, hgprt- or aprt-cells, respectively. Also, antimetabolite resistance can be used as the basis of selection for the following genes: dhfr, which confers resistance to methotrexate (Wigler M et al., (1980) *PNAS* 77(6): 3567-70; O'Hare K et al., (1981) *PNAS* 78: 1527-31); gpt, which confers resistance to mycophenolic acid (Mulligan R C & Berg P (1981) *PNAS* 78(4): 2072-6); neo, which confers resistance to the aminoglycoside G-418 (Wu G Y & Wu C H (1991) *Biotherapy* 3: 87-95; Tolstoshev P (1993) *Ann Rev Pharmacol Toxicol* 32: 573-596; Mulligan R C (1993) *Science* 260: 926-932; and Morgan R A & Anderson W F (1993) *Ann Rev Biochem* 62: 191-217; Nabel G J & Feigner P L (1993) *Trends Biotechnol* 11(5): 211-5); and hygro, which confers resistance to hygromycin (Santerre R F et al., (1984) *Gene* 30(1-3): 147-56). Methods commonly known in the art of recombinant DNA technology can be routinely applied to select the desired recombinant clone and such methods are described, for example, in Ausubel F M et al., (eds.), *Current Protocols in Molecular Biology*, John Wiley & Sons, NY (1993); Kriegler M, Gene Transfer and Expression, *A Laboratory Manual, Stockton Press, NY* (1990); and in Chapters 12 and 13, Dracopoli N C et al., (eds.), *Current Protocols in Human Genetics*, John Wiley & Sons, NY (1994); Colbere-Garapin F et al., (1981) *J Mol Biol* 150: 1-14, which are incorporated by reference herein in their entireties.

The expression levels of an antibody molecule can be increased by vector amplification (for a review, see Bebbington C R & Hentschel C C G, The use of vectors based on gene amplification for the expression of cloned genes in mammalian cells in DNA cloning, Vol. 3 (Academic Press, New York, 1987)). When a marker in the vector system expressing antibody is amplifiable, increase in the level of inhibitor present in culture of host cell will increase the number of copies of the marker gene. Since the amplified region is associated with the antibody gene, production of the antibody will also increase (Crouse G F et al., (1983) *Mol Cell Biol* 3: 257-66).

The host cell can be co-transfected with two or more expression vectors described herein, the first vector encoding a heavy chain derived polypeptide and the second vector encoding a light chain derived polypeptide. The two vectors can contain identical selectable markers which enable equal expression of heavy and light chain polypeptides. The host cells can be co-transfected with different amounts of the two or more expression vectors. For example, host cells can be transfected with any one of the following ratios of a first expression vector and a second expression vector: 1:1, 1:2, 1:3, 1:4, 1:5, 1:6, 1:7, 1:8, 1:9, 1:10, 1:12, 1:15, 1:20, 1:25, 1:30, 1:35, 1:40, 1:45, or 1:50.

Alternatively, a single vector can be used which encodes, and is capable of expressing, both heavy and light chain polypeptides. In such situations, the light chain should be placed before the heavy chain to avoid an excess of toxic free heavy chain (Proudfoot N J (1986) Nature 322: 562-565; and Kohler G (1980) PNAS 77: 2197-2199). The coding sequences for the heavy and light chains can comprise cDNA or genomic DNA. The expression vector can be monocistronic or multicistronic. A multicistronic nucleic acid construct can encode 2, 3, 4, 5, 6, 7, 8, 9, 10 or more, or in the range of 2-5, 5-10 or 10-20 genes/nucleotide sequences. For example, a bicistronic nucleic acid construct can comprise in the following order a promoter, a first gene (e.g., heavy chain of an antibody described herein), and a second gene and (e.g., light chain of an antibody described herein). In such an expression vector, the transcription of both genes can be driven by the promoter, whereas the translation of the mRNA from the first gene can be by a cap-dependent scanning mechanism and the translation of the mRNA from the second gene can be by a cap-independent mechanism, e.g., by an IRES.

Once an antibody molecule described herein has been produced by recombinant expression, it can be purified by any method known in the art for purification of an immunoglobulin molecule, for example, by chromatography (e.g., ion exchange, affinity, particularly by affinity for the specific antigen after Protein A, and sizing column chromatography), centrifugation, differential solubility, or by any other standard technique for the purification of proteins. Further, the antibodies described herein can be fused to heterologous polypeptide sequences described herein or otherwise known in the art to facilitate purification.

In specific embodiments, an antibody or an antigen-binding portion thereof described herein is isolated or purified. Generally, an isolated antibody is one that is substantially free of other antibodies with different antigenic specificities than the isolated antibody. For example, in a particular embodiment, a preparation of an antibody described herein is substantially free of cellular material and/or chemical precursors. The language "substantially free of cellular material" includes preparations of an antibody in which the antibody is separated from cellular components of the cells from which it is isolated or recombinantly produced. Thus, an antibody that is substantially free of cellular material includes preparations of antibody having less than about 30%, 20%, 10%, 5%, 2%, 1%, 0.5%, or 0.1% (by dry weight) of heterologous protein (also referred to herein as a "contaminating protein") and/or variants of an antibody, for example, different post-translational modified forms of an antibody or other different versions of an antibody (or antibody binding portions). When the antibody is recombinantly produced, it is also generally substantially free of culture medium, i.e., culture medium represents less than about 20%>, 10%>, 2%, 1%, 0.5%, or 0.1% of the volume of the protein preparation. When the antibody is produced by chemical synthesis, it is generally substantially free of chemical precursors or other chemicals, i.e., it is separated from chemical precursors or other chemicals which are involved in the synthesis of the protein. Accordingly, such preparations of the antibody have less than about 30%, 20%, 10%, or 5% (by dry weight) of chemical precursors or compounds other than the antibody of interest. In a specific embodiment, antibodies described herein are isolated or purified.

VII. Assays

Antibodies described herein can be tested for binding to FAM19A5 by, for example, standard ELISA. Briefly, microtiter plates are coated with purified FAM19A5 at 1-2 μg/ml in PBS, and then blocked with 5% bovine serum albumin in PBS. Dilutions of antibody (e.g., dilutions of plasma from FAM19A5-immunized mice) are added to each well and incubated for 1-2 hours at 37° C. The plates are washed with PBS/Tween and then incubated with secondary reagent (e.g., for human antibodies, a goat-anti-human IgG Fc-specific polyclonal reagent) conjugated to horseradish peroxidase (HRP) for 1 hour at 37° C. After washing, the plates are developed with ABTS substrate (Moss Inc, product: ABTS-1000) and analyzed by a spectrophotometer at OD 415-495. Sera from immunized mice are then further screened by flow cytometry for binding to a cell line expressing human FAM19A5, but not to a control cell line that does not express FAM19A5. Briefly, the binding of anti-FAM19A5 antibodies is assessed by incubating FAM19A5 expressing CHO cells with the anti-FAM19A5 antibody at 1:20 dilution. The cells are washed and binding is detected with a PE-labeled anti-human IgG Ab. Flow cytometric analyses are performed using a FACS can flow cytometry (Becton Dickinson, San Jose, CA). Preferably, mice which develop the highest titers will be used for fusions.

An ELISA assay as described above can be used to screen for antibodies and, thus, hybridomas that produce antibodies that show positive reactivity with the FAM19A5 immunogen. Hybridomas that produce antibodies that bind, preferably with high affinity, to FAM19A5 can then be subcloned and further characterized. One clone from each hybridoma, which retains the reactivity of the parent cells (by ELISA), can then be chosen for making a cell bank, and for antibody purification.

To purify anti-FAM19A5 antibodies, selected hybridomas can be grown in two-liter spinner-flasks for monoclonal antibody purification. Supernatants can be filtered and concentrated before affinity chromatography with protein A-sepharose (Pharmacia, Piscataway, NJ). Eluted IgG can be checked by gel electrophoresis and high performance liquid chromatography to ensure purity. The buffer solution can be exchanged into PBS, and the concentration can be determined by OD 280 using 1.43 extinction coefficient. The monoclonal antibodies can be aliquoted and stored at −80° C.

To determine if the selected anti-FAM19A5 monoclonal antibodies bind to unique epitopes, each antibody can be biotinylated using commercially available reagents (Pierce, Rockford, IL). Biotinylated MAb binding can be detected with a streptavidin labeled probe. Competition studies using unlabeled monoclonal antibodies and biotinylated monoclonal antibodies can be performed using FAM19A5 coated-ELISA plates as described above.

To determine the isotype of purified antibodies, isotype ELISAs can be performed using reagents specific for antibodies of a particular isotype. For example, to determine the isotype of a human monoclonal antibody, wells of microtiter plates can be coated with 1 μg/ml of anti-human immunoglobulin overnight at 4° C. After blocking with 1% BSA, the plates are reacted with 1 μg/ml or less of test monoclonal antibodies or purified isotype controls, at ambient temperature for one to two hours. The wells can then be reacted with either human IgG1 or human IgM-specific alkaline phosphatase-conjugated probes. Plates are developed and analyzed as described above.

To test the binding of monoclonal antibodies to live cells expressing FAM19A5, flow cytometry can be used, as described in the Examples. Briefly, cell lines expressing membrane-bound FAM19A5 (grown under standard growth conditions) are mixed with various concentrations of monoclonal antibodies in PBS containing 0.1% BSA at 4° C. for 1 hour. After washing, the cells are reacted with Fluorescein-labeled anti-IgG antibody under the same conditions as the primary antibody staining. The samples can be analyzed by FACScan instrument using light and side scatter properties to gate on single cells and binding of the labeled antibodies is determined. An alternative assay using fluorescence microscopy can be used (in addition to or instead of) the flow cytometry assay. Cells can be stained exactly as described above and examined by fluorescence microscopy. This method allows visualization of individual cells, but can have diminished sensitivity depending on the density of the antigen.

Anti-FAM19A5 antibodies can be further tested for reactivity with the FAM19A5 antigen by Western blotting. Briefly, cell extracts from cells expressing FAM19A5 can be prepared and subjected to sodium dodecyl sulfate polyacrylamide gel electrophoresis. After electrophoresis, the separated antigens will be transferred to nitrocellulose membranes, blocked with 20% mouse serum, and probed with the monoclonal antibodies to be tested. IgG binding can be detected using anti-IgG alkaline phosphatase and developed with BCIP/NBT substrate tablets (Sigma Chem. Co., St. Louis, MO).

Methods for analyzing binding affinity, cross-reactivity, and binding kinetics of various anti-FAM19A5 antibodies include standard assays known in the art, for example, BIACORE™ surface plasmon resonance (SPR) analysis using a BIACORE™ 2000 SPR instrument (Biacore AB, Uppsala, Sweden).

In one embodiment, an antibody specifically binds to the soluble form of human FAM19A5. In one embodiment, an antibody specifically binds to the membrane-bound form of human FAM19A5. An antibody can specifically bind to a particular epitope of FAM19A5 (e.g., a SEQ ID NO: 90 or a fragment within SEQ ID NO: 90). In certain embodiments, the antibody specifically binds human FAM19A5, preferably, with high affinity, and does not cross-react to other members of the FAM19 subfamily of proteins.

VIII. Bispecific Molecules

Antibodies described herein can be used for forming bispecific molecules. An anti-FAM19A5 antibody, or antigen-binding portions thereof, can be derivatized or linked to another functional molecule, e.g., another peptide or protein (e.g., another antibody or ligand for a receptor) to generate a bispecific molecule that binds to at least two different binding sites or target molecules. Cytokines such as IL-6, CNTF, LIF, EGF and TGFα, have been implicated as triggers of onset of gliosis and/or reactive astrogliosis (Balasingam et al., *J. Neurosci.* 14(2):846-56 (1994); Winter et al., *Proc. Natl. Acad. Sci. U.S.A* 20; 92(13):5865-9 (1995)) by activating the protein signal transducer and activator of transcription 3 (STAT3), which then regulates many aspects of reactive astrogliosis after CNS injury. Herrmann J. E. et al., *J. Neurosci.* 28(28): 7231-7243 (2008). For example, absence or reduced STAT3 leads to attenuated up-regulation of Glial fibrillary acidic protein (GFAP), failure of astrocyte hypertrophy, and increased spread of inflammation, increased lesion volume and partially attenuated motor recovery after CNS injury. Herrmann J. E. et al., *J. Neurosci.*

28(28): 7231-7243 (2008). Thus, for example, an anti-FAM19A5 antibody can be linked to an antibody or scFv that binds specifically to any protein that is involved in inhibiting onset of gliosis and/or excessive proliferation of reactive astrogliosis for combination treatments, e.g., antibodies to IL-6, CNTF, LIF, EGF or TGFα.

Also, an anti-FAM19A5 antibody can be linked to an antibody or scFv that treats a disease or disorder including a central nervous system damage (e.g., a traumatic brain injury, a cerebrospinal damage, a stroke, or a brain tumor), a cerebrospinal system damage, a degenerative brain disorder (e.g., Huntington's disease, Parkinson's disease, Alzheimer's disease, multiple sclerosis, ALS), a degenerative cerebrospinal or nerve disorder, or a neuropathic pain in a subject (see diseases or disorders in Section XII below). For example, an anti-FAM19A5 antibody can be linked to an antibody or scFv, e.g., Natalizumab (TYSABRI®), Alemtuzumab (LEMTRADA®), that treats multiple sclerosis.

The antibody described herein can in fact be derivatized or linked to more than one other functional molecule to generate multispecific molecules that bind to more than two different binding sites and/or target molecules; such multispecific molecules are also intended to be encompassed by the term "bispecific molecule" as used herein. To create a bispecific molecule described herein, an antibody described herein can be functionally linked (e.g., by chemical coupling, genetic fusion, noncovalent association or otherwise) to one or more other binding molecules, such as another antibody, antibody binding portion thereof, peptide or binding mimetic, such that a bispecific molecule results. In one embodiment, a bispecific molecule binds to FAM19A5 and VEGF. In another embodiment, a bispecific molecule binds to FAM19A5 and EGF.

Accordingly, provided herein are bispecific molecules comprising at least one first binding specificity for FAM19A5 and a second binding specificity for a second target epitope. In an embodiment described herein in which the bispecific molecule is multispecific, the molecule can further include a third binding specificity.

In one embodiment, the bispecific molecules described herein comprise as a binding specificity at least one antibody, or an antibody binding portion thereof, including, e.g., a Fab, Fab', F(ab')2, Fv, or a single chain Fv (scFv). The antibody can also be a light chain or heavy chain dimer, or any minimal fragment thereof such as a Fv or a single chain construct as described in Ladner et al., U.S. Pat. No. 4,946,778, the contents of which is expressly incorporated by reference.

While human monoclonal antibodies are preferred, other antibodies which can be employed in the bispecific molecules described herein are murine, chimeric and humanized monoclonal antibodies.

The bispecific molecules described herein can be prepared by conjugating the constituent binding specificities using methods known in the art. For example, each binding specificity of the bispecific molecule can be generated separately and then conjugated to one another. When the binding specificities are proteins or peptides, a variety of coupling or cross-linking agents can be used for covalent conjugation. Examples of cross-linking agents include protein A, carbodiimide, N-succinimidyl-S-acetyl-thioacetate (SATA), 5,5'-dithiobis(2-nitrobenzoic acid) (DTNB), o-phenylenedimaleimide (oPDM), N-succinimidyl-3-(2-pyridyldithio)propionate (SPDP), and sulfosuccinimidyl 4-(N-maleimidomethyl) cyclohaxane-l-carboxylate (sulfo-SMCC) (see, e.g., Karpovsky et al., (1984) *J. Exp. Med.* 160: 1686; Liu, M A et al., (1985) *Proc. Natl. Acad. Sci. USA* 82:8648). Other methods include those described in Paulus (1985) *Behring Ins. Mitt. No.* 78, 118-132; Brennan et al., (1985) *Science* 229:81-83), and Glennie et al., (1987) *J. Immunol.* 139: 2367-2375). Preferred conjugating agents are SATA and sulfo-SMCC, both available from Pierce Chemical Co. (Rockford, IL).

When the binding specificities are antibodies, they can be conjugated via sulfhydryl bonding of the C-terminus hinge regions of the two heavy chains. In a particularly preferred embodiment, the hinge region is modified to contain an odd number of sulfhydryl residues, preferably one, prior to conjugation.

Alternatively, both binding specificities can be encoded in the same vector and expressed and assembled in the same host cell. This method is particularly useful where the bispecific molecule is a mAb×mAb, mAb×Fab, mAb×(scFv) 2, Fab×F(ab')2 or ligand ×Fab fusion protein. A bispecific antibody can comprise an antibody comprising an scFv at the C-terminus of each heavy chain. A bispecific molecule described herein can be a single chain molecule comprising one single chain antibody and a binding determinant, or a single chain bispecific molecule comprising two binding determinants. Bispecific molecules can comprise at least two single chain molecules. Methods for preparing bispecific molecules are described for example in U.S. Pat. Nos. 5,260,203; 5,455,030; 4,881,175; 5,132,405; 5,091,513; 5,476,786; 5,013,653; 5,258,498; and 5,482,858.

Binding of the bispecific molecules to their specific targets can be confirmed using art-recognized methods, such as enzyme-linked immunosorbent assay (ELISA), radioimmunoassay (RIA), FACS analysis, bioassay (e.g., growth inhibition), or Western Blot assay. Each of these assays generally detects the presence of protein-antibody complexes of particular interest by employing a labeled reagent (e.g., an antibody) specific for the complex of interest.

IX. Diagnosis

In one embodiment the moiety attached to an anti-FAM19A5 antibody is selected from the group consisting of a binding moiety, a labeling moiety, and a biologically active moiety.

Antibodies described herein can be used for diagnostic purposes, including sample testing and in vivo imaging, and for this purpose the antibody (or binding portion thereof) can be conjugated to an appropriate detectable agent, to form an immunoconjugate. For diagnostic purposes, appropriate agents are detectable labels that include radioisotopes, for whole body imaging, and radioisotopes, enzymes, fluorescent labels and other suitable antibody tags for sample testing.

The detectable labels can be any of the various types used currently in the field of in vitro diagnostics, including particulate labels including metal sols such as colloidal gold, isotopes such as $I^{125}$ or $Tc^{99}$ presented for instance with a peptidic chelating agent of the N2S2, N3S or N4 type, chromophores including fluorescent markers, luminescent markers, phosphorescent markers and the like, as well as enzyme labels that convert a given substrate to a detectable marker, and polynucleotide tags that are revealed following amplification such as by polymerase chain reaction. Suitable enzyme labels include horseradish peroxidase, alkaline phosphatase and the like. For instance, the label can be the enzyme alkaline phosphatase, detected by measuring the presence or formation of chemiluminescence following conversion of 1,2 dioxetane substrates such as adamantyl methoxy phosphoryloxy phenyl dioxetane (AMPPD), disodium 3-(4-(methoxyspiro{1,2-dioxetane-3,2'-(5'-chloro)tricyclo{3.3.1.1 3,7}decan}-4-yl) phenyl phosphate (CSPD), as well as CDP and CDP-Star® or other luminescent substrates well-known to those in the art, for example the chelates of suitable lanthanides such as Terbium(III) and Europium(III). The detection means is determined by the chosen label. Appearance of the label or its reaction products can be achieved using the naked eye, in the case where the label is particulate and accumulates at appropriate levels, or using instruments such as a spectrophotometer, a luminometer, a fluorimeter, and the like, all in accordance with standard practice.

Antibodies described herein can also be conjugated to a therapeutic agent to form an immunoconjugate such as an antibody-drug conjugate (ADC). Suitable therapeutic agents include agents modulate onset of gliosis and/or reactive astrogliosis and/or treating degenerative brain disorders, central nervous system damage, or neuropathic pain. Therapeutic agents for treating degenerative brain disorders include drugs for treating Huntington's disease, Parkinson's disease, Alzheimer's disease, multiple sclerosis, and Amyotrophic Lateral Sclerosis (ALS). This include drugs commonly used for treating such degenerative brain disorders, e.g., drugs disclosed infra in Section XII.

Immunoconjugates can be prepared by methods known in the art. Preferably, conjugation methods result in linkages which are substantially (or nearly) non-immunogenic, e.g., peptide- (i.e., amide-), sulfide-, (sterically hindered), disulfide-, hydrazone-, and ether linkages. These linkages are nearly non-immunogenic and show reasonable stability within serum (see, e.g., Senter, P. D., *Curr. Opin. Chem. Biol.* 13 (2009) 235-244; WO 2009/059278; WO 95/17886).

Depending on the biochemical nature of the moiety and the antibody, different conjugation strategies can be employed. In case the moiety is naturally-occurring or recombinant of between 50 to 500 amino acids, there are standard procedures in text books describing the chemistry for synthesis of protein conjugates, which can be easily followed by the skilled artisan (see, e.g., Hackenberger, C. P. R., and Schwarzer, D., *Angew. Chem. Int. Ed. Engl.* 47 (2008) 10030-10074). In one embodiment the reaction of a maleinimido moiety with a cysteine residue within the antibody or the moiety is used. This is an especially suited coupling chemistry in case e.g. a Fab or Fab'-fragment of an antibody is used. Alternatively in one embodiment coupling to the C-terminal end of the antibody or moiety is performed. C-terminal modification of a protein, e.g. of a Fab-fragment can e.g. be performed as described (Sunbul, M. and Yin, *J., Org. Biomol. Chem.* 7 (2009) 3361-3371).

In general, site specific reaction and covalent coupling is based on transforming a natural amino acid into an amino acid with a reactivity which is orthogonal to the reactivity of the other functional groups present. For example, a specific cysteine within a rare sequence context can be enzymatically converted in an aldehyde (see Frese, M. A., and Dierks, T., *ChemBioChem.* 10 (2009) 425-427). It is also possible to obtain a desired amino acid modification by utilizing the specific enzymatic reactivity of certain enzymes with a natural amino acid in a given sequence-context (see, e.g., Taki, M. et al., *Prot. Eng. Des. Sel.* 17 (2004) 119-126; Gautier, A. et al., *Chem. Biol.* 15 (2008) 128-136; and Protease-catalyzed formation of C— N bonds is used by Bordusa, F., Highlights in Bioorganic Chemistry (2004) 389-403).

Site specific reaction and covalent coupling can also be achieved by the selective reaction of terminal amino acids with appropriate modifying reagents. The reactivity of an N-terminal cysteine with benzonitrils (see Ren, H. et al., *Angew. Chem. Int. Ed. Engl.* 48 (2009) 9658-9662) can be used to achieve a site-specific covalent coupling. Native chemical ligation can also rely on C-terminal cysteine residues (Taylor, E. Vogel; Imperiali, B, *Nucleic Acids and Molecular Biology* (2009), 22 (Protein Engineering), 65-96).

EP 1 074 563 describes a conjugation method which is based on the faster reaction of a cysteine within a stretch of negatively charged amino acids with a cysteine located in a stretch of positively charged amino acids.

The moiety can also be a synthetic peptide or peptide mimic. In case a polypeptide is chemically synthesized, amino acids with orthogonal chemical reactivity can be incorporated during such synthesis (see, e.g., de Graaf, A. J. et al., *Bioconjug. Chem.* 20 (2009) 1281-1295). Since a great variety of orthogonal functional groups is at stake and can be introduced into a synthetic peptide, conjugation of such peptide to a linker is standard chemistry.

In order to obtain a mono-labeled polypeptide, the conjugate with 1:1 stoichiometry can be separated by chromatography from other conjugation side-products. This procedure can be facilitated by using a dye labeled binding pair member and a charged linker. By using this kind of labeled and highly negatively charged binding pair member, mono conjugated polypeptides are easily separated from non-labeled polypeptides and polypeptides which carry more than one linker, since the difference in charge and molecular weight can be used for separation. The fluorescent dye can be useful for purifying the complex from un-bound components, like a labeled monovalent binder.

X. Pharmaceutical Compositions

Provided herein are compositions comprising an antibody or antigen-binding portion thereof described herein having the desired degree of purity in a physiologically acceptable carrier, excipient or stabilizer (Remington's Pharmaceutical Sciences (1990) Mack Publishing Co., Easton, PA). Acceptable carriers, excipients, or stabilizers are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN®, PLURONICS® or polyethylene glycol (PEG).

In a specific embodiment, pharmaceutical compositions comprise an antibody or antigen-binding portion thereof, a bispecific molecule, or a immunoconjugate described herein, and optionally one or more additional prophylactic or therapeutic agents, in a pharmaceutically acceptable carrier. In a specific embodiment, pharmaceutical compositions comprise an effective amount of an antibody or antigen-binding portion thereof described herein, and optionally one or more additional prophylactic of therapeutic agents, in a pharmaceutically acceptable carrier. In some embodiments, the antibody is the only active ingredient included in the pharmaceutical composition. Pharmaceutical compositions described herein can be useful in enhancing, inducing or activating a FAM19A5 activity and treating a condition, such as central nervous system damage, a degenerative brain disorder, or a neuropathic pain.

Pharmaceutically acceptable carriers used in parenteral preparations include aqueous vehicles, nonaqueous vehicles, antimicrobial agents, isotonic agents, buffers, antioxidants, local anesthetics, suspending and dispersing agents, emulsifying agents, sequestering or chelating agents and other pharmaceutically acceptable substances. Examples of aqueous vehicles include Sodium Chloride Injection, Ringers Injection, Isotonic Dextrose Injection, Sterile Water Injection, Dextrose and Lactated Ringers Injection. Nonaqueous parenteral vehicles include fixed oils of vegetable origin, cottonseed oil, corn oil, sesame oil and peanut oil. Antimicrobial agents in bacteriostatic or fungistatic concentrations can be added to parenteral preparations packaged in multiple-dose containers which include phenols or cresols, mercurials, benzyl alcohol, chlorobutanol, methyl and propyl p-hydroxybenzoic acid esters, thimerosal, benzalkonium chloride and benzethonium chloride. Isotonic agents include sodium chloride and dextrose. Buffers include phosphate and citrate. Antioxidants include sodium bisulfate. Local anesthetics include procaine hydrochloride. Suspending and dispersing agents include sodium carboxymethylcelluose, hydroxypropyl methylcellulose and polyvinylpyrrolidone. Emulsifying agents include Polysorbate 80 (TWEEN® 80). A sequestering or chelating agent of metal ions includes EDTA. Pharmaceutical carriers also include ethyl alcohol, polyethylene glycol and propylene glycol for water miscible vehicles; and sodium hydroxide, hydrochloric acid, citric acid or lactic acid for pH adjustment.

A pharmaceutical composition can be formulated for any route of administration to a subject. Specific examples of routes of administration include intranasal, oral, parenterally, intrathecally, intra-cerebroventricularly, pulmonarily, subcutaneously, or intraventricularly. Parenteral administration, characterized by either subcutaneous, intramuscular or intravenous injection, is also contemplated herein. Injectables can be prepared in conventional forms, either as liquid solutions or suspensions, solid forms suitable for solution or suspension in liquid prior to injection, or as emulsions. The injectables, solutions and emulsions also contain one or more excipients. Suitable excipients are, for example, water, saline, dextrose, glycerol or ethanol. In addition, if desired, the pharmaceutical compositions to be administered can also contain minor amounts of non-toxic auxiliary substances such as wetting or emulsifying agents, pH buffering agents, stabilizers, solubility enhancers, and other such agents, such as for example, sodium acetate, sorbitan monolaurate, triethanolamine oleate and cyclodextrins.

Preparations for parenteral administration of an antibody include sterile solutions ready for injection, sterile dry soluble products, such as lyophilized powders, ready to be combined with a solvent just prior to use, including hypodermic tablets, sterile suspensions ready for injection, sterile dry insoluble products ready to be combined with a vehicle just prior to use and sterile emulsions. The solutions can be either aqueous or nonaqueous.

If administered intravenously, suitable carriers include physiological saline or phosphate buffered saline (PBS), and solutions containing thickening and solubilizing agents, such as glucose, polyethylene glycol, and polypropylene glycol and mixtures thereof.

Topical mixtures comprising an antibody are prepared as described for the local and systemic administration. The resulting mixture can be a solution, suspension, emulsions or the like and can be formulated as creams, gels, ointments, emulsions, solutions, elixirs, lotions, suspensions, tinctures, pastes, foams, aerosols, irrigations, sprays, suppositories, bandages, dermal patches or any other formulations suitable for topical administration.

An antibody or antigen-binding portion thereof described herein can be formulated as an aerosol for topical application, such as by inhalation (see, e.g., U.S. Pat. Nos. 4,044,126, 4,414,209 and 4,364,923, which describe aerosols for delivery of a steroid useful for treatment of inflammatory diseases, particularly asthma). These formulations for administration to the respiratory tract can be in the form of an aerosol or solution for a nebulizer, or as a microfine powder for insufflations, alone or in combination with an inert carrier such as lactose. In such a case, the particles of the formulation will, in one embodiment, have diameters of less than 50 microns, in one embodiment less than 10 microns.

An antibody or antigen-binding portion thereof described herein can be formulated for local or topical application, such as for topical application to the skin and mucous membranes, such as in the eye, in the form of gels, creams, and lotions and for application to the eye or for intracisternal or intraspinal application. Topical administration is contemplated for transdermal delivery and also for administration to the eyes or mucosa, or for inhalation therapies. Nasal solutions of the antibody alone or in combination with other pharmaceutically acceptable excipients can also be administered.

Transdermal patches, including iontophoretic and electrophoretic devices, are well known to those of skill in the art, and can be used to administer an antibody. For example, such patches are disclosed in U.S. Pat. Nos. 6,267,983, 6,261,595, 6,256,533, 6,167,301, 6,024,975, 6,010,715, 5,985,317, 5,983,134, 5,948,433, and 5,860,957.

In certain embodiments, a pharmaceutical composition comprising an antibody or antigen-binding portion thereof described herein is a lyophilized powder, which can be reconstituted for administration as solutions, emulsions and other mixtures. It can also be reconstituted and formulated as solids or gels. The lyophilized powder is prepared by dissolving an antibody or antigen-binding portion thereof described herein, or a pharmaceutically acceptable derivative thereof, in a suitable solvent. In some embodiments, the lyophilized powder is sterile. The solvent can contain an excipient which improves the stability or other pharmacological component of the powder or reconstituted solution, prepared from the powder. Excipients that can be used include, but are not limited to, dextrose, sorbitol, fructose, corn syrup, xylitol, glycerin, glucose, sucrose or other suitable agent. The solvent can also contain a buffer, such as citrate, sodium or potassium phosphate or other such buffer known to those of skill in the art at, in one embodiment, about neutral pH. Subsequent sterile filtration of the solution followed by lyophilization under standard conditions known to those of skill in the art provides the desired formulation. In one embodiment, the resulting solution will be apportioned into vials for lyophilization. Each vial will contain a single dosage or multiple dosages of the compound. The lyophilized powder can be stored under appropriate conditions, such as at about 4° C. to room temperature.

Reconstitution of this lyophilized powder with water for injection provides a formulation for use in parenteral administration. For reconstitution, the lyophilized powder is added to sterile water or other suitable carrier. The precise amount depends upon the selected compound. Such amount can be empirically determined.

The antibodies or antigen-binding portions thereof, the bispecific molecule, or the immunoconjugate described herein and other compositions provided herein can also be formulated to be targeted to a particular tissue, receptor, or other area of the body of the subject to be treated. Many such targeting methods are well known to those of skill in the art. All such targeting methods are contemplated herein for use in the instant compositions. For non-limiting examples of targeting methods, see, e.g., U.S. Pat. Nos. 6,316,652, 6,274,552, 6,271,359, 6,253,872, 6,139,865, 6,131,570, 6,120,751, 6,071,495, 6,060,082, 6,048,736, 6,039,975, 6,004,534, 5,985,307, 5,972,366, 5,900,252, 5,840,674, 5,759,542, and 5,709,874. In a specific embodiment, an antibody or antigen-binding portion thereof described herein is targeted to treat a central nervous system damage, a degenerative brain disorder, or a neuropathic pain.

The compositions to be used for in vivo administration can be sterile. This is readily accomplished by filtration through, e.g., sterile filtration membranes.

XI. Kits

Provided herein are kits comprising one or more antibodies described herein, or antigen-binding portions thereof, bispecific molecules, or immunoconjugates thereof. In a specific embodiment, provided herein is a pharmaceutical pack or kit comprising one or more containers filled with one or more of the ingredients of the pharmaceutical compositions described herein, such as one or more antibodies provided herein or an antigen-binding portion thereof, optional an instructing for use. In some embodiments, the kits contain a pharmaceutical composition described herein and any prophylactic or therapeutic agent, such as those described herein.

XII. Therapeutic Uses and Methods

Also provided herein are methods for mitigating injury or damage to the CNS in a subject in need there of (e.g., human), comprising administering to the subject an anti-FAM19A5 antibody, a bispecific molecule, or an immunoconjugate described herein, or a composition thereof.

In other aspects, presented herein are methods for inhibiting, slowing down, suppressing, curbing, reducing, reversing, or preventing the beginning or initiation of gliosis and its associated detrimental effects of the CNS in a subject, comprising administering to the subject an anti-FAM19A5 antibody disclosed herein. In some embodiments, presented herein are methods for inhibiting, slowing down, suppressing, curbing, reducing, reversing, or preventing excessive or abnormal proliferation of reactive astrocytes and its associated detrimental effects of the CNS in a subject, comprising administering to the subject an anti-FAM19A5 antibody of the present disclosure. In some embodiments, presented herein are methods for decreasing, inhibiting, or reducing the expression of chondroitin sulfate proteoglycans (including the level of neurocan, NG2, or both), or reducing the activity of, or rendering inactive neurocan, NG2, or both in a subject comprising administering to the subject an anti-FAM19A5 antibody described herein. In some embodiments, presented herein are methods for stimulating, promoting, increasing, or activating the growth of neurons, preferably after injury or damage in a subject comprising administering to the subject an anti-FAM19A5 antibody as described herein. In other embodiments, presented herein are methods for increasing the level of c-fos mRNA, c-fos protein, or c-fos protein activity, and increasing the level of ERK mRNA, ERK protein, or pERK activity, preferably in the nucleus of neurons, in a subject in need thereof, comprising administering to the subject an anti-FAM19A5 antibody of the present disclosure. In certain embodiments, presented herein are methods for enhancing or increasing the level of GAP43 mRNA, GAP43 protein, or increasing the activity of GAP43 protein, preferably in the neurons, in a subject in need thereof, comprising administering to the subject an anti-FAM19A5 antibody as disclosed herein. In certain embodiments, presented herein are methods for enhancing or promoting the survival of neurons and/or promoting the regrowth of an axon, in a subject in need thereof comprising administering to the subject an anti-FAM19A5 antibody disclosed herein. In some embodiments, the subject is a human, preferably a human having an injury or damage to a neuron from e.g., CNS damage, trauma, injury, cerebrospinal damage, brain tumor, infection, ischemia, stroke, autoimmune responses, and/or neurodegenerative disease.

In some aspects, also presented herein are methods for treating a disease, disorder, or condition in a subject in need thereof, comprising administering to the subject an anti-FAM19A5 antibody of the present disclosure. In some embodiments, the disease, disorder, or condition comprises a central nervous system damage, a cerebrospinal system damage, a degenerative brain disorder, a degenerative cerebrospinal or nerve disorder, or a neuropathic pain. In some embodiments, the central nervous system damage is a traumatic brain injury, a cerebrospinal damage, a stroke, a brain tumor, or a combination thereof. In some embodiments, the degenerative brain disorder is Huntington's disease, Parkinson's disease, Alzheimer's disease, multiple sclerosis, Amyotrophic Lateral Sclerosis (ALS), or a combination thereof. Thus, in certain embodiments, disclosed herein is a method for treating a traumatic brain injury, a cerebrospinal damage, a stroke, a brain tumor, or a combination thereof in a subject in need thereof comprising administering to the subject an anti-FAM19A5 antibody disclosed herein or a composition thereof. In some embodiments, disclosed herein is a method for treating Huntington's disease, Parkinson's disease, Alzheimer's disease, multiple sclerosis, ALS in a subject in need thereof comprising administering to the subject an anti-FAM19A5 antibody disclosed herein, or a composition thereof. In some embodiments, the subject is a human.

In some embodiments, an anti-FAM19A5 antibody can be administered in combination with one or more additional agent for treating a central nervous system damage (e.g., a traumatic brain injury, a cerebrospinal damage, a stroke, or a brain tumor), a cerebrospinal system damage, a degenerative brain disorder (e.g., Huntington's disease, Parkinson's disease, Alzheimer's disease, multiple sclerosis, ALS), a degenerative cerebrospinal or nerve disorder, or a neuropathic pain.

In some embodiments, the disease, disorder, or condition comprises a tumor, a fibrosis, a glaucoma, a retinopathy, an age-related macular degeneration, or a mood disorder. In certain embodiments, the disease, disorder, or condition comprises a tumor. In some embodiments, the tumor comprises a melanoma, pancreatic cancer, glioma (e.g., glioblastoma multiforme (GBM)), breast cancer, lymphoma, lung cancer, kidney cancer, prostate cancer, fibrosarcoma, colon adenocarcinoma, liver cancer, or ovarian cancer.

In some embodiments, the anti-FAM19A5 antibody of the present disclosure induces a normalization of blood vessels, e.g., within the tumor. In some embodiments, the normalization of the blood vessels is accompanied by changes in properties of the blood vessels comprising increased connectivity, increased wall thickness, reduced vessel diameter, more regular vessel direction and distribution pattern, increased vessel number, reduction of leakage and permeability, increased pericyte coverage and proximity on the blood vessels, increased oxygenation, or combinations thereof.

In some embodiments, the anti-FAM19A5 antibody of the present disclosure suppresses the growth of the tumor. In some embodiments, the growth of the tumor is suppressed by at least 5%, 10%, 20%, 30%, 40%, 50%, 60%, 70%, 80%, 90%, or 100% compared to a reference (e.g., growth of the tumor in a subject who did not receive the anti-FAM19A5 antibody).

In some embodiments, the anti-FAM19A5 antibody enhances the infiltration of immune cells into the tumor. In some embodiments, the infiltration of immune cells into the tumor is enhanced/increased by at least 5%, 10%, 20%, 30%, 40%, 50%, 60%, 70%, 80%, 90%, or 100% compared to a reference (e.g., a cancer subject who did not receive the anti-FAM19A5 antibody). In certain embodiments, the immune cells comprise macrophages, dendritic cells, T lymphocytes, B lymphocytes, natural killer (NK) cells, or combinations thereof. In some embodiments, the immune cells display hypertrophy. In some embodiments, the infiltration of the immune cells into the tumor is accompanied by increased infiltration of neuronal cells into the tumor. In certain embodiments, the neuronal cells comprise astrocytes, glial cells, or combinations thereof.

In some embodiments, the anti-FAM19A5 antibody of the present disclosure enhances phagocytic activity of a macrophage or a microglia. In some embodiments, the anti-FAM19A5 antibody increases a mitochondrial membrane potential of a macrophage or microglia. In certain embodiments, the phagocytic activity or the mitochondrial membrane potential is enhanced or increased by at least 5%, 10%, 20%, 30%, 40%, 50%, 60%, 70%, 80%, 90%, or 100% compared to a reference (e.g., a cancer subject who did not receive the anti-FAM19A5 antibody).

In some embodiments, the anti-FAM19A5 antibody of the present disclosure reduces necrosis and edema in the tumor. In other embodiments, the anti-FAM19A5 antibody reduces tissue permeability of the tumor. In some embodiments, the necrosis and edema or the tissue permeability of the tumor is reduced by at least 5%, 10%, 20%, 30%, 40%, 50%, 60%, 70%, 80%, 90%, or 100% compared to a reference (e.g., a cancer subject who did not receive the anti-FAM19A5 antibody).

In some embodiments, the anti-FAM19A5 antibody increases the blood flow rate in the tumor. In certain embodiments, the blood flow rate is increased by at least 5%, 10%, 20%, 30%, 40%, 50%, 60%, 70%, 80%, 90%, or 100% compared to a reference (e.g., a cancer subject who did not receive the anti-FAM19A5 antibody).

In some embodiments, the method of treating a tumor comprises administering an additional therapeutic agent. In certain embodiments, the additional therapeutic agent comprises a chemotherapy, immunotherapy, radiotherapy, or combinations thereof. In some embodiments, the immunotherapy comprises a monoclonal antibody, chimeric antigen receptor (CAR) therapy, T-cell therapy, NK-cell therapy, dendritic cell (DC) therapy, adoptive cell transfer (ACT), immune checkpoint modulator, cytokine, cancer vaccine, adjuvant, oncolytic virus, or combinations thereof. In some embodiments, the chemotherapy comprises temozolomide, gemcitabine, paclitaxel, carboplatin, cisplatin, elotuxumab, lenalidomide, dexamethasone, oxaliplatin, or combinations thereof.

In some embodiments, a therapeutically effective amount of an anti-FAM19A5 antibody of the present disclosure, or an composition thereof, is administered. When treating a subject (e.g., a human), a therapeutically effective amount of the anti-FAM19A5 antibody disclosed herein depends on factors such as age, gender, severity of the disease.

In some embodiments, an anti-FAM19A5 antibody of the present disclosure, or a composition thereof, is administered intravenously, orally, parenterally, transthecally, intrathecally, intra-cerebroventricularly, pulmonarily, subcutaneously, intradermally, intramuscularly, or intraventricularly.

The following examples are offered by way of illustration and not by way of limitation.

EXAMPLES

Example 1 Expression and Purification of Human FAM19A5 Protein

Recombinant human FAM19A5 protein was produced and purified as described below and the purified protein was used in an antibody screening assay based on binding affinity analysis. First, LPS-hT plasmid expressing the FAM19A5 gene was transformed into bacteria and protein over-expression was induced. Once produced, the FAM19A5 protein was purified using an Ni-NTA affinity chromatography (Qiagen, Valencia, CA, USA)). Using gradually higher concentration of imidazole, the His-tagged FAM19A5 protein were removed from the Ni-column. The protein expression in the solution is measured using Coomassie Brilliant Blue R-250 Dye. Taking only the FAM19A5 immidazole containing solution, the FAM19A5 protein was concentrated using PBS. When the concentration was complete, both the purity and concentration of the FAM19A5 protein were measured using a Western Blot assay. The concentrated protein was subsequently used to screen for FAM19A5-specific antibodies.

Example 2 Production of Anti-FAM19A5 Antibody Libraries

1. Immunization

The FAM19A5 protein was used as antigen for immunization of a White Leghorn chicken. 50 μg of the synthetic peptide KLH conjugate was mixed in 750 1 phosphate buffered saline (PBS) and incubated at 37° C. for 30 minutes. Afterwards, the toxin is removed in a 2% squalene endotoxin MPL (monophosphorylate lipid A species) and mycobacteria (mycobacteria) of the cell wall components of TDW and CWS containing a water-in-oil emulsion adjuvant (RIBI+MPL+TDM+CWS adjuvant, Sigma, St. Louis, Mo, USA) in emulsified, which was then subcutaneously injected into the chickens. The chickens were immunized for a total of four times with approximately 2-3 weeks apart between immunizations. The titer of the antibodies obtained from the immunized animals were measured via immuno blotting using lysates of HEK293T cells which overexpressed the FAM19A5 protein.

2. Preparation of Single-Chain Variable Fragment (scFv) Library from Immunized Chicken Using TRI reagent (Invitrogen, Carlsbad, CA USA), RNA was extracted from the spleen, bone marrow, and bursa of fabricius of the immunized chickens described above. Oligo-dT primers and SUPERSCRIPT™ III First-Strand Synthesis System (Invitrogen) were used to synthesize the first strand cDNA. For the cDNA obtained from the immune system of the animals, Expand High Fidelity PCR System (Roche Molecular Systems, IN, USA) was used to produce a single chain variable region library. In each reaction, 1 μL of cDNA, 60 pmol of each primer, 10 μL of 10× reaction buffer solution, 8 μL of 2.5 mM dNTP (Promega, Madison, WI, USA), and 0.5 μL of Taq DNA polymerase were mixed with water. The final volume was 100 μL PCR reaction was performed using the following conditions: 30 cycles of (i) 15 seconds at 94° C., (ii) 30 seconds at 56° C., and (iii) 90 seconds at 72° C., followed by a final extension for 10 minutes at 72° C. The PCR products comprising a fragment having a length of about 350 bp where loaded onto a 1.5% agarose gel and after electrophoresis, QIAGEN Gel II Extraction Kit (QIAGEN, Valencia, CA, USA) was used to purify the nucleotide fragment. The purified PCR product was quantified by reading at OD 260 nm. (1 unit OD=50 μg/ml).

Two VH and VL first product from the second PCR was connected randomly by the overlap extension PCR (Overlap extension PCR). Each PCR reaction was mixed with 100 ng of the purified VL and VH product, 60 pmol of each primer, 10 μL 10× reaction buffer, 8 μL of 2.5 mM dNTP, 0.5 μL of Taq DNA polymerase, and water in a final volume of 100 μL. PCR was performed under the following conditions: 25 cycles of (i) 15 seconds at 94° C., (ii) 30 seconds at 56° C., and (iii) 2 minutes at 72° C., followed by final extension for 10 minutes at 72° C. The PCR products comprising a single chain variable region fragment having a length of about 700 bp were loaded onto a 1.5% agarose gel and after electrophoresis, QIAGEN II Gel Extraction Kit (QIAGEN) was used to purify the nucleotide fragment. The purified PCR product was quantified by reading at OD 260 nm. (1 unit OD=50/ml).

3. Library, Ligation and Transformation

The scFv fragment of the PCR product and vector pComb3X-SS (The Scripps Research Institute, CA, USA) were digested with a Sfi I restriction enzyme. 10 μg of the purified overlapping PCT product was mixed with 360 units of Sif I, (μg DNA per 16 units, Roche Molecular Systems, Pleasanton, CA, USA), 20 μL of a 10× reaction buffer, and water to the final volume with 200 μL. 20 g of the pComb3X-SS vector was mixed with 120 units of Sfi I (μg DNA per 6 units), 20 μL of a 10× reaction buffer solution, and water to the final volume to 200 μL. The mixture was digested at 50° C. for 8 hours. Afterwards, the digested product comprising the scFv fragment (about 700 bp) and the vector (about 3400 bp) was loaded onto a 1% agarose gel and purified using a Gel Extraction Kit II QIAGEN (QIAGEN, Valencia, CA, USA). 1400 ng of the Sfi I-restricted pComb3X vector and 700 ng of the digested scFv fragments were mixed with 5× a ligase buffer, 10 μL of T4 DNA ligase (Invitrogen, Carlsbad, CA, USA), and water to a final volume of 200 μL. The mixture was incubated at 16° C. for 16 hours to perform the ligation.

After precipitation with ethanol, the DNA pellet was dissolved in 15 μL of water. To produce a library, the ligation sample was transformed into *E. coli* strain ER2738 (New England Biolabs Inc., Hitchin, Hertfordshine, SG4 OTY, England, UK) via electroporation using the vibrator gene (Gene pulser: Bio-Rad Laboratories, Hercules, CA, USA). Cells were mixed in a 5 ml Super Broth (SB) medium and incubated while stirring at 250 rpm for one hour at 37° C. Then, 3 μL of 100 mg/mL kanamycin was added to 10 mL of SB medium. To determine the library size, 0.1 μL, 1 μL, and 10 μL of the culture sample were smeared onto Luria Broth (LB) agar plates containing 50 μg/ml of kanamycin. After stirring for 1 hour, 4.5 μL of 100 mg/mL kanamycin was added to the LB culture and further stirred for an additional 1 hour. Then, 2 ml of the VCM13 helper phage in water (>$10^{11}$ cfu/ml) was added to the LB medium, along with pre-heated LB (183 mL) containing 92.5 μL of 100 mg/mL kanamycin. This mixture was stirred at 250 rpm at 37° C. for an additional 2 hours. Next, 280 μL (50 mg/mL) of kanamycin was added to the culture and stirred overnight at 37° C. The next day, the bacteria pellet was centrifuged using a high-speed centrifuge (Beckman, JA-10 rotor) at 3,000 g, 4° C. Afterwards, the bacterial pellet was used to extract phagemid DNA, while the supernatant was transferred to sterile centrifuge bottles. Next 8 grams of polyethylene glycol-8000 (PEG-8000, Sigma) and 6 grams of sodium chloride was added (NaCl, Merck) to the supernatant, and then kept for 30 minutes in ice. Afterwards, the supernatant was centrifuged 15 minutes at 15,000 g, 4° C. The supernatant was then discarded, and the phage pellet Tris containing 1% BSA-reproduction was suspended in buffered saline (TBS).

Example 3 Library Panning (Bio-Panning) on an Immobilized Antigen

Bio-panning was performed using magnetic beads (Dynabeads M-270 Epoxy, Invitrogen). At room temperature, approximately $1\times10^7$ beads were coated with 5 μg of recombinant FAM19A5 protein by stirring, while rotating, the beads and the protein together for 20 hours at room temperature. Once the coating was done, the beads were washed 4 times with phosphate buffered saline (PBS) and blocked for one hour in PBS containing 3% BSA at room temperature. Then, the coated beads were cultured for two hours at room temperature with Phage-displayed scFv described above. To remove any phage that was not bound to the antigen coated beads, the beads were washed with 0.05% Tween20/PBS. Then the bound phages were eluted with 50 μL of 0.1 M glycine/hydrogen chloride (0.1 M Glycine-HCl, pH 2.2) and neutralized with 3 μL of 2 M Tris with hydrogen chloride (tris-HCl, pH 9.1). This phage-containing supernatants were used to infect *E. coli* ER2738 cells and VCSM13 helper phage was used to amplify and rescue overnight. Also the input (input) and production (output) by phage titers from the phage-infected cultures were determined by blotting the phage-infected cultures on LB agar plates containing 50 μg/ml of kanamycin. The next day, PEG-8000 and NaCl were used to precipitate phages, which were used subsequently for bio-panning. Bio-panning was performed up to a total of five different times by repeating the above process. With each amplification, the phages were screened and selected for high affinity to the FAM19A5 protein.

Example 4 Selection of Clone by Phage EELISA

To analyze the clones selected from the bio-panning, individual clones were randomly selected from the phase-displayed scFv and confirmed using ELISA that the clones bind to the FAM19A5 recombinant protein. The FAM19A5 recombinant protein was diluted in 0.1 M $NaHCO_3$ buffer, and 100 ng/well of the protein was used to coat 96-well microtiter plates at 4° C. for 16 hours. Next day, the plates were blocked with 3% BSA/PBS at 37° C. for 1 hour. Then, the phage supernatant was mixed with 6% BSA/PBS and was cultured for 2 hours at 37° C. The plates containing the supernatant were then washed with 0.05% Tween-20/PBS. The HRP-conjugated M13 antibody (a-M13-HRP, Pierce Chemical Co, Rockford, IL, USA) was diluted to 1/5000. 50 μl of the diluted antibody was added to the plates and incubated for 1 hour at 37° C. After the incubation and washing, the plates were added with 0.05 M citrate buffer solution, 1 μg/ml of 2,2'-azino-bis (3-ethylbenzothiazoline-6-sulphonic acid) (ABTS, Amresco, Solon, OH, USA), and 0.1% $H_2O_2$ for color development. The absorbance for each well was measured at 405 nm.

Figure 1A:
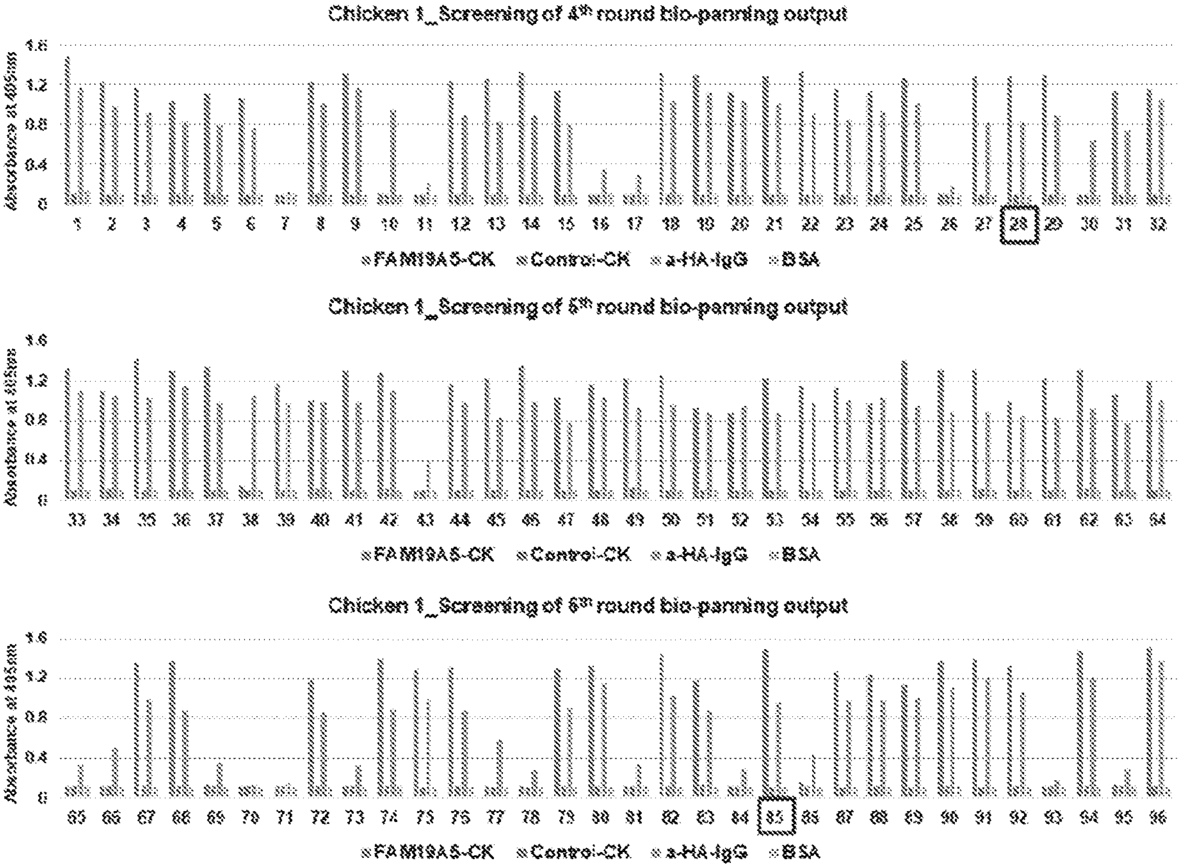
FIGS. 1A, 1B, and 1C provides the binding analysis of individual scFv clones to FAM19A5 protein. The absorbance was measured at 405 nm. The clone numbers provided on the X-axis.
Figure 1B:
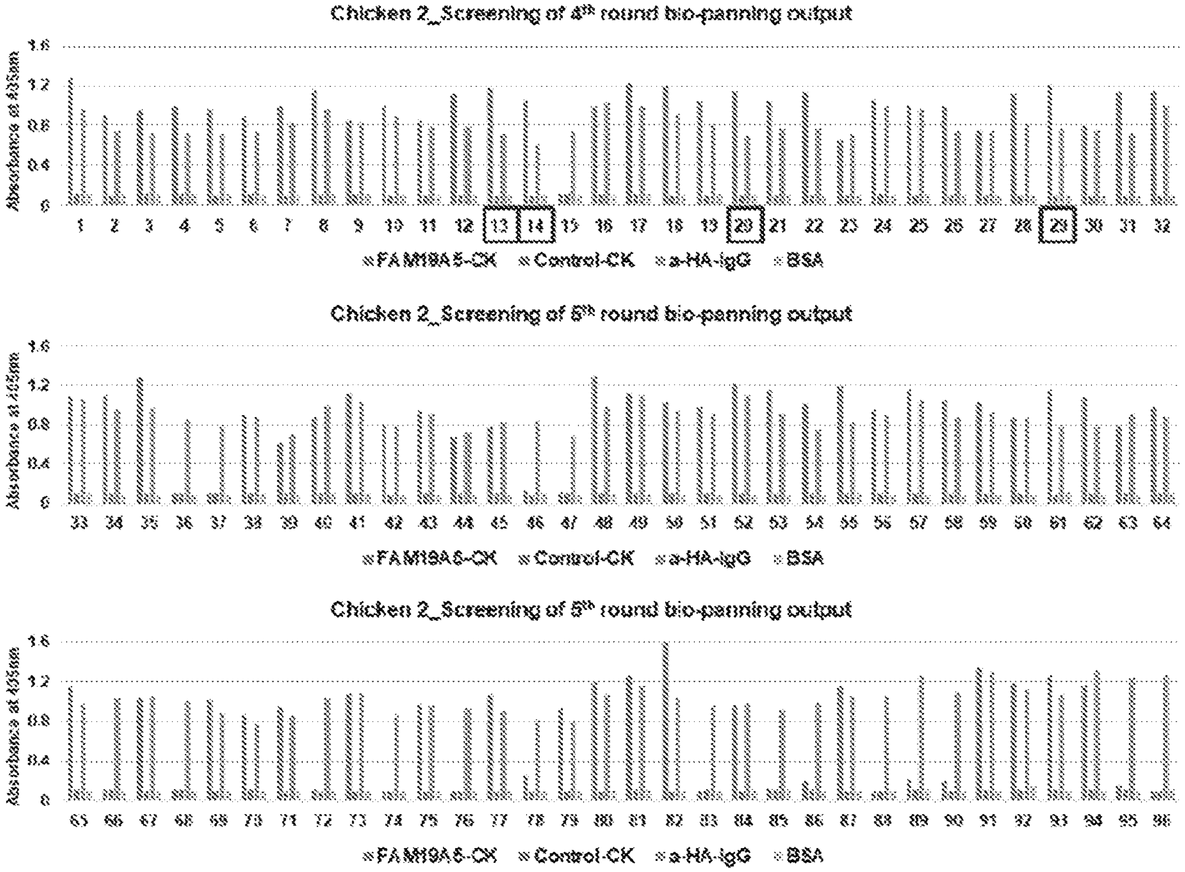
Figure 1C:
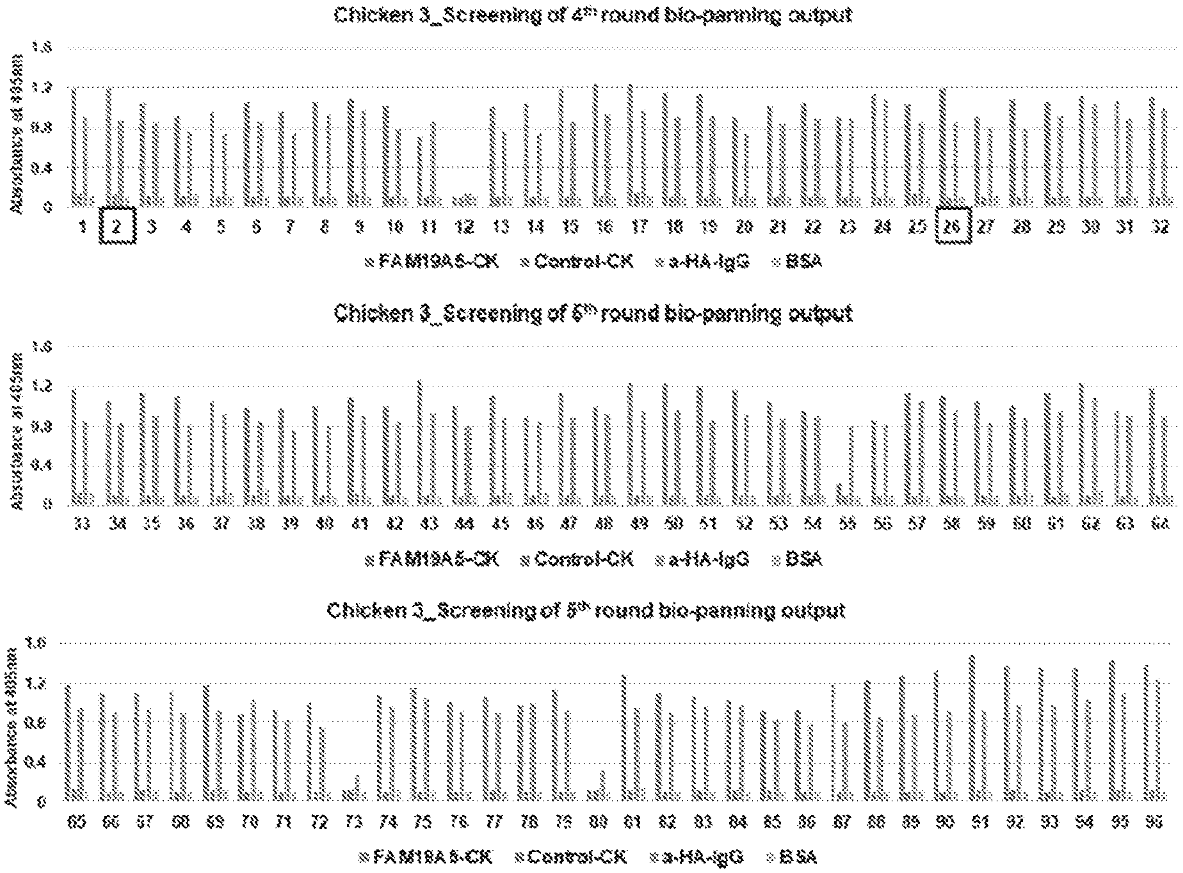

From the 96 clones that were initially identified, 8 scFv clones having unique heavy chain CDR3 (HCDR3) sequences and high binding to FAM19A5 protein were selected for further analysis. FIGS. 1A-IC.

Example 5 Production of Anti-FAM19A5-IGG2/4 Antibody

Anti-FAM19A5 scFv was subcloned into a mammalian expression vector In the FAM19A5 scFv gene sequence, a human Cκ gene was connected to the light chain variable domain, and human immunoglobulin isotype IgG2/4 of CH1, CH2, and CH3 genes were connected to the heavy chain variable region. The antibody having each light chain and each heavy chain was synthesized by adding restriction sites (Genscript, USA). The synthesized gene was inserted into the mammalian cell expression vector having a modified restriction site to facilitate cloning. First, the light chain gene was inserted into the vector using Hind III and Xba I (New England Biolabs, UK) restriction enzymes and then adding the heavy chain gene to the vector by using NheI and BamHI (New England Biolabs, UK) restriction enzymes.

In order to express and purify an anti-FAM19A5-IgG2/4 antibody, mammalian cell transfection and overexpression injection system were used. Approximately 2 μg/ml of the mammalian expression vector was mixed with 4 μg of polyethyleneimine (PEI, Polysciences, Warrington, PA, USA) in 150 mM sodium chloride (NaCl, Merck) corresponding to 1/10 of the cell culture volume. The mixture was allowed to stand for 15 minutes at room temperature. The mixture was added to HEK293F cells ($2\times10^6$ cells/ml, Invitrogen), which were then incubated in the FREESTYLE™ 293 expression culture medium containing 100 U/ml of penicillin and streptomycin (Invitrogen) at 7% $CO_2$ and 37° C. and in a stirring condition of 135 rpm for six days. To purify the expressed anti-FAM19A5 IgG2/4 antibodies from the cell culture supernatant, Protein A bead (RepliGen, Waltham, MA, USA) affinity gel chromatography was used. The protein A chromatography was run on 4~12% Bis-Tris gradient gel electrophoresis. The size and yield of the protein was confirmed by the Coomassie Brilliant Blue staining. The binding ability of the antibodies was measured using an ELISA assay.

Figure 2A:
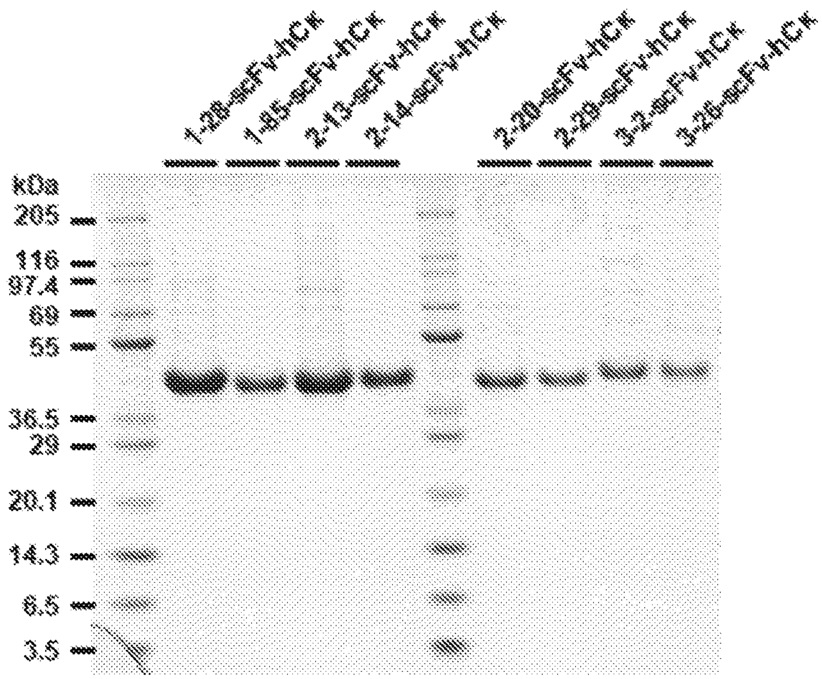
FIGS. 2A and 2B provide the approximate size and binding capability of different anti-FAM19A5 scFv, respectively. The size of the antibodies is shown using SDS-Page, and the binding capability was measured using ELISA. Antibodies shown include (left to right): 1-28, 1-85, 2-13, 2-14, 2-20, 2-29, 3-2, and 3-26.
Figure 2B:
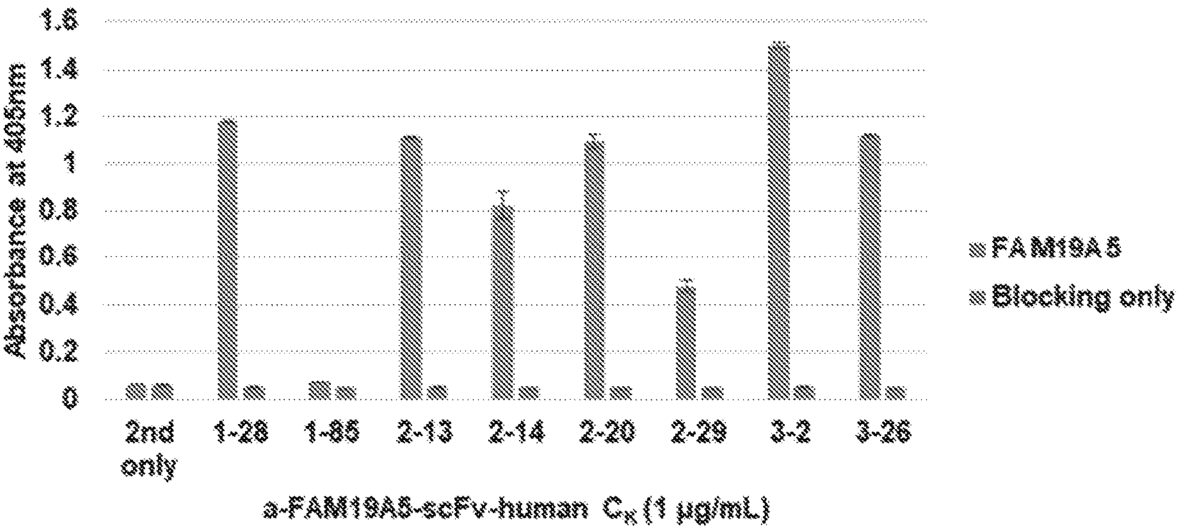

As shown in FIG. 2A, the different antibodies tested (i.e., 1-28, 1-85, 2-13, 2-14, 2-20, 2-29, 3-2, and 3-26) were comparable in size. Except for the 1-85 antibody, the antibodies tested were able to bind to FAM19A5 protein to varying degrees. FIG. 2B.

Example 6 Analysis of the Neutralization Ability of Anti-FAM19A5 Antibodies

To further assess the functional properties of the antibodies, the following methods were used:

1. Preparation of Recombinant FAM19A5 Rabbit Fc Fusion Protein

To construct FAM19A5 expression vectors, genes encoding the human FAM19A5 was chemically synthesized (Genscript, Picataway, NJ, USA). The gene was subcloned into a modified mammalian expression vector encoding the hinge region of human IgG1 and the CH2-CH3 domains of rabbit IgG at the 3' region as reported previously. See Han, J., et al., *Exp Mol Med.* 48(11):e271 (2016).

The expression vector encoding FAM19A5 rabbit Fc fusion was transfected into HEK293F cells (Invitrogen, Carlsbad, CA, USA) using 25-kDa linear polyethyleneimine (Polyscience, Warrington, PA, USA), as reported previously. See Boussif, O., et al., *Proc Natl Acad Sci USA.* 92(16): 7297-301 (1995). The FAM19A5 rabbit fusion protein was purified from the culture supernatants of transiently transfected HEK293F cells using protein A Sepharose column (Repligen, Waltham, MA, USA) according to the manufacturer's instructions.

2. Preparation of Recombinant Anti-FAM19A5 scFv Human CK Fusion Protein

The genes of selected clones were subcloned into the modified pCEP4 vector encoding CK domain (human immunoglobulin κ light chain constant domain) at the 5' region as reported previously. See Lee, Y., et al., *Exp Mol Med.* 46:e114 (2014). The expression vectors encoding anti-FAM19A5 scFv human CK fusion were transfected into HEK293F cells (Invitrogen) as described above. The scFv-hCκ fusion protein was purified from the culture supernatants of transiently transfected HEK293F cells using protein A Sepharose column (Repligen, Waltham, MA, USA) according to the manufacturer's instructions.

3. Neutralizing Efficacy of Anti-FAM19A5 Antibodies on Glial Cells

To evaluate neutralizing efficacy of antibodies was confirmed by flow cytometric analyses, as previously described. See Kim, M., et al., *PLoS One.* 7(4):e35100 (2012). Mouse and human glial cells were seeded into a v-bottom 96-well plate (Corning Inc., Corning, NY, USA) with a final density of $3\times10^5$ cells per well. Cells were treated with 1 μM of recombinant FAM19A5 rabbit Fc and 5 μM of anti-FAM19A5 scFv human Cκ fusion protein in flow cytometry buffer [1% (w/v) BSA in PBS containing 0.05% (w/v) sodium azide] at 37° C. for 1 h. After washing with flow cytometry buffer, the cells were then incubated with Alexa Fluor 488-conjugated anti-rabbit IgG (Fc specific) antibody (Jackson Immuno Research Inc., PA, USA) for 1 h at 37° C. in the dark. After additional washing with the same buffer, the cells were resuspended in 300 μL PBS and analyzed by flow cytometry using a FACSCANTO™ II instrument (BD Bioscience, San Jose, CA, USA) equipped with a 488-nm laser. Data were analyzed with FlowJo software (TreeStar, Ashland, OR, USA).

Figure 3A:
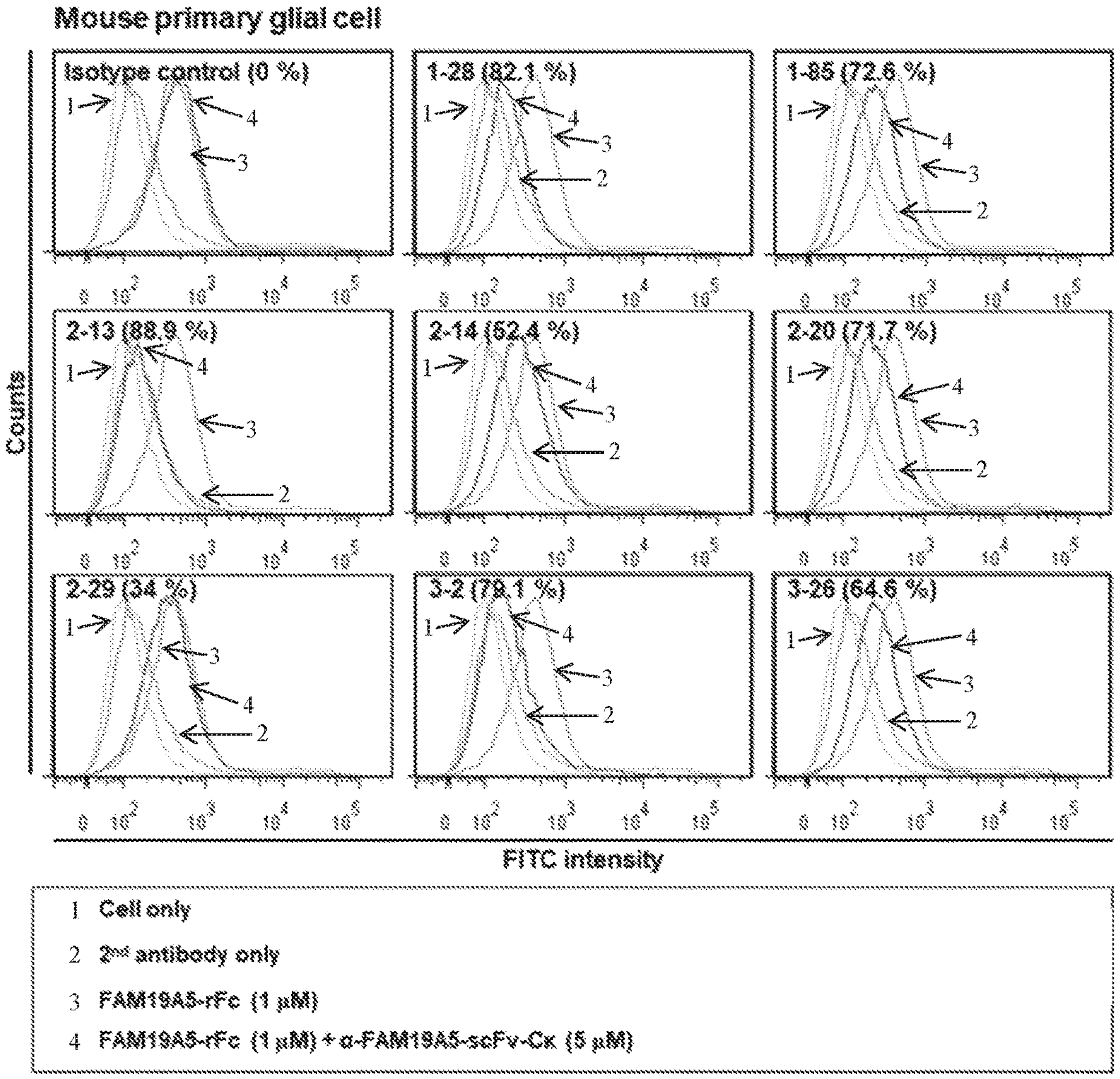
FIGS. 3A and 3B provides a comparison of the ability of different anti-FAM19A5 antibodies to neutralize FAM19A5 expression in mouse and human glial cells, respectively. Neutralization is shown as percent reduction of FAM19A5 expression, which is shown as mean fluorescence intensity (MFI). Percent reduction can be calculated using the following formula: 100%−[((MFI of FAM19A5+anti-FAM19A5 antibody)/(MFI of FAM19A5+control antibody))×100]. Percent reduction for each of the antibodies are shown in parentheses.
Figure 3B:
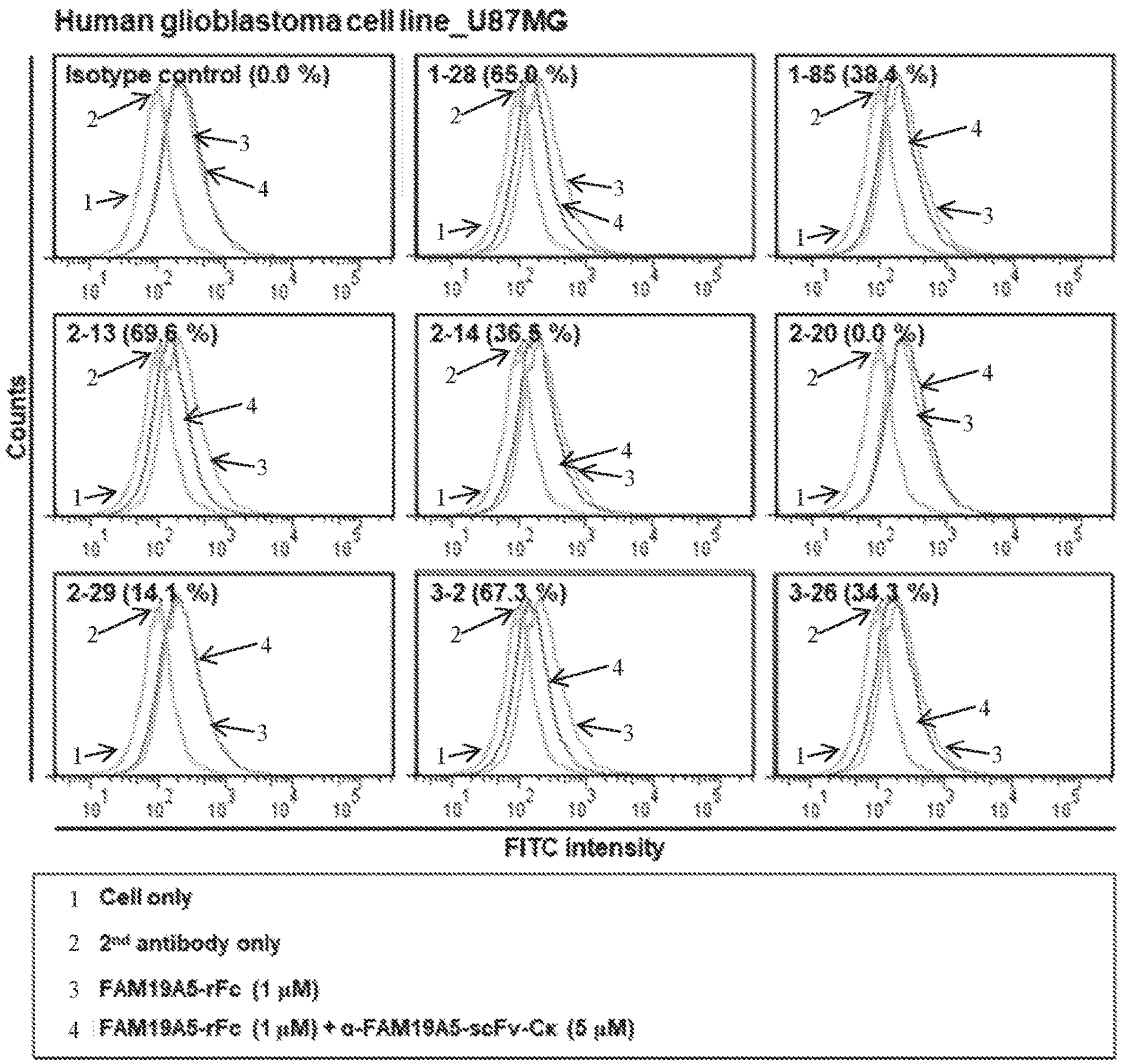

As shown in FIG. 3A, all the antibodies tested (i.e., 1-28, 1-85, 2-13, 2-14, 2-20, 2-29, 3-2, and 3-26) were able to inhibit interaction of FAM19A5 to mouse primary glial cells to varying degrees. In human glioblastoma cell line, the 2-20 antibody was not able to neutralize interaction of FAM19A5 to the cell line. FIG. 3B. The other antibodies were able to neutralize FAM19A5 activity, albeit to varying degrees. The 1-28, 2-13, and 3-2 antibodies showed the greatest neutralizing efficacy in the human glioblastoma cell line.

Example 7 Epitope Mapping Analysis Using FAM19A5 Epitope Fragments F1-F6

Because of its ability to neutralize FAM19A5 expression on both mouse and human glial cells, the 3-2 antibody was selected for epitope mapping analysis. Overlapping peptide fragments (F1-F6, See FIG. 4) of the human FAM19A5 protein were synthesized and conjugated to BSA. Binding of the different anti-FAM19A5 antibodies to the BSA-conjugated peptide fragments F1-F6 was determined by ELISA assay. Briefly, FAM19A5 fragment F1-F6 (diluted to 1 µg/mL in 50 mM carbonate buffer (Biosesang) or to 20 µg/mL for high concentration analysis) were used to coat the wells of 96-well immuno plates (Thermo Scientific) (100 L/well) overnight at 4° C. and then subsequently washed twice in 1×PBS. The plates were then blocked with the blocking buffer (100 µL/well) for 1 hour at room temperature. During the 1-hour incubation, the relevant anti-FAM19A5 antibodies were diluted to 1 µg/mL (or 20 g/mL for high concentration analysis) in the diluent buffer. Once the plates were washed (2× using 1×PBS), the diluted anti-FAM19A5 antibodies were added to the appropriate wells, and the plates were incubated at room temperature for 1 hour. The plates were subsequently washed for a total of five times using the washing buffer. Next, the ODP substrate (prepared by dissolving one ODP tablet (0-phenylenediamine Dihydrochloride, Thermo) into 9 mL of sterilized deionized water and 1 mL of 10× stable Peroxide Stable buffer (Thermo)) was added to each of the wells, and the color change reaction was allowed to occur for 10 minutes. This reaction was stopped by adding 100 µL of 2N H2SO4 (Daejung) to the wells. The absorption value of each of the wells was detected at 492 nm using a 96-well microplate reader (Molecular Device).

Figure 5:
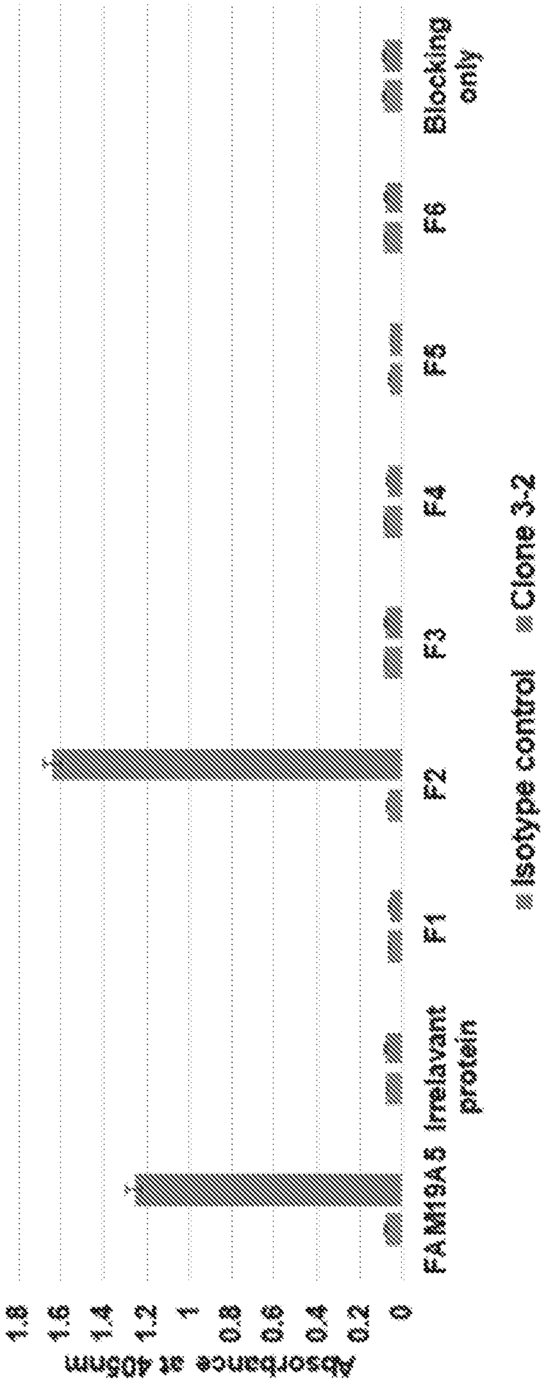
FIG. 5 provides the ELISA results for the binding of the 3-2 antibody to epitope fragments F1 to F6. The left most column ("FAM19A5") represents the positive control and shows the binding of the 3-2 anti-FAM19A5 antibody to whole FAM19A5 protein. "Irrelevant protein" and "blocking only" (i.e., blocking buffer only, i.e., no FAM19A5 protein) groups represent the negative controls. For each of the groups, the bar to the left corresponds to the isotype control and the bar to the right corresponds to the 3-2 antibody.

As shown in FIG. 5, the 3-2 antibody bound strongly to epitope fragment F2 with minimal binding to the other fragments.

Figure 6A:
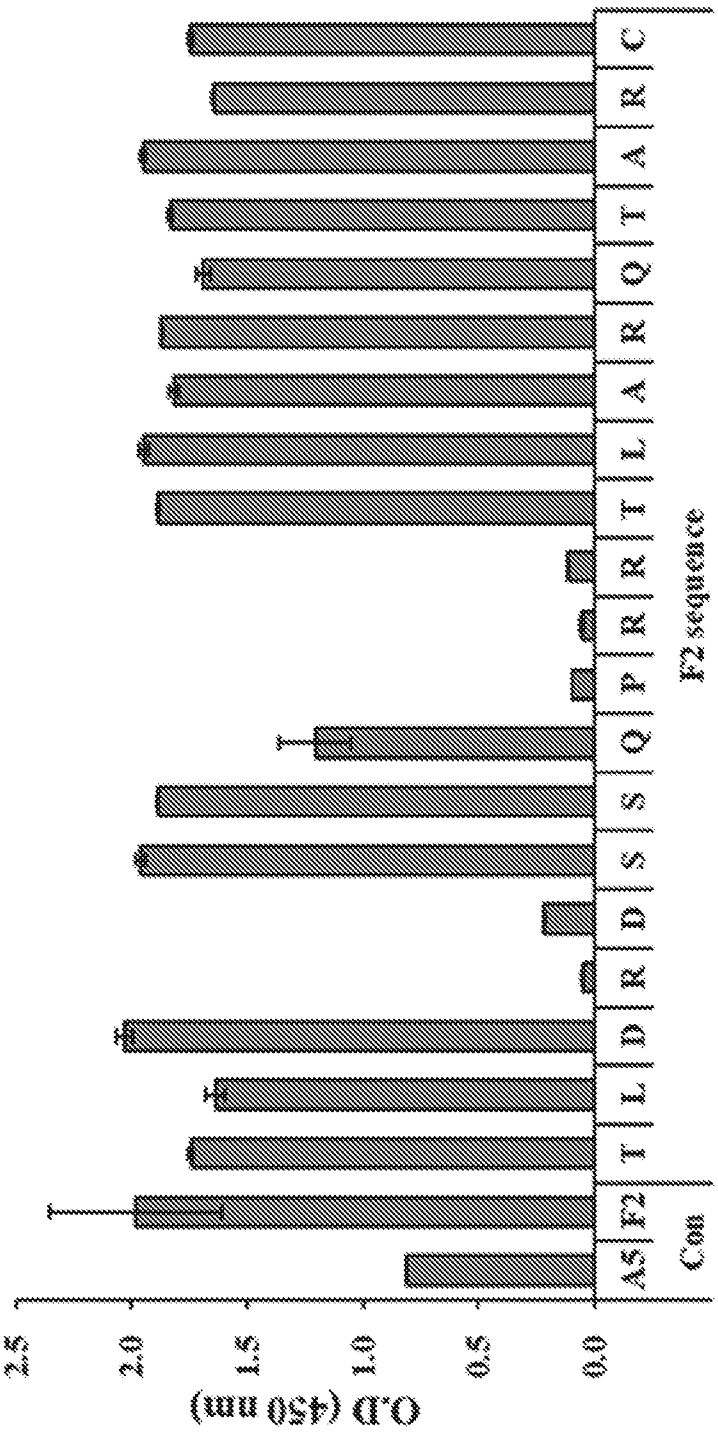
FIGS. 6A, 6B, 6C, 6D, 6E, 6F, 6G, 6H, 6I, and 6J provide the results of the alanine scanning analysis, showing the specific amino acid residues in the epitope F2 fragment (SEQ ID NO: 90) that are important for the binding of the various 3-2 antibody variants to FAM19A5 protein.
Figure 6B:
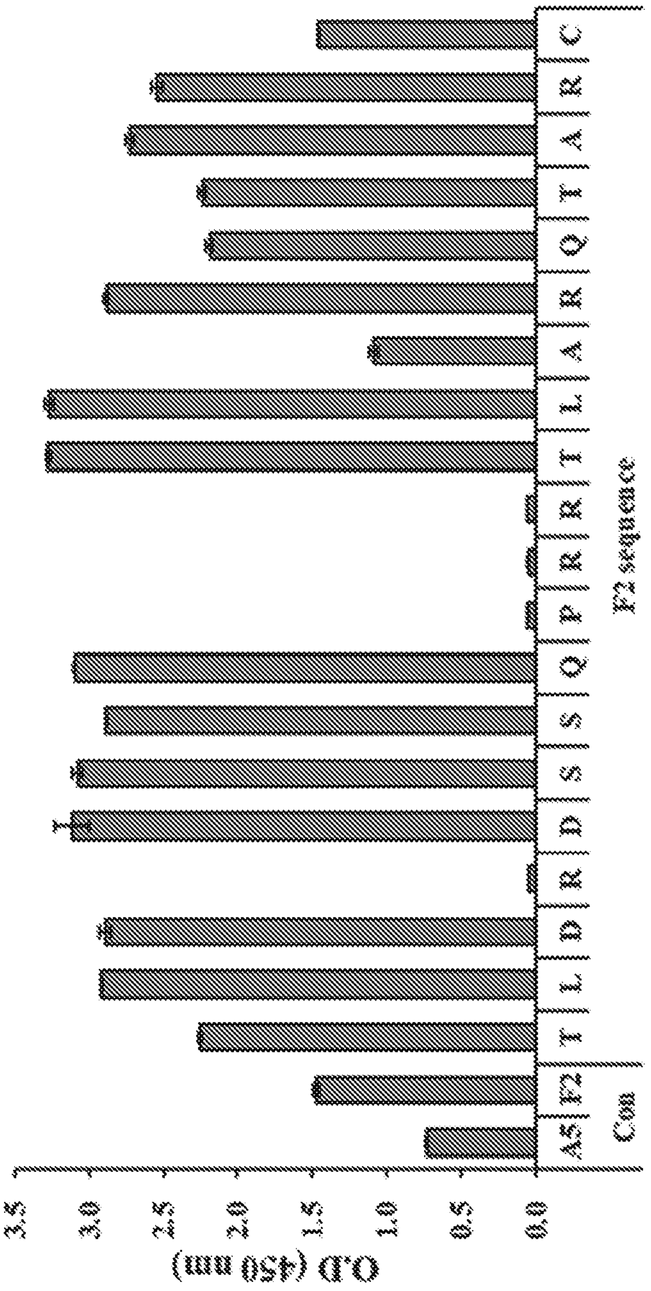
Figure 6C:
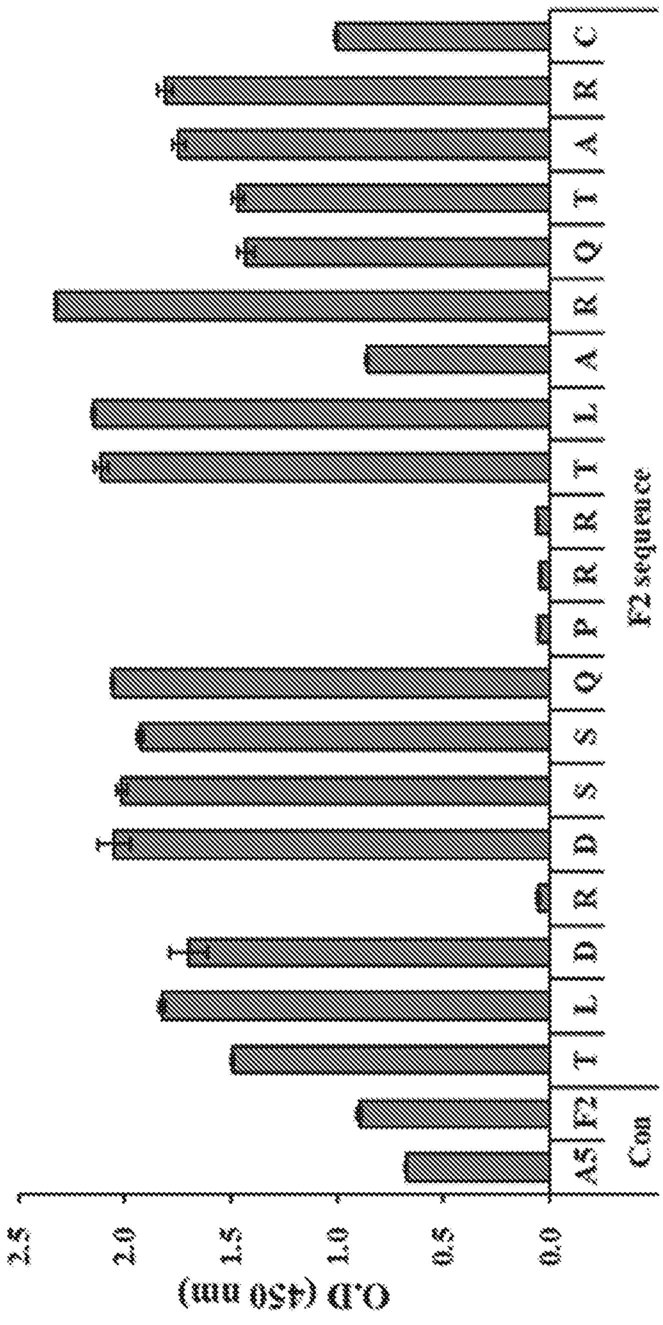
Figure 6D:
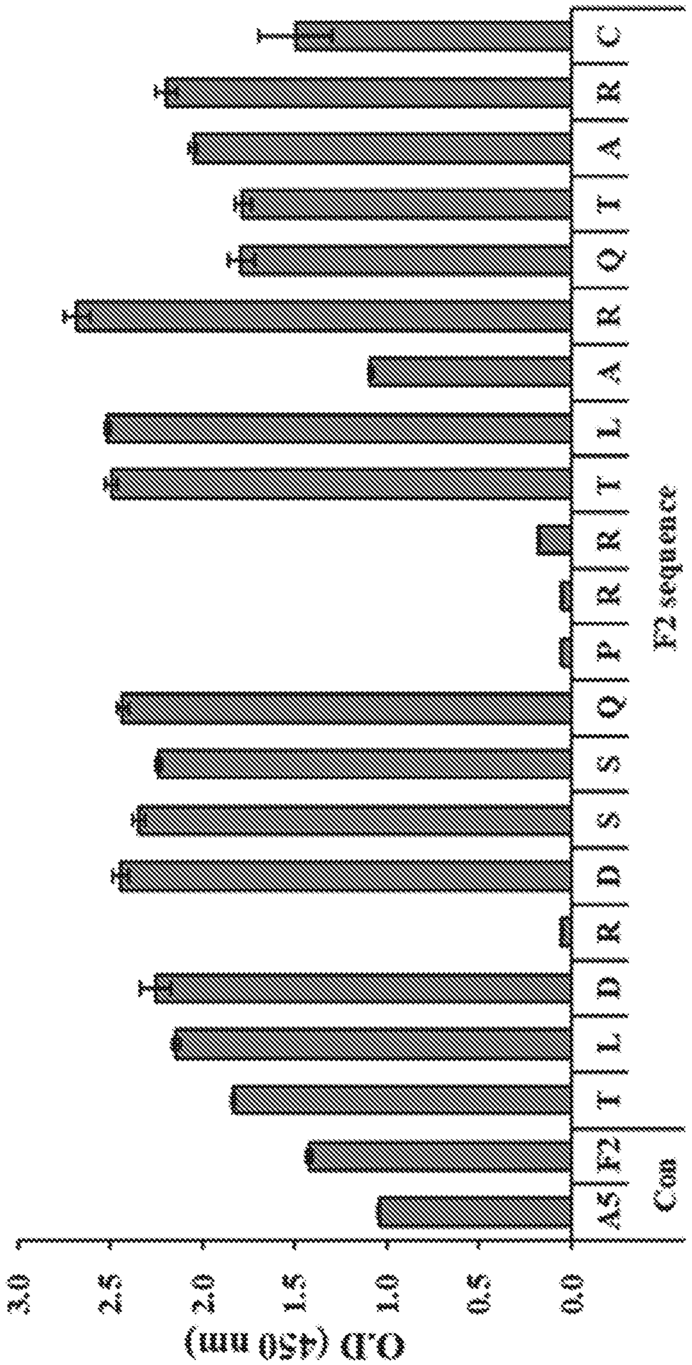
Figure 6E:
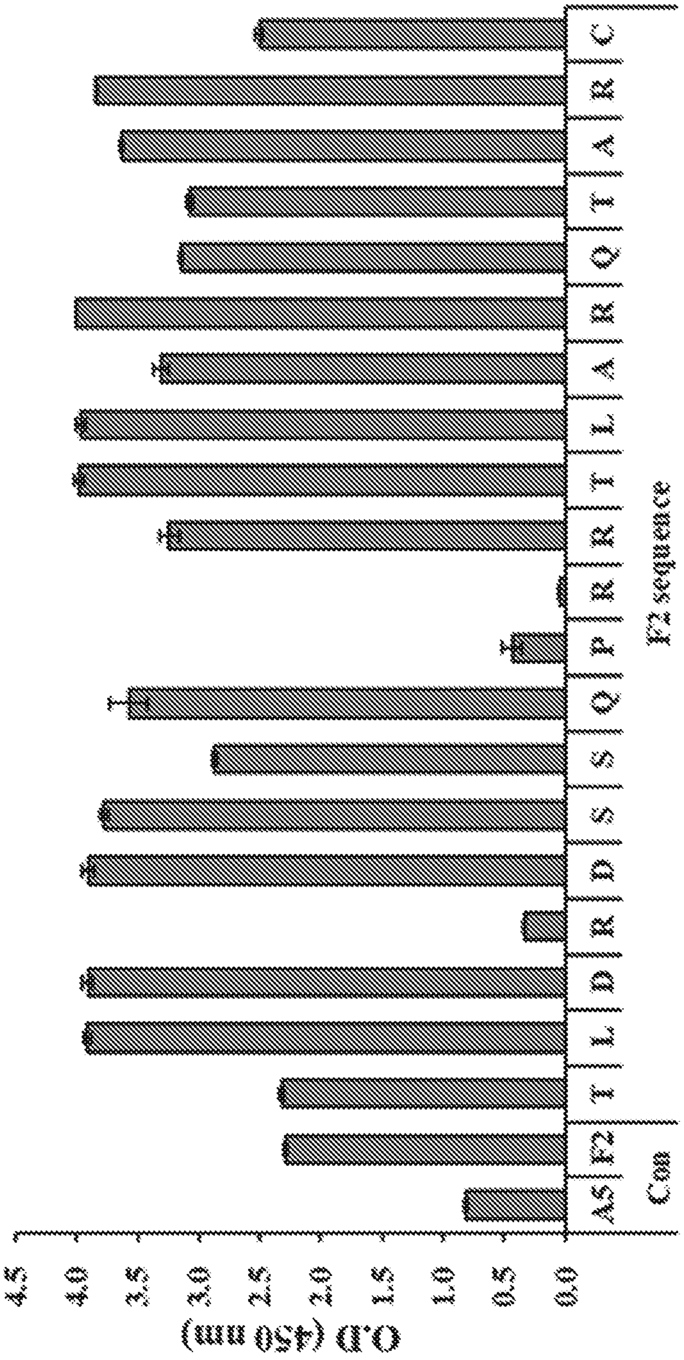
Figure 6F:
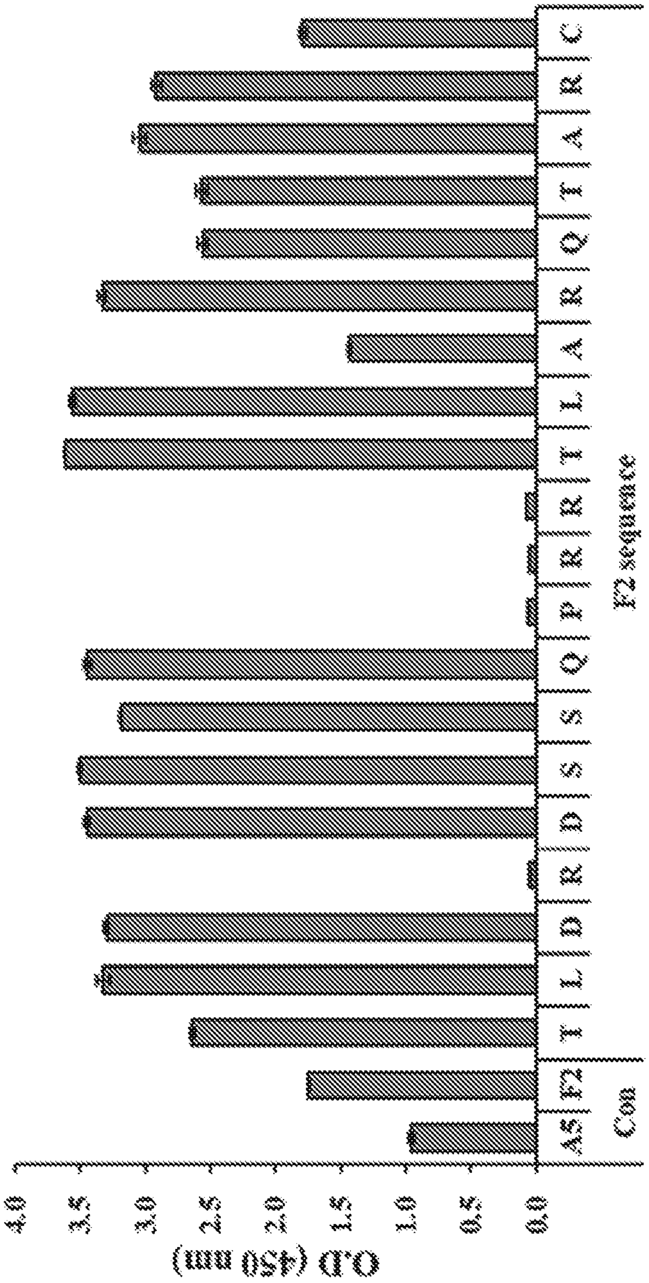
Figure 6G:
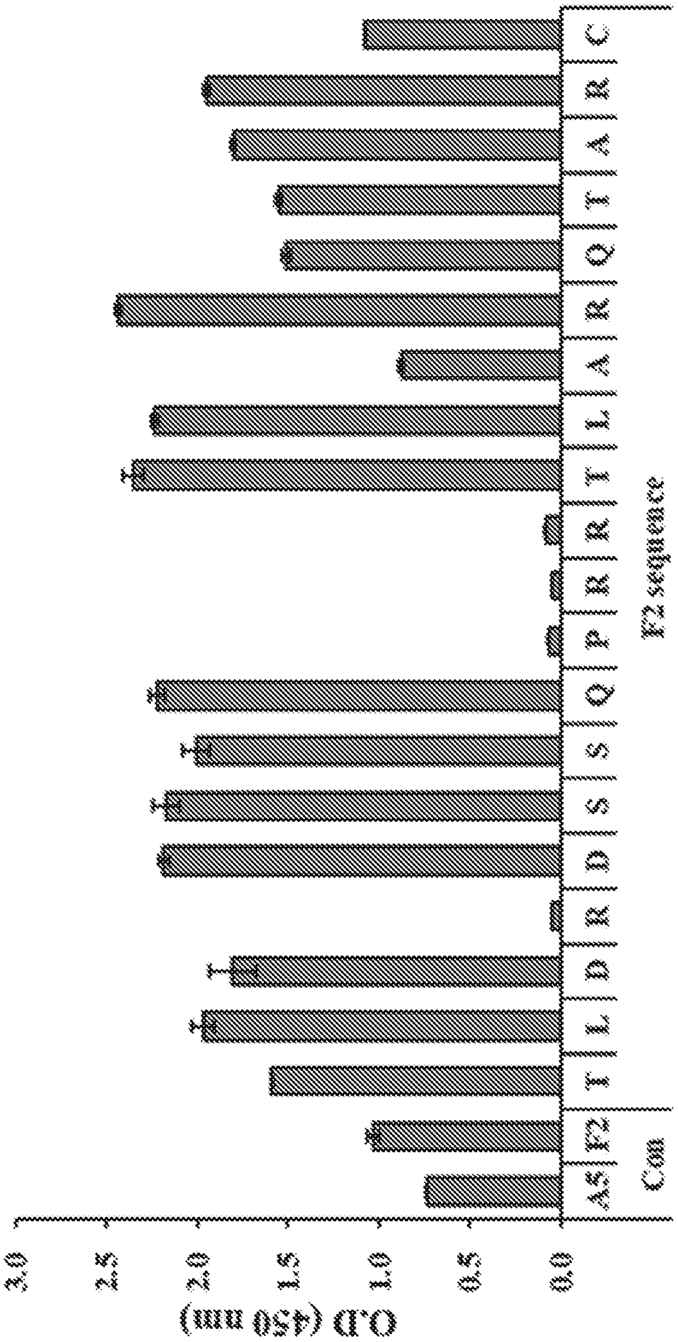
Figure 6H:
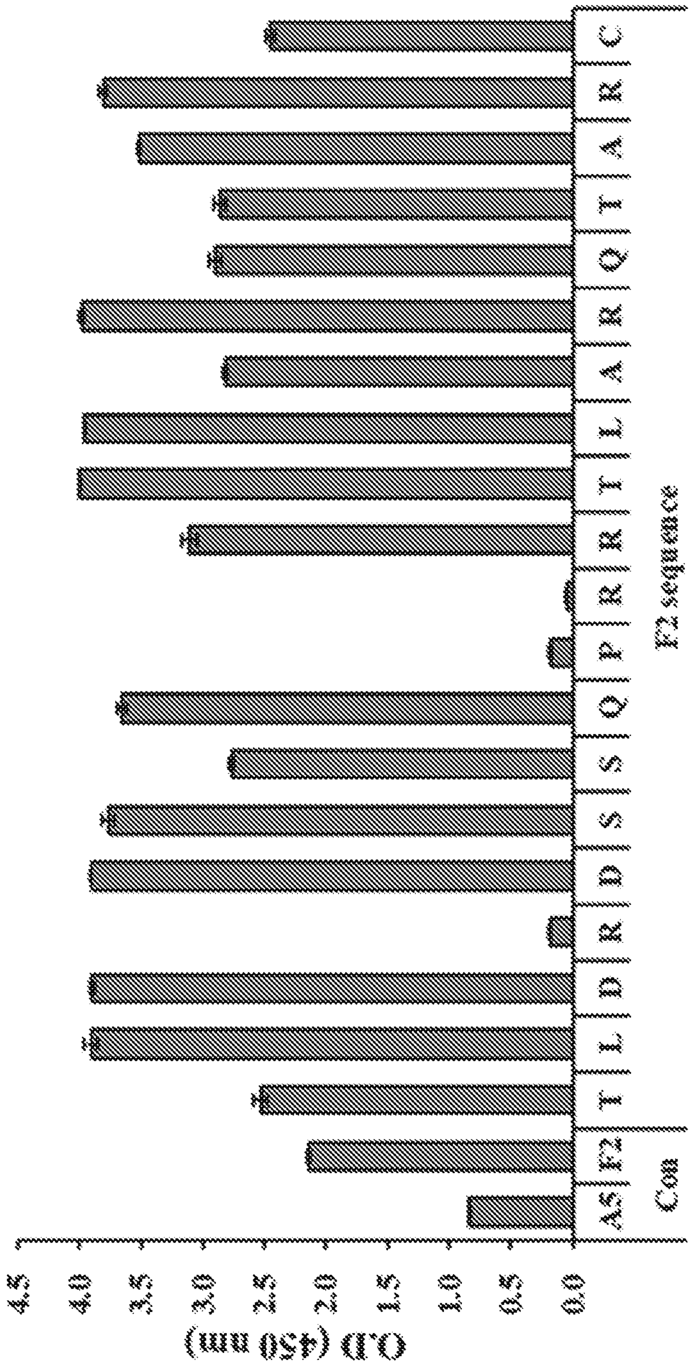
Figure 6I:
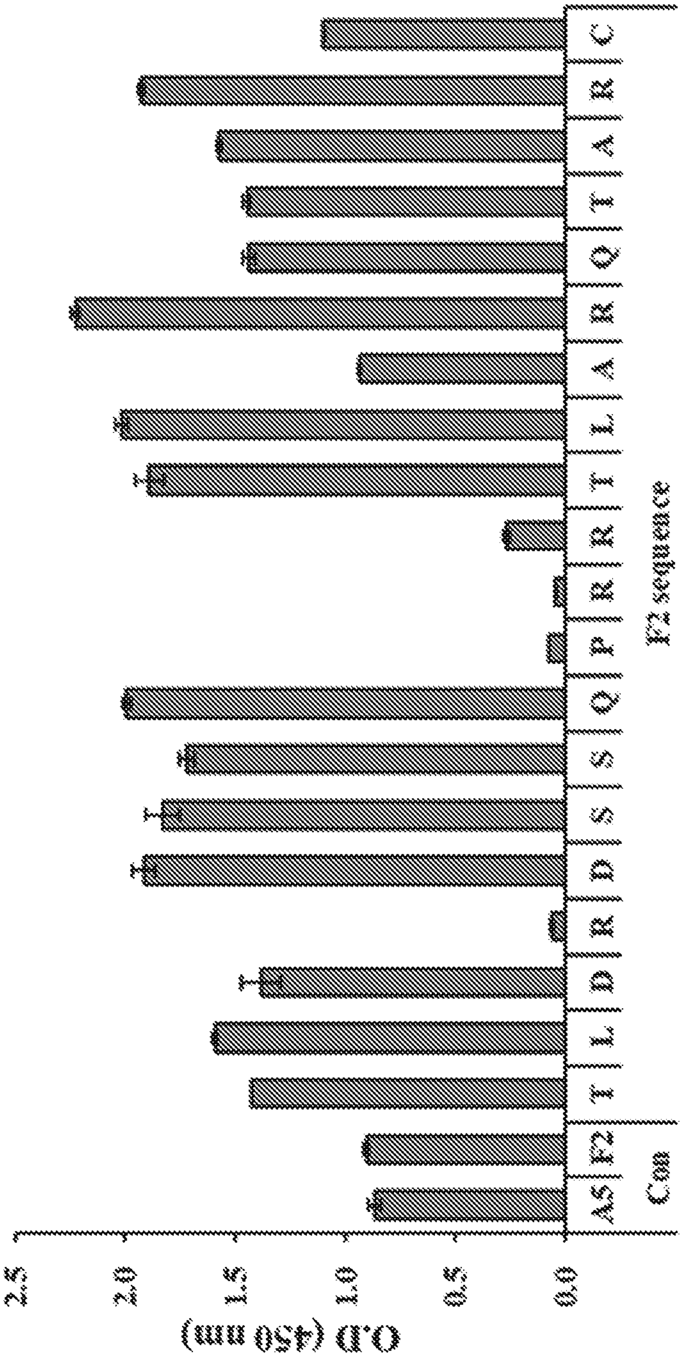
Figure 6J:
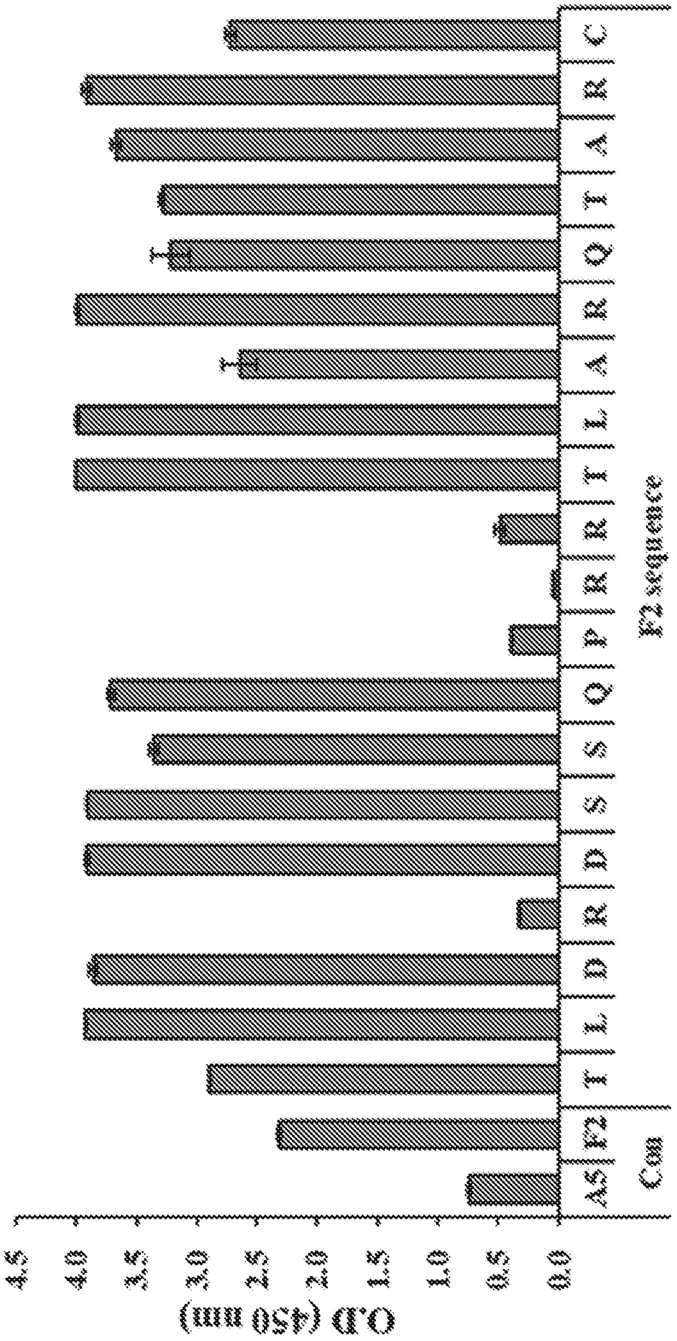

Next, to identify the specific amino acid residues within the epitope fragment F2 that the 3-2 antibody binds to, an alanine scanning analysis was conducted. As shown in FIG. 6A, when amino acid residue R4, D5, P9, R10, or R11 was mutated to alanine, the ability of the 3-2 antibody to bind to epitope fragment F2 was greatly diminished. Similar analysis was conducted for several de-immunized variants of the 3-2 antibody (see Example 8 for details regarding the de-immunization process). As shown in FIGS. 6B, 6C, 6D, 6F, 6G, 6I, and 6J, amino acid residues R4, P9, R10, and R11 were important for binding of antibodies 1-30, 1-32, and 6-10 to FAM19A5. For antibodies, 1-17 and 4-11, amino acid residues R4, P9, and R10 were important (see FIGS. 6E and 6H).

Example 8 De-Immunization of Anti-FAM19A5 Antibody

1. Immunogenicity Assessment in Silico

To reduce the risk of immunogenicity when administered to a human subject, in silico analysis was conducted to identify specific regions of high immunogenicity within the 3-2 and 2-13 anti-FAM19A5 antibodies.

Figure 7:
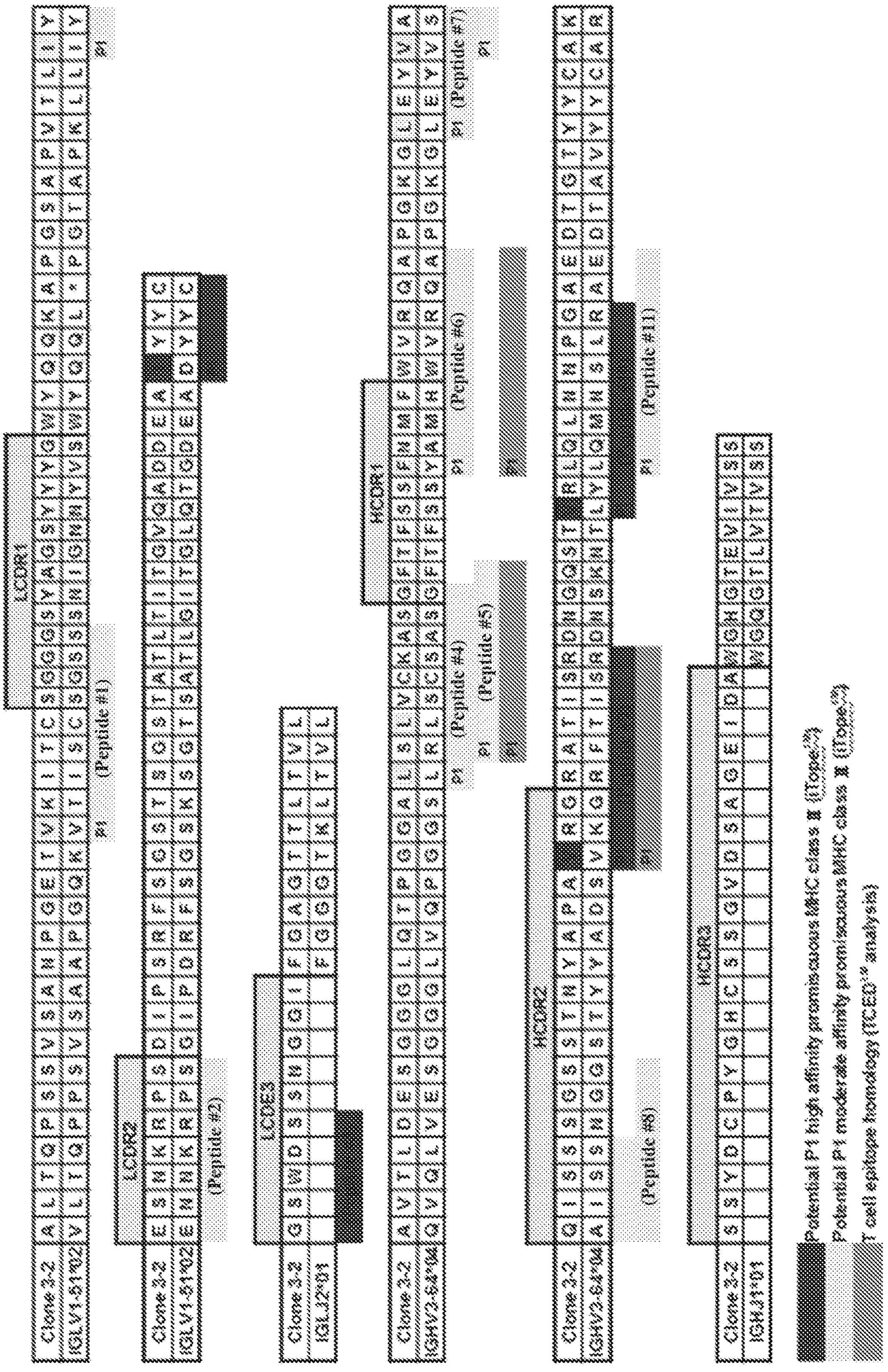
FIG. 7 identifies the potential immunogenicity sites on the light chain variable region (VL) (top three rows) and heavy chain variable region (VH) (bottom three rows) of the 3-2 antibody. The VL corresponds to SEQ ID NO: 12, and the VH corresponds to SEQ ID NO: 11. The sequences for the human germlines used for the framework regions of the 3-2 antibody are also shown: VL=immunoglobulin lambda variable 1-51 (IGLV1-51*02) (SEQ ID NO: 145) and immunoglobulin lambda joining 2 (IGLJ2*01) (SEQ ID NO: 146); VH=immunoglobulin heavy variable 3-64 (IGHV3-64*04) (SEQ ID NO: 147) and immunoglobulin heavy joining 1 (IGHJ1*01) (SEQ ID NO: 148). The human germlines used were the most homologous human germline (IgBLAST, NCBI) to the 3-2 clone. Promiscuous MHC class II binding peptides with high and moderate immunogenicity potential, as determined by ITOPE™ analysis, are indicated. Specifically, the MHCII binding peptides with high immunogenicity potential are as follows: (i) Peptide #3: residues 85-93 of SEQ ID NO: 12 (IYYCGSWDS) (SEQ ID NO: 171); (ii) Peptide #9: residues 64-72 of SEQ ID NO: 11 (VRGRATISR) (SEQ ID NO: 172); and (iii) Peptide #10: residues 79-87 of SEQ ID NO: 11 (VRLQLNNPG) (SEQ ID NO: 173). The MHCII binding peptides with moderate immunogenicity potential are as follows: (i) residues 16-24 of SEQ ID NO: 12 (VKITCSGGG) (SEQ ID NO: 174); (ii) Peptide #2: residues 48-56 of SEQ ID NO: 12 (IYESNKRPS) (SEQ ID NO: 175); (iii) Peptide #4: residues 18-26 of SEQ ID NO: 11 (LSLVCKASG) (SEQ ID NO: 176); (iv) Peptide #5: residues 19-27 of SEQ ID NO: 11 (SLVCKASGF) (SEQ ID NO: 177); (v) Peptide #6: residues 32-40 of SEQ ID NO: 11 (FNMFWVRQA) (SEQ ID NO: 178); (vi) Peptide #7: residues 45-53 of SEQ ID NO: 11 (LEYVAQISS) (SEQ ID NO: 179); (vii) Peptide #8: residues 48-56 of SEQ ID NO: 11 (VAQISSSGS) (SEQ ID NO: 180); and (viii) Peptide #11: residues 81-89 of SEQ ID NO: 11 (LQLNNPGAE) (SEQ ID NO: 181). Homologous peptides from the T cell epitope database are as follows: Peptide #5, Peptide #6, and Peptide #9. A total of 11 binding peptides were identified, which are noted as Peptide #1-#11. "P1" for each of the binding peptides indicates the first anchor position.
Figure 8:
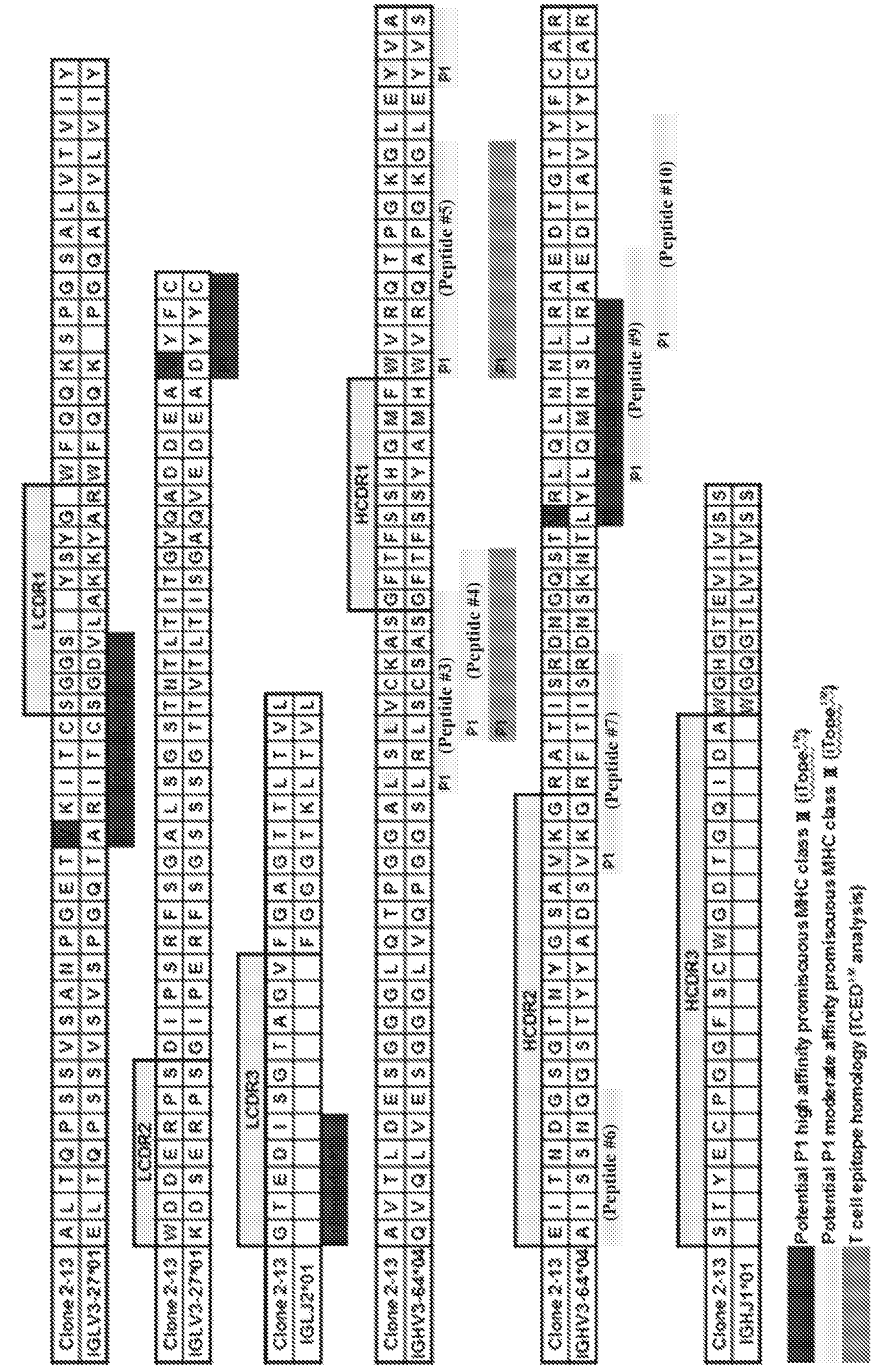
FIG. 8 identifies the potential immunogenicity sites on the light chain variable region (VL) (top three rows) and heavy chain variable region (VH) (bottom three rows) of the 2-13 antibody. The VL corresponds to SEQ ID NO: 45, and the VH corresponds to SEQ ID NO: 35. The sequences for the human germlines used for the framework regions of the 2-13 antibody are also shown: VL=immunoglobulin lambda variable 3-27 (IGLV3-27*01) (SEQ ID NO: 149) and immunoglobulin lambda joining 2 (IGLJ2*01) (SEQ ID NO: 146); VH=immunoglobulin heavy variable 3-64 (IGHV3-64*04) (SEQ ID NO: 147) and immunoglobulin heavy joining 1 (IGHJ1*01) (SEQ ID NO: 148). The human germlines used were the most homologous human germline to the 2-13 clone (IgBLAST, NCBI). Promiscuous MHC class II binding peptides with high and moderate immunogenicity potential, as determined by ITOPE™ analysis, are indicated. Specifically, the MHCII binding peptides with high immunogenicity potential are as follows: (i) Peptide #1: residues 16-24 of SEQ ID NO: 45 (VKITCSGGS) (SEQ ID NO: 182); (ii) Peptide #2: residues 80-88 of SEQ ID NO: 45 (VYFCGTEDI) (SEQ ID NO: 183); and (iii) Peptide #8: residues 79-87 of SEQ ID NO: 35 (VRLQLNNLR) (SEQ ID NO: 184). The MHCII binding peptides with moderate immunogenicity potential are as follows: (i) Peptide #3: residues 18-26 of SEQ ID NO: 35 (LSLVCKASG) (SEQ ID NO: 176); (ii) Peptide #4: residues 20-28 of SEQ ID NO: 35 (LVCKASGFT) (SEQ ID NO: 185); (iii) Peptide #5: residues 36-44 of SEQ ID NO: 35 (WVRQTPGKG) (SEQ ID NO: 186); (iv) Peptide #6: residues 47-55 of SEQ ID NO: 35 (YVAEITNDG) (SEQ ID NO: 187); (v) Peptide #7: residues 64-72 of SEQ ID NO: 35 (VKGRATISR) (SEQ ID NO: 188); (vi) Peptide #9: residues 81-89 of SEQ ID NO: 35 (LQLNNLRAE) (SEQ ID NO: 189); and (vii) Peptide #10: residues 86-94 of SEQ ID NO: 35 (LRAEDTGTY) (SEQ ID NO: 190). Homologous peptides from the T cell epitope database are as follows: Peptide #4, and Peptide #5. A total of 10 binding peptides were identified, which are noted as Peptide #1-#10. "P1" for each of the binding peptides indicates the first anchor position.

In order to identify promiscuous MHC class II binding peptides, iTope™ (Abzena plc., UK) analysis was performed to overlapping 9-mer peptides spanning the entire sequence. Potential T cell epitopes were predicted through analysis of interaction to 34 different MHC class II alleles. As shown in FIGS. 7 and 8, respectively, clone 3-2 contained a total of 11 binding peptides, and clone 2-13 contained a total of 10 non-germline promiscuous MHC class II binding peptides.

Additionally, promiscuous MHC class II binding peptides were analyzed by TCED™ (Abzena plc., UK), which is CD4+ T cell epitope database constructed by T cell stimulation assay against over 10000 peptides. Clone 2-13 revealed that two promiscuous MHC class II binding peptides had high homology to known T cell epitopes. FIG. 8 (highlighted in green). Clone 3-2 had three promiscuous MHC class II binding peptides with high homology to known T cell epitopes. FIG. 7 (highlighted in green).

2. Construction of Composite Antibody Library

Figure 9A:
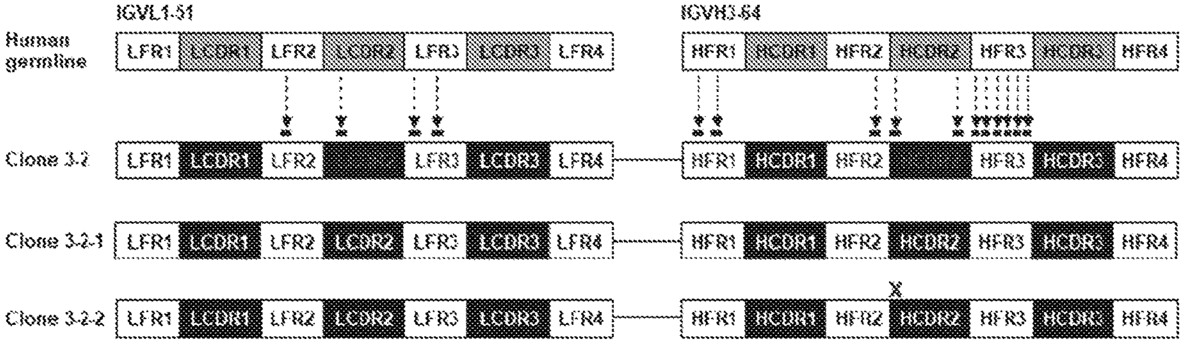
FIGS. 9A, 9B, and 9C provide the binding analysis of de-immunized 3-2 antibodies.
Figure 9B:
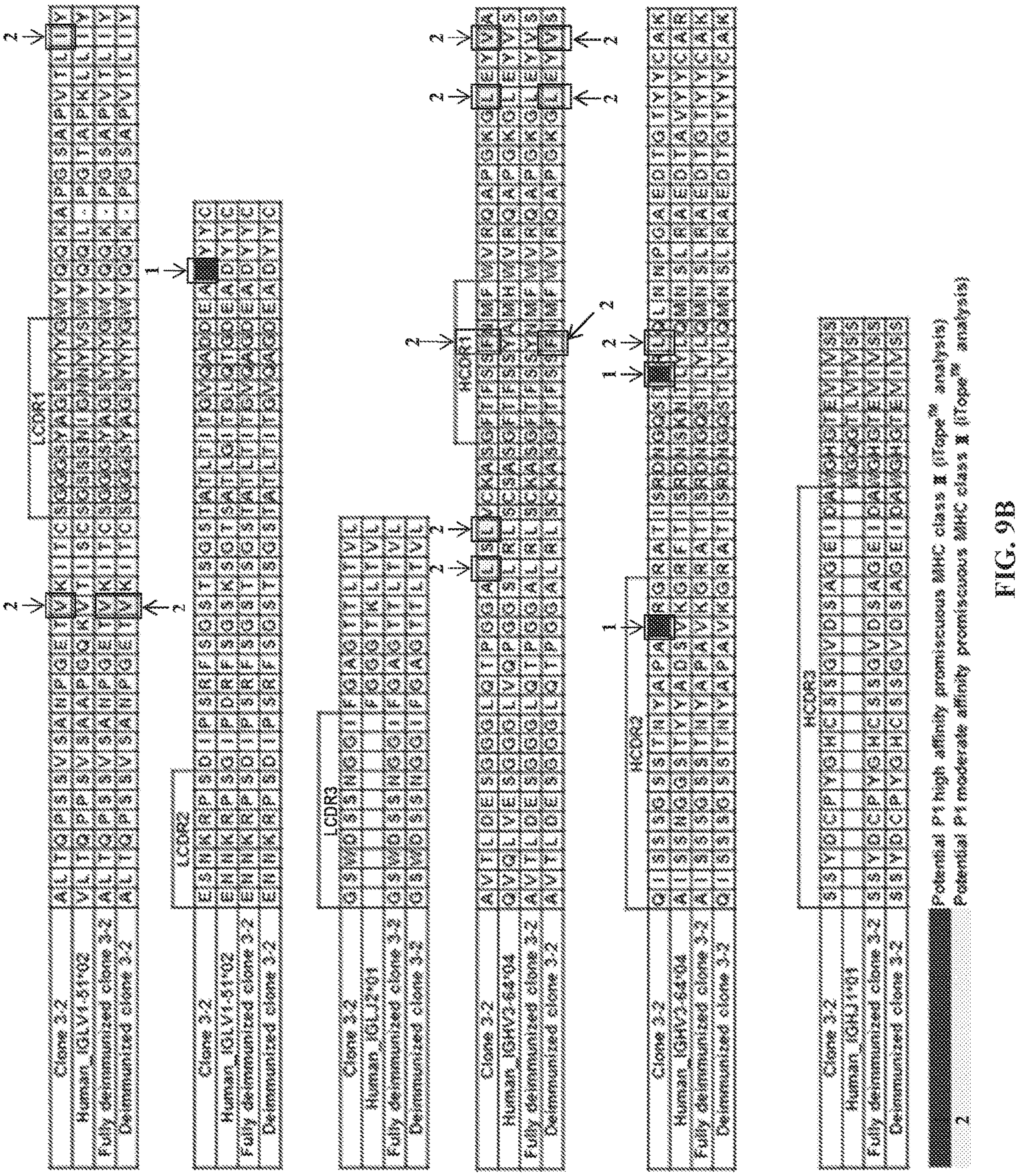

Composite antibody library was designed to avoid CD4+ T cell epitopes related to immunogenicity. To select the most homologous human germline for library construction, framework of clone 2-13 and clone 3-2 was analyzed to IgBLAST database (NCBI). Human germline IGLV1-51*02 (SEQ ID NO: 145), IGLJ2*01 (SEQ ID NO: 146), IGHV3-64*04 (SEQ ID NO: 147) and IGHJ1*01 (SEQ ID NO: 148) genes were chosen for clone 3-2 (FIGS. 9A and 9B). Human germline IGLV3-27*01 (SEQ ID NO: 149), IGLJ2*01 (SEQ ID NO: 146), IGHV3-64*04 (SEQ ID NO: 147) and IGHJ1*01 (SEQ ID NO: 148) genes were chosen for clone 2-13 (FIG. 10).

Library was constructed to substitute certain non-identical amino acid residues in MHC class II binding regions of clone 2-13 and clone 3-2 to corresponding amino acid in the most homologous human germline sequence. Serial overlap extension polymerase chain reaction (PCR) of oligonucleotide encoding degenerate codons to cover both human and chicken amino acid was performed to generate site-directed mutagenesis library, as previously described. Baek D S, Kim Y S. *Biochem Biophys Res Commun.* 463(3):414-20 (2015). PCR product was subcloned into phagemid vector and transformed into *Escherichia coli* strain ER2738 (New England BioLabs, Ipswich, MA, USA) for phage preparation, as previously described. Han, J., et al., *Exp Mol Med.* 48(11): e271 (2016).

3. Biopanning and Clone Selection

To isolate positive clones, biopanning and phage enzyme immunoassay was performed as described previously (Barbas C F., Phage display: a laboratory manual. Cold Spring Harbor, NY: Cold Spring Harbor Laboratory Press; 2001). The phage clones with reactivity against FAM19A5 were selected and their nucleotide sequences were determined by sanger sequencing. The scFv clones with the lowest number of promiscuous MHC class II binding epitopes with retained affinity toward FAM19A5 were finally selected.

Figure 9C:
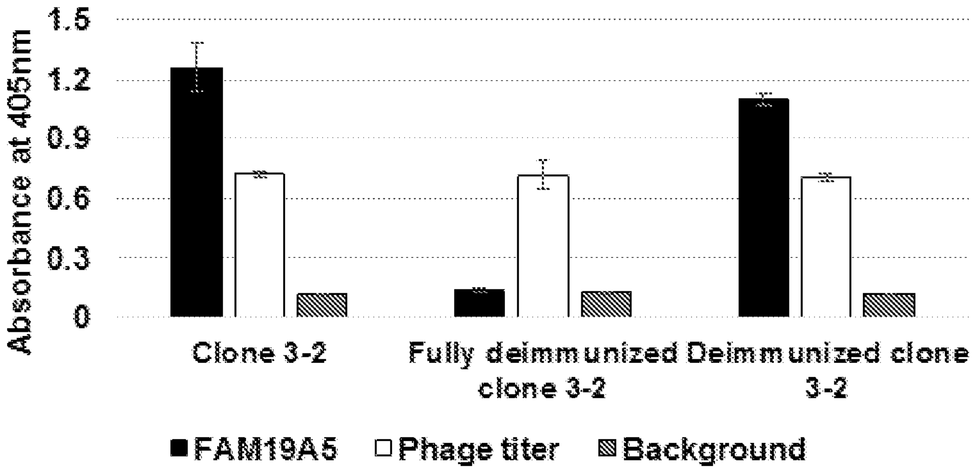

As shown in FIG. 9B, 7 promiscuous MHC class II binding epitopes in clone 3-2 were removed in deimmunized clone 3-2. The removed epitopes correspond to binding peptides #2, 3, 4, 5, 9, 10, and 11 as identified in FIG. 7. Promiscuous MHC class II binding epitopes in CDRH1 could not be removed (i.e., binding peptide #6 in FIG. 7). Also, promiscuous MHC class II binding epitope in HFR2 could not be removed because p3 residue located in the CDRH2 plays a critical role in binding activity (i.e., binding peptide #8 in FIG. 7). As shown in FIG. 9C, completely de-immunizing the 3-2 antibody by mutating all of the above residues resulted in the 3-2 antibody not being able to bind the FAM19A5 protein. However, when the amino acid residue Q50 of the VH was not mutated, the de-immunized 3-2 antibody was able to bind to FAM19A5 protein similar to that of the wild-type 3-2 antibody.

Figure 10A:
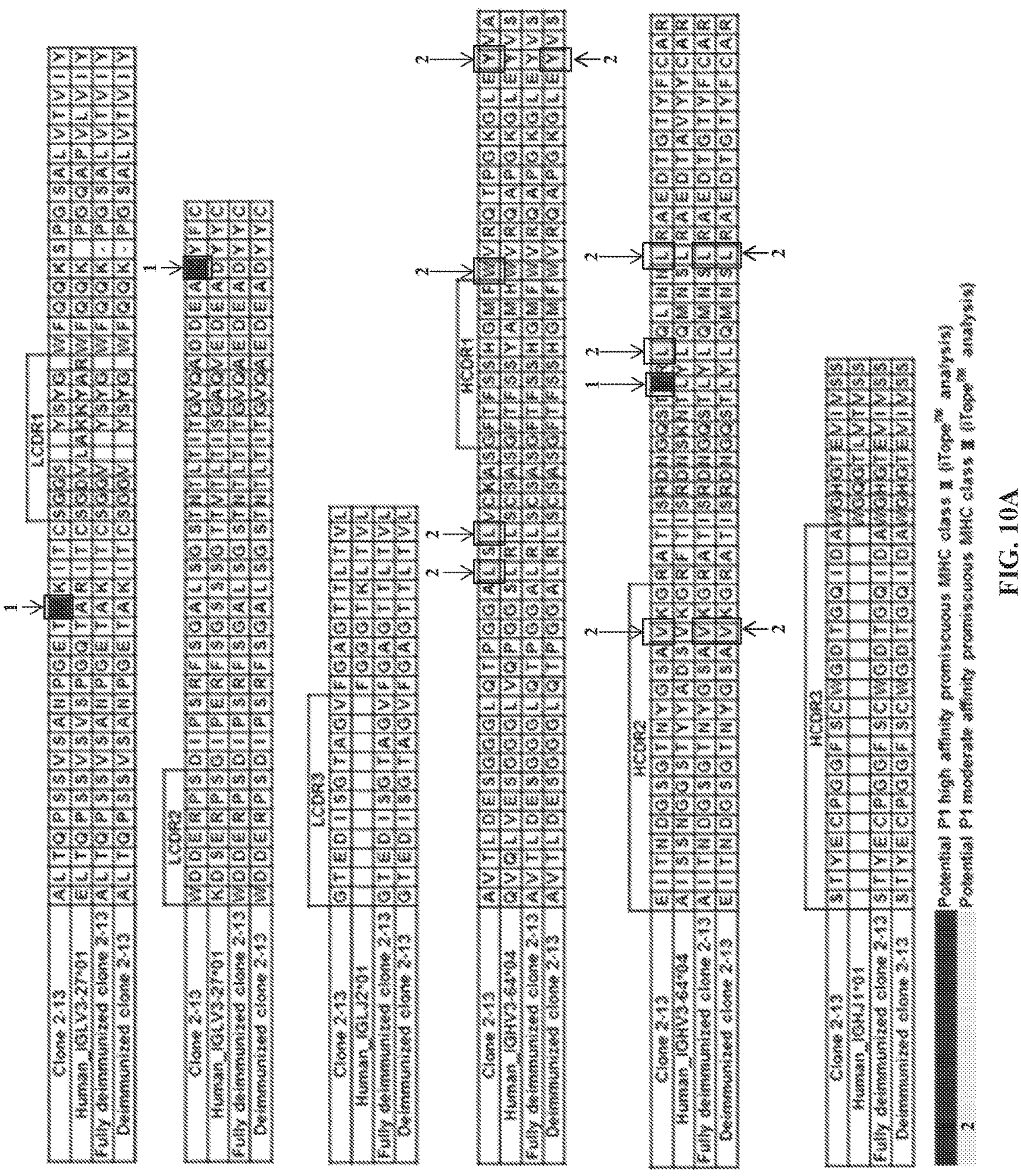
FIGS. 10A and 10B provide analysis for two different de-immunized 2-13 antibodies: (i) fully de-immunized, and (ii) de-immunized except at one amino acid within the heavy chain CDR2) antibody ("de-immunized clone 2-13").
Figure 10B:
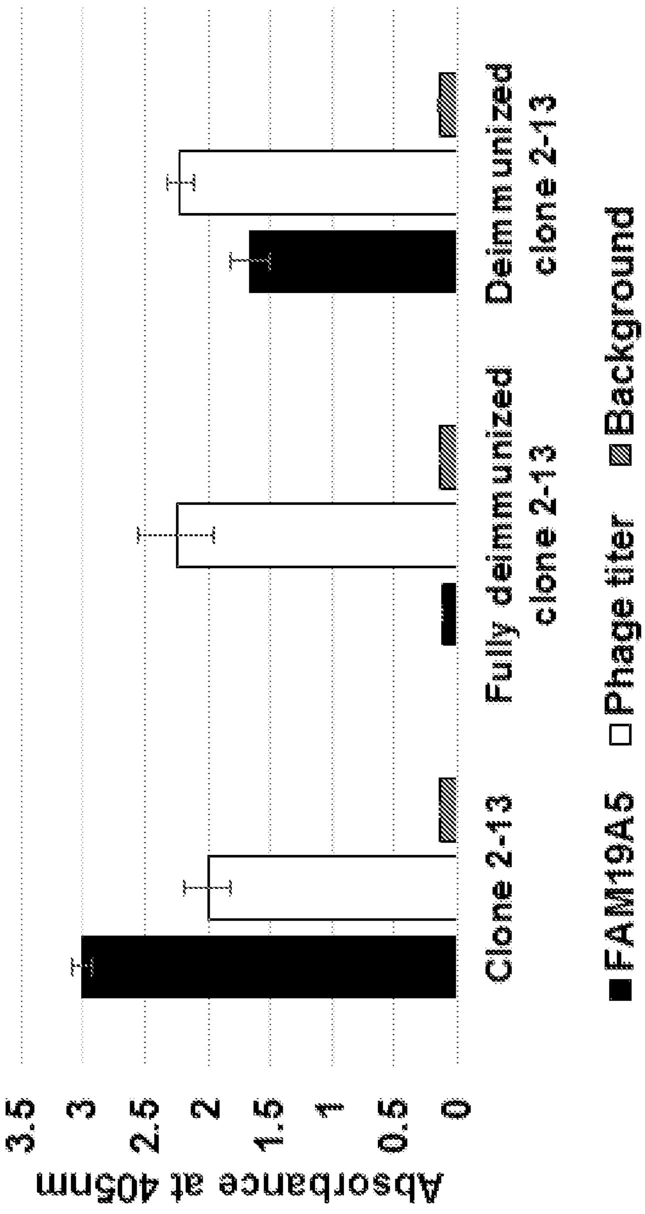

As shown in FIG. 10A, 7 promiscuous MHC class II binding epitopes in clone 2-13 were removed in deimmunized clone 2-13. The removed epitopes correspond to binding peptides #1, 2, 3, 4, 5, 8, and 9 as identified in FIG. 8. Promiscuous MHC class II binding epitope in HFR2 could not be removed because p4 residue located in the CDRH2 plays a critical role in binding activity (i.e., binding peptide #6 in FIG. 8). As with the 3-2 antibody, completely de-immunizing the 2-13 antibody also negatively affected binding to FAM19A5 protein. FIG. 10B.

The above results suggested that it was possible to reduce the immunogenicity of anti-FAM19A5 antibodies without negatively affecting their ability to bind to FAM19A5 protein.

Example 9 Affinity Maturation of De-Immunized 2-13 Antibody

Electrostatic interaction is important in association of antibody and antigen. Lee J. Y., et al., *Nat Commun.* 7:13354 (2016). Each amino acid in 5 CDRs except CDRH3 of deimmunized clone 2-13 was substituted to glutamic acid and aspartic acid to introduce artificially negatively charged R groups. A total of 70 genes encoding point mutated scFvs were chemically synthesized (Integrated DNA Technologies, Coralville, IA, USA) and subcloned into phagemid vector to construct mutant scFvs displaying phage, as described previously. Yoon, A., et al., *PLoS One.* 11(1): e0146907 (2016).

Figure 11:
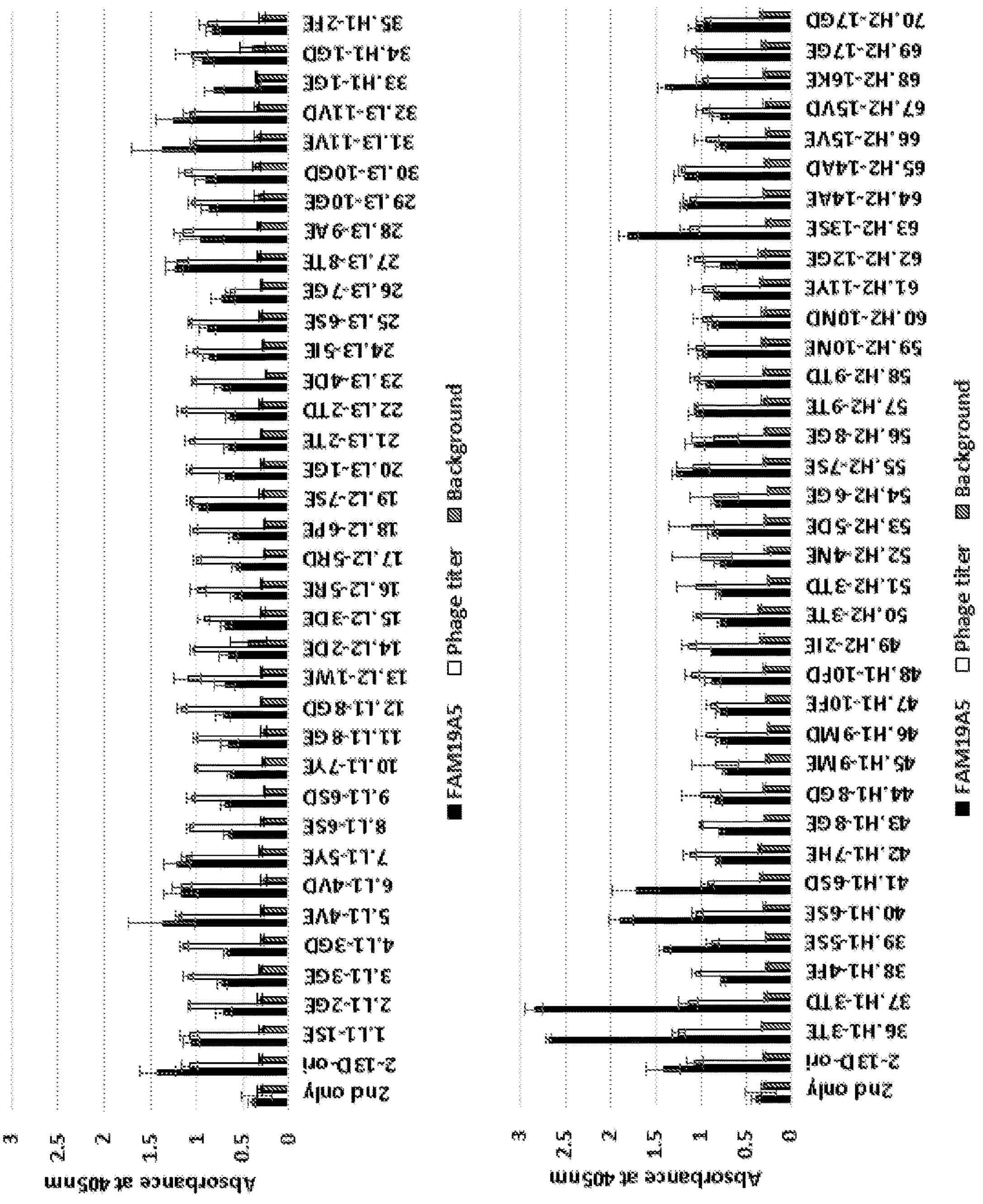
FIG. 11 provides a comparison of the binding ability of different deimmunized clone 2-13 variants. The identity of the different variant antibodies are provided along the x-axis. Each amino acid residue of the CDRL1, CDRL2, CDRL3, CDRH1 and CDRH2 was substituted to glutamic acid and aspartic acid. Reactivity of the 70 variant antibodies was analyzed by phage enzyme immunoassay. Each scFv displayed phage was added to the wells of a microtiter plate coated with FAM19A5 (■) or anti-HA antibody (□). The background signal was measured in control wells that were coated with BSA. The wells were probed with HRP-conjugated anti-M13 antibody. Absorbance at 405 nm was measured. The results are shown as the mean±SD acquired from experiments conducted in triplicate.
Figure 15:
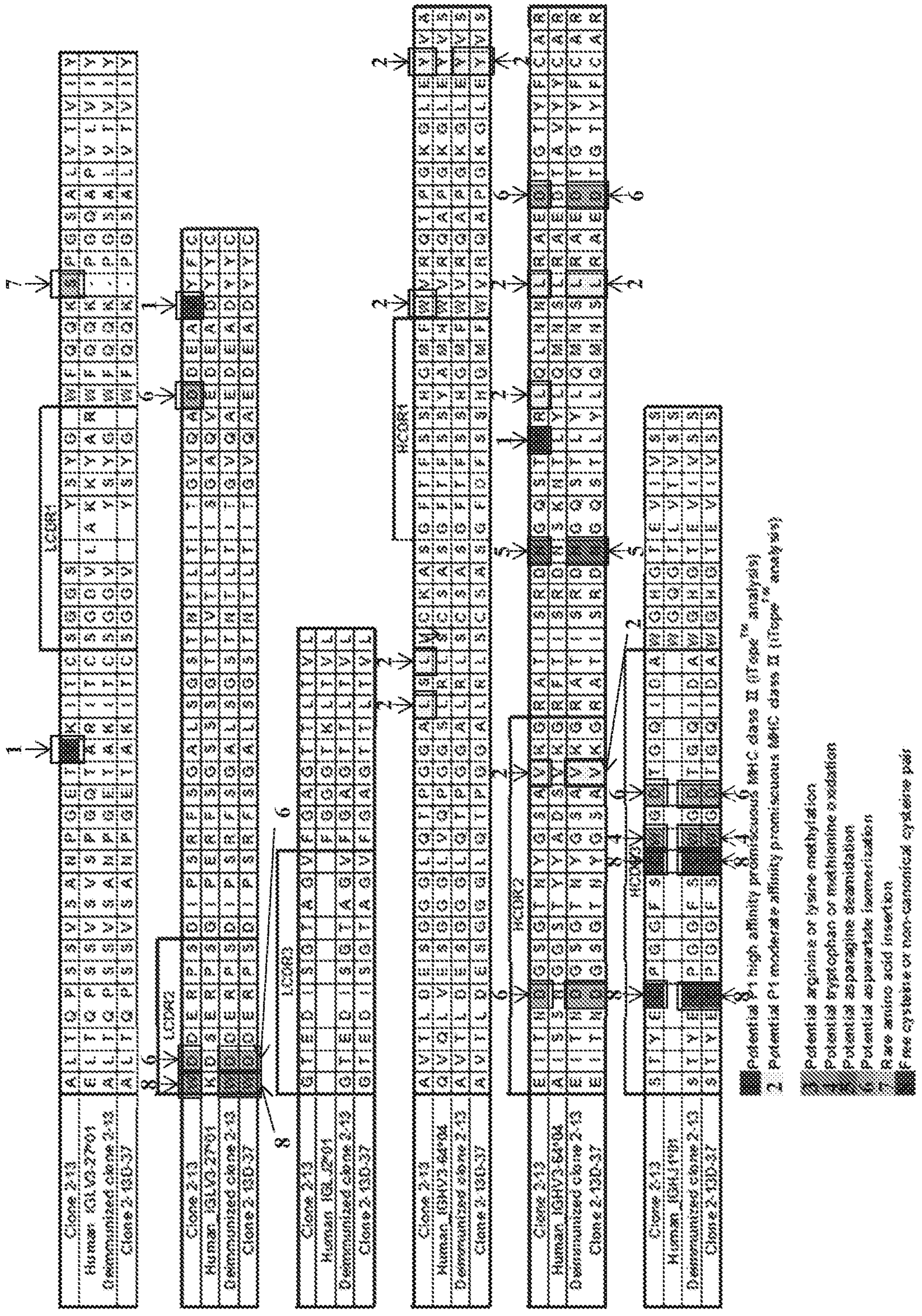
FIG. 15 provides sequence alignment of the light chain variable regions (top three rows) and of the heavy chain variable regions (bottom three rows) for the different de-immunized and/or affinity matured 2-13 antibody variants. The specific VL and VH sequences for the following antibodies are provided: (a) clone 2-13 (SEQ ID NOs: 45 and 35, respectively), (b) de-immunized clone 2-13 (SEQ ID NOs: 46 and 36, respectively), and (c) clone 2-13D-37 (SEQ ID NOs: SEQ ID NOs: 46 and 37, respectively). These variant antibodies are related to the 2-13 antibody in that they are equivalent to the 2-13 antibody, except that they have been de-immunized and/or undergone affinity maturation. Additional sequences shown in FIG. 15 include: (a) immunoglobulin lambda variable 3-27 (IGLV3-27*01) (SEQ ID NO: 149), (b) immunoglobulin lambda joining 2 (IGLJ2*01) (SEQ ID NO: 146), (c) immunoglobulin heavy variable 3-64 (IGHV3-64*04) (SEQ ID NO: 147), and (d) immunoglobulin heavy joining 1 (IGHJ1*01) (SEQ ID NO: 148). Amino acid residues with high and moderate immunogenicity potential, as determined by ITOPE™ analysis, are boxed and indicated with "1" and "2," respectively. Other amino acid residues of interest are also noted: "3"=potential arginine or lysine methylation; "4"=potential tryptophan or methionine oxidation; "5"=potential asparagine deamidation; "6"=potential aspartate isomerization; "7"=rare amino acid insertion; and "8"=free cysteine or non-canonical cysteine pair. Such amino acid residues can lead to product variants during natural cellular processing and degradation events.

Charge-variant mutant scFvs displaying phage were rescued and subjected to a phage enzyme immunoassay as described previously (Barbas C F. Phage display: a laboratory manual. Cold Spring Harbor, NY: Cold Spring Harbor Laboratory Press; 2001). As shown in FIG. 11, all of the clones exhibited FAM19A5 binding activity to varying degrees. Two clones (36.H1-3TE and 37.H1-3TD) exhibited higher binding affinity than de-immunized clone 2-13. Sequence comparison of the VH and VL of (i) wild-type 2-13 antibody, (ii) de-immunized clone 2-13 antibody, and (iii) de-immunized and affinity matured 2-13 antibody (2-13D-37) are provided in FIG. 15.

Example 10 Affinity Maturation of De-Immunized 2-13D-37 Antibody

To construct CDR-H3 site-directed mutagenesis libraries, the gene encoding deimmunized clone 2-13D-37 scFv was used as a template for PCR. Three consecutive residues in the CDR-H3 were randomized with oligonucleotides encoding NNK degenerate codons (N=A, T, G or C, K=G or T), as described previously (Lee Y, Kim H, Chung *J. Exp Mol Med.* 2014; 46:e114). Randomized codons were introduced in CDR-H3 by PCR. Amplified scFv fragments by overlap extension PCR were subcloned into phagemid vector and transformed into ER2738 (New England BioLabs) for phage preparation, as described above. A total of eight CDR-H3 randomized libraries were generated.

Figure 16A:
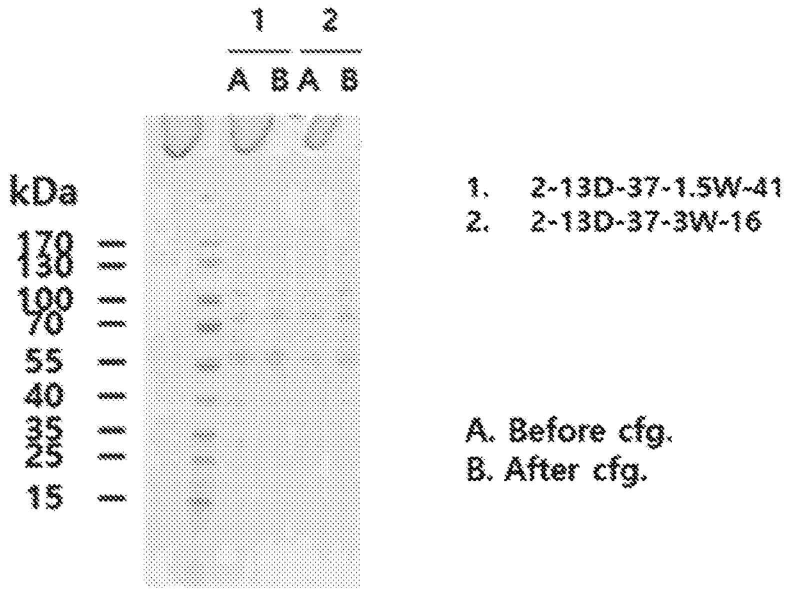
FIGS. 16A, 16B, and 16C provide the expression level of two variants (2-13D-37-1.5W-41 and 2-13D-37-3W-16) of the de-immunized 2-13D-37 antibody, as measured by SDS-PAGE and Western Blotting.
Figure 16B:
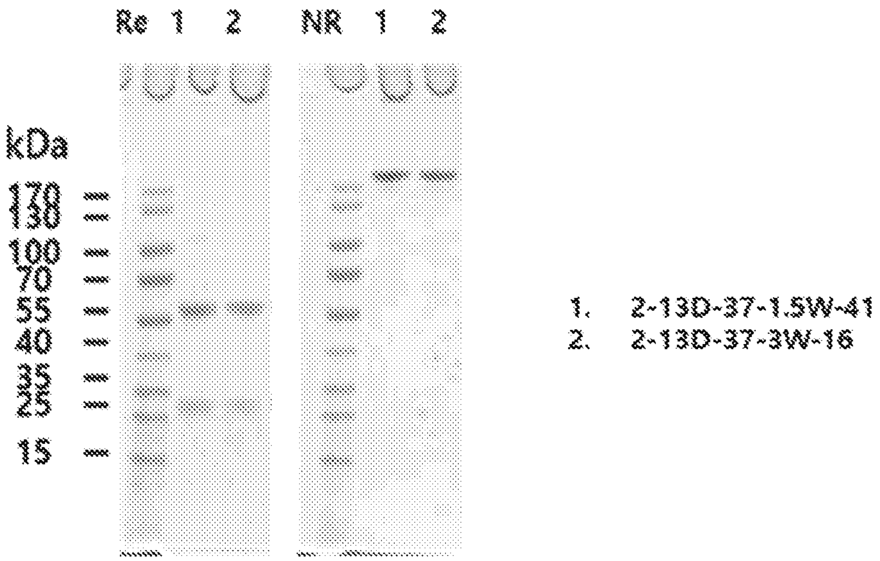
Figure 16C:
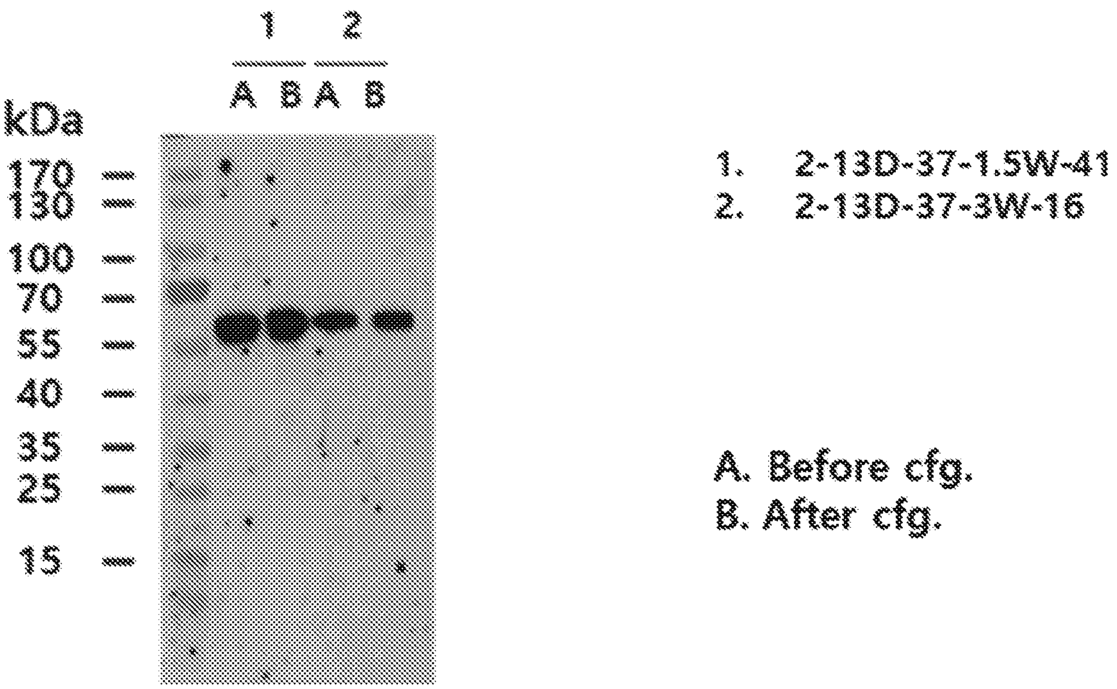
Figure 17A:
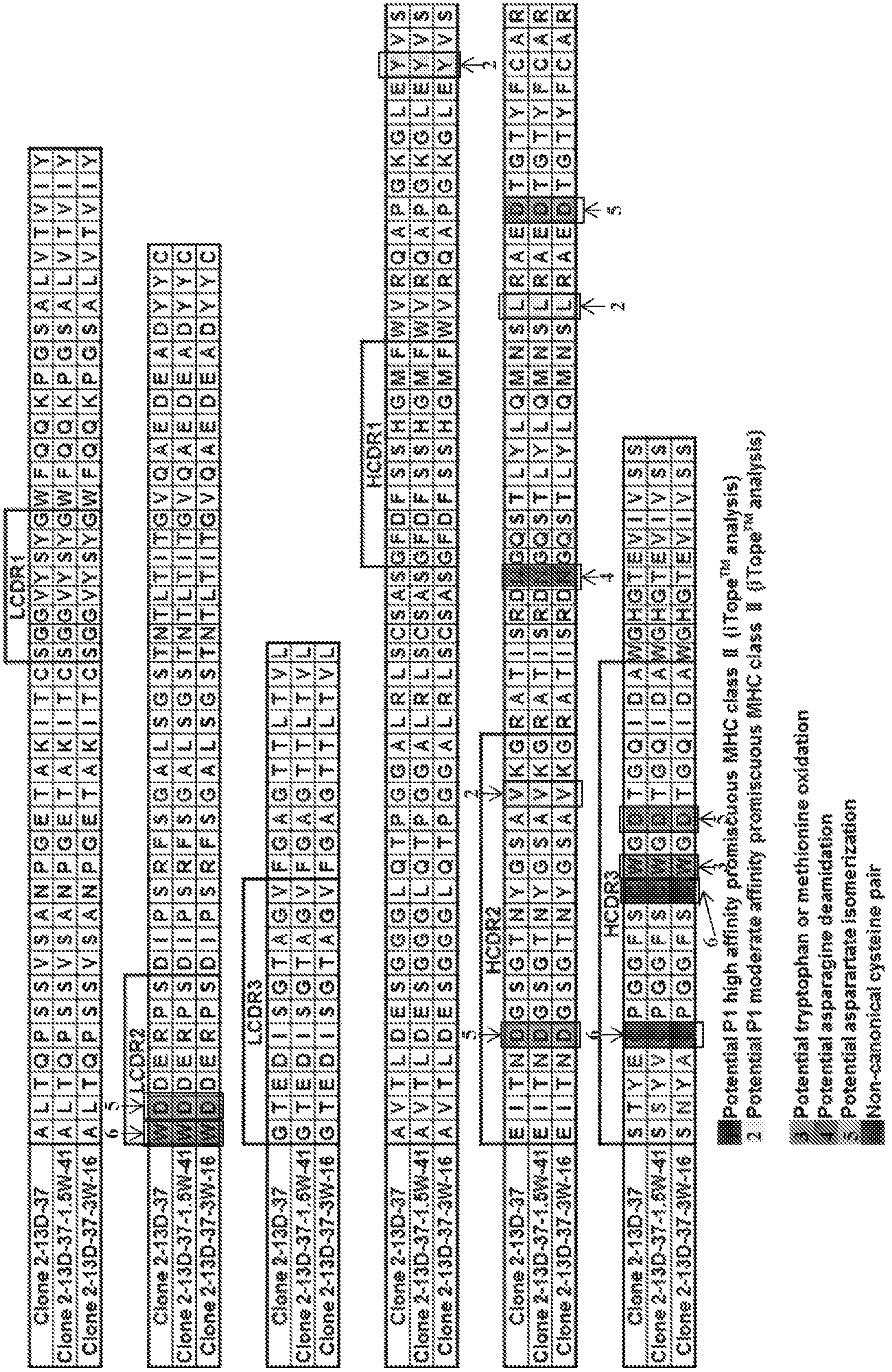
FIGS. 17A and 17B provide analysis of two variants (2-13D-37-1.5W-41 and 2-13D-37-3W-16) of the de-immunized 2-13D-37 antibody, which were generated through affinity maturation.
Figure 17B:
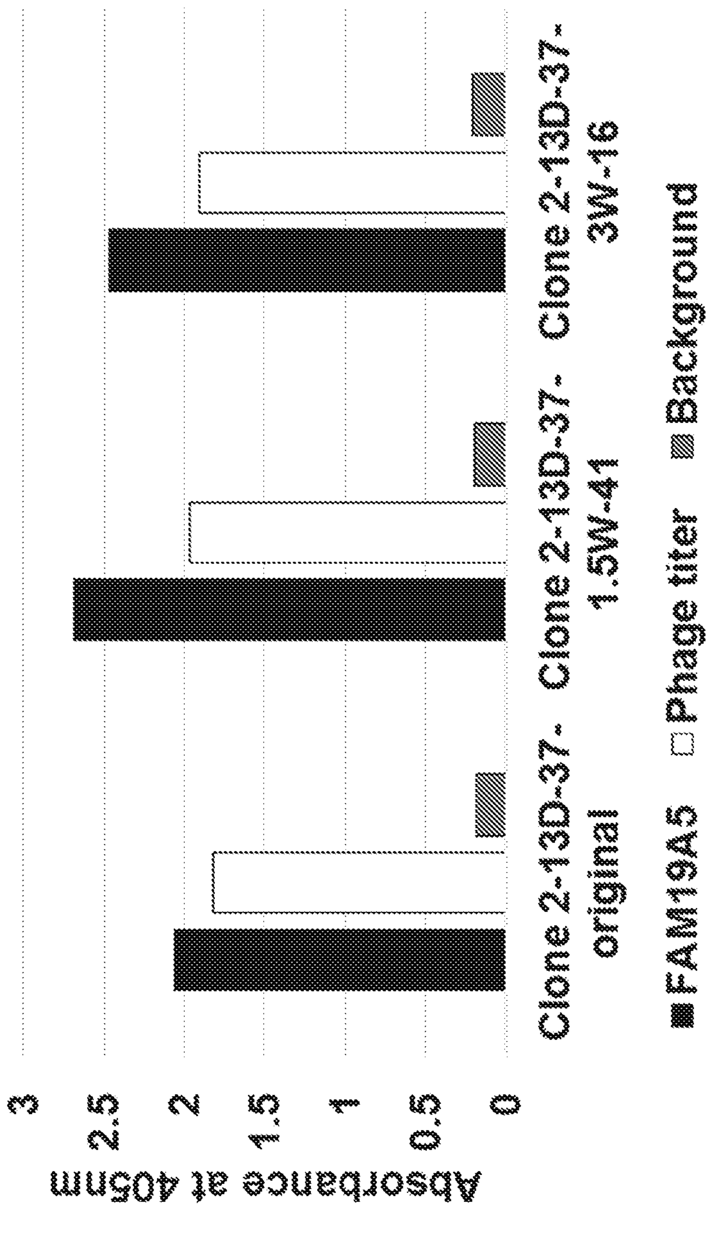

Biopanning and phage enzyme immunoassay were performed to isolate positive clones, as described previously (Barbas C F. Phage display: a laboratory manual. Cold Spring Harbor, NY: Cold Spring Harbor Laboratory Press; 2001; see also Example 8). The phage clones with exhibiting higher reactivity against FAM19A5 were selected and their nucleotide sequences were determined by sanger sequencing. The size and expression level of the candidate clones (i.e., 2-13D-37-1.5W-41 and 2-13D-37-3W-16) as measured using SDS-PAGE and Western Blotting are provided in FIGS. 16B-16C. Sequence comparison of the candidate clones (i.e., 2-13D-37-1.5W-41 and 2-13D-37-3W-16) to deimmunized clone 2-13D-37 is provided in FIG. 17A. Compared to the 2-13D-37 antibody, these affinity matured deimmunized antibodies exhibited greater binding to FAM19A5 protein as measured by ELISA (FIG. 17B).

Figure 12:
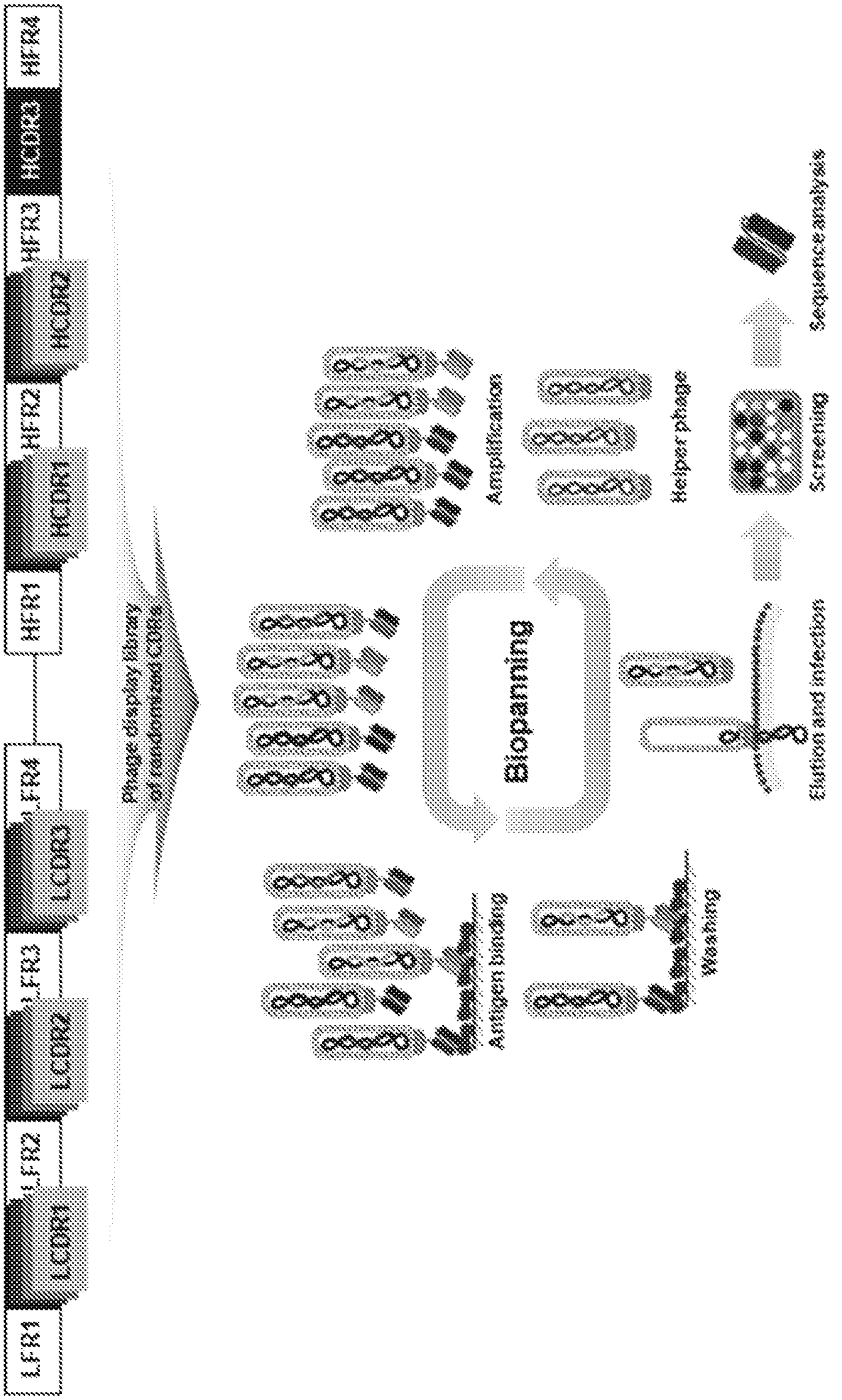
FIG. 12 provides a schematic of the methods used to generate de-immunized anti-FAM19A5 antibodies with improved physicochemical properties.

Example 11 Improving the Physicochemical Properties of De-Immunized 3-2 Antibody To improve the physicochemical properties of the de-immunized anti-FAM19A5 antibodies, a phage display library was constructed using randomized sequences from the light chain CDR 1, CDR2, and CDR3 and from the heavy chain CDR1 and CDR2 of the 3-2 antibody. To construct CDR site-directed mutagenesis libraries, the gene encoding de-immunized clone 3-2 scFv was used as a template for PCR. Four or five consecutive residues in the CDRs were randomized with oligonucleotides encoding NNK degenerate codons (N=A, T, G or C, K=G or T), as described previously. Lee, Y., et al., *J. Exp Mol Med.* 46:e114 (2014). Randomized codons were introduced in five CDRs except CDRH3 by PCR. Amplified scFv fragments by overlap extension PCR were subcloned into phagemid vector and transformed into ER2738 (New England BioLabs) for phage preparation, as described above. FIG. 12.

Figures 13A, 13B:
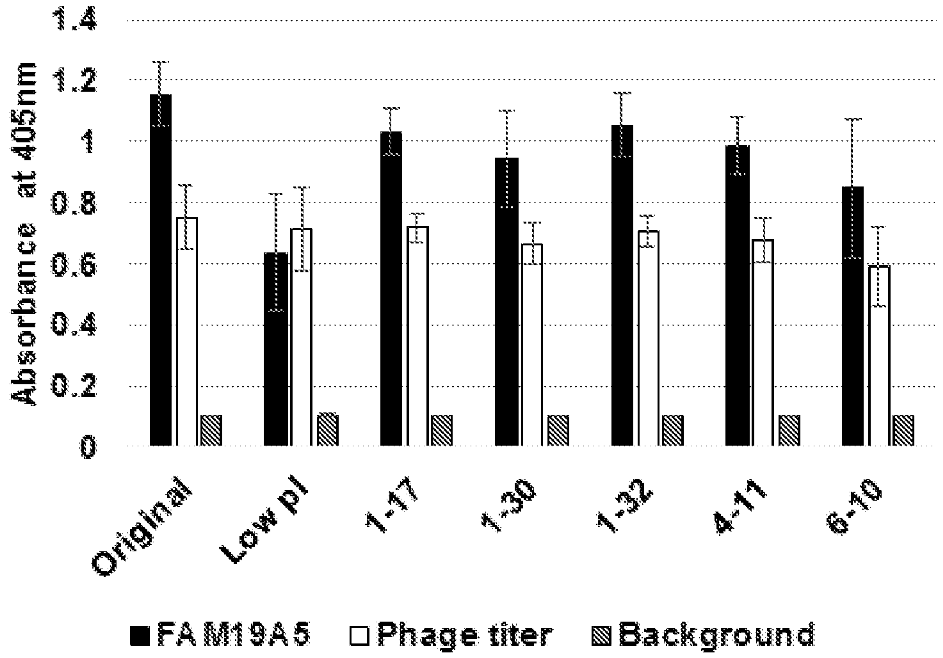
FIGS. 13A and 13B provides a comparison of the physiochemical properties of several deimmunized 3-2 variants to the wild-type (i.e., not deimmunized) 3-2 antibody ("original"). The variant antibodies shown include: (i) antibody with low isoelectric point ("Low PI"), (ii) 1-17, (iii)
Figure 14A:
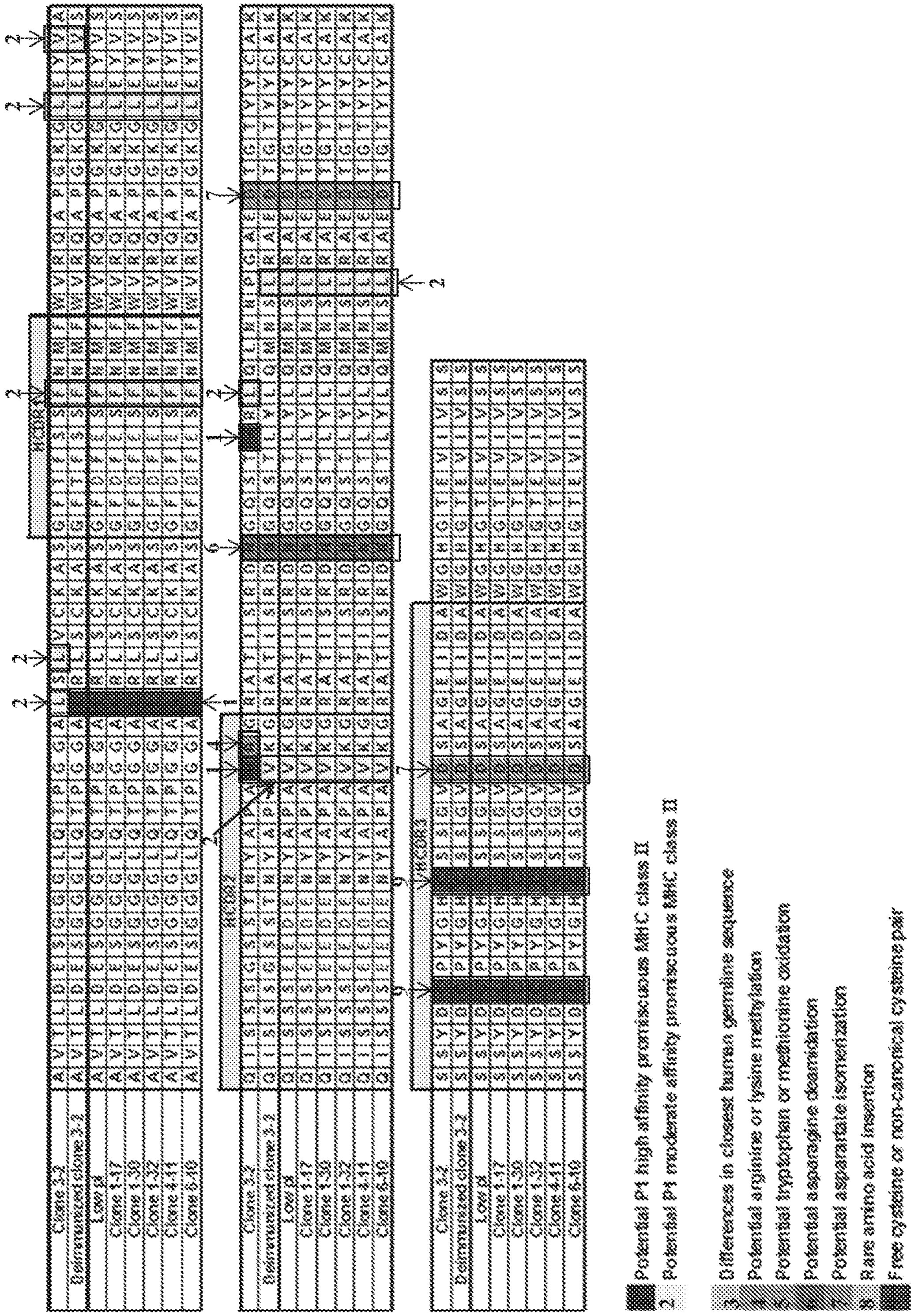
FIGS. 14A and 14B provide sequence alignment of the heavy chain variable regions (FIG. 14A) and of the light chain variable regions (FIG. 14B) for the different deimmunized 3-2 antibody variants. The specific VH and VL sequences for the following antibodies are provided: (a) clone 3-2 (SEQ ID NOs: 11 and 12, respectively), (b) deimmunized clone 3-2 (SEQ ID NOs: 33 and 38, respectively), (c) low PI (SEQ ID NOs: 34 and 39, respectively), (d) clone 1-17 (SEQ ID NOs: 34 and 41, respectively), (e) clone 1-30 (SEQ ID NOs: 34 and 40, respectively), (f) clone 1-32 (SEQ ID NOs: 34 and 42, respectively), (g) clone 4-11 (SEQ ID NOs: 34 and 43, respectively), and (i) clone 6-10 (SEQ ID NOs: 34 and 44, respectively). The deimmunized variant antibodies shown are related to the 3-2 antibody in that the antibodies are equivalent to the 3-2 antibody, except that they have been de-immunized to reduce immunogenicity when administered to human subjects. Amino acid residues with high and moderate immunogenicity potential, as determined by ITOPE™ analysis, are boxed and indicated with "1" and "2," respectively. Other amino acid residues of interest are also noted: "3"=differences in closest human germline sequence; "4"=potential arginine or lysine methylation; "5"=potential tryptophan or methionine oxidation; "6"=potential asparagine deamidation; "7"=potential aspartate isomerization; "8"=rare amino acid insertion; and "9"=free cysteine or non-canonical cysteine pair. Such amino acid residues can lead to product variants during natural cellular processing and degradation events.
Figure 14B:
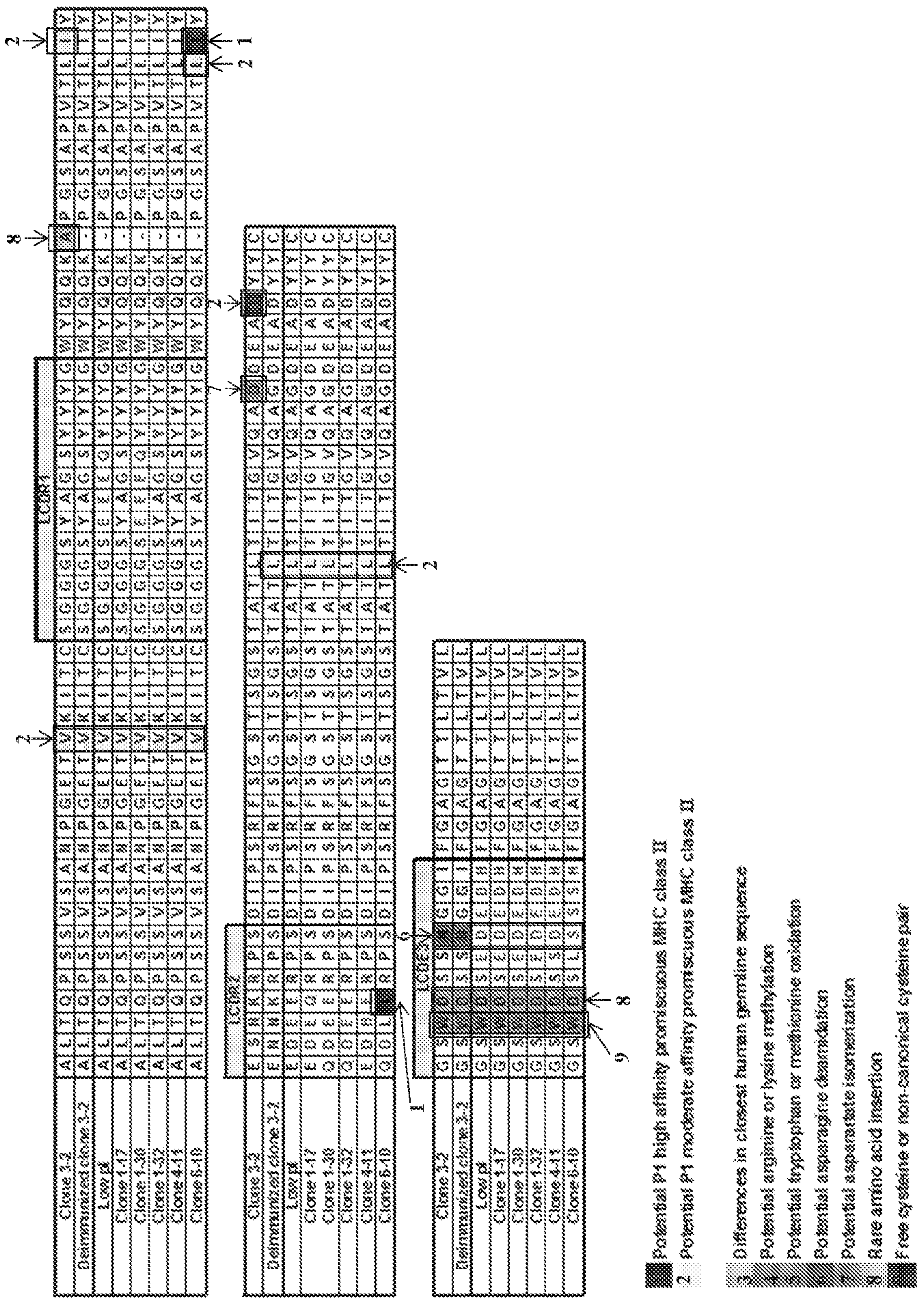

Biopanning and phage enzyme immunoassay were performed to isolate positive clones, as described previously (Barbas C F. Phage display: a laboratory manual. Cold Spring Harbor, NY: Cold Spring Harbor Laboratory Press; 2001). The phage clones with reactivity against FAM19A5 were selected and their nucleotide sequences were determined by sanger sequencing. Intrinsic solubility score and GRAVY score of individual clones were calculated, as described previously. Sormanni, P., et al., *Sci Rep.* 7(1):8200 (2017). Clones with improved solubility while exhibiting similar reactivity against FAM19A5 were selected: (i) antibody with low isoelectric point ("Low PI"), (ii) 1-17, (iii) 1-30, (iv) 1-32, (v) 4-11, and (vi) 6-10. Results are shown in FIGS. 13A and 13B. Sequence comparison of the VH and VL of the different de-immunized variant 3-2 antibodies to wild-type 3-2 antibody is provided in FIGS. 14A and 14B, respectively.

Example 12 HDX-MX Epitope Mapping of 2-13 Antibody

Figure 18:
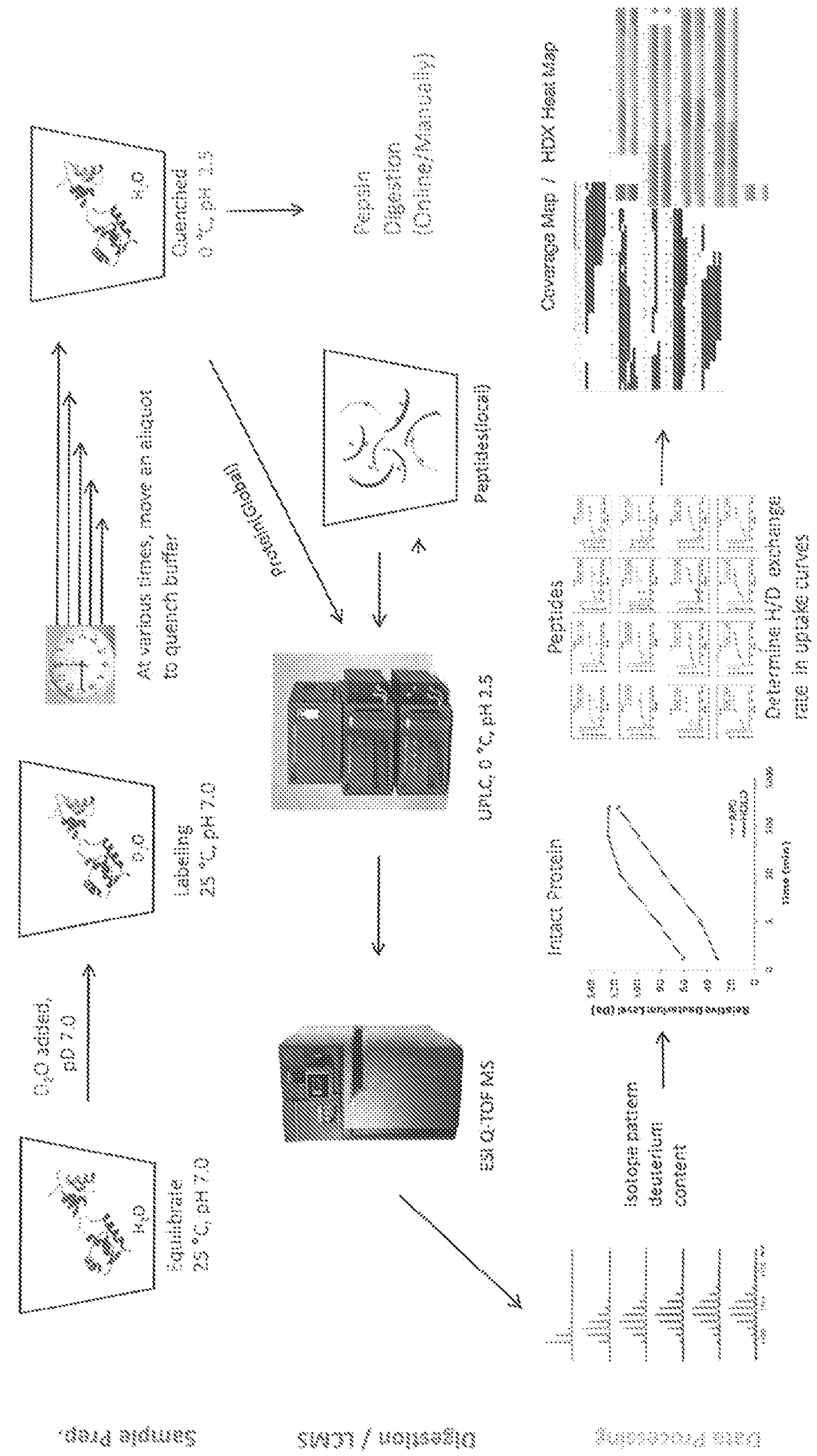
FIG. 18 provides a schematic of the overall workflow of the HDX-MS assay used in Example 11.

Hydrogen/deuterium exchange mass spectrometry (HDX-MS) was utilized as described below to probe the binding epitope of human FAM19A5 for the clone 2-13 anti-FAM19A5 antibody. See FIG. 18.

1. Optimization of Conditions for Maximal FAM19A5 Coverage

Prior to epitope mapping experiments, non-deuteriated experiments were carried out to generate a list of common peptides for FAM19A5 protein. Off-line and on-line pepsin digestion were used to digest the FAM19A5 protein. Houde, D., et al., *Methods Mol Biol* 988:269-89 (2013). With on-line digestion, pepsin immobilized column was used (~20° C.) and the efficiency of the reaction was regulated by adjusting the flow rate. With the off-line method, FAM19A5 protein was digested manually with pepsin at 4° C. for 5 minutes, and then, the mixture was loaded to liquid chromatography column for analysis. To identify the condition for maximal protein coverage, one or more of the following parameters were adjusted: potassium phosphate, sodium phosphate, quench holding time, reducing reagent (TCEP), urea concentration, and pepsin concentration. The Waters PLGS software was used to analyze the raw mass spectrometry (MS) data generated to determine whether maximal protein coverage was obtained. To confirm the reproducibility of the experiments, each of the experimental conditions were repeated at least twice, and peptides that were generated were confirmed. FIG. 19 shows the different experimental conditions used and the percent coverage achieved.

Figure 20A:
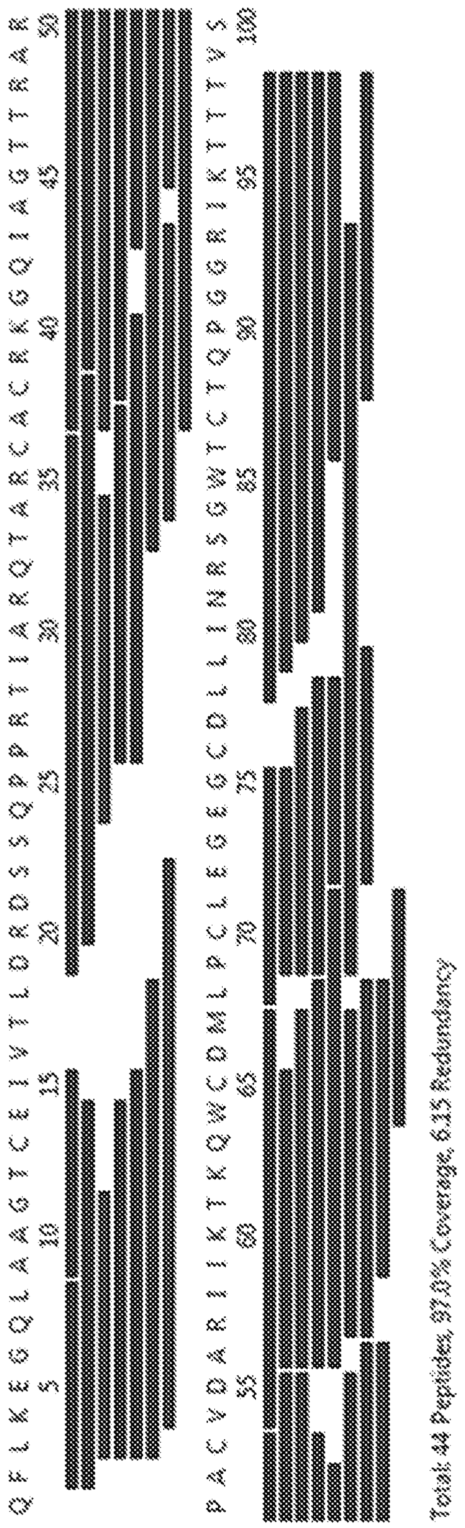

Maximum coverage was observed using the following conditions: 1M TCEP, 2M Urea (pH 2.66), and pepsin at 1:2 concentration. As shown in FIGS. 20A and 20B, using these conditions, 44 peptide fragments were identified, which covered approximately 97% of the FAM19A5 protein.

2. FAM19A5 Epitope Mapping

To obtain maximum (100%) binding ($K_D$=1 nM) even when the antibody-protein complex is diluted 15-fold in the labeling buffer, the antigen-antibody complex samples were incubated for at least 3 hours prior to hydrogen/deuterium labeling. After labeling, the samples were brought to the same volume using equilibrium buffer.

To start the labeling reaction, 2.5 μL of the prepared samples (antigen alone, antibody alone, or antigen-antibody complex) diluted in 1:15 labeling buffer were mixed with the $D_2O$ labeling solution (1.8 μM). The reactions were carried out for different time periods of time: 0 min (i.e., undeuterium), 20 seconds, 10 minutes, 60 minutes, and 240 minutes. For the undeuterium reaction, the prepared sample was mixed instead with the equilibration buffer. At the end of each labeling period, the reaction was stopped with quenching buffer. The samples were then vortexed, immediately frozen in liquid nitrogen, and stored at −80° C. until analysis.

Prior to analysis with the mass spectrometer, the stored frozen samples were allowed to melt and then, digested with pepsin for approximately 5 minutes on ice (i.e., off-line method described above). The resulting relative deuterium levels were plotted versus the exchange time with use of the software program DynamX 3.0™ (Waters). Final sequence coverage and redundancy data are shown in FIG. 21.

Comparison of the deuterium uptake data (single antigen/antibody v. antigen-antibody complex) for each of the identified peptides (see FIG. 21) are shown in FIGS. 22A-22E and 23A-23C. As shown, significant deuterium uptake was observed for the following peptide sequences: (i) ACRKGQIAGTTRARPAC (residues 37-53 of SEQ ID NO: 101) (SEQ ID NO: 110), (ii) ACRKGQIAGTTRARPACVD (residues 37-55 of SEQ ID NO: 101) (SEQ ID NO: 111), (iii) ACRKGQIAGTTRARPACVDA (residues 37-56 of SEQ ID NO: 101) (SEQ ID NO: 112), (iv) ARIIKTKQWC (residues 56-65 of SEQ ID NO: 101) (SEQ ID NO: 113), (v) ARIIKTKQWCDM (residues 56-67 of SEQ ID NO: 101) (SEQ ID NO: 114), (vi) ARIIKTKQWCDML (residues 56-68 of SEQ ID NO: 101) (SEQ ID NO: 115), (vii) ARIIKTKQWCDMLPCL (residues 56-71 of SEQ ID NO: 101) (SEQ ID NO: 116), (viii) RIIKTKQWCDM (residues 57-67 of SEQ ID NO: 101) (SEQ ID NO: 117), and (ix) RIIKTKQWCDML (residues 57-68 of SEQ ID NO: 101) (SEQ ID NO: 118).

Using the above results, a heat map was constructed to identify the regions within FAM19A5 protein with the most significant difference in deuterium uptake between single antigen/antibody sample and antigen-antibody complex. As shown in FIG. 24, amino acid residues 38-50 (CRKGQIAGTTRAR) and 51-64 (PACVDARIIKTKQW) of SEQ ID NO: 101 (SEQ ID NOs: 170 and 97, respectively) were identified as important binding residues for the 2-13 antibody. FIG. 25 shows the location of these residues within the 3-dimensional structure of the FAM19A5 protein.

It is to be appreciated that the Detailed Description section, and not the Summary and Abstract sections, is intended to be used to interpret the claims. The Summary and Abstract sections can set forth one or more but not all exemplary embodiments of the present disclosure as contemplated by the inventor(s), and thus, are not intended to limit the present disclosure and the appended claims in any way.

The present disclosure has been described above with the aid of functional building blocks illustrating the implementation of specified functions and relationships thereof. The boundaries of these functional building blocks have been arbitrarily defined herein for the convenience of the description. Alternate boundaries can be defined so long as the specified functions and relationships thereof are appropriately performed.

The foregoing description of the specific embodiments will so fully reveal the general nature of the disclosure that others can, by applying knowledge within the skill of the art, readily modify and/or adapt for various applications such specific embodiments, without undue experimentation, without departing from the general concept of the present disclosure. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

The breadth and scope of the present disclosure should not be limited by any of the above-described exemplary embodiments, but should be defined only in accordance with the following claims and their equivalents.

All publications, patents, patent applications, internet sites, and accession numbers/database sequences (including both polynucleotide and polypeptide sequences) cited herein are hereby incorporated by reference in their entirety for all purposes to the same extent as if each individual publication, patent, patent application, internet site, or accession number/database sequence were specifically and individually indicated to be so incorporated by reference.

What is claimed is:

1. An isolated antibody, or antigen binding portion thereof, which specifically binds a human family with sequence similarity 19, member AS (FAM19A5) protein ("anti-FAM19A5 antibody"), comprising a heavy chain CDR1, CDR2, and CDR3 and a light chain CDR1, CDR2, and CDR3, wherein (i) the heavy chain CDR1 comprises the amino acid sequence set forth in SEQ ID NO: 14; (ii) the heavy chain CDR2 comprises the amino acid sequence set forth in SEQ ID NO: 15; (iii) the heavy chain CDR3 comprises the amino acid sequence set forth in SEQ ID NO: 7; (iv) the light chain CDR1 comprises the amino acid sequence set forth in SEQ ID NO: 21; (v) the light chain CDR2 comprises the amino acid sequence set forth in SEQ ID NO: 24; and (vi) the light chain CDR3 comprises the amino acid sequence set forth in SEQ ID NO: 23.

2. The anti-FAM19A5 antibody of claim 1, comprising a heavy chain variable region (VH) and a light chain variable region (VL), wherein the VH comprises an amino acid sequence which is at least about 80% identical to the amino acid sequence set forth in SEQ ID NO: 34; and/or wherein the VL comprises an amino acid sequence which is at least about 80% identical to the amino acid sequence set forth in SEQ ID NO: 40.

3. The anti-FAM19A5 antibody of claim 1, which comprises a Fab, a Fab', a F(ab')2, a Fv, or a single chain Fv (scFv).

4. The anti-FAM19A5 antibody of claim 1, which is a chimeric antibody or a humanized antibody.

5. A bispecific molecule comprising the anti-FAM19A5 antibody of claim 1.

6. An immunoconjugate comprising the anti-FAM19A5 antibody of claim 1 linked to a therapeutic agent, wherein the therapeutic agent modulates onset of gliosis and/or reactive astrogliosis and/or treat a degenerative brain disorder, central nervous system damage, or neuropathic pain.

7. A composition comprising the anti-FAM19A5 antibody of claim 1 and a carrier.

8. A composition comprising the anti-FAM19A5 antibody of claim 2 and a carrier.

9. An immunoconjugate comprising the anti-FAM19A5 antibody of claim 2 linked to a therapeutic agent, wherein the therapeutic agent modulates onset of gliosis and/or reactive astrogliosis and/or treat a degenerative brain disorder, central nervous system damage, or neuropathic pain.

10. The anti-FAM19A5 antibody of claim 2, wherein the VH comprises the amino acid sequence set forth in SEQ ID NO: 34 and the VL comprises the amino acid sequence set forth in SEQ ID NO: 40.

11. The anti-FAM19A5 antibody of claim 2, which is a chimeric antibody or a humanized antibody.

12. The anti-FAM19A5 antibody of claim 2, which comprises a Fab, a Fab', a F(ab')2, a Fv, or a single chain Fv (scFv).

13. A bispecific molecule comprising the anti-FAM19A5 antibody of claim 2.

14. An immunoconjugate comprising the anti-FAM19A5 antibody of claim 10 linked to a therapeutic agent, wherein the therapeutic agent modulates onset of gliosis and/or reactive astrogliosis and/or treat a degenerative brain disorder, central nervous system damage, or neuropathic pain.

15. A composition comprising the anti-FAM19A5 antibody of claim 10 and a carrier.

16. The anti-FAM19A5 antibody of claim 10, which is a chimeric antibody or a humanized antibody.

17. The anti-FAM19A5 antibody of claim 10, which comprises a Fab, a Fab', a F(ab')2, a Fv, or a single chain Fv (scFv).

18. A bispecific molecule comprising the anti-FAM19A5 antibody of claim 10.

* * * * *